(12) United States Patent
Paglia et al.

(10) Patent No.: US 10,557,861 B2
(45) Date of Patent: Feb. 11, 2020

(54) SYSTEMS, METHODS, AND BIOMARKERS FOR DETERMINING THE METABOLIC STATE OF RED BLOOD CELLS AND PLATELETS

(71) Applicants: Aarash Bordbar, San Diego, CA (US); University of Iceland, Center for Systems Biology, Reykjavik (IS)

(72) Inventors: Giuseppe Paglia, Reykjavik (IS); Sirus Palsson, San Diego, CA (US); Aarash Bordbar, San Diego, CA (US)

(73) Assignee: UNIVERSITY OF ICELAND, CENTER FOR SYSTEMS BIOLOGY, Reykjavik (IS)

(*) Notice: Subject to any disclaimer, the term of this patent is extended or adjusted under 35 U.S.C. 154(b) by 65 days.

(21) Appl. No.: 15/108,939

(22) PCT Filed: May 15, 2015

(86) PCT No.: PCT/US2015/031235
§ 371 (c)(1),
(2) Date: Jun. 29, 2016

(87) PCT Pub. No.: WO2015/179251
PCT Pub. Date: Nov. 26, 2015

(65) Prior Publication Data
US 2017/0160293 A1    Jun. 8, 2017

Related U.S. Application Data

(60) Provisional application No. 62/002,507, filed on May 23, 2014.

(51) Int. Cl.
*G01N 33/80* (2006.01)
*A61K 35/14* (2015.01)
*A61K 35/18* (2015.01)

(52) U.S. Cl.
CPC .............. *G01N 33/80* (2013.01); *A61K 35/18* (2013.01)

(58) Field of Classification Search
CPC .............. G01N 33/80; G01N 33/56966; G01N 2030/8822; A61K 35/14; A61K 35/18
See application file for complete search history.

(56) References Cited

U.S. PATENT DOCUMENTS

| | | | |
|---|---|---|---|
| 9,903,876 B2 * | 2/2018 | Zimring | ............ G01N 33/80 |
| 2002/0040216 A1 * | 4/2002 | Dumont | ............ A61J 1/10 |
| | | | 604/404 |
| 2007/0285238 A1 | 12/2007 | Batra | |
| 2013/0130298 A1 | 5/2013 | Tarasev et al. | |

FOREIGN PATENT DOCUMENTS

| | | |
|---|---|---|
| CN | 203012785 U | 6/2013 |
| WO | WO-9315402 A1 | 8/1993 |
| WO | WO-2012122154 A2 | 9/2012 |
| WO | WO-2014036183 A2 | 3/2014 |
| WO | WO-2015179251 A1 | 11/2015 |

OTHER PUBLICATIONS

Strumia et al. The preservation of blood for transfusion IX. The effect of increased pH and addition of inosine only or adenine and inosine on the red cell function.The Journal of Laboratory and Clinical Medicine. 79 (5): 863-872 (May 1972). Abstract.*
Uvizl et al. Biochemical changes in the patients plasma after red blood cell transfusion. Signa Vitae 6(2): 64-71 (2001).*
Uvizl et al. Biochemical changes in the patient's plasma after red blood cell transfusion. Signa Vitae 6 (2): 64-71 (2011)—provided to Applicant previously.*
Bordbar et al. Using the reconstructed genome-scale human metabolic network to study physiology and pathology. J Intern Med 271(2):131-141 (2012).
Lewis et al. Constraining the metabolic genotype-phenotype relationship using a phylogeny of in silico methods. Nat Rev Microbiol 10(4):291-305 (2012).
Paglia et al. Biomarkers defining the metabolic age of red blood cells during cold storage. Blood 128(13):e43-50 (2016).
Paglia et al. Comprehensive metabolomic study of platelets reveals the expression of discrete metabolic phenotypes during storage. Transfusion 54(11):2911-2923 (2014).
Paglia et al. Intracellular metabolite profiling of platelets: evaluation of extraction processes and chromatographic strategies. J Chromatogr B Analyt Technol Biomed Life Sci 898:111-120 (2012).
PCT/US2015/031235 International Search Report and Written Opinion dated Sep. 25, 2015.

(Continued)

*Primary Examiner* — Gailene Gabel
(74) *Attorney, Agent, or Firm* — Wilson Sonsini Goodrich & Rosati

(57) ABSTRACT

Disclosed herein are methods, biomarkers, systems, compositions and kits for determining the phase or metabolic state (e.g. First Phase, Second Phase, or Third Phase) of a red blood cell (RBC) sample or for determining the phase or metabolic state (e.g., First Phase or Second Phase) of a platelet (PLT) cell sample. The methods disclosed herein are related to the use of isolated RBC sample or isolated PLT sample and analytical tools for providing information that is relevant to the phase or metabolic state of the RBC sample or the PLT sample. The system disclosed herein utilizes isolated RBC sample or isolated PLT sample and at least one analytical tool or an output from the at least one analytical tool. The compositions and kits described herein utilize RBC samples or PLT samples, including compositions in a form that allows for analysis of the RBC sample or the PLT sample.

20 Claims, 50 Drawing Sheets

(56) References Cited

OTHER PUBLICATIONS

Antonelou et al. Red blood cell aging markers during storage in citrate-phosphate-dextrose-saline-adenine-glucose-mannitol. Transfusion 50(2):376-389 (2010).

Bordbar et al. Identified metabolic signature for assessing red blood cell unit quality is associated with endothelial damage markers and clinical outcomes. Transfusion 56(4):852-862 (2016).

PCT/US2015/031235 International Preliminary Report on Patentability dated Dec. 8, 2016.

\* cited by examiner

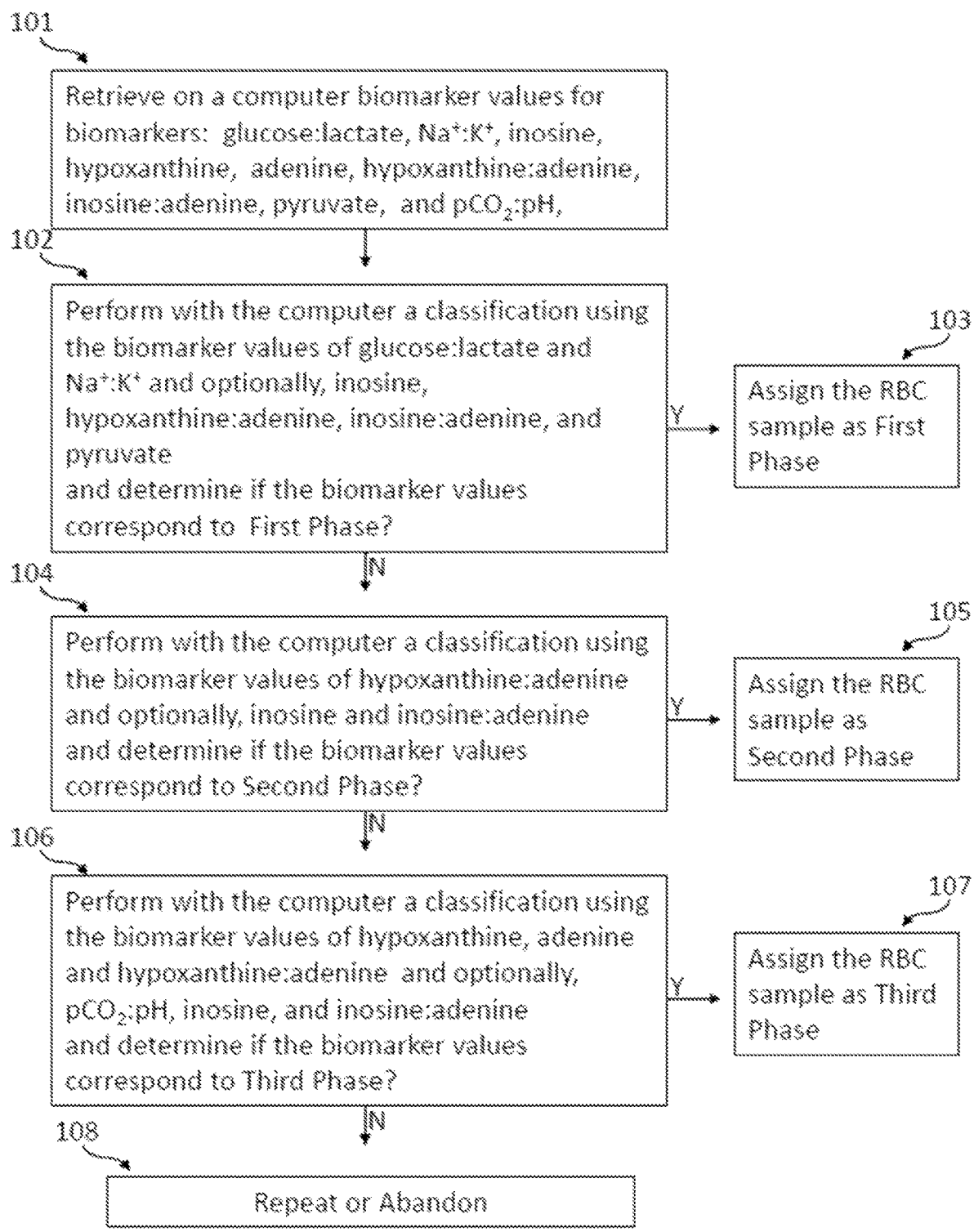

| Time (Days) | Average | SD |
|---|---|---|
| 1 | 7.3 | 1.9 |
| 4 | 3.6 | 0.4 |
| 8 | 2.1 | 0.3 |
| 11 | 1.6 | 0.2 |
| 15 | 1.3 | 0.2 |
| 18 | 1.1 | 0.2 |
| 22 | 0.9 | 0.2 |
| 25 | 0.8 | 0.2 |
| 29 | 0.8 | 0.2 |
| 32 | 0.6 | 0.4 |
| 36 | 0.6 | 0.2 |
| 39 | 0.6 | 0.2 |
| 43 | 0.5 | 0.2 |
| 46 | 0.5 | 0.1 |

| Time (Days) | Average | SD |
|---|---|---|
| 1 | 49.2 | 31.3 |
| 4 | 12.3 | 3.3 |
| 8 | 6.5 | 1.5 |
| 11 | 5.3 | 1.0 |
| 15 | 4.2 | 0.7 |
| 18 | 3.8 | 0.6 |
| 22 | 3.3 | 0.6 |
| 25 | 3.0 | 0.4 |
| 29 | 2.7 | 0.4 |
| 32 | 2.7 | 0.3 |
| 36 | 2.3 | 0.3 |
| 39 | 2.2 | 0.3 |
| 43 | 2.0 | 0.2 |
| 46 | 2.0 | 0.3 |

| Time (Days) | Average | SD |
|---|---|---|
| 1 | 0.0 | 0.0 |
| 4 | 0.0 | 0.0 |
| 8 | 0.2 | 0.3 |
| 11 | 1.65656 | 4.23107 |
| 15 | 6.85427 | 10.54116 |
| 18 | 16.96939 | 19.16265 |
| 22 | 33.60711 | 43.90076 |
| 25 | 68.44441 | 64.75170 |
| 29 | 148.22357 | 130.71317 |
| 32 | 219.81761 | 199.53024 |
| 36 | 261.32447 | 197.45626 |
| 39 | 315.21002 | 248.23370 |
| 43 | 366.19262 | 232.78524 |
| 46 | 398.42447 | 224.68259 |

| Time (Days) | Average | SD |
|---|---|---|
| 1 | 0.0 | 0.0 |
| 4 | 0.0 | 0.0 |
| 8 | 0.0 | 0.0 |
| 11 | 0.0 | 0.0 |
| 15 | 0.0 | 0.0 |
| 18 | 0.0 | 0.0 |
| 22 | 0.1 | 0.0 |
| 25 | 0.1 | 0.0 |
| 29 | 0.2 | 0.0 |
| 32 | 0.2 | 0.1 |
| 36 | 0.3 | 0.1 |
| 39 | 0.3 | 0.1 |
| 43 | 0.3 | 0.1 |
| 46 | 0.4 | 0.1 |

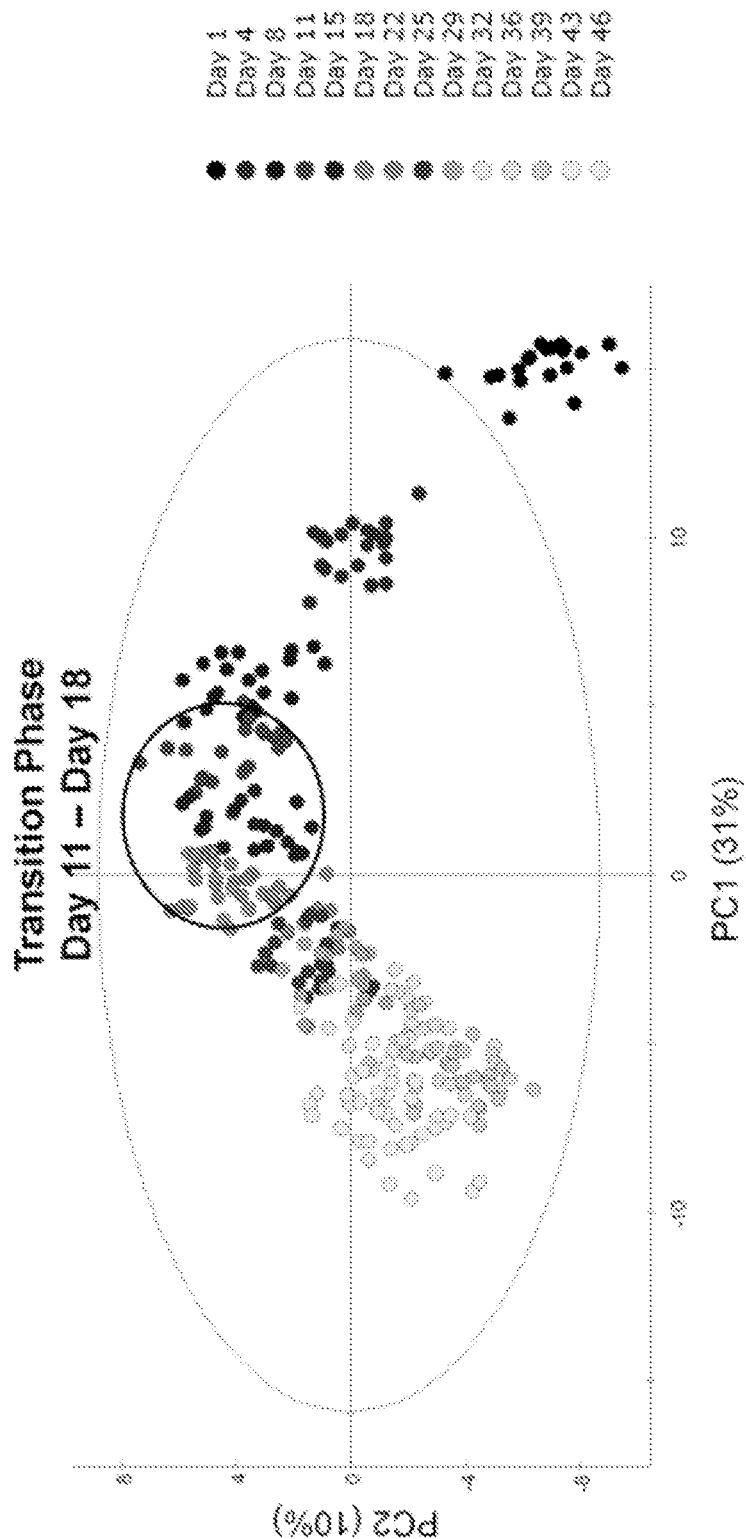

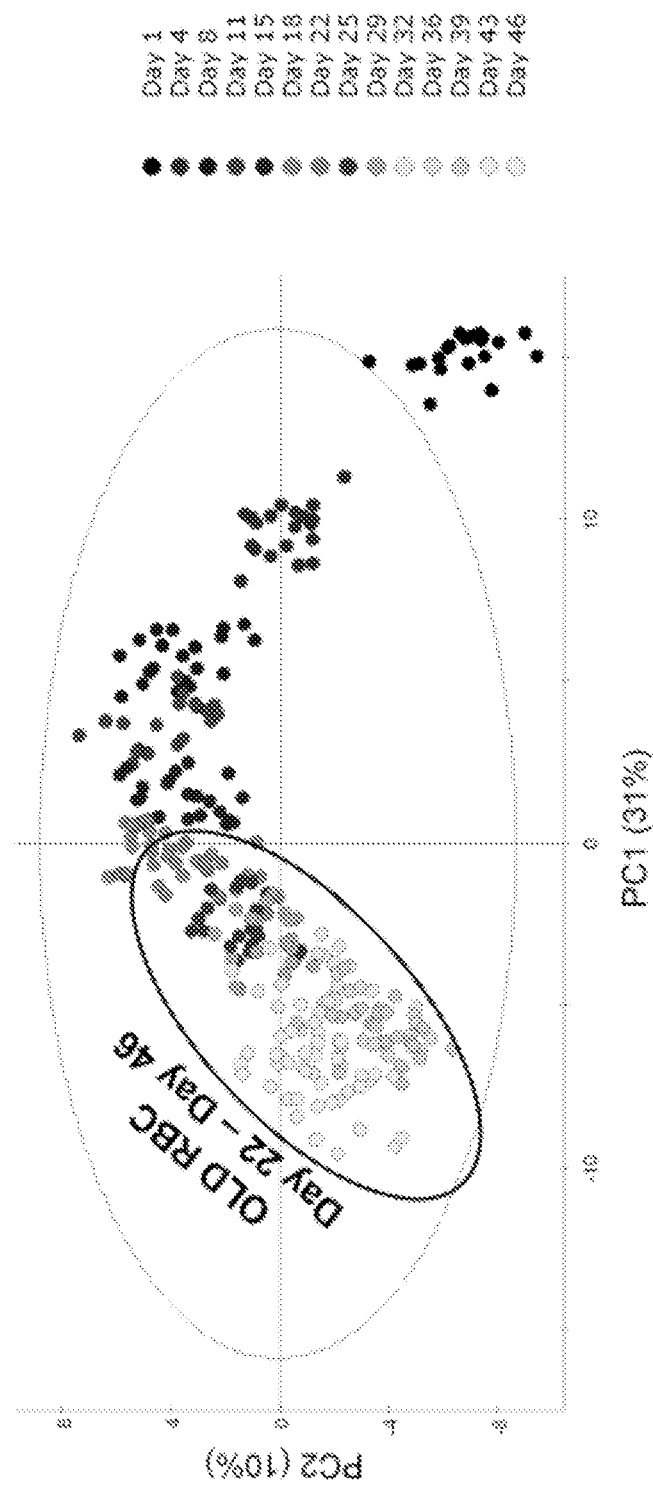

| Time (Days) | Average | SD |
|---|---|---|
| 1 | 0.5 | 0.1 |
| 4 | 0.3 | 0.1 |
| 8 | 0.2 | 0.1 |
| 11 | 0.1 | 0.1 |
| 15 | 0.1 | 0.1 |
| 18 | 0.0 | 0.1 |
| 22 | 0.0 | 0.0 |
| 25 | 0.0 | 0.0 |
| 29 | 0.0 | 0.0 |
| 32 | 0.0 | 0.0 |
| 36 | 0.0 | 0.0 |
| 39 | 0.0 | 0.0 |
| 43 | 0.0 | 0.0 |
| 46 | 0.0 | 0.0 |

| Time (Days) | Average | SD |
| --- | --- | --- |
| 1 | 0.0 | 0.0 |
| 4 | 0.0 | 0.0 |
| 8 | 0.0 | 0.0 |
| 11 | 0.00392 | 0.01688 |
| 15 | 0.02591 | 0.07844 |
| 18 | 0.06924 | 0.14477 |
| 22 | 0.20898 | 0.36318 |
| 25 | 0.40424 | 0.45190 |
| 29 | 0.69798 | 0.54042 |
| 32 | 1.28945 | 1.06674 |
| 36 | 1.57395 | 1.03973 |
| 39 | 2.08586 | 1.37834 |
| 43 | 2.96020 | 2.17471 |
| 46 | 3.44409 | 2.14104 |

| Time (Days) | Average | SD |
|---|---|---|
| 1 | 9.3 | 1.5 |
| 4 | 11.0 | 1.7 |
| 8 | 13.2 | 1.9 |
| 11 | 14.66045 | 1.83684 |
| 15 | 15.89438 | 1.96443 |
| 18 | 16.95794 | 1.78403 |
| 22 | 16.90194 | 2.46310 |
| 25 | 16.67478 | 2.86839 |
| 29 | 16.88445 | 2.62398 |
| 32 | 14.00420 | 1.15729 |
| 36 | 16.27931 | 2.74352 |
| 39 | 16.53693 | 2.76966 |
| 43 | 14.89650 | 2.68353 |
| 46 | 14.98572 | 4.14489 |

| Time (Days) | Average | SD |
|---|---|---|
| 1 | 0 | 0 |
| 4 | 0 | 0 |
| 8 | 0 | 0 |
| 11 | 0.00026 | 0.00019 |
| 15 | 0.00042 | 0.00006 |
| 18 | 0.00044 | 0.00023 |
| 22 | 0.00040 | 0.00018 |
| 25 | 0.00068 | 0.00035 |
| 29 | 0.00086 | 0.00040 |
| 32 | 0.00127 | 0.00066 |
| 36 | 0.00170 | 0.00067 |
| 39 | 0.00213 | 0.00090 |
| 43 | 0.00287 | 0.00130 |
| 46 | 0.00334 | 0.00129 |

SYSTEMS, METHODS, AND BIOMARKERS FOR DETERMINING THE METABOLIC STATE OF RED BLOOD CELLS AND PLATELETS

CROSS-REFERENCE

This application is the National Phase entry of International Application No. PCT/US2015/031235, filed on May 15, 2015, which claims the benefit of U.S. Provisional Application No. 62/002,507 filed May 23, 2014, both of which are incorporated herein by reference in their entireties.

SUMMARY OF THE INVENTION

Disclosed herein in certain embodiments, is a storage device comprising: a container containing a composition comprising red blood cells (RBCs) and an additive solution, wherein the container comprises an indicator which indicates a phase of red blood cells (RBCs) stored therein. In some embodiments, the phase is First Phase, Second Phase, or Third Phase. In some embodiments, the indicator is a non-electronic display system or an electronic display system. In some embodiments, the indicator is a non-electronic display system. In some embodiments, the non-electronic display system comprises a non-electronic label, a color display, a tracking code, a barcode, a test strip, or a combination thereof. In some embodiments, the non-electronic display system displays a set of dates correspond to First Phase, Second Phase, Third Phase, or a combination thereof. In some embodiments, the non-electronic display system is a non-electronic label. In some embodiments, the non-electronic label indicates the phase of RBCs. In some embodiments, the non-electronic label indicates the phase of RBCs through a color. In some embodiments, the non-electronic label indicates a change in phase through a change in color. In some embodiments, the non-electronic label is a non-electronic test label. In some embodiments, the test strip indicates the phase of RBCs. In some embodiments, the test strip indicates the phase of RBCs through a color. In some embodiments, the test strip indicates a change in phase through a change in color. In some embodiments, the indicator is an electronic display system. In some embodiments, the electronic display system comprises an electronic label. In some embodiments, the electronic label is a pictorial label, a color label, an alpha-numerical label, a sound label, or a combination thereof. In some embodiments, the electronic label communicates wirelessly to a digital processing device. In some embodiments, the digital processing device wirelessly communicates a change in phase to the electronic label. In some embodiments, the electronic label updates the change in phase through a pictorial change, a color change, an alpha-numerical change, a sound change, or a combination thereof. In some embodiments, the electronic label displays a set of dates correspond to First Phase, Second Phase, Third Phase, or a combination thereof. In some embodiments, the electronic label displays an updated set of dates with a change in phase. In some embodiments, the electronic label indicates the phase of RBCs. In some embodiments, the electronic label indicates the phase of RBCs through a color. In some embodiments, the electronic label indicates a phase change through a change in color. In some embodiments, the container comprises a wall defining an interior chamber. In some embodiments, the wall comprises a polymeric material. In some embodiments, the polymeric material contains a plasticizer. In some embodiments, the polymeric material is selected from the group consisting of a polyvinyl chloride (PVC) plastic or a non-PVC plastic. In some embodiments, the non-PVC plastic comprises a plasticizer-free polyolefin. In some embodiments, the plasticizer comprises phthalate esters or citrate esters. In some embodiments, the phthalate ester comprises di-2-ethylhexylphthalate (DEHP), mono-(2-ethylhexyl) phthalate (MEHP), or triethylhexyltrimellitate (TEHTM). In some embodiments, the citrate ester comprises acetyltri-n-hexyl citrate, acetyltri-n-(hexyl/octyl/decyl) citrate, acetyl-tri-n-(octyl/decyl) citrate, or n-butyryltri-n-hexyl citrate. In some embodiments, the plasticizer is a non-phthalate plasticizer. In some embodiments, the test strip is adherent to the wall of the container. In some embodiments, the test strip is in contact with the composition comprising red blood cells (RBCs) and an additive solution. In some embodiments, the test strip is visible through the polymeric material. In some embodiments, the color displayed by the test strip is visible through the polymeric material. In some embodiments, the additive solution comprises SAGM, AS-1, AS-3, AS-5, MAP, PAGGSM, PAGGGM or SOLX. In some embodiments, the container is a bag, a box, a bottle, a jar, or a canister.

Disclosed herein in certain embodiments, is a system for determining the phase of a red blood cell (RBC) sample, comprising: (a) a digital processing device comprising an operating system configured to perform executable instructions and an electronic memory; (b) a dataset stored in the electronic memory, wherein the dataset comprises raw data for a biomarker in the RBC sample, wherein the biomarker is concentration of inosine, concentration of hypoxanthine, concentration of adenine, ratio of hypoxanthine:adenine, ratio of glucose:lactate, ratio of $Na^+:K^+$, ratio of $pCO_2:pH$, ratio of inosine:adenine, concentration of pyruvate, or any combinations thereof; and (c) a computer program including instructions executable by the digital processing device to create an application comprising: (i) a first software module configured to analyze the dataset to determine a value of the biomarker; and (ii) a second software module configured to match the value of the biomarker to an equivalent value on a control and assigns a phase to the RBC sample based on the value of the biomarker. In some embodiments, the control is a signature profile of the biomarker. In some embodiments, the control is a signature profile of one, two, or more biomarkers over time. In some embodiments, the signature profile is represented as one, two or more values of the biomarker over time. In some embodiments, the value of the biomarker is determined from one or more RBC samples. In some embodiments, the signature profile is represented as a graph, a chart, a table, or a diagram. In some embodiments, the phase is First Phase, Second Phase, or Third Phase. In some embodiments, the biomarker is hypoxanthine, adenine, inosine, or pyruvate and the value is a range. In some embodiments, the biomarker is glucose:lactate, $Na^+:K^+$, hypoxanthine:adenine, $pCO_2:pH$, or inosine:adenine and the ratio is a range. In some embodiments, the second software module classifies the RBC sample as First Phase when the ratio of glucose:lactate, the ratio of $Na^+:K^+$, the concentration of inosine, the ratio of hypoxanthine:adenine, the ratio of inosine:adenine and the concentration of pyruvate match the values on the control indicated for First Phase. In some embodiments, the second software module classifies the RBC sample as First Phase when the ratio of glucose:lactate and the ratio of $Na^+:K^+$ match the values on the control indicated for First Phase. In some embodiments, the second software module classifies the RBC sample as Second Phase when the ratio of hypoxanthine:adenine, the concentration of inosine, and the ratio of inosine:adenine matches the values on the control indicated for Second Phase. In some embodiments, the second software module classifies the RBC sample as Second Phase when the ratio of hypoxanthine:adenine matches the value on the control indicated for Second Phase. In some embodiments, the second software module classifies the RBC sample as Third Phase when the ratio of hypoxanthine:adenine, the concentration of hypoxanthine, the concentration of adenine, the ratio of $pCO_2$:pH, the ratio of inosine:adenine, and the concentration of inosine match the values on the control indicated for Third Phase. In some embodiments, the second software module classifies the RBC sample as Third Phase when the ratio of hypoxanthine:adenine, the concentration of hypoxanthine, and the concentration of adenine match the values on the control indicated for Third Phase. In some embodiments, the ratio of glucose:lactate greater than 2.0 mM/mM is associated with First Phase and 0-2.0 mM/mM is associated with both Second Phase and Third Phase. In some embodiments, the ratio of $Na^+$:$K^+$ greater than 6.5 mM/mM is associated with First Phase and 0-6.5 mM/mM is associated with both Second Phase and Third Phase. In some embodiments, the ratio of hypoxanthine:adenine between 0-1.0 mM/mM is associated with First Phase, 1.0-16 mM/mM is associated with Second Phase, and greater than 16 mM/mM is associated with Third Phase. In some embodiments, the concentration of hypoxanthine between 0-0.1 mM is associated with both First Phase and Second Phase and greater than 0.1 mM is associated with Third Phase. In some embodiments, the concentration of adenine greater than 0.1 mM is associated with both First Phase and Second Phase and 0-0.1 mM is associated with Third Phase. In some embodiments, the ratio of inosine:adenine at 0 mM/mM is associated with First Phase, 0-0.05 mM/mM is associated with Second Phase, and greater than 0.05 mM/mM is associated with Third Phase. In some embodiments, the ratio of $pCO_2$:pH between 0-16 mmHg/pH is associated with both First Phase and Second Phase and greater than 16 mmHg/pH is associated with Third Phase. In some embodiments, the concentration of inosine at 0 mM is associated with First Phase, 0-0.0005 mM is associated with Second Phase, and greater than 0.0005 mM is associated with Third Phase. In some embodiments, the concentration of pyruvate at 0 mM is associated with First Phase and greater than 0 mM is associated with both Second Phase and Third Phase. In some embodiments, the system for determining the phase of a red blood cell (RBC) sample further comprises an RBC sample. In some embodiments, the RBC sample is an extracellular RBC sample. In some embodiments, the extracellular RBC sample comprises inosine, hypoxanthine, adenine, $Na^+$, $K^+$, glucose, lactate and pyruvate. In some embodiments, the biomarker obtained from the extracellular RBC sample is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, the system for determining the phase of a red blood cell (RBC) sample further comprises an analytical device configured to perform high performance liquid chromatography (HPLC), blood-gas analysis, enzymatic assay, mass spectrometry, photometry, or a combination thereof, to determine the raw data. In some embodiments, the enzymatic assay is a colorimetric assay or a luminescent assay. In some embodiments, the luminescent assay is a fluorometric assay. In some embodiments, the enzymatic assay is monitored by photometric measurements. In some embodiments, the colorimetric assay is monitored by photometric measurements. In some embodiments, the luminescent assay is monitored by photometric measurements. In some embodiments, the fluorometric assay is monitored by photometric measurements. In some embodiments, the analytical device is coupled to the digital processing device. In some embodiments, the digital processing device is connected to a computer network. In some embodiments, the second software module generates a report, wherein the second software module is executed by the digital processing device. In some embodiments, the second software module transmits the report to an end-user, wherein the second software module is executed by the digital processing device. In some embodiments, the RBC sample comprises RBCs and an additive solution. In some embodiments, the additive solution comprises SAGM, AS-1, AS-3, AS-5, MAP, PAGGSM, PAGGGM, or SOLX. In some embodiments, the RBC sample is obtained from a whole blood unit or from an RBC unit.

Disclosed herein in certain embodiments, is a method for determining the phase or metabolic state of a red blood cell (RBC) sample, comprising: (a) determining a value of a biomarker in an RBC sample, wherein the biomarker is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, concentration of pyruvate, or any combinations thereof; (b) matching the value of the biomarker to an equivalent value on a control; and (c) assigning a phase to the RBC sample based on the value of the biomarker. In some embodiments, the control is a signature profile of the biomarker. In some embodiments, the control is a signature profile of one, two or more biomarkers over time. In some embodiments, the signature profile is represented as one, two or more values of the biomarker over time. In some embodiments, the value of the biomarker is determined from one or more RBC samples. In some embodiments, the signature profile is represented as a graph, a chart, a table, or a diagram. In some embodiments, the phase is First Phase, Second Phase, or Third Phase. In some embodiments, the biomarker is hypoxanthine, adenine, inosine, or pyruvate and the value is a range. In some embodiments, the biomarker is glucose:lactate, $Na^+$:$K^+$, hypoxanthine:adenine, $pCO_2$:pH, or inosine:adenine and the ratio is a range. In some embodiments, the method for determining the phase of a red blood cell (RBC) sample further comprises classifying the RBC sample as First Phase when the ratio of glucose:lactate, the ratio of $Na^+$:$K^+$, the concentration of inosine, the ratio of hypoxanthine:adenine, the ratio of inosine:adenine and the concentration of pyruvate match the values on the control indicated for First Phase. In some embodiments, the method for determining the phase of a red blood cell (RBC) sample further comprises classifying the RBC sample as First Phase when the ratio of glucose:lactate and the ratio of $Na^+$:$K^+$ match the values on the control indicated for First Phase. In some embodiments, the method for determining the phase of a red blood cell (RBC) sample further comprises classifying the RBC sample as Second Phase when the ratio of hypoxanthine:adenine, the concentration of inosine, and the ratio of inosine:adenine match the values on the control indicated for Second Phase. In some embodiments, the method for determining the phase of a red blood cell (RBC) sample further comprises classifying the RBC sample as Second Phase when the ratio of hypoxanthine:adenine matches the value on the control indicated for Second Phase. In some embodiments, the method for determining the phase of a red blood cell (RBC) sample further comprises classifying the RBC sample as Third Phase when the ratio of hypoxanthine:adenine, the concentration of hypoxanthine, the concentration of adenine, the ratio of $pCO_2$:pH, the ratio of inosine:adenine, and the concentration of inosine match the values on the control indicated for Third Phase. In some embodiments, the method for determining the phase of a red blood cell (RBC) sample further comprises classifying the RBC sample as Third Phase when the ratio of hypoxanthine:adenine, the concentration of hypoxanthine, and the concentration of adenine match the values on the control indicated for Third Phase. In some embodiments, the ratio of glucose:lactate greater than 2.0 mM/mM is associated with First Phase and 0-2.0 mM/mM is associated with both Second Phase and Third Phase. In some embodiments, the ratio of $Na^+$:$K^+$ greater than 6.5 mM/mM is associated with First Phase and 0-6.5 mM/mM is associated with both Second Phase and Third Phase. In some embodiments, the ratio of hypoxanthine:adenine between 0-1.0 mM/mM is associated with First Phase, 1.0-16 mM/mM is associated with Second Phase and greater than 16 mM/mM is associated with Third Phase. In some embodiments, the concentration of hypoxanthine between 0-0.1 mM is associated with both First Phase and Second Phase and greater than 0.1 mM is associated with Third Phase. In some embodiments, the concentration of adenine greater than 0.1 mM is associated with both First Phase and Second Phase and 0-0.1 mM is associated with Third Phase. In some embodiments, the ratio of inosine:adenine at 0 mM/mM is associated with First Phase, 0-0.05 mM/mM is associated with Second Phase and greater than 0.05 mM/mM is associated with Third Phase. In some embodiments, the ratio of $pCO_2$:pH between 0-16 mmHg/pH is associated with both First Phase and Second Phase and greater than 16 mmHg/pH is associated with Third Phase. In some embodiments, the concentration of inosine at 0 mM is associated with First Phase, 0-0.0005 mM is associated with Second Phase and greater than 0.0005 mM is associated with Third Phase. In some embodiments, the concentration of pyruvate at 0 mM is associated with First Phase and greater than 0 mM is associated with both Second Phase and Third Phase. In some embodiments, step a) further comprises analyzing the RBC sample to determine a raw data for inosine, hypoxanthine, adenine, glucose, lactate, $Na^+$, $K^+$, $pCO_2$, pH, and pyruvate utilizing a method selected from the group consisting of high-performance liquid chromatography (HPLC), blood-gas analysis, enzymatic assay, mass spectrometry, photometry, or a combination thereof, prior to determining the value of the biomarker. In some embodiments, the enzymatic assay is a colorimetric assay or a luminescent assay. In some embodiments, the luminescent assay is a fluorometric assay. In some embodiments, the enzymatic assay is monitored by photometric measurements. In some embodiments, the colorimetric assay is monitored by photometric measurements. In some embodiments, the luminescent assay is monitored by photometric measurements. In some embodiments, the fluorometric assay is monitored by photometric measurements. In some embodiments, the method for determining the phase of a red blood cell (RBC) sample further comprises separating the RBC sample into an extracellular and an intracellular portion. In some embodiments, the extracellular portion is vortexed, centrifuged, dried, and filtered prior to analyzing the RBC sample. In some embodiments, the method for determining the phase of a red blood cell (RBC) sample further comprises adding an internal standard to the extracellular portion prior to analyzing the RBC sample. In some embodiments, the extracellular portion comprises inosine, hypoxanthine, adenine, $Na^+$, $K^+$, glucose, lactate and pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, the raw data for glucose, lactate, $Na^+$, $K^+$, $pCO_2$, and pH are determined using the blood-gas analysis method. In some embodiments, the raw data for inosine, hypoxanthine, adenine, glucose, lactate and pyruvate are determined using an HPLC method. In some embodiments, the raw data for inosine, hypoxanthine, adenine, glucose, lactate and pyruvate are determined using an enzymatic assay. In some embodiments, the measurement is performed at a beginning, an end, or during a time of storage of the RBC sample. In some embodiments, the RBC sample comprises RBCs and an additive solution. In some embodiments, the additive solution comprises SAGM, AS-1, AS-3, AS-5, MAP, PAGGSM, PAGGGM, or SOLX. In some embodiments, the RBC sample is obtained from a whole blood unit or from an RBC unit.

Disclosed herein in certain embodiments, is a kit for determining the phase or metabolic state of a red blood cell (RBC) sample, comprising: (a) a plurality of reagents and analytes for determining a dataset for a biomarker, wherein the biomarker is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, concentration of pyruvate, or any combinations thereof; (b) at least one software module for analyzing the dataset to determine a value of the biomarker, matching the value of the biomarker to an equivalent value on a control; and assigning the RBC sample as First Phase, Second Phase or Third Phase, wherein the value of the biomarker indicates the phase of the RBC sample; and (c) instruction manuals for utilizing the plurality of reagents and analytes and the at least one software module. In some embodiments, the biomarker is hypoxanthine, adenine, inosine, or pyruvate and the value is a range. In some embodiments, the biomarker is glucose:lactate, $Na^+$:$K^+$, hypoxanthine:adenine, $pCO_2$:pH, or inosine:adenine and the ratio is a range. In some embodiments, the kit for determining the phase of a red blood cell (RBC) sample further comprises classifying the RBC sample as First Phase when the ratio of glucose:lactate, the ratio of $Na^+$:$K^+$, the value of inosine, the ratio of hypoxanthine:adenine, the ratio of inosine:adenine and the value of pyruvate match the values on the control indicated for First Phase. In some embodiments, the kit for determining the phase of a red blood cell (RBC) sample further comprises classifying the RBC sample as First Phase when the ratio of glucose:lactate and the ratio of $Na^+$:$K^+$ match the values on the control indicated for First Phase. In some embodiments, the kit for determining the phase of a red blood cell (RBC) sample further comprises classifying the RBC sample as Second Phase when the ratio of hypoxanthine:adenine, the value of inosine and the ratio of inosine:adenine match the values on the control indicated for Third Phase. In some embodiments, the kit for determining the phase of a red blood cell (RBC) sample further comprises classifying the RBC sample as Third Phase when the ratio of hypoxanthine:adenine matches the value on the control indicated for Third Phase. In some embodiments, the kit for determining the phase of a red blood cell (RBC) sample further comprises classifying the RBC sample as Third Phase when the ratio of hypoxanthine:adenine, the value of hypoxanthine, the value of adenine, the ratio of $pCO_2$:pH, the ratio of inosine:adenine, and the value of inosine match the values on the control indicated for Third Phase. In some embodiments, the kit for determining the phase of a red blood cell (RBC) sample further comprises classifying the RBC sample as Third Phase when the ratio of hypoxanthine:adenine, the value of hypoxanthine and the value of adenine match the values on the control indicated for Third Phase. In some embodiments, the plurality of reagents and analytes comprise reagents and analytes for analyzing the RBC sample to determine a raw data for inosine, hypoxanthine, adenine, glucose, lactate, $Na^+$, $K^+$, $pCO_2$, pH, and pyruvate. In some embodiments, the plurality of reagents and analytes comprise reagents and analytes for separating the RBC sample into an extracellular portion and an intracellular portion. In some embodiments, the extracellular portion of the RBC sample comprises inosine, hypoxanthine, adenine, $Na^+$, $K^+$, glucose, lactate and pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, the raw data is determined utilizing a method selected from the group consisting of high-performance liquid chromatography (HPLC), blood-gas analysis, enzymatic assays, mass spectrometry, or photometry. In some embodiments, the enzymatic assay is a colorimetric assay or a luminescent assay. In some embodiments, the luminescent assay is a fluorometric assay. In some embodiments, the enzymatic assay is monitored by photometric measurements. In some embodiments, the colorimetric assay is monitored by photometric measurements. In some embodiments, the luminescent assay is monitored by photometric measurements. In some embodiments, the fluorometric assay is monitored by photometric measurements. In some embodiments, the kit for determining the phase of a red blood cell (RBC) sample further comprises an electronic label. In some embodiments, the kit for determining the phase of a red blood cell (RBC) sample further comprises a non-electronic label. In some embodiments, the non-electronic label is a non-electronic test label. In some embodiments, the non-electronic test label is a test strip. In some embodiments, the test strip indicates the phase of RBCs. In some embodiments, the test strip indicates the phase of RBCs through a color. In some embodiments, the test strip indicates a change in phase through a change in color. In some embodiments, the RBC sample is obtained from a whole blood unit or from an RBC unit.

Disclosed herein, in certain embodiments, is a system for determining the metabolic state of a red blood cell (RBC) sample, comprising: (a) an analytical device configured to provide biomarker data; (b) a digital processing device comprising an operating system configured to perform executable instructions, and an electronic memory; (c) a control dataset stored in the electronic memory for one or more biomarkers selected from the group consisting of concentration of inosine, concentration of hypoxanthine, concentration of adenine, ratio of hypoxanthine:adenine, ratio of glucose:lactate, ratio of $Na^+$:$K^+$, ratio of inosine:adenine, concentration of pyruvate, or any combination thereof, wherein a value in the control dataset defines at least one metabolic state of the RBCs; and (d) a computer program including instructions executable by the digital processing device to create an application comprising: (i) a first software module configured to analyze the biomarker data to determine a measured value for each biomarker; and (ii) a second software module configured to compare the measured value of each biomarker to a respective biomarker value in the control dataset and to assign a first, second, or third metabolic state to the RBC sample based on the value; wherein the second software module classifies the metabolic state of the RBC sample as: First Phase by comparing the measured ratio of glucose:lactate and the ratio of $Na^+$:$K^+$ match the values on the control indicated for the First Phase; and optionally when one or more of the concentration of inosine, the ratio of hypoxanthine:adenine, the ratio of inosine:adenine and the concentration of pyruvate match the values on the control indicated for First Phase; Second Phase when the ratio of hypoxanthine:adenine matches the value on the control indicated for the Second Phase; and optionally when concentration of inosine and/or the ratio of inosine:adenine matches the values on the control indicated for Second Phase; or Third Phase when the ratio of hypoxanthine:adenine, the concentration of hypoxanthine and the concentration of adenine match the values on the control indicated for the Third Phase; and optionally when one or more of pCO2:pH, the ratio of inosine:adenine and the concentration of inosine match the values on the control indicated for the Third Phase.

Disclosed herein, in certain embodiments, is a method for determining the metabolic state of a red blood cell (RBC) sample, comprising: (a) determining a value of a biomarker in an RBC sample by an analytical analysis, wherein the biomarker value is selected from one or more of: concentration of inosine, concentration of hypoxanthine, concentration of adenine, ratio of hypoxanthine:adenine, ratio of glucose:lactate, ratio of $Na^+$:$K^+$, ratio of inosine:adenine, concentration of pyruvate; (b) matching the biomarker value to a respective control value for the biomarker; and; (c) assigning a metabolic state to the RBC sample based on the value of the biomarker which is one of a First Phase, a Second Phase or a Third Phase; wherein: the RBC sample is First Phase when the ratio of glucose:lactate and the ratio of $Na^+$:$K^+$ match the values on the control indicated for First Phase; and optionally when one or more of the concentration of inosine, the ratio of hypoxanthine:adenine, the ratio of inosine:adenine and the concentration of pyruvate match the values on the control indicated for First Phase; the RBC sample is Second Phase when the ratio of hypoxanthine:adenine matches the value on the control indicated for Second Phase; and optionally when one or more of the concentration of inosine, and the ratio of inosine:adenine match the values on the control indicated for Second Phase; or the RBC sample is Third Phase when the ratio of hypoxanthine:adenine, the concentration of hypoxanthine and the concentration of adenine match the values on the control indicated for Third Phase, and optionally when one or more of the ratio of $pCO_2$:pH, the ratio of inosine:adenine, and/or the concentration of inosine match the values on the control indicated for Third Phase.

Disclosed herein, in certain embodiments, is a method for determining the metabolic state of a red blood cell (RBC) sample, comprising: (a) determining a value of a biomarker in an RBC sample by an analytical analysis, wherein the biomarker value is selected from one or more of: concentration of inosine, concentration of hypoxanthine, concentration of adenine, ratio of hypoxanthine:adenine, ratio of glucose:lactate, ratio of $Na^+$:$K^+$, ratio of inosine:adenine, concentration of pyruvate; (b) matching the biomarker value to a respective control value for the biomarker; and; (c) assigning a metabolic state to the RBC sample based on the value of the biomarker which is one of a First Phase, or a Second Phase; wherein: the RBC sample is First Phase when the ratio of glucose:lactate and the ratio of $Na^+$:$K^+$ match the values on the control indicated for First Phase; and optionally when one or more of the concentration of inosine, the ratio of hypoxanthine:adenine, the ratio of inosine:adenine and the concentration of pyruvate match the values on the control indicated for First Phase; or the RBC sample is Second Phase when the ratio of hypoxanthine:adenine matches the value on the control indicated for Second Phase; and optionally when one or more of the concentration of inosine, and the ratio of inosine:adenine match the values on the control indicated for Second Phase. In some embodiments, the control is a signature profile of one, two or more biomarkers over time. In some embodiments, a ratio of glucose:lactate greater than 2.0 mM/mM is associated with First Phase and a ratio in the range 0-2.0 mM/mM is associated with Second Phase. In some embodiments, a ratio of $Na^+$:$K^+$ greater than 6.5 mM/mM is associated with First Phase and a ratio in the range 0-6.5 mM/mM is associated with Second Phase. In some embodiments, a ratio of hypoxanthine:adenine in the range 0-1.0 mM/mM is associated with First Phase, and a ratio in the range 1.0-16 mM/mM is associated with Second Phase. In some embodiments, a concentration of hypoxanthine in the range 0-0.1 mM is associated with both First Phase and Second Phase. In some embodiments, a concentration of adenine greater than 0.1 mM is associated with both First Phase and Second Phase. In some embodiments, a ratio of inosine:adenine of 0 mM/mM is associated with First Phase, and a ratio in the range 0-0.05 is associated with Second Phase. In some embodiments, a ratio of pCO2:pH in the range 0-16 mmHg/pH is associated with First Phase and Second Phase. In some embodiments, a concentration of inosine of 0 mM is associated with First Phase, and a concentration in the range 0-0.0005 mM is associated with Second Phase. In some embodiments, a concentration of pyruvate of 0 mM is associated with First Phase and a concentration greater than 0 mM is associated with Second Phase. In some embodiments, step a) comprises analyzing the RBC sample to determine the amount of at least one of inosine, hypoxanthine, adenine, glucose, lactate, $Na^+$, $K^+$, pCO2, pH and pyruvate. In some embodiments, the analytical analysis is selected from high-performance liquid chromatography (HPLC), blood-gas analysis, enzymatic assay, biochemical assay, luminescence assay, mass spectrometry, photometry, or a combination thereof, prior to determining the value of the biomarker. In some embodiments, the biomarker data obtained from the extracellular RBC sample is concentration of inosine, concentration of hypoxanthine, concentration of adenine, ratio of hypoxanthine:adenine, ratio of glucose:lactate, ratio of $Na^+$:$K^+$, ratio of inosine:adenine, or concentration of pyruvate.

Disclosed herein, in certain embodiments, is a method of screening a red blood cell (RBC) additive solution, comprising: (a) testing a first RBC sample from collected RBCs by the steps of: (i) determining a value of a biomarker in an RBC sample by an analytical analysis, wherein the biomarker value is selected from one or more of: concentration of inosine, concentration of hypoxanthine, concentration of adenine, ratio of hypoxanthine:adenine, ratio of glucose:lactate, ratio of $Na^+$:$K^+$, ratio of inosine:adenine, concentration of pyruvate; (ii) matching the biomarker value to a respective control value for the biomarker; and; (iii) assigning a metabolic state to the RBC sample based on the value of the biomarker which is one of a First Phase, a Second Phase or a Third Phase; wherein: the RBC sample is First Phase when the ratio of glucose:lactate and the ratio of $Na^+$:$K^+$ match the values on the control indicated for First Phase; and optionally when one or more of the concentration of inosine, the ratio of hypoxanthine:adenine, the ratio of inosine:adenine and the concentration of pyruvate match the values on the control indicated for First Phase; the RBC sample is Second Phase when the ratio of hypoxanthine:adenine matches the value on the control indicated for Second Phase; and optionally when one or more of the concentration of inosine, and the ratio of inosine:adenine match the values on the control indicated for Second Phase; or the RBC sample is Third Phase when the ratio of hypoxanthine:adenine, the concentration of hypoxanthine and the concentration of adenine match the values on the control indicated for Third Phase, and optionally when one or more of the ratio of $pCO_2$:pH, the ratio of inosine:adenine, and/or the concentration of inosine match the values on the control indicated for Third Phase; (b) contacting a second sample of RBCs from the collected RBCs with an additive solution and testing the second sample of RBCs by the steps of: (i) determining a value of a biomarker in an RBC sample by an analytical analysis, wherein the biomarker value is selected from one or more of: concentration of inosine, concentration of hypoxanthine, concentration of adenine, ratio of hypoxanthine:adenine, ratio of glucose:lactate, ratio of $Na^+$:$K^+$, ratio of inosine:adenine, concentration of pyruvate; (ii) matching the biomarker value to a respective control value for the biomarker; and; (iii) assigning a metabolic state to the RBC sample based on the value of the biomarker which is one of a First Phase, a Second Phase or a Third Phase; wherein: the RBC sample is First Phase when the ratio of glucose:lactate and the ratio of $Na^+$:$K^+$ match the values on the control indicated for First Phase; and optionally when one or more of the concentration of inosine, the ratio of hypoxanthine:adenine, the ratio of inosine:adenine and the concentration of pyruvate match the values on the control indicated for First Phase; the RBC sample is Second Phase when the ratio of hypoxanthine:adenine matches the value on the control indicated for Second Phase; and optionally when one or more of the concentration of inosine, and the ratio of inosine:adenine match the values on the control indicated for Second Phase; or the RBC sample is Third Phase when the ratio of hypoxanthine:adenine, the concentration of hypoxanthine and the concentration of adenine match the values on the control indicated for Third Phase, and optionally when one or more of the ratio of $pCO_2$:pH, the ratio of inosine:adenine, and/or the concentration of inosine match the values on the control indicated for Third Phase; and (c) selecting the additive solution if duration of First Phase and/or Second Phase of the second RBC sample is extended over duration of First Phase and/or Second Phase of the first RBC sample. In some embodiments, the second sample RBCs is in contact with the additive solution for an extended period of time. In some embodiments, the extended period of time is from about 5 minutes to about 50 days, from about 30 minutes to about 25 days, from about 1 hour to about 20 days, or from about 1 day to about 10 days. In some embodiments, the collected RBCs are from a patient or are stored RBCs.

Disclosed herein, in certain embodiments, is a system for determining the metabolic state of a platelet (PLT) sample, comprising: (a) an analytical device configured to provide biomarker data; (b) a digital processing device comprising an operating system configured to perform executable instructions, and an electronic memory; (c) a control dataset stored in the electronic memory for one or more biomarkers selected from the group consisting of concentration of glutamine, concentration of niacinamide, concentration of glutathione oxidized, concentration of succinic acid, concentration of sCD40L, value of CD41:CD63 (e.g., percentage of cells double positive or expressing both CD41 and CD63+ in a cell population), value of CD41:Annexin-V (e.g., percentage of cells double positive or expressing both CD41 and Annexin-V+ in a cell population), value of CD41:CD42b (e.g., percentage of cells double positive or expressing both CD41 and CD42b in a cell population), ratio of citrate:cis-aconitate, ratio of citrate:malate, ratio of acetate:cis-aconitate, ratio of glucose:lactose, ratio of acetate:succinate, ratio of acetate:lactose, or any combination thereof, wherein a value in the control set dataset defines a transition from a first metabolic state of the platelets to a second metabolic state of the platelets; and (d) a computer program including instructions executable by the digital processing device to create an application comprising: (i) a first software module configured to analyze the biomarker data to determine a measured value for each biomarker; and (ii) a second software module configured to compare the measured value of each biomarker to a respective biomarker value in the control dataset and to assign a first or second metabolic state to the platelet sample based on the value; wherein the second software module classifies the metabolic state of the platelet sample as: First Phase by comparing the measured concentration of glutathione oxidized, ratio of acetate:cis-aconitate, and either ratio of glucose:lactose or ratio of acetate:lactose as greater than the values on the control indicated as the transition from the first metabolic state to the second metabolic state; or Second Phase by comparing the measured concentration of glutathione oxidized, ratio of acetate:cis-aconitate, and either ratio of glucose:lactose or ratio of acetate:lactose as less than the values on the control indicated as the transition from the first metabolic state to the second metabolic state. In some embodiments, the control dataset is a signature profile of one, two, or more biomarkers over time. In some embodiments, the platelet sample is processed by apheresis. In some embodiments, a biomarker associated with the apheresis processed platelet sample is selected from the group consisting of concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combination thereof. In some embodiments, First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state. In some embodiments, the First Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, Second Phase is assigned to the apheresis processed platelet sample where the concentration of glutathione oxidized, ratio of acetate:cis-aconitate, and ratio of glucose:lactose are less than the values on the control indicated as the transition from the first metabolic state to the second metabolic state. In some embodiments, Second Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, the concentration of glutathione oxidized greater than 2.22E-05 mM is associated with First Phase and less than 2.22E-05 mM is associated with Second Phase for the apheresis processed platelet sample. In some embodiments, the concentration of glutathione oxidized is the extracellular concentration of glutathione oxidized. In some embodiments, the concentration of glutamine greater than 0.11 mM is associated with First Phase and less than 0.11 mM is associated with Second Phase for the apheresis processed platelet sample. In some embodiments, the concentration of niacinamide less than 0.0035 mM is associated with First Phase and greater than 0.0035 mM is associated with Second Phase for the apheresis processed platelet sample. In some embodiments, the concentration of sCD40L less than 20.8 ng/mL is associated with First Phase and greater than 20.8 ng/mL is associated with Second Phase for the apheresis processed platelet sample. In some embodiments, the value of CD41:CD63 less than 24.3% is associated with First Phase and greater than 24.3% is associated with Second Phase for the apheresis processed platelet sample. In some embodiments, the ratio of citrate:cis-aconitate greater than 228.3 is associated with First Phase and less than 228.3 is associated with Second Phase for the apheresis processed platelet sample. In some embodiments, the ratio of citrate:malate greater than 470.6 is associated with First Phase and less than 470.6 is associated with Second Phase for the apheresis processed platelet sample. In some embodiments, the ratio of acetate:cis-aconitate greater than 680.6 is associated with First Phase and less than 680.6 is associated with Second Phase for the apheresis processed platelet sample. In some embodiments, the ratio of glucose:lactose greater than 0.569 is associated with First Phase and less than 0.569 is associated with Second Phase for the apheresis processed platelet sample. In some embodiments, the platelet sample is processed by buffy coat method. In some embodiments, a biomarker associated with the buffy coat processed platelet sample is selected from the group consisting of concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combination thereof. In some embodiments, First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, First Phase is assigned to the buffy coat processed platelet where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, Second Phase is assigned to the buffy coat processed platelet sample where the concentration of glutathione oxidized, ratio of acetate:cis-aconitate, and ratio of acetate:lactose are less than the values on the control indicated as the transition from the first metabolic state to the second metabolic state. In some embodiments, Second Phase is assigned to the buffy coat processed platelet where the concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the concentration of glutathione oxidized is the extracellular concentration of glutathione oxidized or the intracellular concentration of glutathione oxidized. In some embodiments, First Phase is assigned to the buffy coat processed platelet where the extracellular concentration of glutathione oxidized, ratio of acetate:cis-aconitate, and ratio of acetate:lactose are greater than the values on the control indicated as the transition from the first metabolic state to the second metabolic state. In some embodiments, First Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state and concentration of succinic acid, concentration of sCD40L, value of CD41:Annexin-V, and value of CD41:CD42b are less than the values on the control indicated as the transition from the first metabolic state to the second metabolic state. In some embodiments, Second Phase is assigned to the buffy coat processed platelet where the extracellular concentration of glutathione oxidized, ratio of acetate:cis-aconitate, and ratio of acetate:lactose are less than the values on the control indicated as the transition from the first metabolic state to the second metabolic state and. In some embodiments, Second Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the extracellular concentration of glutathione oxidized greater than 5.91E-04 mM is associated with First Phase and less than 5.91E-04 mM is associated with Second Phase for the buffy coat processed platelet sample. In some embodiments, the intracellular concentration of glutathione oxidized greater than 3.6E-05 mM is associated with First Phase and less than 3.6E-05 mM is associated with Second Phase for the buffy coat processed platelet sample. In some embodiments, the concentration of glutamine greater than 0.42 mM is associated with First Phase and less than 0.42 mM is associated with Second Phase for the buffy coat processed platelet sample. In some embodiments, the concentration of succinic acid less than 0.0128 mM is associated with First Phase and greater than 0.0128 mM is associated with Second Phase for the buffy coat processed platelet sample. In some embodiments, the value of CD41:Annexin-V less than 3.2% is associated with First Phase and greater than 3.2% is associated with Second Phase for the buffy coat processed platelet sample. In some embodiments, the value of CD41:CD42b less than 1.7% is associated with First Phase and greater than 1.7% is associated with Second Phase for the buffy coat processed platelet sample. In some embodiments, the concentration of sCD40L less than 15 ng/mL is associated with First Phase and greater than 15 ng/mL is associated with Second Phase for the buffy coat processed platelet sample. In some embodiments, the ratio of citrate:cis-aconitate greater than 314 is associated with First Phase and less than 314 is associated with Second Phase for the buffy coat processed platelet sample. In some embodiments, the ratio of acetate:cis-aconitate greater than 835.7 is associated with First Phase and less than 835.7 is associated with Second Phase for the buffy coat processed platelet sample. In some embodiments, the ratio of acetate:succinate greater than 1644 is associated with First Phase and less than 1644 is associated with Second Phase for the buffy coat processed platelet sample. In some embodiments, the ratio of acetate:lactose greater than 3 is associated with First Phase and less than 3 is associated with Second Phase for the buffy coat processed platelet sample. In some embodiments, the system further comprises a platelet sample, wherein the platelet sample comprises extracellular glutamine, niacinamide, succinic acid, and glutathione oxidized, and intracellular glutathione oxidized. In some embodiments, the analytical device performs high performance liquid chromatography (HPLC), enzymatic assay, biochemical assay, luminescence assay, mass spectrometry, photometry, or a combination thereof. In some embodiments, the analytical device is coupled to the digital processing device. In some embodiments, the platelet sample comprises platelets and an additive solution.

Disclosed herein, in certain embodiments, is a system for determining the metabolic state of a platelet (PLT) sample, comprising: (a) an analytical device configured to provide biomarker data; (b) a digital processing device comprising an operating system configured to perform executable instructions, and an electronic memory; (c) a control dataset stored in the electronic memory for one or more biomarkers selected from the group consisting of concentration of glutamine, concentration of niacinamide, concentration of glutathione oxidized, concentration of succinic acid, concentration of sCD40L, value of CD41:CD63 (e.g., percentage of cells double positive or expressing both CD41 and CD63+ in a cell population), value of CD41:Annexin-V (e.g., percentage of cells double positive or expressing both CD41 and Annexin-V+ in a cell population), value of CD41:CD42b (e.g., percentage of cells double positive or expressing both CD41 and CD42b in a cell population), ratio of citrate:cis-aconitate, ratio of citrate:malate, ratio of acetate:cis-aconitate, ratio of glucose:lactose, ratio of acetate:succinate, ratio of acetate:lactose, or any combination thereof, wherein a value in the control set dataset defines a transition from a first metabolic state of the platelets to a second metabolic state of the platelets; and (d) a computer program including instructions executable by the digital processing device to create an application comprising: (i) a first software module configured to analyze the biomarker data to determine a measured value for each biomarker; and (ii) a second software module configured to compare the measured value of each biomarker to a respective biomarker value in the control dataset and to assign a first metabolic state to the platelet sample based on the value; wherein the second software module classifies the metabolic state of the platelet sample as First Phase by comparing the measured concentration of glutathione oxidized, ratio of acetate:cis-aconitate, and either ratio of glucose:lactose or ratio of acetate:lactose as greater than the values on the control indicated as the transition from the first metabolic state to the second metabolic state. In some embodiments, the platelet sample is processed by apheresis. In some embodiments, a biomarker associated with the apheresis processed platelet is selected from the group consisting of concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combination thereof. In some embodiments, First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state. In some embodiments, the First Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, the platelet sample is processed by buffy coat method. In some embodiments, a biomarker associated with the buffy coat processed platelet sample is selected from the group consisting of concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combination thereof. In some embodiments, First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, First Phase is assigned to the buffy coat processed platelet where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the concentration of glutathione oxidized is the extracellular concentration of glutathione oxidized or the intracellular concentration of glutathione oxidized. In some embodiments, First Phase is assigned to the buffy coat processed platelet where the extracellular concentration of glutathione oxidized, ratio of acetate:cis-aconitate, and ratio of acetate:lactose are greater than the values on the control indicated as the transition from the first metabolic state to the second metabolic state. In some embodiments, First Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state.

Disclosed herein, in certain embodiments, is a method for determining the metabolic state of a platelet (PLT) sample, comprising: (a) determining a value of a biomarker in a platelet sample by an analytical analysis, wherein the biomarker value is selected from one or more of: concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose; (b) matching the biomarker value to a respective control value for the biomarker, wherein a value in the control defines a transition from a first metabolic state of the platelets to a second metabolic state of the platelets; and (c) assigning a metabolic state to the platelet sample based on the value of the biomarker; wherein the sample is First Phase when the measured concentration of glutathione oxidized, ratio of acetate:cis-aconitate, and either ratio of glucose:lactose or ratio of acetate:lactose are greater than the values on the control indicated as the transition from the first metabolic state to the second metabolic state. In some embodiments, the platelet sample is processed by apheresis. In some embodiments, a biomarker associated with the apheresis processed platelet sample is selected from the group consisting of concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combination thereof. In some embodiments, the First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state. In some embodiments, the First Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, the concentration of glutathione oxidized is an intracellular concentration of glutathione oxidized. In some embodiments, the platelet sample is processed by buffy coat method. In some embodiments, a biomarker associated with the buffy coat processed platelet sample is selected from the group consisting of concentration of glutamine, concentration of glutathione oxidized, concentration of succinic acid, concentration of sCD40L, value of CD41:CD63, value of CD41:CD42b, ratio of citrate:cis-aconitate, ratio of acetate:cis-aconitate, ratio of acetate:succinate, ratio of acetate:lactose, or any combination thereof. In some embodiments, the First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:CD63, and value of CD41:CD42b are less than the values on the control indicated as the transition from the first metabolic state to the second metabolic state. In some embodiments, the concentration of glutathione oxidized is the extracellular concentration of glutathione oxidized or the intracellular concentration of glutathione oxidized. In some embodiments, the First Phase is assigned to the buffy coat processed platelet sample where the extracellular concentration of glutathione oxidized, ratio of acetate:cis-aconitate, and ratio of acetate:lactose are greater than the values on the control indicated as the transition from the first metabolic state to the second metabolic state and concentration of sCD40L, value of CD41:Annexin-V, and value of CD41:CD42b are less than the values on the control indicated as the transition from the first metabolic state to the second metabolic state. In some embodiments, the First Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:CD63, and value of CD41:CD42b are less than the values on the control indicated as the transition from the first metabolic state to the second metabolic state.

Disclosed herein, in certain embodiments, is a method of screening a platelet additive solution, comprising: (a) testing a first PLT sample from collected PLTs by the steps of: (i) determining a value of a biomarker in a platelet sample by an analytical analysis, wherein the biomarker value is selected from one or more of: concentration of glutamine, concentration of niacinamide, concentration of glutathione oxidized, concentration of succinic acid, concentration of sCD40L, value of CD41:CD63 (e.g., percentage of cells double positive or expressing both CD41 and CD63+ in a cell population), value of CD41:Annexin-V (e.g., percentage of cells double positive or expressing both CD41 and Annexin-V+ in a cell population), value of CD41:CD42b (e.g., percentage of cells double positive or expressing both CD41 and CD42b in a cell population), ratio of citrate:cis-aconitate, ratio of citrate:malate, ratio of acetate:cis-aconitate, ratio of glucose:lactose, ratio of acetate:succinate, or ratio of acetate:lactose; (ii) matching the biomarker value to a respective control value for the biomarker, wherein a value in the control defines a transition from a first metabolic state of the platelets to a second metabolic state of the platelets; and (iii) assigning a metabolic state to the platelet sample based on the value of the biomarker which is one of First Phase or Second Phase; wherein: the sample is First Phase when the measured concentration of glutathione oxidized, ratio of acetate:cis-aconitate, and either ratio of glucose:lactose or ratio of acetate:lactose are greater than the values on the control indicated as the transition from the first metabolic state to the second metabolic state; or the sample is Second Phase when the measured concentration of glutathione oxidized, ratio of acetate:cis-aconitate, and either ratio of glucose:lactose or ratio of acetate:lactose are less than the values on the control indicated as the transition from the first metabolic state to the second metabolic state; (b) contacting a second sample of PLTs from the collected PLTs with an additive solution and testing the second sample of PLTs by the steps of: (i) determining a value of a biomarker in a platelet sample by an analytical analysis, wherein the biomarker value is selected from one or more of: concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose; (ii) matching the biomarker value to a respective control value for the biomarker, wherein a value in the control defines a transition from a first metabolic state of the platelets to a second metabolic state of the platelets; and (iii) assigning a metabolic state to the platelet sample based on the value of the biomarker which is one of First Phase or Second Phase; wherein: the sample is First Phase when the measured concentration of glutathione oxidized, ratio of acetate:cis-aconitate, and either ratio of glucose:lactose or ratio of acetate:lactose are greater than the values on the control indicated as the transition from the first metabolic state to the second metabolic state; or the sample is Second Phase when the measured concentration of glutathione oxidized, ratio of acetate:cis-aconitate, and either ratio of glucose:lactose or ratio of acetate:lactose are less than the values on the control indicated as the transition from the first metabolic state to the second metabolic state; and (c) selecting the additive solution if duration of First Phase of the second PLT sample is extended over duration of First Phase of the first PLT sample. In some embodiments, the second sample of PLTs is in contact with the additive solution for an extended period of time. In some embodiments, the extended period of time is from about 5 minutes to about 50 days, from about 30 minutes to about 25 days, from about 1 hour to about 20 days, or from about 1 day to about 10 days. In some embodiments, the collected PLTs are obtained from a patient or are stored PLTs. In some embodiments, the control dataset is a signature profile of one, two, or more biomarkers over time. In some embodiments, the platelet sample is processed by apheresis. In some embodiments, a biomarker associated with the apheresis processed platelet sample is selected from the group consisting of concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combination thereof. In some embodiments, the First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state. In some embodiments, the First Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, the Second Phase is assigned to the apheresis processed platelet sample where the concentration of glutathione oxidized, ratio of acetate:cis-aconitate, and ratio of glucose:lactose are less than the values on the control indicated as the transition from the first metabolic state to the second metabolic state. In some embodiments, the Second Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, concentration of glutathione oxidized is an intracellular concentration of glutathione oxidized. In some embodiments, the concentration of glutathione oxidized greater than 2.22E-05 mM is associated with First Phase and less than 2.22E-05 mM is associated with Second Phase for the apheresis processed platelet sample. In some embodiments, the concentration of glutamine greater than 0.11 mM is associated with First Phase and less than 0.11 mM is associated with Second Phase for the apheresis processed platelet sample. In some embodiments, the concentration of niacinamide less than 0.0035 mM is associated with First Phase and greater than 0.0035 mM is associated with Second Phase for the apheresis processed platelet sample. In some embodiments, the concentration of sCD40L less than 20.8 ng/mL is associated with First Phase and greater than 20.8 ng/mL is associated with Second Phase for the apheresis processed platelet sample. In some embodiments, the value of CD41:CD63 less than 24.3% is associated with First Phase and greater than 24.3% is associated with Second Phase for the apheresis processed platelet sample. In some embodiments, the ratio of citrate:cis-aconitate greater than 228.3 is associated with First Phase and less than 228.3 is associated with Second Phase for the apheresis processed platelet sample. In some embodiments, the ratio of citrate:malate greater than 470.6 is associated with First Phase and less than 470.6 is associated with Second Phase for the apheresis processed platelet sample. In some embodiments, the ratio of acetate:cis-aconitate greater than 680.6 is associated with First Phase and less than 680.6 is associated with Second Phase for the apheresis processed platelet sample. In some embodiments, the ratio of glucose:lactose greater than 0.569 is associated with First Phase and less than 0.569 is associated with Second Phase for the apheresis processed platelet sample. In some embodiments, the platelet sample is processed by buffy coat method. In some embodiments, a biomarker associated with the buffy coat processed platelet sample is selected from the group consisting of concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combination thereof. In some embodiments, the First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the Second Phase is assigned to the buffy coat processed platelet sample where the concentration of glutathione oxidized, ratio of acetate:cis-aconitate, and ratio of acetate:lactose are less than the values on the control indicated as the transition from the first metabolic state to the second metabolic state. In some embodiments, the Second Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the concentration of glutathione oxidized is an extracellular concentration of glutathione oxidized or an intracellular concentration of glutathione oxidized. In some embodiments, the First Phase is assigned to the buffy coat processed platelet sample where the extracellular concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the Second Phase is assigned to the buffy coat processed platelet sample where the extracellular concentration of glutathione oxidized, ratio of acetate:cis-aconitate, and ratio of acetate:lactose are less than the values on the control indicated as the transition from the first metabolic state to the second metabolic state. In some embodiments, the Second Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the extracellular concentration of glutathione oxidized greater than 5.91E-04 mM is associated with First Phase and less than 5.91E-04 mM is associated with Second Phase for the buffy coat processed platelet sample. In some embodiments, the intracellular concentration of glutathione oxidized greater than 3.6E-05 mM is associated with First Phase and less than 3.6E-05 mM is associated with Second Phase for the buffy coat processed platelet sample. In some embodiments, the concentration of glutamine greater than 0.42 mM is associated with First Phase and less than 0.42 mM is associated with Second Phase for the buffy coat processed platelet sample. In some embodiments, the concentration of succinic acid less than 0.0128 mM is associated with First Phase and greater than 0.0128 mM is associated with Second Phase for the buffy coat processed platelet sample. In some embodiments, the value of CD41:Annexin-V less than 3.2% is associated with First Phase and greater than 3.2% is associated with Second Phase for the buffy coat processed platelet sample. In some embodiments, the value of CD41:CD42b less than 1.7% is associated with First Phase and greater than 1.7% is associated with Second Phase for the buffy coat processed platelet sample. In some embodiments, the concentration of sCD40L less than 15 ng/mL is associated with First Phase and greater than 15 ng/mL is associated with Second Phase for the buffy coat processed platelet sample. In some embodiments, the ratio of citrate:cis-aconitate greater than 314 is associated with First Phase and less than 314 is associated with Second Phase for the buffy coat processed platelet sample. In some embodiments, the ratio of acetate:cis-aconitate greater than 835.7 is associated with First Phase and less than 835.7 is associated with Second Phase for the buffy coat processed platelet sample. In some embodiments, the ratio of acetate:succinate greater than 1644 is associated with First Phase and less than 1644 is associated with Second Phase for the buffy coat processed platelet sample. In some embodiments, the ratio of acetate:lactose greater than 3 is associated with First Phase and less than 3 is associated with Second Phase for the buffy coat processed platelet sample. In some embodiments, the method further comprises a platelet sample, wherein the platelet sample comprises extracellular glutamine, niacinamide, succinic acid, and glutathione oxidized, and intracellular glutathione oxidized. In some embodiments, the analytical analysis is a high performance liquid chromatography (HPLC) analysis, enzymatic assay, biochemical assay, luminescence assay, mass spectrometry analysis, photometry analysis, or a combination thereof. In some embodiments, the platelet sample comprises platelets and an additive solution.

Disclosed herein, in certain embodiments, is a method for storing red blood cells (RBCs), comprising: (a) obtaining an RBC sample from the RBCs; (b) testing the RBC sample by the steps of: (i) determining a value of a biomarker in an RBC sample by an analytical analysis, wherein the biomarker value is selected from one or more of: concentration of inosine, concentration of hypoxanthine, concentration of adenine, ratio of hypoxanthine:adenine, ratio of glucose:lactate, ratio of $Na^+$:$K^+$, ratio of inosine:adenine, concentration of pyruvate; (ii) matching the biomarker value to a respective control value for the biomarker; and (iii) assigning a metabolic state to the RBC sample based on the value of the biomarker which is one of a First Phase, a Second Phase or a Third Phase; wherein: the RBC sample is First Phase when the ratio of glucose:lactate and the ratio of $Na^+$:$K^+$ match the values on the control indicated for First Phase; and optionally when one or more of the concentration of inosine, the ratio of hypoxanthine:adenine, the ratio of inosine:adenine and the concentration of pyruvate match the values on the control indicated for First Phase; the RBC sample is Second Phase when the ratio of hypoxanthine:adenine matches the value on the control indicated for Second Phase; and optionally when one or more of the concentration of inosine, and the ratio of inosine:adenine match the values on the control indicated for Second Phase; or the RBC sample is Third Phase when the ratio of hypoxanthine:adenine, the concentration of hypoxanthine and the concentration of adenine match the values on the control indicated for Third Phase, and optionally when one or more of the ratio of $pCO_2$:pH, the ratio of inosine:adenine, and/or the concentration of inosine match the values on the control indicated for Third Phase; (c) assigning a range of days associated with First Phase, Second Phase, or Third Phase to the RBCs to indicate storage duration of the RBC sample in First Phase, Second Phase, or Third Phase; and (d) recommending the disposal of RBCs in Third Phase. In some embodiments, the range of days associated with First Phase is from day 0 to day 10. In some embodiments, the range of days associated with Second Phase is from day 11 to day 18. In some embodiments, the range of days associated with Third Phase is after day 19. In some embodiments, the control is a signature profile of one, two or more biomarkers over time. In some embodiments, a ratio of glucose:lactate greater than 2.0 mM/mM is associated with First Phase and a ratio in the range 0-2.0 mM/mM is associated with both Second Phase and Third Phase. In some embodiments, a ratio of $Na^+$:$K^+$ greater than 6.5 mM/mM is associated with First Phase and a ratio in the range 0-6.5 mM/mM is associated with both Second Phase and Third Phase. In some embodiments, a ratio of hypoxanthine:adenine in the range 0-1.0 mM/mM is associated with First Phase, a ratio in the range 1.0-16 mM/mM is associated with Second Phase and a ratio greater than 16 mM/mM is associated with Third Phase. In some embodiments, a concentration of hypoxanthine in the range 0-0.1 mM is associated with both First Phase and Second Phase and a concentration greater than 0.1 mM is associated with Third Phase. In some embodiments, a concentration of adenine greater than 0.1 mM is associated with both First Phase and Second Phase and concentration in the range 0-0.1 mM is associated with Third Phase. In some embodiments, a ratio of inosine:adenine of 0 mM/mM is associated with First Phase, a ratio in the range 0-0.05 is associated with Second Phase and a ratio greater than 0.05 is associated Third Phase. In some embodiments, a ratio of pCO2:pH in the range 0-16 mmHg/pH is associated with First Phase and Second Phase, and a ratio greater than 16 mmg/pH is associated with Third Phase. In some embodiments, a concentration of inosine of 0 mM is associated with First Phase, a concentration in the range 0-0.0005 mM is associated with Second Phase and a concentration greater than 0.0005 mM is associated with Third Phase. In some embodiments, a concentration of pyruvate of 0 mM is associated with First Phase and a concentration greater than 0 mM is associated with both Second Phase and Third Phase. In some embodiments, step b) comprises analyzing the RBC sample to determine the amount of at least one of inosine, hypoxanthine, adenine, glucose, lactate, $Na^+$, $K^+$, $pCO2$, pH and pyruvate. In some embodiments, the analytical analysis is selected from high-performance liquid chromatography (HPLC), blood-gas analysis, enzymatic assay, biochemical assay, luminescence assay, mass spectrometry, photometry, or a combination thereof, prior to determining the value of the biomarker. In some embodiments, the RBC sample is an extracellular RBC sample comprising inosine, hypoxanthine, adenine, $Na^+$, $K^+$, glucose, lactate and pyruvate. In some embodiments, the biomarker data obtained from the extracellular RBC sample is concentration of inosine, concentration of hypoxanthine, concentration of adenine, ratio of hypoxanthine:adenine, ratio of glucose:lactate, ratio of $Na^+:K^+$, ratio of inosine:adenine, or concentration of pyruvate. In some embodiments, the RBC sample comprises RBCs and an additive solution.

Disclosed herein, in certain embodiments, is a method for storing platelets (PLTs), comprising: (a) obtaining a PLT sample from the PLTs; (b) testing the PLT sample by the steps of: (i) determining a value of a biomarker in a platelet sample by an analytical analysis, wherein the biomarker value is selected from one or more of: concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose; (ii) matching the biomarker value to a respective control value for the biomarker, wherein a value in the control defines a transition from a first metabolic state of the platelets to a second metabolic state of the platelets; and (iii) assigning a metabolic state to the platelet sample based on the value of the biomarker which is one of First Phase or Second Phase; wherein: the sample is First Phase when the measured concentration of glutathione oxidized, ratio of acetate:cis-aconitate, and either ratio of glucose:lactose or ratio of acetate:lactose are greater than the values on the control indicated as the transition from the first metabolic state to the second metabolic state; or the sample is Second Phase when the measured concentration of glutathione oxidized, ratio of acetate:cis-aconitate, and either ratio of glucose:lactose or ratio of acetate:lactose are less than the values on the control indicated as the transition from the first metabolic state to the second metabolic state; (c) assigning a range of days associated with First Phase or Second Phase to the PLTs to indicate storage duration of the PLT sample in First Phase or Second Phase; and (d) recommending disposal of PLTs in Second Phase. In some embodiments, the range of days associated with First Phase is from day 0 to day 3. In some embodiments, the range of days associated with Second Phase is after day 4. In some embodiments, the control dataset is a signature profile of one, two, or more biomarkers over time. In some embodiments, the platelet sample is processed by apheresis. In some embodiments, a biomarker associated with the apheresis processed platelet sample is selected from the group consisting of concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combination thereof. In some embodiments, the First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state. In some embodiments, the First Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, the Second Phase is assigned to the apheresis processed platelet sample where the concentration of glutathione oxidized, ratio of acetate:cis-aconitate, and ratio of glucose:lactose are less than the values on the control indicated as the transition from the first metabolic state to the second metabolic state. In some embodiments, the Second Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, concentration of glutathione oxidized is an intracellular concentration of glutathione oxidized. In some embodiments, the concentration of glutathione oxidized greater than 2.22E-05 mM is associated with First Phase and less than 2.22E-05 mM is associated with Second Phase for the apheresis processed platelet sample. In some embodiments, the concentration of glutamine greater than 0.11 mM is associated with First Phase and less than 0.11 mM is associated with Second Phase for the apheresis processed platelet sample. In some embodiments, the concentration of niacinamide less than 0.0035 mM is associated with First Phase and greater than 0.0035 mM is associated with Second Phase for the apheresis processed platelet sample. In some embodiments, the concentration of sCD40L less than 20.8 ng/mL is associated with First Phase and greater than 20.8 ng/mL is associated with Second Phase for the apheresis processed platelet sample. In some embodiments, the value of CD41:CD63 less than 24.3% is associated with First Phase and greater than 24.3% is associated with Second Phase for the apheresis processed platelet sample. In some embodiments, the ratio of citrate:cis-aconitate greater than 228.3 is associated with First Phase and less than 228.3 is associated with Second Phase for the apheresis processed platelet sample. In some embodiments, the ratio of citrate:malate greater than 470.6 is associated with First Phase and less than 470.6 is associated with Second Phase for the apheresis processed platelet sample. In some embodiments, the ratio of acetate:cis-aconitate greater than 680.6 is associated with First Phase and less than 680.6 is associated with Second Phase for the apheresis processed platelet sample. In some embodiments, the ratio of glucose:lactose greater than 0.569 is associated with First Phase and less than 0.569 is associated with Second Phase for the apheresis processed platelet sample. In some embodiments, the platelet sample is processed by buffy coat method. In some embodiments, a biomarker associated with the buffy coat processed platelet sample is selected from the group consisting of concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combination thereof. In some embodiments, the First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the Second Phase is assigned to the buffy coat processed platelet sample where the concentration of glutathione oxidized, ratio of acetate:cis-aconitate, and ratio of acetate:lactose are less than the values on the control indicated as the transition from the first metabolic state to the second metabolic state. In some embodiments, the Second Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the concentration of glutathione oxidized is an extracellular concentration of glutathione oxidized or an intracellular concentration of glutathione oxidized. In some embodiments, the First Phase is assigned to the buffy coat processed platelet sample where the extracellular concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the Second Phase is assigned to the buffy coat processed platelet sample where the extracellular concentration of glutathione oxidized, ratio of acetate:cis-aconitate, and ratio of acetate:lactose are less than the values on the control indicated as the transition from the first metabolic state to the second metabolic state. In some embodiments, the Second Phase is assigned to the buffy coat processed platelet sample where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the extracellular concentration of glutathione oxidized greater than 5.91E-04 mM is associated with First Phase and less than 5.91E-04 mM is associated with Second Phase for the buffy coat processed platelet sample. In some embodiments, the intracellular concentration of glutathione oxidized greater than 3.6E-05 mM is associated with First Phase and less than 3.6E-05 mM is associated with Second Phase for the buffy coat processed platelet sample. In some embodiments, the concentration of glutamine greater than 0.42 mM is associated with First Phase and less than 0.42 mM is associated with Second Phase for the buffy coat processed platelet sample. In some embodiments, the concentration of succinic acid less than 0.0128 mM is associated with First Phase and greater than 0.0128 mM is associated with Second Phase for the buffy coat processed platelet sample. In some embodiments, the value of CD41:Annexin-V less than 3.2% is associated with First Phase and greater than 3.2% is associated with Second Phase for the buffy coat processed platelet sample. In some embodiments, the value of CD41:CD42b less than 1.7% is associated with First Phase and greater than 1.7% is associated with Second Phase for the buffy coat processed platelet sample. In some embodiments, the concentration of sCD40L less than 15 ng/mL is associated with First Phase and greater than 15 ng/mL is associated with Second Phase for the buffy coat processed platelet sample. In some embodiments, the ratio of citrate:cis-aconitate greater than 314 is associated with First Phase and less than 314 is associated with Second Phase for the buffy coat processed platelet sample. In some embodiments, the ratio of acetate:cis-aconitate greater than 835.7 is associated with First Phase and less than 835.7 is associated with Second Phase for the buffy coat processed platelet sample. In some embodiments, the ratio of acetate:succinate greater than 1644 is associated with First Phase and less than 1644 is associated with Second Phase for the buffy coat processed platelet sample. In some embodiments, the ratio of acetate:lactose greater than 3 is associated with First Phase and less than 3 is associated with Second Phase for the buffy coat processed platelet sample. In some embodiments, the method further comprises a platelet sample, wherein the platelet sample comprises extracellular glutamine, niacinamide, succinic acid, and glutathione oxidized, and intracellular glutathione oxidized. In some embodiments, the analytical analysis is a high performance liquid chromatography (HPLC) analysis, enzymatic assay, biochemical assay, luminescence assay, mass spectrometry analysis, photometry analysis, or a combination thereof. In some embodiments, the platelet sample comprises platelets and an additive solution.

Disclosed herein, in certain embodiments, is a method for characterizing red blood cells (RBCs) for transfusion, comprising: (a) obtaining an RBC sample from the RBCs; (b) determining a value of a biomarker in the RBC sample by an analytical analysis, wherein the biomarker value is selected from one or more of: concentration of inosine, concentration of hypoxanthine, concentration of adenine, ratio of hypoxanthine:adenine, ratio of glucose:lactate, ratio of $Na^+$:$K^+$, ratio of inosine:adenine, concentration of pyruvate; (c) matching the biomarker value to a respective control value for the biomarker; and; (d) assigning a metabolic state to the RBC sample based on the value of the biomarker which is one of a First Phase, a Second Phase or a Third Phase; wherein: the RBC sample is First Phase when the ratio of glucose:lactate and the ratio of $Na^+$:$K^+$ match the values on the control indicated for First Phase; and optionally when one or more of the concentration of inosine, the ratio of hypoxanthine:adenine, the ratio of inosine:adenine and the concentration of pyruvate match the values on the control indicated for First Phase; the RBC sample is Second Phase when the ratio of hypoxanthine:adenine matches the value on the control indicated for Second Phase; and optionally when one or more of the concentration of inosine, and the ratio of inosine:adenine match the values on the control indicated for Second Phase; or the RBC sample is Third Phase when the ratio of hypoxanthine:adenine, the concentration of hypoxanthine and the concentration of adenine match the values on the control indicated for Third Phase, and optionally when one or more of the ratio of $pCO_2$:pH, the ratio of inosine:adenine, and/or the concentration of inosine match the values on the control indicated for Third Phase; and (e) recommending First Phase or Second Phase RBCs for transfusion. In some embodiments, Third Phase RBCs is not recommended for transfusion. In some embodiments, the control is a signature profile of one, two or more biomarkers over time. In some embodiments, a ratio of glucose:lactate greater than 2.0 mM/mM is associated with First Phase and a ratio in the range 0-2.0 mM/mM is associated with both Second Phase and Third Phase. In some embodiments, a ratio of $Na^+$:$K^+$ greater than 6.5 mM/mM is associated with First Phase and a ratio in the range 0-6.5 mM/mM is associated with both Second Phase and Third Phase. In some embodiments, a ratio of hypoxanthine:adenine in the range 0-1.0 mM/mM is associated with First Phase, a ratio in the range 1.0-16 mM/mM is associated with Second Phase and a ratio greater than 16 mM/mM is associated with Third Phase. In some embodiments, a concentration of hypoxanthine in the range 0-0.1 mM is associated with both First Phase and Second Phase and a concentration greater than 0.1 mM is associated with Third Phase. In some embodiments, a concentration of adenine greater than 0.1 mM is associated with both First Phase and Second Phase and concentration in the range 0-0.1 mM is associated with Third Phase. In some embodiments, a ratio of inosine:adenine of 0 mM/mM is associated with First Phase, a ratio in the range 0-0.05 is associated with Second Phase and a ratio greater than 0.05 is associated Third Phase. In some embodiments, a ratio of pCO2:pH in the range 0-16 mmHg/pH is associated with First Phase and Second Phase, and a ratio greater than 16 mmg/pH is associated with Third Phase. In some embodiments, a concentration of inosine of 0 mM is associated with First Phase, a concentration in the range 0-0.0005 mM is associated with Second Phase and a concentration greater than 0.0005 mM is associated with Third Phase. In some embodiments, a concentration of pyruvate of 0 mM is associated with First Phase and a concentration greater than 0 mM is associated with both Second Phase and Third Phase. In some embodiments, step b) comprises analyzing the RBC sample to determine the amount of at least one of inosine, hypoxanthine, adenine, glucose, lactate, $Na^+$, $K^+$, pCO2, pH and pyruvate. In some embodiments, the analytical analysis is selected from high-performance liquid chromatography (HPLC), blood-gas analysis, enzymatic assay, biochemical assay, luminescence assay, mass spectrometry, photometry, or a combination thereof, prior to determining the value of the biomarker. In some embodiments, the RBC sample is an extracellular RBC sample comprising inosine, hypoxanthine, adenine, $Na^+$, $K^+$, glucose, lactate and pyruvate. In some embodiments, the biomarker data obtained from the extracellular RBC sample is concentration of inosine, concentration of hypoxanthine, concentration of adenine, ratio of hypoxanthine:adenine, ratio of glucose:lactate, ratio of $Na^+$:$K^+$, ratio of inosine:adenine, or concentration of pyruvate. In some embodiments, the RBC sample comprises RBCs and an additive solution.

Disclosed herein, in certain embodiments, is a storage device comprising: a container; a composition comprising red blood cells (RBCs) and an additive solution in the container; and an indicator which displays the metabolic state of RBCs stored therein; wherein the indicator has a testing module which contains reagents and analytes for carrying out a test reaction to allow detection of one or more biomarkers; and the metabolic state of the RBCs is displayed as one of a First, a Second or a Third Phase; wherein the metabolic state of the RBCs is classified as: (a) First Phase by comparing the measured ratio of glucose:lactate and the ratio of $Na^+$:$K^+$ match the values on the control indicated for the First Phase; and optionally when one or more of the concentration of inosine, the ratio of hypoxanthine:adenine, the ratio of inosine:adenine and the concentration of pyruvate match the values on the control indicated for First Phase; (b) Second Phase when the ratio of hypoxanthine:adenine matches the value on the control indicated for the Second Phase; and optionally when concentration of inosine and/or the ratio of inosine:adenine matches the values on the control indicated for Second Phase; or (c) Third Phase when the ratio of hypoxanthine:adenine, the concentration of hypoxanthine and the concentration of adenine match the values on the control indicated for the Third Phase; and optionally when one or more of pCO2:pH, the ratio of inosine:adenine and the concentration of inosine match the values on the control indicated for the Third Phase. In some embodiments, the indicator indicates the phase of RBCs through a colour. In some embodiments, the indicator indicates a change in phase through a change in colour. In some embodiments, the container comprises a wall defining an interior chamber. In some embodiments, the indicator is adherent to the wall of the container. In some embodiments, the test strip is visible through the wall of the container. In some embodiments, the control is a signature profile of one, two or more biomarkers over time. In some embodiments, a ratio of glucose:lactate greater than 2.0 mM/mM is associated with First Phase and a ratio in the range 0-2.0 mM/mM is associated with both Second Phase and Third Phase. In some embodiments, a ratio of $Na^+$:$K^+$ greater than 6.5 mM/mM is associated with First Phase and a ratio in the range 0-6.5 mM/mM is associated with both Second Phase and Third Phase. In some embodiments, a ratio of hypoxanthine:adenine in the range 0-1.0 mM/mM is associated with First Phase, a ratio in the range 1.0-16 mM/mM is associated with Second Phase and a ratio greater than 16 mM/mM is associated with Third Phase. In some embodiments, a concentration of hypoxanthine in the range 0-0.1 mM is associated with both First Phase and Second Phase and a concentration greater than 0.1 mM is associated with Third Phase. In some embodiments, a concentration of adenine greater than 0.1 mM is associated with both First Phase and Second Phase and concentration in the range 0-0.1 mM is associated with Third Phase. In some embodiments, a ratio of inosine:adenine of 0 mM/mM is associated with First Phase, a ratio in the range 0-0.05 is associated with Second Phase and a ratio greater than 0.05 is associated Third Phase. In some embodiments, a ratio of pCO2:pH in the range 0-16 mmHg/pH is associated with First Phase and Second Phase, and a ratio greater than 16 mmg/pH is associated with Third Phase. In some embodiments, a concentration of inosine of 0 mM is associated with First Phase, a concentration in the range 0-0.0005 mM is associated with Second Phase and a concentration greater than 0.0005 mM is associated with Third Phase. In some embodiments, a concentration of pyruvate of 0 mM is associated with First Phase and a concentration greater than 0 mM is associated with both Second Phase and Third Phase. In some embodiments, step b) comprises analyzing the RBC sample to determine the amount of at least one of inosine, hypoxanthine, adenine, glucose, lactate, $Na^+$, $K^+$, pCO2, pH and pyruvate. In some embodiments, the analytical analysis is selected from high-performance liquid chromatography (HPLC), blood-gas analysis, enzymatic assay, biochemical assay, luminescence assay, mass spectrometry, photometry, or a combination thereof, prior to determining the value of the biomarker. In some embodiments, the RBC sample is an extracellular RBC sample comprising inosine, hypoxanthine, adenine, $Na^+$, $K^+$, glucose, lactate and pyruvate. In some embodiments, the biomarker data obtained from the extracellular RBC sample is concentration of inosine, concentration of hypoxanthine, concentration of adenine, ratio of hypoxanthine:adenine, ratio of glucose:lactate, ratio of $Na^+$:$K^+$, ratio of inosine:adenine, or concentration of pyruvate. In some embodiments, the RBC sample comprises RBCs and an additive solution.

Disclosed herein, in certain embodiments, is a method for characterizing platelets (PLTs) for transfusion, comprising: (a) obtaining a PLT sample from the PLTs; (b) determining a value of a biomarker in the PLT sample by an analytical analysis, wherein the biomarker value is selected from one or more of: concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose; (c) matching the biomarker value to a respective control value for the biomarker, wherein a value in the control defines a transition from a first metabolic state of the platelets to a second metabolic state of the platelets; (d) assigning a metabolic state to the platelet sample based on the value of the biomarker which is one of First Phase or Second Phase; wherein: the sample is First Phase when the measured concentration of glutathione oxidized, ratio of acetate:cis-aconitate, and either ratio of glucose:lactose or ratio of acetate:lactose are greater than the values on the control indicated as the transition from the first metabolic state to the second metabolic state; or the sample is Second Phase when the measured concentration of glutathione oxidized, ratio of acetate:cis-aconitate, and either ratio of glucose:lactose or ratio of acetate:lactose are less than the values on the control indicated as the transition from the first metabolic state to the second metabolic state; and (e) recommending First Phase PLTs for transfusion. In some embodiments, Second Phase PLTs is not recommended for transfusion. In some embodiments, the control dataset is a signature profile of one, two, or more biomarkers over time. In some embodiments, the platelet sample is processed by apheresis. In some embodiments, a biomarker associated with the apheresis processed platelet sample is selected from the group consisting of concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combination thereof. In some embodiments, the First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state. In some embodiments, the First Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, the Second Phase is assigned to the apheresis processed platelet sample where the concentration of glutathione oxidized, ratio of acetate:cis-aconitate, and ratio of glucose:lactose are less than the values on the control indicated as the transition from the first metabolic state to the second metabolic state. In some embodiments, the Second Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, concentration of glutathione oxidized is an intracellular concentration of glutathione oxidized. In some embodiments, the concentration of glutathione oxidized greater than 2.22E-05 mM is associated with First Phase and less than 2.22E-05 mM is associated with Second Phase for the apheresis processed platelet sample. In some embodiments, the concentration of glutamine greater than 0.11 mM is associated with First Phase and less than 0.11 mM is associated with Second Phase for the apheresis processed platelet sample. In some embodiments, the concentration of niacinamide less than 0.0035 mM is associated with First Phase and greater than 0.0035 mM is associated with Second Phase for the apheresis processed platelet sample. In some embodiments, the concentration of sCD40L less than 20.8 ng/mL is associated with First Phase and greater than 20.8 ng/mL is associated with Second Phase for the apheresis processed platelet sample. In some embodiments, the value of CD41:CD63 less than 24.3% is associated with First Phase and greater than 24.3% is associated with Second Phase for the apheresis processed platelet sample. In some embodiments, the ratio of citrate:cis-aconitate greater than 228.3 is associated with First Phase and less than 228.3 is associated with Second Phase for the apheresis processed platelet sample. In some embodiments, the ratio of citrate:malate greater than 470.6 is associated with First Phase and less than 470.6 is associated with Second Phase for the apheresis processed platelet sample. In some embodiments, the ratio of acetate:cis-aconitate greater than 680.6 is associated with First Phase and less than 680.6 is associated with Second Phase for the apheresis processed platelet sample. In some embodiments, the ratio of glucose:lactose greater than 0.569 is associated with First Phase and less than 0.569 is associated with Second Phase for the apheresis processed platelet sample. In some embodiments, the platelet sample is processed by buffy coat method. In some embodiments, a biomarker associated with the buffy coat processed platelet sample is selected from the group consisting of concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combination thereof. In some embodiments, the First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the Second Phase is assigned to the buffy coat processed platelet sample where the concentration of glutathione oxidized, ratio of acetate:cis-aconitate, and ratio of acetate:lactose are less than the values on the control indicated as the transition from the first metabolic state to the second metabolic state. In some embodiments, the Second Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the concentration of glutathione oxidized is an extracellular concentration of glutathione oxidized or an intracellular concentration of glutathione oxidized. In some embodiments, the First Phase is assigned to the buffy coat processed platelet sample where the extracellular concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the Second Phase is assigned to the buffy coat processed platelet sample where the extracellular concentration of glutathione oxidized, ratio of acetate:cis-aconitate, and ratio of acetate:lactose are less than the values on the control indicated as the transition from the first metabolic state to the second metabolic state. In some embodiments, the Second Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the extracellular concentration of glutathione oxidized greater than 5.91E-04 mM is associated with First Phase and less than 5.91E-04 mM is associated with Second Phase for the buffy coat processed platelet sample. In some embodiments, the intracellular concentration of glutathione oxidized greater than 3.6E-05 mM is associated with First Phase and less than 3.6E-05 mM is associated with Second Phase for the buffy coat processed platelet sample. In some embodiments, the concentration of glutamine greater than 0.42 mM is associated with First Phase and less than 0.42 mM is associated with Second Phase for the buffy coat processed platelet sample. In some embodiments, the concentration of succinic acid less than 0.0128 mM is associated with First Phase and greater than 0.0128 mM is associated with Second Phase for the buffy coat processed platelet sample. In some embodiments, the value of CD41:Annexin-V less than 3.2% is associated with First Phase and greater than 3.2% is associated with Second Phase for the buffy coat processed platelet sample. In some embodiments, the value of CD41:CD42b less than 1.7% is associated with First Phase and greater than 1.7% is associated with Second Phase for the buffy coat processed platelet sample. In some embodiments, the concentration of sCD40L less than 15 ng/mL is associated with First Phase and greater than 15 ng/mL is associated with Second Phase for the buffy coat processed platelet sample. In some embodiments, the ratio of citrate:cis-aconitate greater than 314 is associated with First Phase and less than 314 is associated with Second Phase for the buffy coat processed platelet sample. In some embodiments, the ratio of acetate:cis-aconitate greater than 835.7 is associated with First Phase and less than 835.7 is associated with Second Phase for the buffy coat processed platelet sample. In some embodiments, the ratio of acetate:succinate greater than 1644 is associated with First Phase and less than 1644 is associated with Second Phase for the buffy coat processed platelet sample. In some embodiments, the ratio of acetate:lactose greater than 3 is associated with First Phase and less than 3 is associated with Second Phase for the buffy coat processed platelet sample. In some embodiments, the method further comprises a platelet sample, wherein the platelet sample comprises extracellular glutamine, niacinamide, succinic acid, and glutathione oxidized, and intracellular glutathione oxidized. In some embodiments, the analytical analysis is a high performance liquid chromatography (HPLC) analysis, enzymatic assay, biochemical assay, luminescence assay, mass spectrometry analysis, photometry analysis, or a combination thereof. In some embodiments, the platelet sample comprises platelets and an additive solution.

Disclosed herein, in certain embodiments, is a storage device comprising: (a) a container; (b) a composition comprising platelets (PLTs) in the container; and (c) an indicator which displays the metabolic state of platelets stored therein; wherein the indicator has a testing module which contains reagents and analytes for carrying out a test reaction to allow detection of one or more biomarkers; and the metabolic state of the platelets is displayed as one of First Phase or Second Phase; wherein the metabolic state of the RBCs is classified as: First Phase by comparing the measured concentration of glutathione oxidized, ratio of acetate:cis-aconitate, and either ratio of glucose:lactose or ratio of acetate:lactose as greater than the values on the control indicated as the transition from the first metabolic state to the second metabolic state; or Second Phase by comparing the measured concentration of glutathione oxidized, ratio of acetate:cis-aconitate, and either ratio of glucose:lactose or ratio of acetate:lactose as less than the values on the control indicated as the transition from the first metabolic state to the second metabolic state. In some embodiments, the indicator indicates the phase of platelets through a colour. In some embodiments, the indicator indicates a change in phase through a change in colour. In some embodiments, the container comprises a wall defining an interior chamber. In some embodiments, the indicator is adherent to the wall of the container. In some embodiments, the test strip is visible through the wall of the container. In some embodiments, the control dataset is a signature profile of one, two, or more biomarkers over time. In some embodiments, the platelet sample is processed by apheresis. In some embodiments, a biomarker associated with the apheresis processed platelet sample is selected from the group consisting of concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combination thereof. In some embodiments, the First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state. In some embodiments, the First Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, the Second Phase is assigned to the apheresis processed platelet sample where the concentration of glutathione oxidized, ratio of acetate:cis-aconitate, and ratio of glucose:lactose are less than the values on the control indicated as the transition from the first metabolic state to the second metabolic state. In some embodiments, the Second Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, concentration of glutathione oxidized is an intracellular concentration of glutathione oxidized. In some embodiments, the concentration of glutathione oxidized greater than 2.22E-05 mM is associated with First Phase and less than 2.22E-05 mM is associated with Second Phase for the apheresis processed platelet sample. In some embodiments, the concentration of glutamine greater than 0.11 mM is associated with First Phase and less than 0.11 mM is associated with Second Phase for the apheresis processed platelet sample. In some embodiments, the concentration of niacinamide less than 0.0035 mM is associated with First Phase and greater than 0.0035 mM is associated with Second Phase for the apheresis processed platelet sample. In some embodiments, the concentration of sCD40L less than 20.8 ng/mL is associated with First Phase and greater than 20.8 ng/mL is associated with Second Phase for the apheresis processed platelet sample. In some embodiments, the value of CD41:CD63 less than 24.3% is associated with First Phase and greater than 24.3% is associated with Second Phase for the apheresis processed platelet sample. In some embodiments, the ratio of citrate:cis-aconitate greater than 228.3 is associated with First Phase and less than 228.3 is associated with Second Phase for the apheresis processed platelet sample. In some embodiments, the ratio of citrate:malate greater than 470.6 is associated with First Phase and less than 470.6 is associated with Second Phase for the apheresis processed platelet sample. In some embodiments, the ratio of acetate:cis-aconitate greater than 680.6 is associated with First Phase and less than 680.6 is associated with Second Phase for the apheresis processed platelet sample. In some embodiments, the ratio of glucose:lactose greater than 0.569 is associated with First Phase and less than 0.569 is associated with Second Phase for the apheresis processed platelet sample. In some embodiments, the platelet sample is processed by buffy coat method. In some embodiments, a biomarker associated with the buffy coat processed platelet sample is selected from the group consisting of concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combination thereof. In some embodiments, the First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the Second Phase is assigned to the buffy coat processed platelet sample where the concentration of glutathione oxidized, ratio of acetate:cis-aconitate, and ratio of acetate:lactose are less than the values on the control indicated as the transition from the first metabolic state to the second metabolic state. In some embodiments, the Second Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the concentration of glutathione oxidized is an extracellular concentration of glutathione oxidized or an intracellular concentration of glutathione oxidized. In some embodiments, the First Phase is assigned to the buffy coat processed platelet sample where the extracellular concentration of glutathione oxidized, ratio of acetate:cis-aconitate, and ratio of acetate:lactose are greater than the values on the control indicated as the transition from the first metabolic state to the second metabolic state. In some embodiments, the First Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the Second Phase is assigned to the buffy coat processed platelet sample where the extracellular concentration of glutathione oxidized, ratio of acetate:cis-aconitate, and ratio of acetate:lactose are less than the values on the control indicated as the transition from the first metabolic state to the second metabolic state. In some embodiments, the Second Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state. In some embodiments, the extracellular concentration of glutathione oxidized greater than 5.91E-04 mM is associated with First Phase and less than 5.91E-04 mM is associated with Second Phase for the buffy coat processed platelet sample. In some embodiments, the intracellular concentration of glutathione oxidized greater than 3.6E-05 mM is associated with First Phase and less than 3.6E-05 mM is associated with Second Phase for the buffy coat processed platelet sample. In some embodiments, the concentration of glutamine greater than 0.42 mM is associated with First Phase and less than 0.42 mM is associated with Second Phase for the buffy coat processed platelet sample. In some embodiments, the concentration of succinic acid less than 0.0128 mM is associated with First Phase and greater than 0.0128 mM is associated with Second Phase for the buffy coat processed platelet sample. In some embodiments, the value of CD41:Annexin-V less than 3.2% is associated with First Phase and greater than 3.2% is associated with Second Phase for the buffy coat processed platelet sample. In some embodiments, the value of CD41:CD42b less than 1.7% is associated with First Phase and greater than 1.7% is associated with Second Phase for the buffy coat processed platelet sample. In some embodiments, the concentration of sCD40L less than 15 ng/mL is associated with First Phase and greater than 15 ng/mL is associated with Second Phase for the buffy coat processed platelet sample. In some embodiments, the ratio of citrate:cis-aconitate greater than 314 is associated with First Phase and less than 314 is associated with Second Phase for the buffy coat processed platelet sample. In some embodiments, the ratio of acetate:cis-aconitate greater than 835.7 is associated with First Phase and less than 835.7 is associated with Second Phase for the buffy coat processed platelet sample. In some embodiments, the ratio of acetate:succinate greater than 1644 is associated with First Phase and less than 1644 is associated with Second Phase for the buffy coat processed platelet sample. In some embodiments, the ratio of acetate:lactose greater than 3 is associated with First Phase and less than 3 is associated with Second Phase for the buffy coat processed platelet sample. In some embodiments, the method further comprises a platelet sample, wherein the platelet sample comprises extracellular glutamine, niacinamide, succinic acid, and glutathione oxidized, and intracellular glutathione oxidized. In some embodiments, the analytical analysis is a high performance liquid chromatography (HPLC) analysis, enzymatic assay, biochemical assay, luminescence assay, mass spectrometry analysis, photometry analysis, or a combination thereof. In some embodiments, the platelet sample comprises platelets and an additive solution.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1B illustrates a conceptual classification scheme for assignment of First Phase, Second Phase (Transition Phase) or Third Phase to an RBC sample based on the values of biomarkers described herein.

FIG. 5A illustrates the ratio of glucose:lactate during storage from Day 1 to Day 46. The gray region indicates Second Phase (Transition Phase). FIG. 5B depicts ratio time profile of glucose:lactate. FIG. 5C and FIG. 5D depict time profiles of glucose and lactate concentrations. In FIG. 5E, principal component analysis correlates the signature profile of glucose:lactate to the RBC metabolism during storage. First principal component (PC1) accounts for 31% of the total variance in the dataset. PC1 illustrates metabolic concentration variance over time. Second principal component (PC2) accounts for 10% of total variance.

FIG. 6A illustrates the ratio of $Na^+$:$K^+$ during storage from Day 1 to Day 46. The gray region indicates Second Phase (Transition Phase). FIG. 6B depicts ratio time profile of $Na^+$:$K^+$. FIG. 6C and FIG. 6D depict time profiles of $K^+$ and $Na^+$ concentrations. In FIG. 6E, principal component analysis correlates the signature profile of $Na^+$:$K^+$ to the RBC metabolism during storage. First principal component (PC1) accounts for 31% of the total variance in the dataset. PC1 illustrates metabolic concentration variance over time. Second principal component (PC2) accounts for 10% of total variance.

FIG. 7A illustrates the ratio of hypoxanthine:adenine during storage from Day 1 to Day 46. The gray region indicates Second Phase (Transition Phase). FIG. 7B depicts ratio time profile of hypoxanthine:adenine. FIG. 7C and FIG. 7D depict time profiles of hypoxanthine and adenine concentrations. In FIGS. 7E-7F, principal component analysis correlates the signature profile of hypoxanthine:adenine to the RBC metabolism during storage. First principal component (PC1) accounts for 31% of the total variance in the dataset. PC1 illustrates metabolic concentration variance over time. Second principal component (PC2) accounts for 10% of total variance.

FIGS. 8A-8D illustrate an exemplary signature profile of hypoxanthine. FIG. 8A and FIG. 8B illustrate the concentration of hypoxanthine during storage from Day 1 to Day 46. In FIG. 8A, the gray region indicates Second Phase (Transition Phase). In FIG. 8C and FIG. 8D, principal component analysis correlates the signature profile of hypoxanthine to the RBC metabolism during storage. First principal component (PC1) accounts for 31% of the total variance in the dataset. PC1 illustrates metabolic concentration variance over time. Second principal component (PC2) accounts for 10% of total variance.

FIG. 9A and FIG. 9B illustrate the concentration of adenine during storage from Day 1 to Day 46. In FIG. 9A, the gray region indicates Second Phase (Transition Phase). In FIG. 9C and FIG. 9D, principal component analysis correlates the signature profile of adenine to the RBC metabolism during storage. First principal component (PC1) accounts for 31% of the total variance in the dataset. PC1 illustrates metabolic concentration variance over time. Second principal component (PC2) accounts for 10% of total variance.

FIG. 10A illustrates the ratio of inosine:adenine during storage from Day 1 to Day 46. The gray region indicates Second Phase (Transition Phase). FIG. 10B depicts ratio time profile of inosine:adenine.

FIG. 10C and FIG. 10D depict time profiles of inosine and adenine concentrations. In FIG. 10E and FIG. 10F, principal component analysis correlates the signature profile of inosine:adenine to the RBC metabolism during storage. First principal component (PC1) accounts for 31% of the total variance in the dataset. PC1 illustrates metabolic concentration variance over time. Second principal component (PC2) accounts for 10% of total variance.

FIG. 11A illustrates the ratio of $pCO_2$:pH during storage from Day 1 to Day 46. The gray region indicates Second Phase (Transition Phase). FIG. 11B depicts ratio time profile of $pCO_2$:pH. FIG. 11C and FIG. 11D depict time profiles of $pCO_2$ and pH concentrations. In FIG. 11E and FIG. 11F, principal component analysis correlates the signature profile of $pCO_2$:pH to the RBC metabolism during storage. First principal component (PC1) accounts for 31% of the total variance in the dataset. PC1 illustrates metabolic concentration variance over time. Second principal component (PC2) accounts for 10% of total variance.

FIG. 12A and FIG. 12B illustrate the ratio of inosine during storage from Day 1 to Day 46. The gray region indicates Second Phase (Transition Phase). In FIG. 12C and FIG. 12D, principal component analysis correlates the signature profile of inosine to the RBC metabolism during storage. First principal component (PC1) accounts for 31% of the total variance in the dataset. PC1 illustrates metabolic concentration variance over time. Second principal component (PC2) accounts for 10% of total variance.

FIG. 15A illustrates a signature profile of platelets processed by apheresis by principal component analysis.

FIG. 15B illustrates a signature profile of platelets processed by buffy coat method by principal component analysis. Stage 1 illustrates First Phase. Stage 2 illustrates Second Phase.

FIG. 16A illustrates signature profile of glutathione oxidized from platelets processed by apheresis. The glutathione oxidized was obtained from the intracellular medium of the apheresis processed platelets. FIG. 16B illustrates signature profile of glutathione oxidized from platelets processed by buffy coat method. The glutathione oxidized was obtained from the intracellular medium of the buffy coat processed platelets.

FIG. 17A illustrates signature profile of glutamine from platelets processed by apheresis. FIG. 17B illustrates signature profile of niacinamide from platelets processed by apheresis. FIG. 17C illustrates signature profile of glutamine from platelets processed by buffy coat method. FIG. 17D illustrates signature profile of succinic acid from platelets processed by buffy coat method. FIG. 17E illustrates a second signature profile of glutathione oxidized from platelets processed by buffy coat method. The glutathione oxidized used to generate the second signature profile was obtained from the extracellular medium of the buffy coat processed platelets.

DETAILED DESCRIPTION OF THE INVENTION

Certain Terminology

Figure 1A:
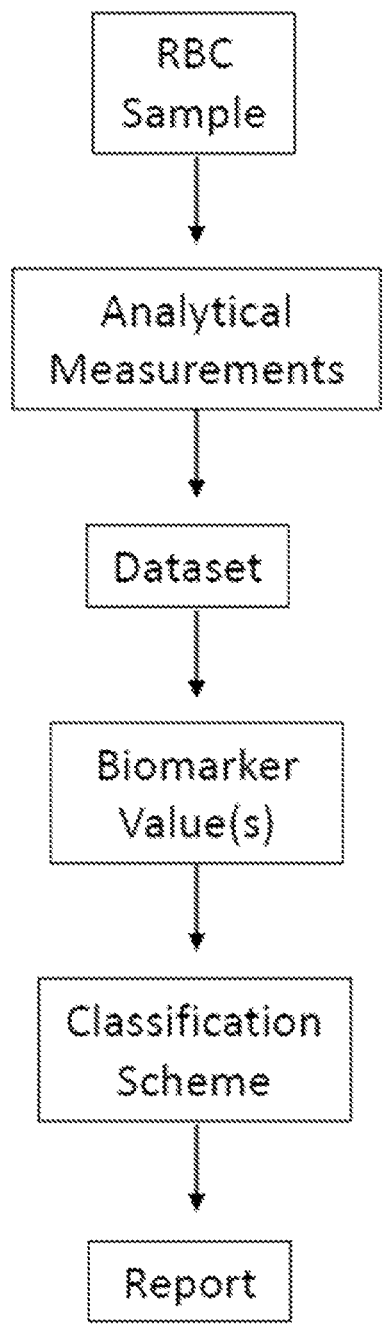
FIG. 1A illustrates a conceptual schematic for determination of a phase of a red blood cell (RBC) sample.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

As used herein, "value," "value of a biomarker" and "biomarker value" are used interchangeably to refer to a measurement that is made using any analytical method for detecting the biomarker in an red blood cell (RBC) sample or a platelet (PLT) sample and indicates the presence, absence, absolute amount, relative amount, normalized amount, a level, a ratio of measured amount or level, or the like, of, for, or corresponding to the biomarker in the RBC sample or the PLT sample. In some embodiments, when "value" is used in the context of value of inosine, value of hypoxanthine, value of adenine, and value of pyruvate, "value" refers to concentration of inosine, concentration of hypoxanthine, concentration of adenine, and concentration of pyruvate. In some embodiments, when "value" is used in the context of value of CD41:CD63, value of CD41:Annexin-V, or value of CD41:CD42b, "value" refers to percentage of cells double positive or expressing both CD41 and CD63 in a cell population, percentage of cells double positive or expressing both CD41 and Annexin-V in a cell population, or percentage of cells double positive or expressing both CD41 and CD42b in a cell population.

As used herein, "metabolic state(s)", "metabolic phase(s)" and "phase(s)" are used interchangeably to refer to at least one defined state of RBCs or PLTs. In some embodiments, in the context of RBCs, a metabolic state, a metabolic phase, or a phase is at least one defined state; preferably one of a first, a second or a third defined state. Such defined states in reference to RBCs correspond to the First Phase, Second Phase or Third Phase for RBCs described herein. In some embodiments, in the context of PLTs, a metabolic state, a metabolic phase, or a phase is at least one defined state; preferably one of a first or a second defined state. Such defined states in reference to PLTs correspond to the First Phase or Second Phase for PLTs described herein.

As used herein, the term "additive solution" refers to any RBC or PLT additive solution which is added to preserve and/or extend the shelf-life of the RBC or PLT. Examplary RBC additive solutions include, but are not limited to, SAG, SAGM, AS-1 (Adsol), AS-3 (Nutricel), AS-5 (Optisol), MAP, PAGGSM (Macopharma), PAGGGM, SOLX (AS-7), BAGP-M, ErythroSol-1, ErythroSol-2, ErythroSol-4, and EAS-81. Examplary PLT additive solutions include, but are not limited to, PAS-1 (PAS-I plasmalyte), PAS-B (PAS-II or T-Sol), PAS-C(PAS-III or Intersol), PAS-D (ComposolPS), PAS-E (PAS-IIIM SSP+), PAS-F (PlasmaLyte A, Isoplate), PAS-G, or M-Sol.

Red Blood Cell Storage and Storage Lesion

Red blood cell (RBC) transfusion represents one of the most widely practiced medical interventions worldwide. In general, RBC units, red blood cells (RBCs) packaged in a storage bag or unit, is available for transfusion for up to for example 42 days post collection in appropriate storage additive solutions. During storage, RBCs are subject to both functional and morphological changes. These reversible and irreversible changes or "storage lesions," alters the RBC properties, ability to function, and recovery after transfusion. For example, RBCs are known to undergo corpuscular changes, such as a decrease in 2,3-diphosphoglycerate (DPG) levels which results in impaired oxygen delivery, a decrease in adenosine trisphosphate (ATP) pool which reduces Na+-K+-ATPase activity, and a decrease in antioxidant capacities which alters reduction of methemoglobin and generates reactive oxygen species (ROS) through a Fenton reaction. Membrane alterations such as changes in protein band 3 and release of procoagulant vesicles lead to deformable sphero-echinocytes with increased adherence to the endothelium and increased susceptibility to phagocytosis. An increase in rigidity, osmotic fragility, haemolytic rate, vesiculation rate, and potassium concentration, a decrease in pH and oxygen off-loading capacity, and a release of proinflammatory molecules further contribute to RBC storage lesion. Although some storage lesions are reversible, such as depletion of ATP and DPG levels, nevertheless, stored RBCs are generally known to have a mean duration of storage between 16 and 21 days with maximum storage duration of for example 42 days.

In general, increased storage time correlates to increased RBC storage lesion. However, factors related to inherent donor-related variability have also contributed to the complexity of the RBC storage. For example, genetics, age, health and lifestyle factors may all contribute to the complexity of RBC storage. Further, current RBC assessment generally requires a haemolysis test where haemolysis is less than 1% in the US and less than 0.8% in Europe and a post 24 h recovery test in which ≥75% cell remain in circulation 24 h after infusion is required. However, post 24 h recovery test is done on healthy volunteers and presumption is made on a global bases. In addition, current RBC assessments do not take into account the various parameters of donor variability and storage conditions. Therefore, a comprehensive test is needed.

Disclosed herein in certain embodiments, are systems, methods, compositions, device and kits for determining the phase or metabolic state of a red blood cell (RBC) sample. Further disclosed herein in certain embodiments, are systems and methods for determining the quality of an RBC sample. In certain embodiments, disclosed herein is a method for characterizing red blood cells (RBCs) for transfusion, comprising: (a) obtaining an RBC sample from the RBCs; (b) determining a value of a biomarker in the RBC sample by an analytical analysis, wherein the biomarker value is selected from one or more of: concentration of inosine, concentration of hypoxanthine, concentration of adenine, ratio of hypoxanthine:adenine, ratio of glucose:lactate, ratio of $Na^+:K^+$, ratio of inosine:adenine, concentration of pyruvate; (c) matching the biomarker value to a respective control value for the biomarker; and; (d) assigning a metabolic state to the RBC sample based on the value of the biomarker which is one of a First Phase, a Second Phase or a Third Phase; wherein: the RBC sample is First Phase when the ratio of glucose:lactate and the ratio of $Na^+:K^+$ match the values on the control indicated for First Phase; and optionally when one or more of the concentration of inosine, the ratio of hypoxanthine:adenine, the ratio of inosine:adenine and the concentration of pyruvate match the values on the control indicated for First Phase; the RBC sample is Second Phase when the ratio of hypoxanthine:adenine matches the value on the control indicated for Second Phase; and optionally when one or more of the concentration of inosine, and the ratio of inosine:adenine match the values on the control indicated for Second Phase; or the RBC sample is Third Phase when the ratio of hypoxanthine:adenine, the concentration of hypoxanthine and the concentration of adenine match the values on the control indicated for Third Phase, and optionally when one or more of the ratio of $pCO_2$:pH, the ratio of inosine:adenine, and/or the concentration of inosine match the values on the control indicated for Third Phase; and (e) recommending First Phase or Second Phase RBCs for transfusion.

Disclosed herein, in certain embodiments, is a storage device comprising: a container; a composition comprising red blood cells (RBCs) and an additive solution in the container; and an indicator which displays the metabolic state of RBCs stored therein; wherein the indicator has a testing module which contains reagents and analytes for carrying out a test reaction to allow detection of one or more biomarkers; and the metabolic state of the RBCs is displayed as one of a First, a Second or a Third Phase; wherein the metabolic state of the RBCs is classified as: (a) First Phase by comparing the measured ratio of glucose:lactate and the ratio of $Na^+:K^+$ match the values on the control indicated for the First Phase; and optionally when one or more of the concentration of inosine, the ratio of hypoxanthine:adenine, the ratio of inosine:adenine and the concentration of pyruvate match the values on the control indicated for First Phase; (b) Second Phase when the ratio of hypoxanthine:adenine matches the value on the control indicated for the Second Phase; and optionally when concentration of inosine and/or the ratio of inosine:adenine matches the values on the control indicated for Second Phase; or (c) Third Phase when the ratio of hypoxanthine:adenine, the concentration of hypoxanthine and the concentration of adenine match the values on the control indicated for the Third Phase; and optionally when one or more of pCO2:pH, the ratio of inosine:adenine and the concentration of inosine match the values on the control indicated for the Third Phase.

Disclosed herein, in certain embodiments, is a system for determining the phase or metabolic state of a red blood cell (RBC) sample, comprising: (a) a digital processing device comprising an operating system configured to perform executable instructions and an electronic memory; (b) a dataset stored in the electronic memory, wherein the dataset comprises raw data for a biomarker in the RBC sample, wherein the biomarker is concentration of inosine, concentration of hypoxanthine, concentration of adenine, ratio of hypoxanthine:adenine, ratio of glucose:lactate, ratio of $Na^+:K^+$, ratio of $pCO_2$:pH, ratio of inosine:adenine, or concentration of pyruvate; and (c) a computer program including instructions executable by the digital processing device to create an application comprising: (i) a first software module configured to analyze the dataset to determine a value of the biomarker; and (ii) a second software module configured to match the value of the biomarker to an equivalent value on a control and assigns a phase to the RBC sample based on the value of the biomarker.

Disclosed herein in certain embodiments, is a method for determining the phase or metabolic state of a red blood cell (RBC) sample, comprising: (a) determining a value of a biomarker in an RBC sample, wherein the biomarker is concentration of inosine, concentration of hypoxanthine, concentration of adenine, ratio of hypoxanthine:adenine, ratio of glucose:lactate, ratio of $Na^+:K^+$, ratio of $pCO_2$:pH, ratio of inosine:adenine, or concentration of pyruvate; (b) matching the value of the biomarker to an equivalent value on a control; and (c) assigning a phase to the RBC sample based on the value of the biomarker.

Disclosed herein in certain embodiments, is a storage device comprising: a container containing a composition comprising red blood cells (RBCs) and an additive solution, wherein the container comprises an indicator which indicates a phase of red blood cells (RBCs) stored therein.

Disclosed herein in certain embodiments, is a kit for determining the phase or metabolic state of a red blood cell (RBC) sample, comprising: (a) a plurality of reagents for determining a dataset for a biomarker, wherein the biomarker is concentration of inosine, concentration of hypoxanthine, concentration of adenine, ratio of hypoxanthine:adenine, ratio of glucose:lactate, ratio of $Na^+:K^+$, ratio of $pCO_2$:pH, ratio of inosine:adenine, concentration of pyruvate, or any combinations thereof; (b) at least one software module for analyzing the dataset to determine a value of the biomarker, matching the value of the biomarker to an equivalent value on a control; and assigning the RBC sample as First Phase, Second Phase or Third Phase, wherein the value of the biomarker indicates the phase of the RBC sample; and (c) instruction manuals for utilizing the plurality of reagents and the at least one software module.

Red Blood Cell (RBC) Biomarkers

RBC functions by producing metabolites (e.g. ATP, NADPH, NADH) for maintaining its osmotic balance and electroneutrality and by fighting oxidative stresses in order to maintain biological functionalities and cell membrane integrity. For example, RBC utilizes a plurality of metabolic pathways to maintain homeostasis and integrity of the blood environment. Maintaining a reducing state within an RBC and protecting hemoglobin from oxidation requires reduced form of glutathione (GSH), which is synthesized from the glutathione peroxidase reaction pathway. Glutathione reductase, a product of the pentose phosphate pathway, recycles oxidized glutathione (GSSH) into GSH with cofactor NADPH. NADPH, along with ATP and 2,3-DPG, are generated through the anaerobic glycolytic pathway. In some instances, ATP and 2,3-DPG is also generated through the Luebering-Rapoport shunt.

In some embodiments, any suitable metabolite is used as a biomarker. In some embodiments, the metabolite is a product of glycolysis, pentose pathway, purine and pyrimidine metabolisms, TCA cycle, glutathione metabolism, glycerophospholipid metabolism and 2,3-bisphosphoglycerate (2,3-BPG, also known as 2,3-diphosphoglycerate or 2,3-DPG, or Luebering-Rapapport) metabolism.

In some embodiments, any suitable RBC component or any physiological, biochemical or molecular parameters associated with the presence of a specific physiological state or process of the RBC are used as a biomarker. In some embodiments, RBC components include hemoglobin, oxygen which hemoglobin transports, carbon dioxide which hemoglobin removes, iron which interacts with hemoglobin, and additional components such as electrolytes including sodium, potassium, chlorides, and so forth. In some embodiments, the RBC components are extracellular components. In some embodiments, the RBC components are located in the RBC medium. In some embodiments, the RBC components are intracellular components. In some embodiments, the physiological, biochemical or molecular parameters include pressure of oxygen, pressure of carbon dioxide, pH and so forth.

In some embodiments, the biomarkers are selected from values of glucose, glyceric acid, 6-phosphogluconic acid, 6-phosphogluconate, glucose 6-phosphate, 6-phosphogluconolactone, fructose 6-phosphate, fructose-1,6-diphosphate, pentose-5-phosphate, hexose-6-phosphate, fructose, lactic acid, sedoheptulose-7-phosphate, pyruvate, phosphoenolpyruvate, phosphoglyceric acid, dihydroxyacetone phosphate (DHAP), glyceraldehydes-3-phosphate (GAD-3-P), 1,3-diphosphoglycerate, 3-phosphoglycerate, 2-phosphoglycerate, 2,3-bisphosphoglycerate (2,3-BPG, also known as 2,3-diphosphoglycerate or 2,3-DPG), mannose, lactate, ribulose-5-phosphate, xylulose-5-phosphate, ribose-5-phosphate, erythrose-4-phosphate, 5-phosphoribosyl-1-pyrophosphate, xanthosine, xanthosine monphosphate (XMP), xanthine, adenine, guanine, hypoxanthine, guanosine, inosine, inosine monophosphate (IMP), adenosine, adenosine monophosphate (AMP), adenosine diphosphate (ADP), adenosine triphosphate (ATP), uric acid, guanosine monophosphate (GMP), guanosine diphosphate (GDP), ADP-ribose, ribose-1-phosphate, nicotinamide adenine dinucleotide (NAD$^+$), nicotinamide adenine dinucleotide reduced (NADH), nicotinamide adenine dinucleotide phosphate (NADP$^+$), nicotinamide adenine dinucleotide phosphate reduced (NADPH), cytidine 5' triphosphate (CTP), cytidine 5' diphosphate (CDP), cytidine 5' monophosphate (CMP), cytosine, cytidine, uridine, uracil, dyhydrouracil, 5-methylcytidine, N4-acetylcytidine, 5'-deoxy-5'-(methylthio)adenosine (5-MTA), adenylosuccinate, inorganic phosphate, ammonia, pCO$_2$, citric acid, fumaric acid, phosphenolpyruvate, aconitic acid, succinic acid, malic acid, aconitic acid, succinic acid, 5-oxoproline, glutathione (oxidized and reduced, GSH, GSSG), cysteine-glutathione disulfide, α-tocopherol, ergothioneine, S-adenosylmethionine (SAMe), S-adenosylhomocysteine (SAH), homocysteine, cysteine, glutamate, glycine, methionine, 2-hydroxybutyrate, 2-aminobutyrate, ophthalmate, cysteinyl-glycine, cysteineglycine disulfide, arginine, alanine, asparagines, carnitine, choline, citrulline, aspartic acid, glutamic acid, glutamine, histidine, hydroxyproline, isoleucine, lysine, mannitol, methyl histidine, nicotinamide, pantothenic acid, phenylalanine, serine, taurine, threonine, tryptophan, tyrosine, valine, acetyl-carnitine, asymmetric dimethylarginine (ADMA), asparagines, citrulline, creatine, ascorbic acid, raffinose, 5-oxoproline, glutamic acid, glycerol monophosphate, choline, phosphocholine, sn-glycero-3-phosphocholine, O-phosphryletha-nolamine, choline, CDP-choline, CDP-ethanolamine, glycerol-phospho-inositol, 2,3-BPG (2,3-DPG), 9,10-epoxystearate, cholesterol, 7-α-hydroxycholesterol, 7-β-hydroxycholesterol, 7-ketocholesterol, 1-palmitoylglycerophosphoinositol, 1-stearoylglycerophosphoinositol, phospholipid, lysophospholipids, phospholipase A, archidonate, linoleic acid, prostaglandin E2, (±)-13-hydroxy-9Z, 11E-octadecadienoic acid (13-HODE), (±)-9-hydroxy-10E, 12Z-octadecadienoic acid (9-HODE), 5-hydroxyeicosatetraenoic acid (5-HETE), 12-hydroxyeicosatetraenoic acid (12-HETE), 15-hydroxyeicosatetraenoic acid (15-HETE), D-glucose, L(+)-lactate, citrate, malate, fumarate, urate, allantoin, hemoglobin, bilirubin, calcium, sodium, potassium, chloride, pCO$_2$, pO$_2$, pH, hypoxanthine: adenine, glucose:lactate, Na$^+$:K$^+$, pCO$_2$:pH, and inosine: adenine.

In some embodiments, the biomarkers are selected from values of fructose-6-phosphate, fructose-1,6-diphosphate, 6-phosphogluconate, pentose-5-phosphate, 1,3-diphosphoglycerate, 3-phosphoglycerate, 2-phosphoglycerate, hexose-6-phosphate, adenosine triphosphate (ATP), adenosine monophosphate (AMP), adenosine diphosphate (ADP), inosine monophosphate (IMP), glutathione (oxidized and reduced, GSH, GSSG), cysteinyl-glycine, S-adenosylmethionine (SAMe), S-adenosylhomocysteine (SAH), 5'-(methylthio)adenosine (5-MTA), 2,3-diphosphoglycerate (2,3-DPG), fructose, mannose, phosphocholine, uric acid, glutamic acid, citrate, citric acid, malate, fumarate, glucose 6-phosphate, phosphoenolpyruvate, glyceric acid, carnitine, 5-oxoproline, alanine, cysteine, cysteinyl-glycine, cysteineglycine disulfide, homocysteine, acetyl-carnitine, arginine, glutamine, glutamate, uridine, xanthine, inosine, hypoxanthine, adenine, glucose, lactate, sodium, potassium, chloride, pCO$_2$, pO$_2$, pH, hypoxanthine:adenine, glucose: lactate, Na$^+$:K$^+$, pCO$_2$:pH, inosine:adenine, and pyruvate. In some embodiments, the biomarkers are selected from values of inosine, hypoxanthine, adenine, hypoxanthine:adenine, glucose:lactate, Na$^+$:K$^+$, pCO$_2$:pH, inosine:adenine, and pyruvate.

In some embodiments, biomarkers for determining the phase of the red blood cells include concentration of inosine, concentration of hypoxanthine, concentration of adenine, ratio of hypoxanthine:adenine, ratio of glucose:lactate, ratio of Na$^+$:K$^+$, ratio of pCO$_2$:pH, ratio of inosine:adenine, and concentration of pyruvate. In some embodiments, the biomarker is concentration of inosine, concentration of hypoxanthine, concentration of adenine, ratio of hypoxanthine: adenine, ratio of glucose:lactate, ratio of Na$^+$:K$^+$, ratio of pCO$_2$:pH, ratio of inosine:adenine, and concentration of pyruvate. In some embodiments, the biomarker is concentration of inosine. In some embodiments, the biomarker is concentration of hypoxanthine. In some embodiments, the biomarker is concentration of adenine. In some embodiments, the biomarker is ratio of hypoxanthine:adenine. In some embodiments, the biomarker is ratio of glucose:lactate. In some embodiments, the biomarker is ratio of Na$^+$:K$^+$. In some embodiments, the biomarker is ratio of pCO$_2$:pH. In some embodiments, the biomarker is ratio of inosine:adenine. In some embodiments, the biomarker is concentration of pyruvate.

In some embodiments, the biomarkers are obtained from values of the extracellular portion of the RBC sample. In some embodiments, the extracellular portion refers to the RBC medium. In some embodiments, the extracellular portion refers to the RBC supernatant. In some embodiments, the RBC sample is an extracellular RBC sample. In some embodiments, the biomarkers for determining the phase of the red blood cells are obtained from the extracellular portion. In some embodiments, the biomarkers obtained from the extracellular portion include concentration of inosine, concentration of hypoxanthine, concentration of adenine, ratio of hypoxanthine:adenine, ration of $Na^+$:$K^+$, ratio of glucose:lactate, ratio of inosine:adenine, and concentration of pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, the biomarker obtained from the extracellular portion is concentration of inosine. In some embodiments, the biomarker obtained from the extracellular portion is concentration of hypoxanthine. In some embodiments, the biomarker obtained from the extracellular portion is concentration of adenine. In some embodiments, the biomarker obtained from the extracellular portion is ratio of hypoxanthine:adenine. In some embodiments, the biomarker obtained from the extracellular portion is ratio of glucose:lactate. In some embodiments, the biomarker obtained from the extracellular portion is ratio of $Na^+$:$K^+$. In some embodiments, the biomarker obtained from the extracellular portion is ratio of $pCO_2$:pH. In some embodiments, the biomarker obtained from the extracellular portion is ratio of inosine:adenine. In some embodiments, the biomarker obtained from the extracellular portion is concentration of pyruvate.

RBC Metabolic Phases

RBCs are classified based on their metabolic state or phase. FIG. 1A illustrates a conceptual schematic for determining a phase of a red blood cell (RBC) sample. The RBC sample is analyzed by assays or analytical chemistry techniques and methods described herein to generate raw data used to determine one or more of the biomarkers described herein. The raw data is compiled into a dataset and analyzed by a computer program to determine the value of one or more biomarkers. The value of one or more biomarkers is then used by the computer program to classify the RBC sample into a phase based on the classification scheme illustrated in FIG. 1B. A report is then generated to indicate either an assignment of a phase to the RBC sample or a failure to assign a phase to the RBC sample.

In some embodiments, the RBCs have 1, 2, 3, 4, 5, or more phases. In some embodiments, the RBCs are classified into three phases. The three phases are First Phase (Healthy Phase), Second Phase (Transition Phase) and Third Phase (Old Phase). The phases (e.g., three phases) indicate a metabolic state of the RBCs. In some embodiments, the RBCs are classified into First Phase, Second Phase, and/or Third Phase. In some embodiments, the RBCs are classified into First Phase and/or Second Phase. In some embodiments, the RBCs are classified into First Phase and/or Third Phase. In some embodiments, the RBCs are classified into First Phase. In some embodiments, the RBCs are classified into Second Phase. In some embodiments, the RBCs are classified into Third Phase. In some embodiments, the metabolic state of the RBC refers to the metabolic state of the RBC during storage. In some embodiments, metabolic state is at least one defined state; preferably one of a first, a second or a third defined state. Such defined states correspond to the First Phase, Second Phase or Third Phase described herein. In some embodiments, a first defined metabolic state corresponds to First Phase. In some embodiments, a second defined metabolic state corresponds to Second Phase. In some embodiments, a third defined metabolic state corresponds to Third Phase.

In some embodiments, the three phases or metabolic states are characterized by a set of biomarkers. In some embodiments, the set of biomarkers is selected from the group consisting of concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine and concentration of pyruvate. In some embodiments, First Phase (Healthy Phase) is characterized by the set of biomarkers selected from the group consisting of concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine and concentration of pyruvate. In some embodiments, Second Phase (Transition Phase) is characterized by the set of biomarkers selected from the group consisting of concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine and concentration of pyruvate. In some embodiments, Third Phase (Old Phase) is characterized by the set of biomarkers selected from the group consisting of concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine and concentration of pyruvate.

In some embodiments, the biomarkers are obtained from the extracellular portion of the RBC sample. In some embodiments, the set of biomarkers obtained from the extracellular portion include concentration of inosine, concentration of hypoxanthine, concentration of adenine, ratio of hypoxanthine:adenine, ration of $Na^+$:$K^+$, ratio of glucose:lactate, ratio of inosine:adenine, and concentration of pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, First Phase (Healthy Phase) is characterized by the set of biomarkers obtained from the extracellular portion. In some embodiments, Second Phase (Transition Phase) is characterized by the set of biomarkers obtained from the extracellular portion. In some embodiments, Third Phase (Old Phase) is characterized by the set of biomarkers obtained from the extracellular portion.

In some embodiments, a biomarker is a single value or is a range of values. In some embodiments, the value or the range of values is from about 0 to about 100, about 0 to about 50, about 0 to about 20 or about 0 to about 10. In some embodiments, the value or the range of values of a biomarker is represented with a unit (e.g., M, mM, µM, nM, mmHg) or is unitless. In some embodiment, the unit is a mass, concentration, volume, pressure, signal, absorbance, distance, time or a ratio of two or more units (e.g. absorbance/time or concentration/volume).

In some embodiments, the value is represented as a ratio of two or more biomarkers. In some embodiments, the ratio is about 0 to about 10,000, about 0 to about 5000, about 0 to about 2000 or about 0 to about 1000.

In some embodiments, the value of the biomarker is correlated to time. In some embodiments, the time is represented as minutes, hours, days, months or years. In some embodiments, the time is represented as days. In some embodiments, the time indicates a range of days. In some embodiments, the time is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 days. In some instances, day 1 correlates to the day in which the RBCs are processed for storage. In some embodiments, day 0 indicates the day in which RBCs as whole blood is harvested from a patient. In some instances, day 2 correlates to 24 hours of storage. In some embodiments, a set of values is correlated to time. In some embodiments, the three phases are correlated to time.

In some embodiments, a phase or metabolic state is assigned to the RBC sample based on the value of the biomarker by a computer program (see FIG. 1B, 101). In some embodiments, the computer program matches the value of the biomarker to an equivalent value on a control to assign phases. In some embodiments, the control is represented as a signature profile. As described elsewhere herein, a signature profile characterizes a measurement of a metabolite, an RBC component, a physiological, biochemical or molecular parameter at a specific biological condition, or a ratio of these measurements. In some embodiments, the equivalent value on a control is associated with one of the three phases. In some embodiments, the ratio of glucose:lactate, the ratio of $Na^+:K^+$, the value of inosine, the ratio of hypoxanthine:adenine, the ratio of inosine:adenine, and the value of pyruvate match the values on the control indicated for First Phase (Healthy Phase) (FIG. 1B, 102). In some embodiments, First Phase (Healthy Phase) is assigned by the computer program to the RBC sample when the ratio of glucose:lactate, the ratio of $Na^+:K^+$, the value of inosine, the ratio of hypoxanthine:adenine, the ratio of inosine:adenine and the value of pyruvate match the values on the control indicated for First Phase (Healthy Phase) (FIG. 1B, 103). In some embodiment, the ratio of glucose:lactate and the ratio of $Na^+:K^+$ match the values on the control indicated for First Phase (Healthy Phase) (FIG. 1B, 102). In some embodiments, First Phase (Healthy Phase) is assigned by the computer program to the RBC sample when the ratio of glucose:lactate and the ratio of $Na^+:K^+$ match the values on the control indicated for First Phase (Healthy Phase) (FIG. 1B, 103). In some embodiments, the ratio of hypoxanthine:adenine, the value of inosine, and the ratio of inosine:adenine match the values on the control indicated for Second Phase (Transition Phase) (FIG. 1B, 104). In some embodiments, Second Phase (Transition Phase) is assigned by the computer program to the RBC sample when the ratio of hypoxanthine:adenine, the value of inosine, and the ratio of inosine:adenine match the values on the control indicated for Second Phase (Transition Phase) (FIG. 1B, 105). In some embodiments, the ratio of hypoxanthine:adenine match the values on the control indicated for Second Phase (Transition Phase) (FIG. 1B, 104). In some embodiments, Second Phase (Transition Phase) is assigned by the computer program to the RBC sample when the ratio of hypoxanthine:adenine match the values on the control indicated for Second Phase (Transition Phase) (FIG. 1B, 105). In some embodiments, the ratio of hypoxanthine:adenine, the value of hypoxanthine, the value of adenine, the ratio of $pCO_2$:pH, the ratio of inosine:adenine and the value of inosine match the values on the control indicated for Third Phase (Old Phase) (FIG. 1B, 106). In some embodiments, Third Phase (Old Phase) is assigned by the computer program to the RBC sample when the ratio of hypoxanthine:adenine, the value of hypoxanthine, the value of adenine, the ratio of $pCO_2$:pH, the ratio of inosine:adenine and the value of inosine match the values on the control indicated for Third Phase (Old Phase) (FIG. 1B, 107). In some embodiments, the ratio of hypoxanthine:adenine, the value of hypoxanthine, and the value of adenine match the values on the control indicated for Third Phase (Old Phase) (FIG. 1B, 106). In some embodiments, Third Phase (Old Phase) is assigned by the computer program to the RBC sample when the ratio of hypoxanthine:adenine, the value of hypoxanthine, and the value of adenine match the values on the control indicated for Third Phase (Old Phase) (FIG. 1B, 107). In some embodiments, the phase indicates the quality of the RBC sample.

In some embodiments, the value of a biomarker is used to predict the duration of the RBC sample in a particular phase or metabolic state. In some embodiments, when the ratio of glucose:lactate and the ratio of $Na^+:K^+$ match values that correspond to the terminal portion of First Phase (Healthy Phase), this indicates that the RBC sample will likely undergo a metabolic shift into Second Phase (Transition Phase) soon. In some embodiments, the value of the biomarker is used to predict how long the RBC sample remains in First Phase (Healthy Phase). In some embodiments, the value of the biomarker is used to predict how long the RBC sample remains in Second Phase (Transition Phase). In some embodiments, the value of the biomarker is used to predict how long the RBC sample remains in Third Phase (Old Phase).

In some embodiments, the three phases or metabolic states correspond to the quality of the RBC. In some embodiments, First Phase (Healthy Phase) indicates the quality of the RBC as near to fresh blood (e.g. blood that is freshly drawn from a donor). In some embodiments, First Phase (Healthy Phase) indicates the quality of the RBC as containing a set of biomarkers that would be similar to the set of biomarkers found in fresh blood. In some embodiment, Second Phase (Transition Phase) indicates the quality of the RBC in a transition state from First Phase (Healthy Phase) to Third Phase (Old Phase). In some embodiments, Third Phase (Old Phase) indicates the quality of the RBC as aged blood.

First Phase (Healthy Phase)—RBC

In some embodiments, First Phase (Healthy Phase) is characterized by a set of biomarkers. In some embodiments, the set of biomarkers is selected from concentration of inosine, concentration of hypoxanthine, concentration of adenine, ratio of hypoxanthine:adenine, ratio of glucose:lactate, ratio of $Na^+:K^+$, ratio of $pCO_2$:pH, ratio of inosine:adenine and concentration of pyruvate. In some embodiments, the set of biomarkers is the ratio of glucose:lactate, the ratio of $Na^+:K^+$, the concentration of inosine, the ratio of hypoxanthine:adenine, the ratio of inosine:adenine and the concentration of pyruvate. In some embodiments, the set of biomarkers is the ratio of glucose:lactate and the ratio of $Na^+:K^+$. In some embodiments, First Phase (Healthy Phase) is characterized by the ratio of glucose:lactate, the ratio of $Na^+:K^+$, the concentration of inosine, the ratio of hypoxanthine:adenine, the ratio of inosine:adenine and the concentration of pyruvate. In some embodiments, First Phase (Healthy Phase) is characterized by the ratio of glucose:lactate and the ratio of $Na^+:K^+$. In some embodiments, the RBC sample is classified as First Phase (Healthy Phase) based on the ratio of glucose:lactate, the ratio of $Na^+$:$K^+$, the concentration of inosine, the ratio of hypoxanthine:adenine, the ratio of inosine:adenine and the concentration of pyruvate. In some embodiments, the RBC sample is classified as First Phase (Healthy Phase) based on the ratio of glucose:lactate and the ratio of $Na^+$:$K^+$. In some embodiments, the quality of the RBC sample is determined based on the ratio of glucose:lactate, the ratio of $Na^+$:$K^+$, the concentration of inosine, the ratio of hypoxanthine:adenine, the ratio of inosine:adenine and the concentration of pyruvate. In some embodiments, the quality of the RBC sample is determined based on the ratio of glucose:lactate and the ratio of $Na^+$:$K^+$.

In some embodiments, the biomarkers are obtained from the extracellular portion of the RBC sample. In some embodiments, the set of biomarkers obtained from the extracellular portion include concentration of inosine, concentration of hypoxanthine, concentration of adenine, ratio of hypoxanthine:adenine, ration of $Na^+$:$K^+$, ratio of glucose:lactate, ratio of inosine:adenine, and concentration of pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, First Phase (Healthy Phase) is characterized by the set of biomarkers obtained from the extracellular portion.

In some embodiments, the set of biomarkers selected from concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine and concentration of pyruvate are indicated with a set of values or a set of ratios. In some embodiments, the concentration of inosine, the concentration of hypoxanthine, the concentration of adenine and the concentration of pyruvate are each indicated with a value. In some embodiments, the values of inosine, hypoxanthine, adenine and pyruvate are represented as ranges. In some embodiments, the value is associated with a unit or is unitless. In some embodiments, the unit is in millimolar (mM) concentration. In some embodiments, the ratio of hypoxanthine:adenine, the ratio of glucose:lactate, the ratio of $Na^+$:$K^+$, the ratio of $pCO_2$:pH and the ratio of inosine:adenine are indicated as ranges. In some embodiments, the ratio is associated with a unit or is unitless. In some embodiments, the unit is in millimolar/millimolar (mM/mM) concentration or mmHg/pH.

In some embodiments, the range of values of inosine is from about 0 mM to about 1 mM, about 0 mM to about 0.1 mM, about 0 mM to about 0.01 mM, about 0 mM to about 0.005 mM, about 0 mM to about 0.002 mM, about 0 mM to about 0.001 mM, about 0 mM to about 0.0009 mM, about 0 mM to about 0.0008 mM, about 0 mM to about 0.0007 mM, about 0 mM to about 0.0006 mM, or about 0 mM to about 0.0005 mM. In some embodiments, the value of inosine is about 0 mM. In some embodiments, the value of inosine is 0 mM.

In some embodiments, the range of values of hypoxanthine is from about 0 mM to about 1 mM, about 0 mM to about 0.5 mM, about 0 mM to about 0.2 mM, about 0 mM to about 0.15 mM, about 0 mM to about 0.14 mM, about 0 mM to about 0.13 mM, about 0 mM to about 0.12 mM, about 0 mM to about 0.11 mM, or about 0 mM to about 0.1 mM. In some embodiments, the range of values of hypoxanthine is from about 0 mM to about 0.1 mM. In some embodiments, the range of values of hypoxanthine is from 0 mM to 0.1 mM.

In some embodiments, the value of adenine is greater than 1 mM, greater than 0.9 mM, greater than 0.8 mM, greater than 0.7 mM, greater than 0.6 mM, greater than 0.5 mM, greater than 0.4 mM, greater than 0.3 mM, greater than 0.2 mM, or greater than 0.1 mM. In some embodiments, the value of adenine is greater than 0.1 mM.

In some embodiments, the value of pyruvate is greater than 1 mM, greater than 0.5 mM, greater than 0.1 mM, or greater than 0 mM. In some embodiments, the value of pyruvate is about 0 mM. In some embodiments, the value of pyruvate is 0 mM.

In some embodiments, the ratio of glucose:lactate is greater than 10 mM/mM, greater than 9 mM/mM, greater than 8 mM/mM, greater than 7 mM/mM, greater than 6 mM/mM, greater than 5 mM/mM, greater than 4 mM/mM, greater than 3 mM/mM, or greater than 2 mM/mM. In some embodiments, the ratios of glucose:lactate is greater than 2.0 mM/mM.

In some embodiments, the ratios of $Na^+$:$K^+$ is greater than 100 mM/mM, greater than 50 mM/mM, greater than 20 mM/mM, greater than 10 mM/mM, greater than 9 mM/mM, greater than 8.5 mM/mM, greater than 8 mM/mM, greater than 7.5 mM/mM, greater than 7 mM/mM, or greater than 6.5 mM/mM. In some embodiments, the ratios of $Na^+$:$K^+$ is greater than 6.5 mM/mM.

In some embodiments, the range of ratios of hypoxanthine:adenine is from about 0 mM/mM to about 1000 mM/mM, about 0 mM/mM to about 100 mM/mM, about 0 mM/mM to about 20 mM/mM, about 0 mM/mM to about 18 mM/mM, about 0 mM/mM to about 16 mM/mM, about 0 mM/mM to about 14 mM/mM, about 0 mM/mM to about 12 mM/mM, about 0 mM/mM to about 10 mM/mM, about 0 mM/mM to about 8 mM/mM, about 0 mM/mM to about 6 mM/mM, about 0 mM/mM to about 4 mM/mM, about 0 mM/mM to about 2 mM/mM, about 0 mM/mM to about 1.5 mM/mM, or about 0 mM/mM to about 1 mM/mM. In some embodiments, the range of ratios of hypoxanthine:adenine is from about 0 mM/mM to about 1.0 mM/mM. In some embodiments, the range of ratios of hypoxanthine:adenine is from 0 mM/mM to 1.0 mM/mM.

In some embodiments, the range of ratios of $pCO_2$:pH is from about 0 mmHg/pH to about 30 mmHg/pH, about 0 mmHg/pH to about 25 mmHg/pH, about 0 mmHg/pH to about 20 mmHg/pH, about 0 mmHg/pH to about 19 mmHg/pH, about 0 mmHg/pH to about 18 mmHg/pH, about 0 mmHg/pH to about 17 mmHg/pH, or about 0 mmHg/pH to about 16 mmHg/pH. In some embodiments, the range of ratios of $pCO_2$:pH is from about 0 mmHg/pH to about 16 mmHg/pH. In some embodiments, the range of ratios of $pCO_2$:pH is from 0 mmHg/pH to 16 mmHg/pH.

In some embodiments, the range of ratios of inosine:adenine is from about 0 mM/mM to about 10 mM/mM, about 0 mM/mM to about 5 mM/mM, about 0 mM/mM to about 1 mM/mM, about 0 mM/mM to about 0.5 mM/mM, about 0 mM/mM to about 0.1 mM/mM, or about 0 mM/mM to about 0.05 mM/mM. In some embodiments, the range of ratios of inosine:adenine is about 0 mM/mM. In some embodiments, the range of ratios of inosine:adenine is 0 mM/mM.

In some embodiments, First Phase (Healthy Phase) is characterized by the ratio of glucose:lactate greater than 2.0 mM/mM, the ratio of $Na^+$:$K^+$ greater than 6.5 mM/mM, the value of inosine at about 0 mM, the ratio of hypoxanthine:adenine from about 0 mM/mM to about 1.0 mM/mM, the ratio of inosine:adenine at about 0 mM/mM, and the value of pyruvate at about 0 mM. In some embodiments, First Phase (Healthy Phase) is characterized by the ratio of glucose:lactate greater than 2.0 mM/mM, the ratio of $Na^+$:$K^+$ greater than 6.5 mM/mM, the value of inosine at 0 mM, the ratio of hypoxanthine:adenine from 0 mM/mM to 1.0 mM/mM, the ratio of inosine:adenine at 0 mM/mM, and the value of pyruvate at 0 mM. In some embodiments, First Phase (Healthy Phase) is characterized by the ratio of glucose:lactate greater than 2.0 mM/mM and the ratio of $Na^+$:$K^+$ greater than 6.5 mM/mM.

In some embodiments, the RBC sample is classified as First Phase (Healthy Phase) based on the ratio of glucose:lactate greater than 2.0 mM/mM, the ratio of $Na^+$:$K^+$ greater than 6.5 mM/mM, the value of inosine at about 0 mM, the ratio of hypoxanthine:adenine from about 0 mM/mM to about 1.0 mM/mM, the ratio of inosine:adenine at about 0 mM/mM and the value of pyruvate at about 0 mM. In some embodiments, the RBC sample is classified as First Phase (Healthy Phase) based on the ratio of glucose:lactate greater than 2.0 mM/mM, the ratio of $Na^+$:$K^+$ greater than 6.5 mM/mM, the value of inosine at 0 mM, the ratio of hypoxanthine:adenine from 0 mM/mM to 1.0 mM/mM, the ratio of inosine:adenine at 0 mM/mM and the value of pyruvate at 0 mM. In some embodiments, the RBC sample is classified as First Phase (Healthy Phase) based on the ratio of glucose:lactate greater than 2.0 mM/mM and the ratio of $Na^+$:$K^+$ greater than 6.5 mM/mM.

In some embodiments, the quality of the RBC sample is determined based on the ratio of glucose:lactate greater than 2.0 mM/mM, the ratio of $Na^+$:$K^+$ greater than 6.5 mM/mM, the value of inosine at about 0 mM, the ratio of hypoxanthine:adenine from about 0 mM/mM to about 1.0 mM/mM, the ratio of inosine:adenine at about 0 mM and the value of pyruvate at about 0 mM. In some embodiments, the quality of the RBC sample is determined based on the ratio of glucose:lactate greater than 2.0 mM/mM, the ratio of $Na^+$:$K^+$ greater than 6.5 mM/mM, the value of inosine at 0 mM, the ratio of hypoxanthine:adenine from 0 mM/mM to 1.0 mM/mM, the ratio of inosine:adenine at 0 mM/mM and the value of pyruvate at 0 mM. In some embodiments, the quality of the RBC sample is determined based on the ratio of glucose:lactate greater than 2.0 mM/mM and the ratio of $Na^+$:$K^+$ greater than 6.5 mM/mM.

In some embodiments, First Phase (Healthy Phase) is correlated to about day 1 to about day 60, about day 1 to about day 30, about day 1 to about day 20, about day 1 to about day 12, about day 1 to about day 11 or about day 1 to about day 10 of storage. In some embodiments, First Phase (Healthy Phase) is correlated to about day 1, 2, 3, 4, 5, 6, 7, 8, 9 or day 10 of storage. In some instances, day 1 correlates to the day in which the RBCs are processed for storage. In some instances, day 2 correlates to 24 hours of storage.

In some embodiments, the value of a biomarker is used to predict how long the RBC sample remains in First Phase (Healthy Phase). In some embodiments, when the ratio of glucose:lactate, the ratio of $Na^+$:$K^+$, the value of inosine, the ratio of hypoxanthine:adenine, the ratio of inosine:adenine, and the value of pyruvate match the values that correspond to an initial portion of First Phase (Healthy Phase), this indicates that the RBC sample remains in First Phase (Healthy Phase) for 1, 2, 3, 4, 5, 6, 7, 8, 9, 10 or more days. In some embodiments, when the ratio of glucose:lactate and the ratio of $Na^+$:$K^+$ match the values that correspond to an initial portion of First Phase (Healthy Phase), this indicates that the RBC sample remains in First Phase (Healthy Phase) for 1, 2, 3, 4, 5, 6, 7, 8, 9, 10 or more days. In some embodiments, when the ratio of glucose:lactate, the ratio of $Na^+$:$K^+$, the value of inosine, the ratio of hypoxanthine:adenine, the ratio of inosine:adenine, and the value of pyruvate match the values that correspond to a terminal portion of First Phase (Healthy Phase), this indicates that the RBC sample remains in First Phase (Healthy Phase) for less than 1, 2, 3, 4, 5, 6, 7, 8, 9, or 10 days. In some embodiments, when the ratio of glucose:lactate and the ratio of $Na^+$:$K^+$ match the values that correspond to a terminal portion of First Phase (Healthy Phase), this indicates that the RBC sample remains in First Phase (Healthy Phase) for less than 1, 2, 3, 4, 5, 6, 7, 8, 9, or 10 days. In some embodiments, when the ratio of glucose:lactate, the ratio of $Na^+$:$K^+$, the value of inosine, the ratio of hypoxanthine:adenine, the ratio of inosine:adenine, and the value of pyruvate match the values that correspond to between an initial and a terminal portion of First Phase (Healthy Phase), this indicates that the RBC sample remains in First Phase (Healthy Phase) for about 1, 2, 3, 4, 5, 6, 7, 8, 9, 10 or more days. In some embodiments, when the ratio of glucose:lactate and the ratio of $Na^+$:$K^+$ match the values that correspond to between an initial and a terminal portion of First Phase (Healthy Phase), this indicates that the RBC sample remains in First Phase (Healthy Phase) for about 1, 2, 3, 4, 5, 6, 7, 8, 9, 10 or more days.

In some embodiments, any RBC sample is characterized as First Phase (Healthy Phase) regardless of storage age, storage condition (e.g. storage temperature or addition of an additive solution) or donor genetic variations (e.g. age, sex or a donor's health). In some embodiments, an RBC sample stored for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 days is characterized as First Phase (Healthy Phase). In some embodiments, an RBC sample which has been in storage for about 15 days or for about 25 days is characterized as First Phase (Healthy Phase) if the ratio of glucose:lactate is greater than 2.0 mM/mM, the ratio of $Na^+$:$K^+$ is greater than 6.5 mM/mM, the value of inosine is about 0 mM, the ratio of hypoxanthine:adenine is from about 0 mM/mM to about 1.0 mM/mM, the ratio of inosine:adenine is about 0 mM/mM, and the value of pyruvate is about 0 mM. In some embodiments, an RBC sample which has been in storage for about 15 days or for about 25 days is characterized as First Phase (Healthy Phase) if the ratio of glucose:lactate is greater than 2.0 mM/mM, the ratio of $Na^+$:$K^+$ is greater than 6.5 mM/mM, the value of inosine is 0 mM, the ratio of hypoxanthine:adenine is from 0 mM/mM to 1.0 mM/mM, the ratio of inosine:adenine is 0 mM/mM, and the value of pyruvate is 0 mM. In some embodiments, an RBC sample which has been in storage for about 15 days or for about 25 days is characterized as First Phase (Healthy Phase) if the ratio of glucose:lactate is greater than 2.0 mM/mM and the ratio of $Na^+$/$K^+$ is greater than 6.5 mM/mM.

In some embodiments, an RBC sample stored under any storage condition is characterized as First Phase (Healthy Phase). In some embodiments, the storage condition is a storage temperature or the addition of an additive solution. In some embodiments, the additive solution includes SAG, SAGM, AS-1 (Adsol), $AS_{-3}$ (Nutricel), AS-5 (Optisol), MAP, PAGGSM (Macopharma), PAGGGM, SOLX (AS-7), BAGP-M, ErythroSol-1, ErythroSol-2, ErythroSol-4, and EAS-81. In some embodiments, the additive solution is SAGM, AS-1 (Adsol), AS-3 (Nutricel), AS-5 (Optisol), MAP, PAGGSM (Macopharma), PAGGGM, or SOLX (AS-7). In some embodiments, the additive solution is SAGM.

In some embodiments, the storage condition is a storage temperature. In some embodiments, the storage temperature is from about −80° C. to about 25° C., about −10° C. to about 10° C., about 0° C. to about 8° C. In some embodiments, the storage temperature is about 4° C.

In some embodiments, the RBC sample stored under any temperature is characterized as First Phase (Healthy Phase). In some embodiments, an RBC sample stored under any temperature is characterized as First Phase (Healthy Phase) if the ratio of glucose:lactate is greater than 2.0 mM/mM, the ratio of $Na^+$:$K^+$ is greater than 6.5 mM/mM, the value of inosine is about 0 mM, the ratio of hypoxanthine:adenine is from about 0 mM/mM to about 1.0 mM/mM, the ratio of inosine:adenine is about 0 mM/mM, and the value of pyruvate is about 0 mM. In some embodiments, an RBC sample stored under any temperature is characterized as First Phase (Healthy Phase) if the ratio of glucose:lactate is greater than 2.0 mM/mM, the ratio of $Na^+$:$K^+$ is greater than 6.5 mM/mM, the value of inosine is 0 mM, the ratio of hypoxanthine:adenine is from 0 mM/mM to 1.0 mM/mM, the ratio of inosine:adenine is 0 mM/mM, and the value of pyruvate is 0 mM. In some embodiments, an RBC sample stored under any temperature is characterized as First Phase (Healthy Phase) if the ratio of glucose:lactate is greater than 2.0 mM/mM and the ratio of $Na^+$:$K^+$ is greater than 6.5 mM/mM.

In some embodiments, an RBC sample regardless of donor genetic variation (e.g. age, sex or a donor's health) is characterized as First Phase (Healthy Phase). In some embodiments, an RBC sample regardless of donor genetic variation is characterized as First Phase (Healthy Phase) if the ratio of glucose:lactate is greater than 2.0 mM/mM, the ratio of $Na^+$:$K^+$ is greater than 6.5 mM/mM, the value of inosine is about 0 mM, the ratio of hypoxanthine:adenine is from about 0 mM/mM to about 1.0 mM/mM, the ratio of inosine:adenine is about 0 mM/mM, and the value of pyruvate is about 0 mM. In some embodiments, an RBC sample regardless of donor genetic variation is characterized as First Phase (Healthy Phase) if the ratio of glucose:lactate is greater than 2.0 mM/mM, the ratio of $Na^+$:$K^+$ is greater than 6.5 mM/mM, the value of inosine is 0 mM, the ratio of hypoxanthine:adenine is from 0 mM/mM to 1.0 mM/mM, the ratio of inosine:adenine is 0 mM/mM, and the value of pyruvate is 0 mM. In some embodiments, an RBC sample regardless of donor genetic variation is characterized as First Phase (Healthy Phase) if the ratio of glucose:lactate is greater than 2.0 mM/mM and the ratio of $Na^+$:$K^+$ is greater than 6.5 mM/mM.

Second Phase (Transition Phase)—RBC

In some embodiments, Second Phase (Transition Phase) is characterized by a set of biomarkers. In some embodiments, the set of biomarkers is selected from concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine and concentration of pyruvate. In some embodiments, the set of biomarkers is the ratio of hypoxanthine:adenine, the concentration of inosine, and the ratio of inosine:adenine. In some embodiments, the set of biomarkers is the ratio of hypoxanthine:adenine. In some embodiments, Second Phase (Transition Phase) is characterized by the ratio of hypoxanthine:adenine, the concentration of inosine, and the ratio of inosine:adenine. In some embodiments, Second Phase (Transition Phase) is characterized by the ratio of hypoxanthine:adenine. In some embodiments, the RBC sample is classified as Second Phase (Transition Phase) based on the ratio of hypoxanthine:adenine, the concentration of inosine, and the ratio of inosine:adenine. In some embodiments, the RBC sample is classified as Second Phase (Transition Phase) based on the ratio of hypoxanthine:adenine. In some embodiments, the quality of the RBC sample is determined based on the ratio of hypoxanthine:adenine, the concentration of inosine, and the ratio of inosine:adenine. In some embodiments, the quality of the RBC sample is determined based on the ratio of hypoxanthine:adenine.

In some embodiments, the biomarkers are obtained from the extracellular portion of the RBC sample. In some embodiments, the set of biomarkers obtained from the extracellular portion include concentration of inosine, concentration of hypoxanthine, concentration of adenine, ratio of hypoxanthine:adenine, ration of $Na^+$:$K^+$, ratio of glucose:lactate, ratio of inosine:adenine, and concentration of pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, Second Phase (Transition Phase) is characterized by the set of biomarkers obtained from the extracellular portion.

In some embodiments, the set of biomarkers selected from concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine and concentration of pyruvate are indicated with a set of values or a set of ratios. In some embodiments, the concentration of inosine, the concentration of hypoxanthine, the concentration of adenine, and the concentration of pyruvate are each indicated with a value. In some embodiments, the concentration of inosine, the concentration of hypoxanthine, the concentration of adenine, and the concentration of pyruvate are represented as ranges. In some embodiments, the value is associated with a unit or is unitless. In some embodiments, the unit is in milimolar (mM) concentration. In some embodiments, the ratio of hypoxanthine:adenine, the ratio of glucose:lactate, the ratio of $Na^+$:$K^+$, the ratio of $pCO_2$:pH and the ratio of inosine:adenine are indicated as ranges. In some embodiments, the ratio is associated with a unit or is unitless. In some embodiments, the unit is in millimolar/millimolar (mM/mM) concentration or mmHg/pH.

In some embodiments, the concentration of hypoxanthine is from about 0 mM to about 1 mM, about 0 mM to about 0.5 mM, about 0 mM to about 0.2 mM, about 0 mM to about 0.15 mM, about 0 mM to about 0.14 mM, about 0 mM to about 0.13 mM, about 0 mM to about 0.12 mM, about 0 mM to about 0.11 mM, or about 0 mM to about 0.1 mM. In some embodiments, the range of values of hypoxanthine is from about 0 mM to about 0.1 mM. In some embodiments, the range of values of hypoxanthine is from 0 mM to 0.1 mM.

In some embodiments, the value of adenine is greater than 1 mM, greater than 0.9 mM, greater than 0.8 mM, greater than 0.7 mM, greater than 0.6 mM, greater than 0.5 mM, greater than 0.4 mM, greater than 0.3 mM, greater than 0.2 mM, or greater than 0.1 mM. In some embodiments, the value of adenine is greater than 0.1 mM.

In some embodiments, the range of values of inosine is from about 0 mM to about 1 mM, about 0 mM to about 0.1 mM, about 0 mM to about 0.01 mM, about 0 mM to about 0.005 mM, about 0 mM to about 0.002 mM, about 0 mM to about 0.001 mM, about 0 mM to about 0.0009 mM, about 0 mM to about 0.0008 mM, about 0 mM to about 0.0007 mM, about 0 mM to about 0.0006 mM, or about 0 mM to about 0.0005 mM. In some embodiments, the range of values of inosine is from about 0 mM to about 0.0005 mM. In some embodiments, the range of values of inosine is from 0 mM to 0.0005 mM.

In some embodiments, the value of pyruvate is greater than 1 mM, greater than 0.5 mM, greater than 0.1 mM, or greater than 0 mM. In some embodiments, the value of pyruvate is greater than 0 mM.

In some embodiments, the range of ratios of hypoxanthine:adenine is from about 0 mM/mM to about 1000 mM/mM, about 1 mM/mM to about 100 mM/mM, about 1 mM/mM to about 20 mM/mM, about 1 mM/mM to about 19 mM/mM, about 1 mM/mM to about 18 mM/mM, about 1 mM/mM to about 17 mM/mM, or about 1 mM/mM to about 16 mM/mM. In some embodiments, the range of ratios of hypoxanthine:adenine is from about 1.0 mM/mM to about 16 mM/mM. In some embodiments, the range of ratios of hypoxanthine:adenine is from 1.0 mM/mM to 16 mM/mM.

In some embodiments, the range of ratios of $pCO_2$:pH is from about 0 mmHg/pH to about 30 mmHg/pH, about 0 mmHg/pH to about 25 mmHg/pH, about 0 mmHg/pH to about 20 mmHg/pH, about 0 mmHg/pH to about 19 mmHg/pH, about 0 mmHg/pH to about 18 mmHg/pH, about 0 mmHg/pH to about 17 mmHg/pH, or about 0 mmHg/pH to about 16 mmHg/pH. In some embodiments, the range of ratios of $pCO_2$:pH is from about 0 mmHg/pH to about 16 mmHg/pH. In some embodiments, the range of ratios of $pCO_2$:pH is from 0 mmHg/pH to 16 mmHg/pH.

In some embodiments, the range of ratios of inosine:adenine is from about 0 mM/mM to about 10 mM/mM, about 0 mM/mM to about 5 mM/mM, about 0 mM/mM to about 1 mM/mM, about 0 mM/mM to about 0.5 mM/mM, about 0 mM/mM to about 0.1 mM/mM, or about 0 mM/mM to about 0.05 mM/mM. In some embodiments, the range of ratios of inosine:adenine is from about 0 mM/mM to about 0.05 mM/mM. In some embodiments, the range of ratios of inosine:adenine is from 0 mM/mM to 0.05 mM/mM.

In some embodiments, the range of ratios of glucose:lactate is from about 0 mM/mM to about 10 mM/mM, about 0 mM/mM to 9 mM/mM, about 0 mM/mM to 8 mM/mM, about 0 mM/mM to 7 mM/mM, about 0 mM/mM to 6 mM/mM, about 0 mM/mM to 5 mM/mM, about 0 mM/mM to 4 mM/mM, about 0 mM/mM to 3 mM/mM, or about 0 mM/mM to 2 mM/mM. In some embodiments, the range of ratios of glucose:lactate is from about 0 mM/mM to about 2.0 mM/mM. In some embodiments, the range of ratios of glucose:lactate is from 0 mM/mM to 2.0 mM/mM.

In some embodiments, the range of ratios of $Na^+$:$K^+$ is from about 0 mM/mM to 100 mM/mM, about 0 mM/mM to 50 mM/mM, about 0 mM/mM to 20 mM/mM, about 0 mM/mM to 10 mM/mM, about 0 mM/mM to 9 mM/mM, about 0 mM/mM to 8.5 mM/mM, about 0 mM/mM to 8 mM/mM, about 0 mM/mM to 7.5 mM/mM, about 0 mM/mM to 7 mM/mM, or about 0 mM/mM to 6.5 mM/mM. In some embodiments, the range of ratios of $Na^+$:$K^+$ is from about 0 mM/mM to about 6.5 mM/mM. In some embodiments, the range of ratios of $Na^+$:$K^+$ is from 0 mM/mM to 6.5 mM/mM.

In some embodiments, Second Phase (Transition Phase) is characterized by the ratio of hypoxanthine:adenine from about 1.0 mM/mM to about 16 mM/mM, the value of inosine from about 0 mM to about 0.0005 mM, and the ratio of inosine:adenine from about 0 mM/mM to about 0.05 mM/mM. In some embodiments, Second Phase (Transition Phase) is characterized by the ratio of hypoxanthine:adenine from 1.0 mM/mM to 16 mM/mM, the value of inosine from 0 mM to 0.0005 mM, and the ratio of inosine:adenine from 0 mM/mM to 0.05 mM/mM. In some embodiments, Second Phase (Transition Phase) is characterized by the ratio of hypoxanthine:adenine from about 1.0 mM/mM to about 16 mM/mM. In some embodiments, Second Phase (Transition Phase) is characterized by the ratio of hypoxanthine:adenine from 1.0 mM/mM to 16 mM/mM.

In some embodiments, the RBC sample is classified as Second Phase (Transition Phase) based on the ratio of hypoxanthine:adenine from about 1.0 mM/mM to about 16 mM/mM, the value of inosine from about 0 mM to about 0.0005 mM, and the ratio of inosine:adenine from about 0 mM/mM to about 0.05 mM/mM. In some embodiments, the RBC sample is classified as Second Phase (Transition Phase) based on the ratio of hypoxanthine:adenine from 1.0 mM/mM to 16 mM/mM, the value of inosine from 0 mM to 0.0005 mM, and the ratio of inosine:adenine from 0 mM/mM to 0.05 mM/mM. In some embodiments, the RBC sample is classified as Second Phase (Transition Phase) based on the ratio of hypoxanthine:adenine from about 1.0 mM/mM to about 16 mM/mM. In some embodiments, the RBC sample is classified as Second Phase (Transition Phase) based on the ratio of hypoxanthine:adenine from 1.0 mM/mM to 16 mM/mM.

In some embodiments, the quality of the RBC sample is determined based on the ratio of hypoxanthine:adenine from about 1.0 mM/mM to about 16 mM/mM, the value of inosine from about 0 mM to about 0.0005 mM, and the ratio of inosine:adenine from about 0 mM/mM to about 0.05 mM/mM. In some embodiments, the quality of the RBC sample is determined based on the ratio of hypoxanthine:adenine from 1.0 mM/mM to 16 mM/mM, the value of inosine from 0 mM to 0.0005 mM, and the ratio of inosine:adenine from 0 mM/mM to 0.05 mM/mM. In some embodiments, the quality of the RBC sample is determined based on the ratio of hypoxanthine:adenine from about 1.0 mM/mM to about 16 mM/mM. In some embodiments, the quality of the RBC sample is determined based on the ratio of hypoxanthine:adenine from 1.0 mM/mM to 16 mM/mM.

In some embodiments, Second Phase (Transition Phase) is correlated to about day 1 to about day 60, about day 5 to about day 30, about day 8 to about day 20, about day 10 to about day 19 or about day 11 to about day 18. In some embodiments, Second Phase (Transition Phase) is correlated to about day 11, 12, 13, 14, 15, 16, 17 or day 18 of storage.

In some embodiments, the value of a biomarker is used to predict how long the RBC sample remains in Second Phase (Transition Phase). In some embodiments, when the ratio of hypoxanthine:adenine, the value of inosine, and the ratio of inosine:adenine match the values that correspond to an initial portion of Second Phase (Transition Phase), this indicates that the RBC sample remains in Second Phase (Transition Phase) for 1, 2, 3, 4, 5, 6, 7, 8 or more days. In some embodiments, when the ratio of hypoxanthine:adenine match the values that correspond to an initial portion of Second Phase (Transition Phase), this indicates that the RBC sample remains in Second Phase (Transition Phase) for 1, 2, 3, 4, 5, 6, 7, 8 or more days. In some embodiments, when the ratio of hypoxanthine:adenine, the value of inosine, and the ratio of inosine:adenine match the values that correspond to a terminal portion of Second Phase (Transition Phase), this indicates that the RBC sample remains in Second Phase (Transition Phase) for less than 1, 2, 3, 4, 5, 6, 7, or 8 days. In some embodiments, when the ratio of hypoxanthine:adenine match the values that correspond to a terminal portion of Second Phase (Transition Phase), this indicates that the RBC sample remains in Second Phase (Transition Phase) for less than 1, 2, 3, 4, 5, 6, 7, or 8 days. In some embodiments, when the ratio of hypoxanthine:adenine, the value of inosine, and the ratio of inosine:adenine match the values that correspond to between an initial and a terminal portion of Second Phase (Transition Phase), this indicates that the RBC sample remains in Second Phase (Transition Phase) for about 1, 2, 3, 4, 5, 6, 7, 8 or more days. In some embodiments, when the ratio of hypoxanthine:adenine match the values that correspond to between an initial and a terminal portion of Second Phase (Transition Phase), this indicates that the RBC sample remains in Second Phase (Transition Phase) for about 1, 2, 3, 4, 5, 6, 7, 8 or more days.

In some embodiments, any RBC sample is characterized as Second Phase (Transition Phase) regardless of storage age, storage condition (e.g. storage temperature or addition of an additive solution) or donor genetic variations (e.g. age, sex or a donor's health). In some embodiments, an RBC sample stored for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 days is characterized as Second Phase (Transition Phase). In some embodiments, an RBC sample which has been in storage for about 5 days or for about 30 days is characterized as Second Phase (Transition Phase) if the ratio of hypoxanthine:adenine is from about 1.0 mM/mM to about 16 mM/mM, the value of inosine is from about 0 mM to about 0.0005 mM, and the ratio of inosine:adenine is from about 0 mM/mM to about 0.05 mM/mM. In some embodiments, an RBC sample which has been in storage for about 5 days or for about 30 days is characterized as Second Phase (Transition Phase) if the ratio of hypoxanthine:adenine is from 1.0 mM/mM to 16 mM/mM, the value of inosine is from 0 mM to 0.0005 mM, and the ratio of inosine:adenine is from 0 mM/mM to 0.05 mM/mM. In some embodiments, an RBC sample which has been in storage for about 5 days or for about 30 days is characterized as Second Phase (Transition Phase) if the ratio of hypoxanthine:adenine is from about 1.0 mM/mM to about 16 mM/mM. In some embodiments, an RBC sample which has been in storage for about 5 days or for about 30 days is characterized as Second Phase (Transition Phase) if the ratio of hypoxanthine:adenine is from 1.0 mM/mM to 16 mM/mM.

In some embodiments, an RBC sample stored under any storage condition is characterized as Second Phase (Transition Phase). In some embodiments, the storage condition is a storage temperature or the addition of an additive solution. In some embodiments, the additive solution includes SAG, SAGM, AS-1 (Adsol), AS-3 (Nutricel), AS-5 (Optisol), MAP, PAGGSM (Macopharma), PAGGGM, SOLX (AS-7), BAGP-M, ErythroSol-1, ErythroSol-2, ErythroSol-4, and EAS-81. In some embodiments, the additive solution is SAGM, AS-1 (Adsol), AS-3 (Nutricel), AS-5 (Optisol), MAP, PAGGSM (Macopharma), PAGGGM, or SOLX (AS-7). In some embodiments, the additive solution is SAGM.

In some embodiments, the storage condition is a storage temperature. In some embodiments, the storage temperature is from about −80° C. to about 25° C., about −10° C. to about 10° C., about 0° C. to about 8° C. In some embodiments, the storage temperature is about 4° C.

In some embodiments, an RBC sample stored at any temperature is characterized as Second Phase (Transition Phase). In some embodiments, an RBC sample stored at any temperature is characterized as Second Phase (Transition Phase) if the ratio of hypoxanthine:adenine is from about 1.0 mM/mM to about 16 mM/mM, the value of inosine is from about 0 mM to about 0.0005 mM, and the ratio of inosine:adenine is from about 0 mM/mM to about 0.05 mM/mM. In some embodiments, an RBC sample stored at any temperature is characterized as Second Phase (Transition Phase) if the ratio of hypoxanthine:adenine is from 1.0 mM/mM to 16 mM/mM, the value of inosine is from 0 mM to 0.0005 mM, and the ratio of inosine:adenine is from 0 mM/mM to 0.05 mM/mM. In some embodiments, an RBC sample stored at any temperature is characterized as Second Phase (Transition Phase) if the ratio of hypoxanthine:adenine is from about 1.0 mM/mM to about 16 mM/mM. In some embodiments, an RBC sample stored at any temperature is characterized as Second Phase (Transition Phase) if the ratio of hypoxanthine:adenine is from 1.0 mM/mM to 16 mM/mM.

In some embodiments, an RBC sample regardless of donor genetic variation (e.g. age, sex or a donor's health) is characterized as Second Phase (Transition Phase). In some embodiments, an RBC sample regardless of donor genetic variation is characterized as Second Phase (Transition Phase) if the ratio of hypoxanthine:adenine is from about 1.0 mM/mM to about 16 mM/mM, the value of inosine is from about 0 mM to about 0.0005 mM, and the ratio of inosine:adenine is from about 0 mM/mM to about 0.05 mM/mM. In some embodiments, an RBC sample regardless of donor genetic variation is characterized as Second Phase (Transition Phase) if the ratio of hypoxanthine:adenine is from 1.0 mM/mM to 16 mM/mM, the value of inosine is from 0 mM to 0.0005 mM, and the ratio of inosine:adenine is from 0 mM/mM to 0.05 mM/mM. In some embodiments, an RBC sample regardless of donor genetic variation is characterized as Second Phase (Transition Phase) if the ratio of hypoxanthine:adenine is from about 1.0 mM/mM to about 16 mM/mM. In some embodiments, an RBC sample regardless of donor genetic variation is characterized as Second Phase (Transition Phase) if the ratio of hypoxanthine:adenine is from 1.0 mM/mM to 16 mM/mM.

Third Phase (Old Phase)—RBC

In some embodiments, Third Phase (Old Phase) is characterized by a set of biomarkers. In some embodiments, the set of biomarkers is selected from concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, and concentration of pyruvate. In some embodiments, the set of biomarkers is the ratio of hypoxanthine:adenine, the concentration of hypoxanthine, the concentration of adenine, the ratio of $pCO_2$:pH, the ratio of inosine:adenine and the concentration of inosine. In some embodiments, the set of biomarkers is the ratio of hypoxanthine:adenine, the concentration of hypoxanthine and the concentration of adenine. In some embodiments, Third Phase (Old Phase) is characterized by the ratio of hypoxanthine:adenine, the concentration of hypoxanthine, the concentration of adenine, the ratio of $pCO_2$:pH, the ratio of inosine:adenine and the concentration of inosine. In some embodiments, Third Phase (Old Phase) is characterized by the ratio of hypoxanthine:adenine, the concentration of hypoxanthine and the concentration of adenine. In some embodiments, the RBC sample is classified as Third Phase (Old Phase) based on the ratio of hypoxanthine:adenine, the concentration of hypoxanthine, the concentration of adenine, the ratio of $pCO_2$:pH, the ratio of inosine:adenine and the concentration of inosine. In some embodiments, the RBC sample is classified as Third Phase (Old Phase) based on the ratio of hypoxanthine:adenine, the concentration of hypoxanthine and the concentration of adenine. In some embodiments, the quality of the RBC sample is determined based on the ratio of hypoxanthine:adenine, the concentration of hypoxanthine, the concentration of adenine, the ratio of $pCO_2$:pH, the ratio of inosine:

adenine and the concentration of inosine. In some embodiments, the quality of the RBC sample is determined based on the ratio of hypoxanthine:adenine, the concentration of hypoxanthine and the concentration of adenine.

In some embodiments, the biomarkers are obtained from the extracellular portion of the RBC sample. In some embodiments, the set of biomarkers obtained from the extracellular portion include concentration of inosine, concentration of hypoxanthine, concentration of adenine, ratio of hypoxanthine:adenine, ratio of $Na^+$:$K^+$, ratio of glucose: lactate, ratio of inosine:adenine, and concentration of pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, Third Phase (Old Phase) is characterized by the set of biomarkers obtained from the extracellular portion.

In some embodiments, the set of biomarkers selected from concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine and concentration of pyruvate are indicated with a set of values or a set of ratios. In some embodiments, the concentration of inosine, the concentration of hypoxanthine, the concentration of adenine, and the concentration of pyruvate are each indicated with a value. In some embodiments, the values of inosine, hypoxanthine, adenine and pyruvate are represented as a range. In some embodiments, the value is associated with a unit or is unitless. In some embodiments, the unit is in millimolar (mM) concentration. In some embodiments, the ratio of hypoxanthine:adenine, the ratio of glucose: lactate, the ratio of $Na^+$:$K^+$, the ratio of $pCO_2$:pH and the ratio of inosine:adenine are indicated as ranges. In some embodiments, the ratio is associated with a unit or is unitless. In some embodiments, the unit is in millimolar/ millimolar (mM/mM) concentration or mmHg/pH.

In some embodiments, the value of hypoxanthine is greater than 1 mM, greater than 0.5 mM, greater than 0.2 mM, greater than 0.15 mM, greater than 0.14 mM, greater than 0.13 mM, greater than 0.12 mM, greater than 0.11 mM, or greater than 0.1 mM. In some embodiments, the value of hypoxanthine is greater than 0.1 mM.

In some embodiments, the range of values of adenine is from about 0 mM to about 1 mM, about 0 mM to about 0.9 mM, about 0 mM to about 0.8 mM, about 0 mM to about 0.7 mM, about 0 mM to about 0.6 mM, about 0 mM to about 0.5 mM, about 0 mM to about 0.4 mM, about 0 mM to about 0.3 mM, about 0 mM to about 0.2 mM, or about 0 mM to about 0.1 mM. In some embodiments, the range of values of adenine is from about 0 mM to about 0.1 mM. In some embodiments, the range of values of adenine is from 0 mM to 0.1 mM.

In some embodiments, the value of inosine is greater than 1 mM, greater than 0.1 mM, greater than 0.01 mM, greater than 0.005 mM, greater than 0.002 mM, greater than 0.001 mM, greater than 0.0009 mM, greater than 0.0008 mM, greater than 0.0007 mM, greater than 0.0006 mM, or greater than 0.0005 mM. In some embodiments, the value of inosine is greater than 0.0005 mM.

In some embodiments, the value of pyruvate is greater than 1 mM, greater than 0.5 mM, greater than 0.1 mM, or greater than 0 mM. In some embodiments, the value of pyruvate is greater than 0 mM.

In some embodiments, the range of ratios of glucose: lactate is from about 0 mM/mM to about 10 mM/mM, about 0 mM/mM to 9 mM/mM, about 0 mM/mM to 8 mM/mM, about 0 mM/mM to 7 mM/mM, about 0 mM/mM to 6 mM/mM, about 0 mM/mM to 5 mM/mM, about 0 mM/mM to 4 mM/mM, about 0 mM/mM to 3 mM/mM, or about 0 mM/mM to 2 mM/mM. In some embodiments, the range of ratios of glucose:lactate is from about 0 mM/mM to about 2.0 mM/mM. In some embodiments, the range of ratios of glucose:lactate is from 0 mM/mM to 2.0 mM/mM.

In some embodiments, the range of ratios of $Na^+$:$K^+$ is from about 0 mM/mM to 100 mM/mM, about 0 mM/mM to 50 mM/mM, about 0 mM/mM to 20 mM/mM, about 0 mM/mM to 10 mM/mM, about 0 mM/mM to 9 mM/mM, about 0 mM/mM to 8.5 mM/mM, about 0 mM/mM to 8 mM/mM, about 0 mM/mM to 7.5 mM/mM, about 0 mM/mM to 7 mM/mM, or about 0 mM/mM to 6.5 mM/mM. In some embodiments, the range of ratios of $Na^+$:$K^+$ is from about 0 mM/mM to about 6.5 mM/mM. In some embodiments, the range of ratios of $Na^+$:$K^+$ is from 0 mM/mM to 6.5 mM/mM.

In some embodiments, the ratio of hypoxanthine:adenine is greater than 1000 mM/mM, greater than 500 mM/mM, greater than 100 mM/mM, greater than 20 mM/mM, greater than 19 mM/mM, greater than 18 mM/mM, greater than 17 mM/mM, or greater than 16 mM/mM. In some embodiments, the ratio of hypoxanthine:adenine is greater than 16 mM/mM.

In some embodiments, the ratio of $pCO_2$:pH is greater than 30 mmHg/pH, greater than 25 mmHg/pH, greater than 20 mmHg/pH, greater than 19 mmHg/pH, greater than 18 mmHg/pH, greater than 17 mmHg/pH, or greater than 16 mmHg/pH. In some embodiments, the ratio of $pCO_2$:pH is greater than 16 mmHg/pH.

In some embodiments, the ratio of inosine:adenine is greater than 10 mM/mM, greater than 5 mM/mM, greater than 1 mM/mM, greater than 0.5 mM/mM, greater than 0.1 mM/mM, or greater than 0.05 mM/mM. In some embodiments, the ratio of inosine:adenine is greater than 0.05 mM/mM.

In some embodiments, Third Phase (Old Phase) is characterized by the ratio of hypoxanthine:adenine greater than 16 mM/mM, the value of hypoxanthine greater than 0.1 mM, the value of adenine from about 0 mM to about 0.1 mM, the ratio of $pCO_2$:pH greater than 16 mmHg/pH, the ratio of inosine:adenine greater than 0.05 mM/mM and the value of inosine greater than 0.0005 mM. In some embodiments, Third Phase (Old Phase) is characterized by the ratio of hypoxanthine:adenine greater than 16 mM/mM, the value of hypoxanthine greater than 0.1 mM, the value of adenine from 0 mM to 0.1 mM, the ratio of $pCO_2$:pH greater than 16 mmHg/pH, the ratio of inosine:adenine greater than 0.05 mM/mM and the value of inosine greater than 0.0005 mM. In some embodiments, Third Phase (Old Phase) is characterized by the ratio of hypoxanthine:adenine greater than 16 mM/mM, the value of hypoxanthine greater than 0.1 mM and the value of adenine from about 0 mM to about 0.1 mM. In some embodiments, Third Phase (Old Phase) is characterized by the ratio of hypoxanthine:adenine greater than 16 mM/mM, the value of hypoxanthine greater than 0.1 mM and the value of adenine from 0 mM to 0.1 mM.

In some embodiments, the RBC sample is classified as Third Phase (Old Phase) based on the ratio of hypoxanthine: adenine greater than 16 mM/mM, the value of hypoxanthine greater than 0.1 mM, the value of adenine from about 0 mM to about 0.1 mM, the ratio of $pCO_2$:pH greater than 16 mmHg/pH, the ratio of inosine:adenine greater than 0.05 mM/mM and the value of inosine greater than 0.0005 mM. In some embodiments, the RBC sample is classified as Third Phase (Old Phase) based on the ratio of hypoxanthine:adenine greater than 16 mM/mM, the value of hypoxanthine greater than 0.1 mM, the value of adenine from 0 mM to 0.1 mM, the ratio of $pCO_2$:pH greater than 16 mmHg/pH, the ratio of inosine:adenine greater than 0.05 mM/mM and the value of inosine greater than 0.0005 mM. In some embodiments, the RBC sample is classified as Third Phase (Old Phase) based on the ratio of hypoxanthine:adenine greater than 16 mM/mM, the value of hypoxanthine greater than 0.1 mM and the value of adenine from about 0 mM to about 0.1 mM. In some embodiments, the RBC sample is classified as Third Phase (Old Phase) based on the ratio of hypoxanthine:adenine greater than 16 mM/mM, the value of hypoxanthine greater than 0.1 mM and the value of adenine from 0 mM to 0.1 mM.

In some embodiments, the quality of the RBC sample is determined based on the ratio of hypoxanthine:adenine greater than 16 mM/mM, the value of hypoxanthine greater than 0.1 mM, the value of adenine from about 0 mM to about 0.1 mM, the ratio of $pCO_2$:pH greater than 16 mmHg/pH, the ratio of inosine:adenine greater than 0.05 mM/mM and the value of inosine greater than 0.0005 mM. In some embodiments, the quality of the RBC sample is determined based on the ratio of hypoxanthine:adenine greater than 16 mM/mM, the value of hypoxanthine greater than 0.1 mM, the value of adenine from 0 mM to 0.1 mM, the ratio of $pCO_2$:pH greater than 16 mmHg/pH, the ratio of inosine:adenine greater than 0.05 mM/mM and the value of inosine greater than 0.0005 mM. In some embodiments, the quality of the RBC sample is determined based on the ratio of hypoxanthine:adenine greater than 16 mM/mM, the value of hypoxanthine greater than 0.1 mM and the value of adenine from about 0 mM to about 0.1 mM. In some embodiments, the quality of the RBC sample is determined based on the ratio of hypoxanthine:adenine greater than 16 mM/mM, the value of hypoxanthine greater than 0.1 mM and the value of adenine from 0 mM to 0.1 mM.

In some embodiments, Third Phase (Old Phase) is correlated to about day 1 to about day 60, about day 10 to about day 50, about day 16 to about day 48, about day 17 to about day 47, about day 18 to about day 46 or about day 19 to about day 46. In some embodiments, Third Phase (Old Phase) is correlated to about day 18, 19, 20, 21, 22, 23, 24, 25, 26, 27, 28, 29, 30, 31, 32, 33, 34, 35, 36, 37, 38, 39, 40, 41, 42, 43, 44, 45 or day 46 of storage.

In some embodiments, the value of a biomarker is used to predict how long the RBC sample remains in Third Phase (Old Phase). In some embodiments, when the ratio of hypoxanthine:adenine, the value of hypoxanthine, the value of adenine, the ratio of $pCO_2$:pH, the ratio of inosine:adenine and the value of inosine match the values that correspond to an initial portion of Third Phase (Old Phase), this indicates that the RBC sample remains in Third Phase (Old Phase) for 1, 2, 3, 4, 5, 6, 7, 8, 9, 10, 11, 12, 13, 14, 15, 16, 17, 18, 19, 20, 21, 22, 23, 24, 25, 26, 27, 28, or more days. In some embodiments, when the ratio of hypoxanthine:adenine, the value of hypoxanthine, the value of adenine match the values that correspond to an initial portion of Third Phase (Old Phase), this indicates that the RBC sample remains in Third Phase (Old Phase) for 1, 2, 3, 4, 5, 6, 7, 8, 9, 10, 11, 12, 13, 14, 15, 16, 17, 18, 19, 20, 21, 22, 23, 24, 25, 26, 27, 28, or more days. In some embodiments, when the ratio of hypoxanthine:adenine, the value of hypoxanthine, the value of adenine, the ratio of $pCO_2$:pH, the ratio of inosine:adenine and the value of inosine match the values that correspond to a terminal portion of Third Phase (Old Phase), this indicates that the RBC sample remains in Third Phase (Old Phase) for less than 1, 2, 3, 4, 5, 6, 7, 8, 9, 10, 11, 12, 13, 14, 15, 16, 17, 18, 19, 20, 21, 22, 23, 24, 25, 26, 27, or 28 days. In some embodiments, when the ratio of hypoxanthine:adenine, the value of hypoxanthine, the value of adenine match the values that correspond to a terminal portion of Third Phase (Old Phase), this indicates that the RBC sample remains in Third Phase (Old Phase) for less than 1, 2, 3, 4, 5, 6, 7, 8, 9, 10, 11, 12, 13, 14, 15, 16, 17, 18, 19, 20, 21, 22, 23, 24, 25, 26, 27, or 28 days. In some embodiments, when the ratio of hypoxanthine:adenine, the value of hypoxanthine, the value of adenine, the ratio of $pCO_2$:pH, the ratio of inosine:adenine and the value of inosine match the values that correspond to between an initial and a terminal portion of Third Phase (Old Phase), this indicates that the RBC sample remains in Third Phase (Old Phase) for about 1, 2, 3, 4, 5, 6, 7, 8, 9, 10, 11, 12, 13, 14, 15, 16, 17, 18, 19, 20, 21, 22, 23, 24, 25, 26, 27, 28 or more days. In some embodiments, when the ratio of hypoxanthine:adenine, the value of hypoxanthine, the value of adenine match the values that correspond to between an initial and a terminal portion of Third Phase (Old Phase), this indicates that the RBC sample remains in Third Phase (Old Phase) for about 1, 2, 3, 4, 5, 6, 7, 8, 9, 10, 11, 12, 13, 14, 15, 16, 17, 18, 19, 20, 21, 22, 23, 24, 25, 26, 27, 28 or more days.

In some embodiments, any RBC sample is characterized as Third Phase (Old Phase) regardless of storage age, storage condition (e.g. storage temperature or the addition of an additive solution) or donor genetic variations (e.g. age, sex or a donor's health). In some embodiments, an RBC sample stored for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 days is characterized as Third Phase (Old Phase). In some embodiments, an RBC sample which has been in storage for about 5 days or for about 15 days is characterized as Third Phase (Old Phase) if the ratio of hypoxanthine:adenine is greater than 16 mM/mM, the value of hypoxanthine is greater than 0.1 mM, the value of adenine is from about 0 mM to about 0.1 mM, the ratio of $pCO_2$:pH is greater than 16 mmHg/pH, the ratio of inosine:adenine is greater than 0.05 mM/mM and the value of inosine is greater than 0.0005 mM. In some embodiments, an RBC sample which has been in storage for about 5 days or for about 15 days is characterized as Third Phase (Old Phase) if the ratio of hypoxanthine:adenine is greater than 16 mM/mM, the value of hypoxanthine is greater than 0.1 mM, the value of adenine is from 0 mM to 0.1 mM, the ratio of $pCO_2$:pH is greater than 16 mmHg/pH, the ratio of inosine:adenine is greater than 0.05 mM/mM and the value of inosine is greater than 0.0005 mM. In some embodiments, an RBC sample which has been in storage for about 5 days or for about 15 days is characterized as Third Phase (Old Phase) if the ratio of hypoxanthine:adenine is greater than 16 mM/mM, the value of hypoxanthine is greater than 0.1 mM and the value of adenine is from about 0 mM to about 0.1 mM. In some embodiments, an RBC sample which has been in storage for about 5 days or for about 15 days is characterized as Third Phase (Old Phase) if the ratio of hypoxanthine:adenine is greater than 16 mM/mM, the value of hypoxanthine is greater than 0.1 mM and the value of adenine is from 0 mM to 0.1 mM.

In some embodiments, an RBC sample stored under any storage condition is characterized as Third Phase (Old Phase). In some embodiments, the storage condition is a storage temperature or the addition of an additive solution.

In some embodiments, the additive solution includes SAG, SAGM, AS-1 (Adsol), AS-3 (Nutricel), AS-5 (Optisol), MAP, PAGGSM (Macopharma), PAGGGM, SOLX (AS-7), BAGP-M, ErythroSol-1, ErythroSol-2, ErythroSol-4, and EAS-81. In some embodiments, the additive solution is SAGM, AS-1 (Adsol), AS-3 (Nutricel), AS-5 (Optisol), MAP, PAGGSM (Macopharma), PAGGGM, or SOLX (AS-7). In some embodiments, the additive solution is SAGM.

In some embodiments, the storage condition is a storage temperature. In some embodiments, the storage temperature is from about −80° C. to about 25° C., about −10° C. to about 10° C., about 0° C. to about 8° C. In some embodiments, the storage temperature is about 4° C.

In some embodiments, an RBC sample stored at any temperature is characterized as Third Phase (Old Phase). In some embodiments, an RBC sample stored at any temperature is characterized as Third Phase (Old Phase) if the ratio of hypoxanthine:adenine is greater than 16 mM/mM, the value of hypoxanthine is greater than 0.1 mM, the value of adenine is from about 0 mM to about 0.1 mM, the ratio of $pCO_2$:pH is greater than 16 mmHg/pH, the ratio of inosine:adenine is greater than 0.05 mM/mM and the value of inosine is greater than 0.0005 mM. In some embodiments, an RBC sample stored at any temperature is characterized as Third Phase (Old Phase) if the ratio of hypoxanthine:adenine is greater than 16 mM/mM, the value of hypoxanthine is greater than 0.1 mM, the value of adenine is from 0 mM to 0.1 mM, the ratio of $pCO_2$:pH is greater than 16 mmHg/pH, the ratio of inosine:adenine is greater than 0.05 mM/mM and the value of inosine is greater than 0.0005 mM. In some embodiments, an RBC sample stored at any temperature is characterized as Third Phase (Old Phase) if the ratio of hypoxanthine:adenine is greater than 16 mM/mM, the value of hypoxanthine is greater than 0.1 mM and the value of adenine is from about 0 mM to about 0.1 mM. In some embodiments, an RBC sample stored at any temperature is characterized as Third Phase (Old Phase) if the ratio of hypoxanthine:adenine is greater than 16 mM/mM, the value of hypoxanthine is greater than 0.1 mM and the value of adenine is from 0 mM to 0.1 mM.

In some embodiments, an RBC sample regardless of donor genetic variation (e.g. age, sex or a donor's health) is characterized as Third Phase (Old Phase). In some embodiments, an RBC sample regardless of donor genetic variation is characterized as Third Phase (Old Phase) if the ratio of hypoxanthine:adenine is greater than 16 mM/mM, the value of hypoxanthine is greater than 0.1 mM, the value of adenine is from about 0 mM to about 0.1 mM, the ratio of $pCO_2$:pH is greater than 16 mmHg/pH, the ratio of inosine:adenine is greater than 0.05 mM/mM and the value of inosine is greater than 0.0005 mM. In some embodiments, an RBC sample regardless of donor genetic variation is characterized as Third Phase (Old Phase) if the ratio of hypoxanthine:adenine is greater than 16 mM/mM, the value of hypoxanthine is greater than 0.1 mM, the value of adenine is from 0 mM to 0.1 mM, the ratio of $pCO_2$:pH is greater than 16 mmHg/pH, the ratio of inosine:adenine is greater than 0.05 mM/mM and the value of inosine is greater than 0.0005 mM. In some embodiments, an RBC sample regardless of donor genetic variation is characterized as Third Phase (Old Phase) if the ratio of hypoxanthine:adenine is greater than 16 mM/mM, the value of hypoxanthine is greater than 0.1 mM and the value of adenine is from about 0 mM to about 0.1 mM. In some embodiments, an RBC sample regardless of donor genetic variation is characterized as Third Phase (Old Phase) if the ratio of hypoxanthine:adenine is greater than 16 mM/mM, the value of hypoxanthine is greater than 0.1 mM and the value of adenine is from 0 mM to 0.1 mM.

Platelet Storage

Platelet concentrates are generally used within about 5 to about 7 days of room temperature storage. During storage, platelets (PLTs) develop platelet storage lesion, characterized by biomolecular and morphological changes related to platelet metabolism, activation, and apoptosis. As is similar to RBCs, increased storage time for PLTs correlates to increased PLT storage lesion. Further, storage conditions and the use of additive solutions in some instances contribute to the complexity of PLT storage.

Disclosed herein in certain embodiments, are systems, methods, compositions, device and kits for determining the phase or metabolic state of a platelet (PLT) sample. Further disclosed herein are systems and methods for determining the quality of a PLT sample.

In some embodiments, disclosed herein is a method for characterizing platelets (PLTs) for transfusion, which comprises (a) obtaining a PLT sample from the PLTs; (b) determining a value of a biomarker in the PLT sample by an analytical analysis, wherein the biomarker value is selected from one or more of: concentration of glutamine, concentration of niacinamide, concentration of glutathione oxidized, concentration of succinic acid, concentration of sCD40L, value of CD41:CD63 (e.g., percentage of cells double positive or expressing both CD41 and CD63+ in a cell population), value of CD41:Annexin-V (e.g., percentage of cells double positive or expressing both CD41 and Annexin-V+ in a cell population), value of CD41:CD42b (e.g., percentage of cells double positive or expressing both CD41 and CD42b in a cell population), ratio of citrate:cis-aconitate, ratio of citrate:malate, ratio of acetate:cis-aconitate, ratio of glucose:lactose, ratio of acetate:succinate, or ratio of acetate:lactose; (c) matching the biomarker value to a respective control value for the biomarker, wherein a value in the control defines a transition from a first metabolic state of the platelets to a second metabolic state of the platelets; (d) assigning a metabolic state to the platelet sample based on the value of the biomarker which is one of First Phase or Second Phase; wherein: the sample is First Phase when the measured concentration of glutathione oxidized, ratio of acetate:cis-aconitate, and either ratio of glucose:lactose or ratio of acetate:lactose are greater than the values on the control indicated as the transition from the first metabolic state to the second metabolic state; or the sample is Second Phase when the measured concentration of glutathione oxidized, ratio of acetate:cis-aconitate, and either ratio of glucose:lactose or ratio of acetate:lactose are less than the values on the control indicated as the transition from the first metabolic state to the second metabolic state; and (e) recommending First Phase PLTs for transfusion.

In some embodiments, disclosed herein is a method for storing platelets (PLTs), comprises (a) obtaining a PLT sample from the PLTs; (b) testing the PLT sample by the steps of: (i) determining a value of a biomarker in a platelet sample by an analytical analysis, wherein the biomarker value is selected from one or more of: concentration of glutamine, concentration of niacinamide, concentration of glutathione oxidized, concentration of succinic acid, concentration of sCD40L, value of CD41:CD63 (e.g., percentage of cells double positive or expressing both CD41 and CD63+ in a cell population), value of CD41:Annexin-V (e.g., percentage of cells double positive or expressing both CD41 and Annexin-V+ in a cell population), value of CD41:CD42b (e.g., percentage of cells double positive or expressing both CD41 and CD42b in a cell population), ratio of citrate:cis-aconitate, ratio of citrate:malate, ratio of acetate:cis-aconitate, ratio of glucose:lactose, ratio of acetate:succinate, or ratio of acetate:lactose; (ii) matching the biomarker value to a respective control value for the biomarker, wherein a value in the control defines a transition from a first metabolic state of the platelets to a second metabolic state of the platelets; and (iii) assigning a metabolic state to the platelet sample based on the value of the biomarker which is one of First Phase or Second Phase; wherein: the sample is First Phase when the measured concentration of glutathione oxidized, ratio of acetate:cis-aconitate, and either ratio of glucose:lactose or ratio of acetate:lactose are greater than the values on the control indicated as the transition from the first metabolic state to the second metabolic state; or the sample is Second Phase when the measured concentration of glutathione oxidized, ratio of acetate:cis-aconitate, and either ratio of glucose:lactose or ratio of acetate:lactose are less than the values on the control indicated as the transition from the first metabolic state to the second metabolic state; (c) assigning a range of days associated with First Phase or Second Phase to the PLTs to indicate storage duration of the PLT sample in First Phase or Second Phase; and (d) recommending disposal of PLTs in Second Phase.

In some embodiments, disclosed herein is a storage device comprising: (a) a container; (b) a composition comprising platelets (PLTs) in the container; and (c) an indicator which displays the metabolic state of platelets stored therein; wherein the indicator has a testing module which contains reagents and analytes for carrying out a test reaction to allow detection of one or more biomarkers; and the metabolic state of the platelets is displayed as one of First Phase or Second Phase; wherein the metabolic state of the RBCs is classified as: First Phase by comparing the measured concentration of glutathione oxidized, ratio of acetate:cis-aconitate, and either ratio of glucose:lactose or ratio of acetate:lactose as greater than the values on the control indicated as the transition from the first metabolic state to the second metabolic state; or Second Phase by comparing the measured concentration of glutathione oxidized, ratio of acetate:cis-aconitate, and either ratio of glucose:lactose or ratio of acetate:lactose as less than the values on the control indicated as the transition from the first metabolic state to the second metabolic state.

Also disclosed herein are assays, kits, and systems for one or more of the platelet biomarkers described herein for determining the metabolic phase or metabolic state of a platelet (PLT) sample. In some embodiments, disclosed herein is a kit for determining the phase or metabolic state of a platelet (PLT) sample, comprising: (a) a plurality of reagents and analytes for determining a dataset for a biomarker, wherein the biomarker is concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combination thereof; (b) at least one software module for analyzing the dataset to determine a value of the biomarker, comparing the value of the biomarker to a respective biomarker value in a control dataset; and assigning the PLT sample as First Phase or Second Phase, wherein the value of the biomarker indicates the phase of the PLT sample; and (c) instruction manuals for utilizing the plurality of reagents and analytes and the at least one software module.

Platelets Biomarkers

In some embodiments, any suitable metabolite is used as a biomarker for PLT. In some embodiments, the metabolite is a product of glycolysis (or gluconeogenesis), pentose phosphate pathway, purine and pyrimidine metabolisms, citrate cycle (TCA cycle), glycerophospholipid metabolism, glutathione metabolism, amino sugar and nucleotide sugar metabolism, propanoate metabolism, pentose and glucuronate interconversions, glyoxylate and dicarboxylate metabolism, cysteine and methionine metabolism, sphingolipid metabolism, galactose metabolism, starch and sucrose metabolism, pyrimidine metabolism, glycerolipid metabolism, butanoate metabolism, arginine and proline metabolism, alanine, aspartate and glutamate metabolism, glycine, serine and threonine metabolism, tyrosine metabolism, D-glutamine and D-glutamate metabolism, ascorbate and aldarate metabolism, methane metabolism, phenylalanine metabolism, riboflavin metabolism, nitrogen metabolism, ether lipid metabolism, pyruvate metabolism, thiamine metabolism, nicotinate and nicotinamide metabolism, primary bile acid biosynthesis, taurine and hypotaurine metabolism, porphyrin and chlorophyll metabolism, histidine metabolism, aminoacyl-tRNA biosynthesis, beta-alanine metabolism, phenylalanine, tyrosine and tryptophan biosynthesis, D-arginine and D-ornithine metabolism, valine, leucine and isoleucine biosynthesis, selenoamino acid metabolism, cyanoamino acid metabolism, ubiquinone and other terpenoid-quinone biosynthesis, valine, leucine and isoleucine degradation, pantothenate and CoA biosynthesis, lysine biosynthesis, tryptophan metabolism, lysine degradation, biotin metabolism, caffeine metabolism, or sulfur metabolism.

In some embodiments, the metabolite is selected from: dimethylglycine, choline, proline, nicotinamide, hydroxyproline, isoleucine, asparagine, adenine, hypoxanthine, lysine, methionine, guanine, histidine, carnitine, phenylalanine, methyl histidine, arginine, citrulline, fructose, glucose, mannose, phosphocholine, ADMA, acetylcarnitine, tryptophan, cystine, cytidine, thiamine, 5-MTA, glutathione reduced, S-adenosylhomocysteine (SAH), S-adenosylmethionine (SAMe), glutathione oxidized, alanine, serine, glyceric acid, fumaric acid, valine, succinic acid, threonine, 5-oxoproline, aspartic acid, malate, glutamine, xanthine, uric acid, aconitic acid, ascorbic acid, tyrosine, citric acid, uridine, inosine, guanosine, lactic acid, taurine, glutamic acid, phosphoenolpyruvate, glycerol-P, 2-phosphoglycerate, fructose 6-P, glucose 6-P, 6-phosphogluconate, CMP, UMP, fructose-1,6-diP, AMP, IMP. GMP, UDP, ADP, GDP, ATP, ADP-ribose, FAD, glycerophospho-inositol, ascorbate-phosphate, C3 Carnitine, C4 Carnitine, C5 Carnitine, CDP-choline, CDP-ethanolamine, dihydroxy stearic acid, disaccharide, HETEs, LPC 16:0, LPC 16:1, LPC 18:0, LPC 18:1, LPC 18:2, LPC 18:3, acetylneuraminic acid, phosphorylethanolamine, pentose-5-phosphate, phtalic acid, sedoheptulose-7-phosphate, glycero-phosphocholine, sphingosine, sphingosine-1-phosphate, tetrasaccharide, trisaccharide, UDP-glucuronate, UDP-acetylglucosamine, niacinamide, sCD40L, CD41, CD63+, Annexin-V+, CD42b, citrate, cis-aconitate, malate, acetate, lactose, or any combinations thereof.

In some embodiments, the biomarkers are selected from values of dimethylglycine, choline, proline, nicotinamide, hydroxyproline, isoleucine, asparagine, adenine, hypoxanthine, lysine, methionine, guanine, histidine, carnitine, phenylalanine, methyl histidine, arginine, citrulline, fructose, glucose, mannose, phosphocholine, ADMA, acetylcarnitine, tryptophan, cystine, cytidine, thiamine, 5-MTA, glutathione reduced, S-adenosylhomocysteine (SAH), S-adenosylmethionine (SAMe), glutathione oxidized, alanine, serine, glyceric acid, fumaric acid, valine, succinic acid, threonine, 5-oxoproline, aspartic acid, malate, glutamine, xanthine, uric acid, aconitic acid, ascorbic acid, tyrosine, citric acid, uridine, inosine, guanosine, lactic acid, taurine, glutamic acid, phosphoenolpyruvate, glycerol-P, 2-phosphoglycerate, fructose 6-P, glucose 6-P, 6-phosphogluconate, CMP, UMP, fructose-1,6-diP, AMP, IMP. GMP, UDP, ADP, GDP, ATP, ADP-ribose, FAD, glycerophospho-inositol, ascorbate-phosphate, C3 Carnitine, C4 Carnitine, C5 Carnitine, CDP-choline, CDP-ethanolamine, dihydroxy stearic acid, disaccharide, HETEs, LPC 16:0, LPC 16:1, LPC 18:0, LPC 18:1, LPC 18:2, LPC 18:3, acetylneuraminic acid, phosphoryl-ethanolamine, pentose-5-phosphate, phtalic acid, sedoheptulose-7-phosphate, glycero-phosphocholine, sphingosine, sphingosine-1-phosphate, tetrasaccharide, trisaccharide, UDP-glucuronate, UDP-acetylglucosamine, niacinamide, sCD40L, CD41, CD63+, Annexin-V+, CD42b, citrate, cis-aconitate, malate, acetate, lactose, CD41 and CD63+, CD41 and Annexin-V+, CD41 and CD42b, citrate:cis-aconitate, citrate:malate, acetate:cis-aconitate, glucose:lactose, acetate:succinate, acetate:lactose, or any combinations thereof.

In some embodiments, the biomarkers are selected from values of glutamine, niacinamide, glutathione oxidized, succinic acid, sCD40L, CD41, CD63 (or CD63+), Annexin-V+ (or Annexin-V), CD42b, citrate, cis-aconitate, malate, acetate, lactose, CD41:CD63, CD41:Annexin-V+, CD41:CD42b, citrate:cis-aconitate, citrate:malate, acetate:cis-aconitate, glucose:lactose, acetate:succinate, acetate:lactose, or any combinations thereof.

In some embodiments, biomarkers for determining the phase of platelets include concentration of glutamine, concentration of niacinamide, concentration of glutathione oxidized, concentration of succinic acid, concentration of sCD40L, value of CD41:CD63 (e.g., percentage of cells double positive or expressing both CD41 and CD63+ in a cell population), value of CD41:Annexin-V (e.g., percentage of cells double positive or expressing both CD41 and Annexin-V+ in a cell population), value of CD41:CD42b (e.g., percentage of cells double positive or expressing both CD41 and CD42b in a cell population), ratio of citrate:cis-aconitate, ratio of citrate:malate, ratio of acetate:cis-aconitate, ratio of glucose:lactose, ratio of acetate:succinate, ratio of acetate:lactose, or any combinations thereof. In some embodiments, the biomarker is concentration of glutamine. In some embodiments, the biomarker is concentration of niacinamide. In some embodiments, the biomarker is concentration of glutathione oxidized. In some embodiments, the biomarker is concentration of succinic acid. In some embodiments, the biomarker is concentration of sCD40L. In some embodiments, the biomarker is value of CD41:CD63. In some instances, the value of CD41:CD63 is the percentage of cells double positive or expressing both CD41 and CD63+ in a cell population. In some embodiments, the biomarker is value of CD41:Annexin-V. In some embodiments, the value of CD41:Annexin-V is the percentage of cells double positive or expressing both CD41 and Annexin-V+ in a cell population. In some embodiments, the biomarker is value of CD41:CD42b. In some embodiments, the value of CD41:CD42b is the percentage of cells double positive or expressing both CD41 and CD42b in a cell population. In some embodiments, the biomarker is ratio of citrate:cis-aconitate. In some embodiments, the biomarker is ratio of citrate:malate. In some embodiments, the biomarker is ratio of acetate:cis-aconitate. In some embodiments, the biomarker is ratio of glucose:lactose. In some embodiments, the biomarker is ratio of acetate:succinate. In some embodiments, the biomarker is ratio of acetate:lactose.

In some embodiments, any suitable platelet component or any physiological, biochemical or molecular parameters associated with the presence of a specific physiological state or process of the platelet are used as a biomarker.

In some embodiments, the platelet components are extracellular components. In some embodiments, the platelet components are located in the platelet medium. In some embodiments, the platelet components are located in the surrounding blood plasma. In some embodiments, the platelet components are intracellular components. In some embodiments, the platelet component comprises surface markers. In some embodiments, the platelet is processed by apheresis, by buffy coat method, or by platelet-rich-plasma (PRP) method. In some embodiments, the platelet is processed by apheresis or buffy coat method.

In some embodiments, the platelet is processed by apheresis. Apheresis (also known as pheresis, or hemapheresis) is a process in which whole blood is separated into individual components such as RBCs, platelets, and plasma, and from which an individual component (e.g., platelet) is harvested. In some instances, apheresis allows for removal of disease-provoking components to be removed. In some instances, the process involves whole blood obtained from a patient is passed through an apparatus that separates out one particular component from the blood by such as a centrifugation method and returning the remainder of the blood back to the patient. In some instances, multiple units of platelets are obtained from a single patient.

In some embodiments, a metabolite associated with the apheresis processed platelet is selected from: dimethylglycine, choline, proline, nicotinamide, hydroxyproline, isoleucine, asparagine, adenine, hypoxanthine, lysine, methionine, guanine, histidine, carnitine, phenylalanine, methyl histidine, arginine, citrulline, fructose, glucose, mannose, phosphocholine, ADMA, acetylcarnitine, tryptophan, cystine, cytidine, thiamine, 5-MTA, glutathione reduced, S-adenosylhomocysteine (SAH), S-adenosylmethionine (SAMe), glutathione oxidized, alanine, serine, glyceric acid, fumaric acid, valine, succinic acid, threonine, 5-oxoproline, aspartic acid, malate, glutamine, xanthine, uric acid, aconitic acid, ascorbic acid, tyrosine, citric acid, uridine, inosine, guanosine, lactic acid, taurine, glutamic acid, phosphoenolpyruvate, glycerol-P, 2-phosphoglycerate, fructose 6-P, glucose 6-P, 6-phosphogluconate, CMP, UMP, fructose-1,6-diP, AMP, IMP. GMP, UDP, ADP, GDP, ATP, ADP-ribose, FAD, glycerophospho-inositol, ascorbate-phosphate, C3 Carnitine, C4 Carnitine, C5 Carnitine, CDP-choline, CDP-ethanolamine, dihydroxy stearic acid, disaccharide, HETEs, LPC 16:0, LPC 16:1, LPC 18:0, LPC 18:1, LPC 18:2, LPC 18:3, acetylneuraminic acid, phosphoryl-ethanolamine, pentose-5-phosphate, phtalic acid, sedoheptulose-7-phosphate, glycero-phosphocholine, sphingosine, sphingosine-1-phosphate, tetrasaccharide, trisaccharide, UDP-glucuronate, UDP-acetylglucosamine, niacinamide, sCD40L, CD41, CD63+, Annexin-V+, CD42b, citrate, cis-aconitate, malate, acetate, lactose, or any combinations thereof.

In some embodiments, the biomarkers associated with the apheresis processed platelet are selected from values of dimethylglycine, choline, proline, nicotinamide, hydroxyproline, isoleucine, asparagine, adenine, hypoxanthine, lysine, methionine, guanine, histidine, carnitine, phenylalanine, methyl histidine, arginine, citrulline, fructose, glucose, mannose, phosphocholine, ADMA, acetylcarnitine, tryptophan, cystine, cytidine, thiamine, 5-MTA, glutathione reduced, S-adenosylhomocysteine (SAH), S-adenosylmethionine (SAMe), glutathione oxidized, alanine, serine, glyceric acid, fumaric acid, valine, succinic acid, threonine, 5-oxoproline, aspartic acid, malate, glutamine, xanthine, uric acid, aconitic acid, ascorbic acid, tyrosine, citric acid, uridine, inosine, guanosine, lactic acid, taurine, glutamic acid, phosphoenolpyruvate, glycerol-P, 2-phosphoglycerate, fructose 6-P, glucose 6-P, 6-phosphogluconate, CMP, UMP, fructose-1,6-diP, AMP, IMP. GMP, UDP, ADP, GDP, ATP, ADP-ribose, FAD, glycerophospho-inositol, ascorbate-phosphate, C3 Carnitine, C4 Carnitine, C5 Carnitine, CDP-choline, CDP-ethanolamine, dihydroxy stearic acid, disaccharide, HETEs, LPC 16:0, LPC 16:1, LPC 18:0, LPC 18:1, LPC 18:2, LPC 18:3, acetylneuraminic acid, phosphoryl-ethanolamine, pentose-5-phosphate, phtalic acid, sedoheptulose-7-phosphate, glycero-phosphocholine, sphingosine, sphingosine-1-phosphate, tetrasaccharide, trisaccharide, UDP-glucuronate, UDP-acetylglucosamine, niacinamide, sCD40L, CD41, CD63+, Annexin-V+, CD42b, citrate, cis-aconitate, malate, acetate, lactose, CD41 and CD63+, CD41 and Annexin-V+, CD41 and CD42b, citrate:cis-aconitate, citrate:malate, acetate:cis-aconitate, glucose:lactose, acetate:succinate, acetate:lactose, or any combinations thereof.

In some embodiments, the biomarkers associated with the apheresis processed platelet are selected from values of glutamine, niacinamide, glutathione oxidized, succinic acid, sCD40L, CD41, CD63+(or CD63), Annexin-V+(Annexin-V), CD42b, citrate, cis-aconitate, malate, acetate, lactose, CD41:CD63+, CD41:Annexin-V, CD41:CD42b, citrate:cis-aconitate, citrate:malate, acetate:cis-aconitate, glucose:lactose, acetate:succinate, acetate:lactose, or any combinations thereof.

In some embodiments, biomarkers associated with the apheresis processed platelet for determining the phase of platelets include concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combinations thereof.

In some embodiments, a biomarker associated with the apheresis processed platelet is selected from concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combinations thereof.

In some embodiments, the platelet is processed by buffy coat method. In some instances, buffy coat method involves obtaining a fraction of a whole blood sample that contains white blood cells (or leukocytes) and platelets following centrifugation of the blood. In some instances, the fraction containing white blood cells and platelets is the buffy coat. In some instances, the buffy coat is subjected to an additional centrifugation and/or filtration step to separate platelets from the white blood cells. In some instances, multiple collections of buffy coat are pooled together prior to the additional centrifugation and/or filtration step to harvest platelets. In some instances, multiple collections of buffy coat are pooled together to obtain one unit of platelets.

In some embodiments, a metabolite associated with the buffy coat processed platelet is selected from: dimethylglycine, choline, proline, nicotinamide, hydroxyproline, isoleucine, asparagine, adenine, hypoxanthine, lysine, methionine, guanine, histidine, carnitine, phenylalanine, methyl histidine, arginine, citrulline, fructose, glucose, mannose, phosphocholine, ADMA, acetylcarnitine, tryptophan, cystine, cytidine, thiamine, 5-MTA, glutathione reduced, S-adenosylhomocysteine (SAH), S-adenosylmethionine (SAMe), glutathione oxidized, alanine, serine, glyceric acid, fumaric acid, valine, succinic acid, threonine, 5-oxoproline, aspartic acid, malate, glutamine, xanthine, uric acid, aconitic acid, ascorbic acid, tyrosine, citric acid, uridine, inosine, guanosine, lactic acid, taurine, glutamic acid, phosphoenolpyruvate, glycerol-P, 2-phosphoglycerate, fructose 6-P, glucose 6-P, 6-phosphogluconate, CMP, UMP, fructose-1,6-diP, AMP, IMP. GMP, UDP, ADP, GDP, ATP, ADP-ribose, FAD, glycerophospho-inositol, ascorbate-phosphate, C3 Carnitine, C4 Carnitine, C5 Carnitine, CDP-choline, CDP-ethanolamine, dihydroxy stearic acid, disaccharide, HETEs, LPC 16:0, LPC 16:1, LPC 18:0, LPC 18:1, LPC 18:2, LPC 18:3, acetylneuraminic acid, phosphoryl-ethanolamine, pentose-5-phosphate, phtalic acid, sedoheptulose-7-phosphate, glycero-phosphocholine, sphingosine, sphingosine-1-phosphate, tetrasaccharide, trisaccharide, UDP-glucuronate, UDP-acetylglucosamine, niacinamide, sCD40L, CD41, CD63+, Annexin-V+, CD42b, citrate, cis-aconitate, malate, acetate, lactose, or any combinations thereof.

In some embodiments, the biomarkers associated with the buffy coat processed platelet are selected from values of dimethylglycine, choline, proline, nicotinamide, hydroxyproline, isoleucine, asparagine, adenine, hypoxanthine, lysine, methionine, guanine, histidine, carnitine, phenylalanine, methyl histidine, arginine, citrulline, fructose, glucose, mannose, phosphocholine, ADMA, acetylcarnitine, tryptophan, cystine, cytidine, thiamine, 5-MTA, glutathione reduced, S-adenosylhomocysteine (SAH), S-adenosylmethionine (SAMe), glutathione oxidized, alanine, serine, glyceric acid, fumaric acid, valine, succinic acid, threonine, 5-oxoproline, aspartic acid, malate, glutamine, xanthine, uric acid, aconitic acid, ascorbic acid, tyrosine, citric acid, uridine, inosine, guanosine, lactic acid, taurine, glutamic acid, phosphoenolpyruvate, glycerol-P, 2-phosphoglycerate, fructose 6-P, glucose 6-P, 6-phosphogluconate, CMP, UMP, fructose-1,6-diP, AMP, IMP. GMP, UDP, ADP, GDP, ATP, ADP-ribose, FAD, glycerophospho-inositol, ascorbate-phosphate, C3 Carnitine, C4 Carnitine, C5 Carnitine, CDP-choline, CDP-ethanolamine, dihydroxy stearic acid, disaccharide, HETEs, LPC 16:0, LPC 16:1, LPC 18:0, LPC 18:1, LPC 18:2, LPC 18:3, acetylneuraminic acid, phosphoryl-ethanolamine, pentose-5-phosphate, phtalic acid, sedoheptulose-7-phosphate, glycero-phosphocholine, sphingosine, sphingosine-1-phosphate, tetrasaccharide, trisaccharide, UDP-glucuronate, UDP-acetylglucosamine, niacinamide, sCD40L, CD41, CD63+, Annexin-V+, CD42b, citrate, cis-aconitate, malate, acetate, lactose, CD41 and CD63+, CD41 and Annexin-V+, CD41 and CD42b, citrate:cis-aconitate, citrate:malate, acetate:cis-aconitate, glucose:lactose, acetate:succinate, acetate:lactose, or any combinations thereof.

In some embodiments, the biomarkers associated with the buffy coat processed platelet are selected from values of glutamine, niacinamide, glutathione oxidized, succinic acid, sCD40L, CD41, CD63+, Annexin-V+, CD42b, citrate, cis-aconitate, malate, acetate, lactose, CD41:CD63+, CD41:Annexin-V+, CD41:CD42b, citrate:cis-aconitate, citrate:malate, acetate:cis-aconitate, glucose:lactose, acetate:succinate, acetate:lactose, or any combinations thereof.

In some embodiments, biomarkers associated with the buffy coat processed platelet for determining the phase of platelets include concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combinations thereof.

In some embodiments, a biomarker associated with the buffy coat processed platelet is selected from concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combinations thereof.

In some embodiments, the platelet components are extracellular components. In some embodiments, the biomarker obtained from the extracellular portion is concentration of glutamine, concentration of niacinamide, concentration of glutathione oxidized, or concentration of succinic acid. In some instances, the biomarker obtained from the extracellular portion through apheresis is concentration of glutamine, and concentration of niacinamide. In some instances, the biomarker obtained from the extracellular portion through apheresis is concentration of glutamine. In some instances, the biomarker obtained from the extracellular portion through apheresis is concentration of niacinamide. In some instances, the biomarker obtained from the extracellular portion through buffy coat method is concentration of glutamine, concentration of glutathione oxidized, and concentration of succinic acid. In some instances, the biomarker obtained from the extracellular portion through buffy coat method is concentration of glutamine. In some instances, the biomarker obtained from the extracellular portion through buffy coat method is concentration of glutathione oxidized. In some instances, the biomarker obtained from the extracellular portion through buffy coat method is concentration of succinic acid.

In some embodiments, the platelet components are intracellular components. In some embodiments, the biomarker obtained from the intracellular portion is concentration of glutamine, concentration of niacinamide, concentration of glutathione oxidized, or concentration of succinic acid. In some instances, the biomarker obtained from the intracellular portion through apheresis is concentration of glutathione oxidized. In some instances, the biomarker obtained from the intracellular portion through buffy coat method is concentration of glutathione oxidized.

Platelets Metabolic Phases

Figure 14:
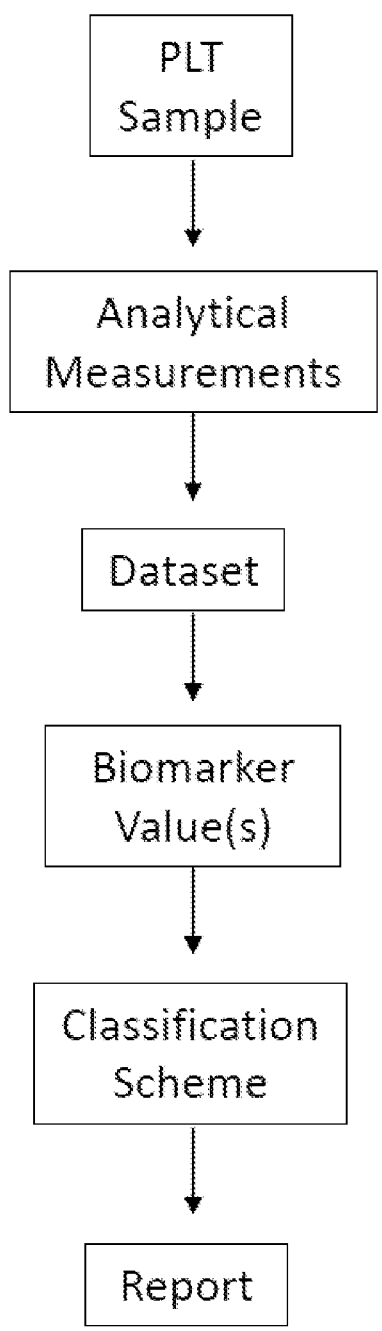
FIG. 14 illustrates a conceptual schematic for determination of a phase of a platelet (PLT) sample
Figure 15A:
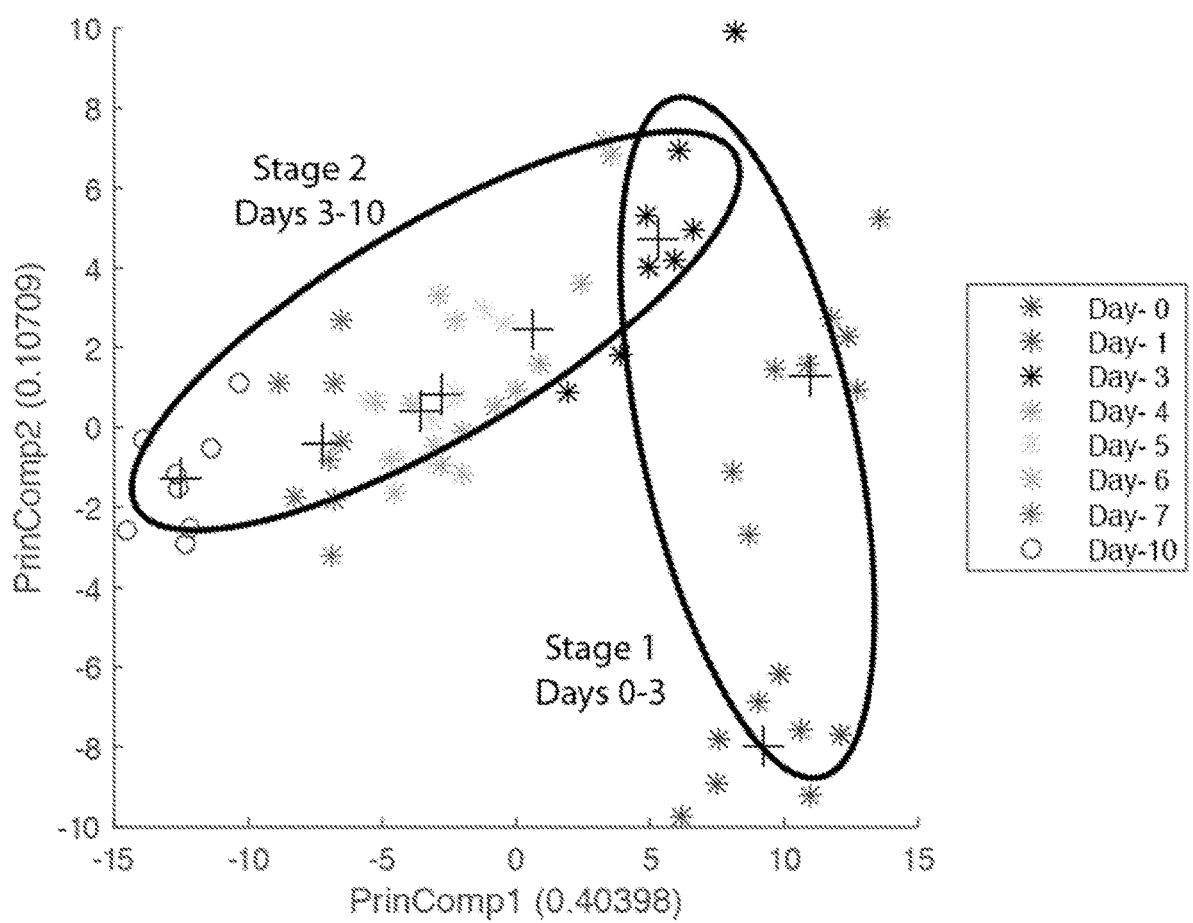
FIG. 15A and FIG. 15B illustrate exemplary signature profiles of platelets.
Figure 15B:
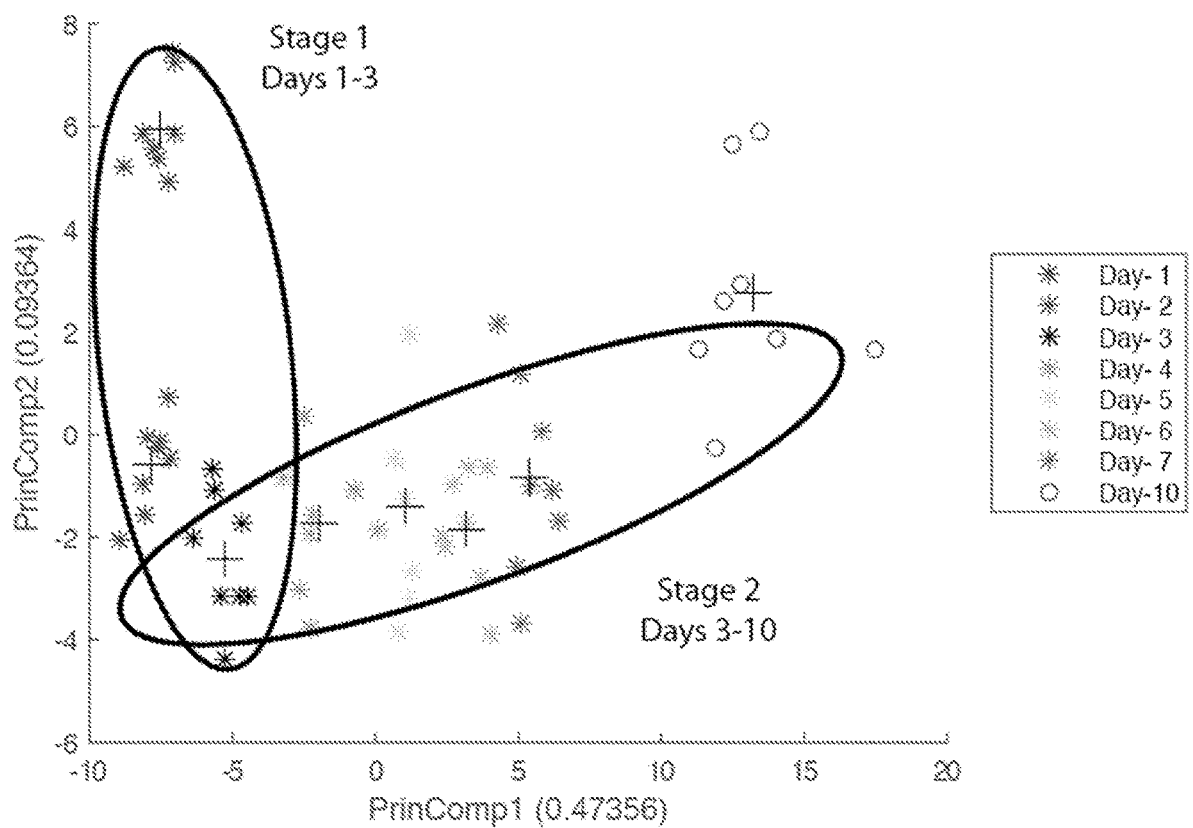
Figure 16A:
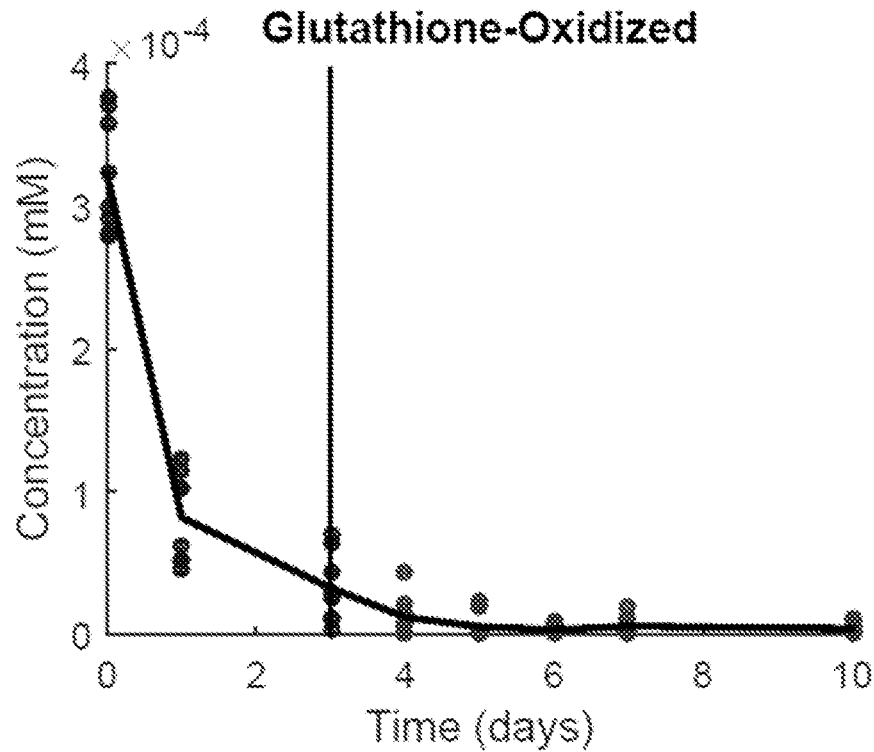
FIG. 16A and FIG. 16B illustrate exemplary signature profiles of glutathione oxidized.
Figure 16B:
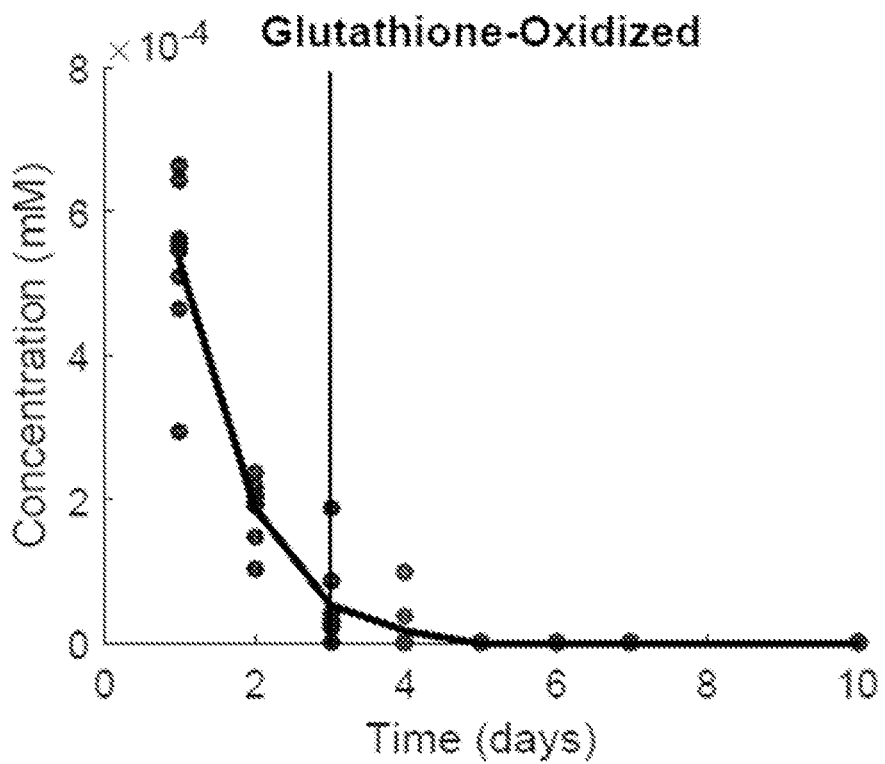

Platelets (PLTs) are classified based on their metabolic state or phase. FIG. 14 illustrates a conceptual schematic for determining a phase of a platelet (PLT) sample. The platelet sample is analyzed by assays or analytical chemistry techniques and methods described herein to generate raw data used to determine one or more of the biomarkers described herein. The raw data is compiled into a dataset and analyzed by a computer program to determine the value of one or more biomarkers. The value of one or more biomarkers is then used by the computer program to classify the platelet sample into a metabolic phase based on their values as greater than or less than the transition values in the control, whereby the transition values indicate the transition from a first metabolic state to a second metabolic state. A report is then generated to indicate either an assignment of a phase to the platelet sample or a failure to assign a phase to the platelet sample.

In some embodiments, the platelets have 1, 2, 3, 4, 5, or more phases. In some embodiments, the platelets are classified into two phases. The two phases are First Phase and Second Phase. The two phases indicate a metabolic state of the platelets. In some embodiments, the platelets are classified into First Phase, and/or Second Phase. In some embodiments, the platelets are classified into First Phase. In some embodiments, the platelets are classified into Second Phase. In some embodiments, the metabolic state or phase of the platelets refers to the metabolic state of the platelet during storage. In some embodiments, the metabolic state is at least one defined state; preferably one of a first or a second. Such defined states correspond to the First Phase or Second Phase of the platelets described herein. In some embodiments, a first defined metabolic state corresponds to First Phase. In some embodiments, a second defined metabolic state corresponds to Second Phase.

In some embodiments, the two phases or metabolic states are characterized by a set of biomarkers. In some embodiments, the set of biomarkers is selected from the group consisting of concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, and ratio of acetate:lactose. In some instances, First Phase is characterized by the set of biomarkers selected from the group consisting of concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, and ratio of acetate:lactose. In some instances, Second Phase is characterized by the set of biomarkers selected from the group consisting of concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, and ratio of acetate:lactose.

In some embodiments, the biomarkers are obtained from the extracellular portion of the platelet sample. In some instants, the set of biomarkers obtained from the extracellular portion include concentration of glutamine, concentration of niacinamide, concentration of glutathione oxidized, and concentration of succinic acid. In some aspects, the biomarkers obtained from the extracellular portion are concentration of glutamine, concentration of niacinamide, concentration of glutathione oxidized, and concentration of succinic acid. In some embodiments, First Phase is characterized by the set of biomarkers obtained from the extracellular portion. In some embodiments, Second Phase is characterized by the set of biomarkers obtained from the extracellular portion.

In some embodiments, the biomarkers are obtained from the intracellular portion of the platelet sample. In some instants, the set of biomarkers obtained from the intracellular portion include concentration of glutathione oxidized. In some embodiments, First Phase is characterized by the set of biomarkers obtained from the intracellular portion. In some embodiments, Second Phase is characterized by the set of biomarkers obtained from the intracellular portion.

As disclosed elsewhere herein, a biomarker is a single value or is a range of values. In some embodiments, the value or the range of values is from about 0 to about 100, about 0 to about 50, about 0 to about 20 or about 0 to about 10. In some embodiments, the value or the range of values of a biomarker is represented with a unit (e.g., M, mM, µM, nM, mmHg) or is unitless. In some embodiment, the unit is a mass, concentration, volume, pressure, signal, absorbance, distance, time or a ratio of two or more units (e.g. absorbance/time or concentration/volume).

In some embodiments, the value is represented as a ratio of two or more biomarkers. In some embodiments, the ratio is about 0 to about 10,000, about 0 to about 5000, about 0 to about 2000 or about 0 to about 1000.

In some embodiments, the value of the biomarker is correlated to time. In some embodiments, the time is represented as minutes, hours, days, months or years. In some embodiments, the time is represented as days. In some embodiments, the time indicates a range of days. In some embodiments, the time is about 1, 2, 3, 4, 5, 6, 7, 8, 9, 10, 11, 12, 13, 14, 15, 16, 17, 18, 19, or 20 days. In some embodiments, a set of values is correlated to time. In some embodiments, the two phases are correlated to time.

In some embodiments, a phase is assigned to the platelet sample based on the value of the biomarker by a computer program. In some embodiments, the computer program determines if the value of the biomarker is greater than or less than a value on a control indicated as a transition value from first phase to second phase. Based on the value, the computer in some cases assigns a phase to the sample. In some embodiments, the control is represented as a signature profile. As described elsewhere herein, a signature profile characterizes a measurement of a metabolite, a platelet component, a physiological, biochemical or molecular parameter at a specific biological condition, or a ratio of these measurements. In some embodiments, the concentration of glutathione oxidized, ratio of acetate:cis-aconitate, and either ratio of glucose:lactose or ratio of acetate:lactose are greater than the values on the control indicated as the transition from the first metabolic state to the second metabolic state. In some instances, First Phase is assigned by the computer program to the platelet sample when the concentration of glutathione oxidized, ratio of acetate:cis-aconitate, and either ratio of glucose:lactose or ratio of acetate:lactose are greater than the values on the control indicated as the transition from the first metabolic state to the second metabolic state. In some embodiments, the concentration of glutathione oxidized, ratio of acetate:cis-aconitate, and either ratio of glucose:lactose or ratio of acetate:lactose are less than the values on the control indicated as the transition from the first metabolic state to the second metabolic state. In some instances, Second Phase is assigned by the computer program to the platelet sample when the concentration of glutathione oxidized, ratio of acetate:cis-aconitate, and either ratio of glucose:lactose or ratio of acetate:lactose are less than the values on the control indicated as the transition from the first metabolic state to the second metabolic state.

In some embodiments, the platelets are processed by apheresis. In some embodiments, the platelets are processed by buffy coat method.

In some embodiments, the value of a biomarker is used to predict the duration of the platelet sample in a particular phase. In some embodiments, when the concentration of glutathione oxidized, ratio of acetate:cis-aconitate, and either ratio of glucose:lactose or ratio of acetate:lactose are closer to the values on the control indicated as the transition from the first metabolic state to the second metabolic state, this indicates that the platelet sample will likely undergo a metabolic shift into Second Phase. In some embodiments, the value of the biomarker is used to predict how long the platelet sample remains in First Phase.

In some embodiments, the two phases or metabolic states correspond to the quality of the platelet. In some embodiments, First Phase indicates the quality of the platelet as near to fresh platelets (e.g. from blood that is freshly drawn from a donor). In some embodiments, First Phase indicates the quality of the platelet as containing a set of biomarkers that would be similar to the set of biomarkers found in fresh platelet. In some embodiment, Second Phase indicates the quality of the platelet in as aged platelet.

First Phase—Platelets

In some embodiments, First Phase is characterized by a set of biomarkers. In some embodiments, the set of biomarkers is selected from concentration of glutamine, concentration of niacinamide, concentration of glutathione oxidized, concentration of succinic acid, concentration of sCD40L, value of CD41:CD63 (e.g., percentage of cells double positive or expressing both CD41 and CD63+ in a cell population), value of CD41:Annexin-V (e.g., percentage of cells double positive or expressing both CD41 and Annexin-V+ in a cell population), value of CD41:CD42b (e.g., percentage of cells double positive or expressing both CD41 and CD42b in a cell population), ratio of citrate:cis-aconitate, ratio of citrate:malate, ratio of acetate:cis-aconitate, ratio of glucose:lactose, ratio of acetate:succinate, ratio of acetate:lactose, or any combination thereof. In some embodiments, the set of biomarkers is concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose. In some embodiments, the platelet sample is classified as First Phase based on the concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose. In some instances, the quality of the platelet sample is determined based on the concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose.

In some embodiments, the biomarkers are obtained from the extracellular portion of the platelet sample. In some embodiments, the set of biomarkers obtained from the extracellular portion include concentration of glutamine, concentration of niacinamide, concentration of glutathione oxidized, and concentration of succinic acid. In some embodiments, the set of biomarkers obtained from the extracellular portion is concentration of glutamine, concentration of niacinamide, concentration of glutathione oxidized, and concentration of succinic acid. In some embodiments, First Phase is characterized by the set of biomarkers obtained from the extracellular portion.

In some embodiments, the biomarkers are obtained from the intracellular portion of the platelet sample. In some embodiments, the set of biomarkers obtained from the intracellular portion include concentration of glutamine, concentration of niacinamide, concentration of glutathione oxidized, and concentration of succinic acid. In some embodiments, the set of biomarkers obtained from the intracellular portion is concentration of glutamine, concentration of niacinamide, concentration of glutathione oxidized, and concentration of succinic acid. In some embodiments, First Phase is characterized by the set of biomarkers obtained from the intracellular portion.

In some embodiments, the set of biomarkers selected from concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose are indicated with a set of values. In some embodiments, the value is associated with a unit or is unitless. In some embodiments, the value is a ratio. In some embodiments, the unit is in millimolar (mM) concentration, ng/mL, or as a percentage.

Apheresis

In some embodiments, the biomarkers are obtained from an apheresis processed platelet sample. In some embodiments, biomarkers associated with the apheresis processed platelet sample for determining the phase of platelets include concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combinations thereof. In some embodiments, a biomarker associated with the apheresis processed platelet is selected from concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combinations thereof. In some embodiments, a biomarker associated with the apheresis processed platelet is selected from concentration of glutathione oxidized, ratio of acetate:cis-aconitate, and ratio of glucose:lactose.

In some embodiments, First Phase is assigned the apheresis processed platelet sample based on concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combinations thereof. In some embodiments, First Phase is assigned the apheresis processed platelet sample based on concentration of glutathione oxidized, ratio of acetate:cis-aconitate, ratio of glucose:lactose, concentration of sCD40L, and value of CD41:CD63. In some embodiments, First Phase is assigned the apheresis processed platelet sample based on concentration of glutathione oxidized, ratio of acetate:cis-aconitate, and ratio of glucose:lactose.

In some embodiments, First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state. In some embodiments, First Phase is assigned to the apheresis processed platelet sample where the concentration of glutathione oxidized, ratio of acetate:cis-aconitate, and ratio of glucose:lactose are greater than the values on the control indicated as the transition from the first metabolic state to the second metabolic state and concentration of sCD40L, and value of CD41:CD63 are less than the values on the control indicated as the transition from the first metabolic state to the second metabolic state. In some embodiments, First Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some instances, the concentration of glutathione oxidized is the intracellular concentration of gluthione oxidized. In some embodiments, First Phase is assigned to the apheresis processed platelet sample where the intracellular concentration of glutathione oxidized, ratio of acetate:cis-aconitate, and ratio of glucose:lactose are greater than the values on the control indicated as the transition from the first metabolic state to the second metabolic state. In some embodiments, First Phase is assigned to the apheresis processed platelet sample where the intracellular concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of sCD40L, and value of CD41:CD63 are less than the values on the control indicated as the transition from the first metabolic state to the second metabolic state. In some embodiments, First Phase is assigned to the apheresis processed platelet sample where the extracellular concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state.

In some embodiments, the concentration of glutathione oxidized greater than 2.22E-05 mM is associated with First Phase. In some embodiments, the concentration of glutathione oxidized is the intracellular concentration of glutathione oxidized. In some embodiments, the intracellular concentration of glutathione oxidized greater than 2.22E-05 mM is associated with First Phase.

In some embodiments, the concentration of glutamine greater than 0.11 mM is associated with First Phase.

In some embodiments, the concentration of niacinamide less than 0.0035 mM is associated with First Phase.

In some embodiments, the concentration of sCD40L less than 20.8 ng/mL is associated with First Phase.

In some embodiments, the value of CD41:CD63 less than 24.3% is associated with First Phase.

In some embodiments, the ratio of citrate:cis-aconitate greater than 228.3 is associated with First Phase.

In some embodiments, the ratio of citrate:malate greater than 470.6 is associated with First Phase.

In some embodiments, the ratio of acetate:cis-aconitate greater than 680.6 is associated with First Phase.

In some embodiments, the ratio of glucose:lactose greater than 0.569 is associated with First Phase.

Buffy Coat

In some embodiments, the biomarkers are obtained from a buffy coat processed platelet sample. In some embodiments, biomarkers associated with the buffy coat processed platelet sample for determining the phase of platelets include concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combinations thereof. In some embodiments, a biomarker associated with the buffy coat processed platelet sample is selected from concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combination thereof. In some embodiments, a biomarker associated with the buffy coat processed platelet sample is selected from concentration of glutathione oxidized, ratio of acetate:cis-aconitate, and ratio of acetate:lactose.

In some embodiments, First Phase is assigned to the buffy coat processed platelet sample based on concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, and ratio of acetate:lactose. In some embodiments, First Phase is assigned to the buffy coat processed platelet sample based on concentration of glutathione oxidized, concentration of sCD40L, value of CD41:Annexin-V, value of CD41:CD42b, ratio of acetate:cis-aconitate, and ratio of acetate:lactose. In some embodiments, First Phase is assigned to the buffy coat processed platelet sample based on concentration of glutathione oxidized, ratio of acetate:cis-aconitate, and ratio of acetate:lactose.

In some embodiments, First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, First Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state and the concentration of sCD40L, value of CD41:Annexin-V, and value of CD41:CD42b are less than the values on the control indicated as the transition from the first metabolic state to the second metabolic state. In some embodiments, First Phase is assigned to the buffy coat processed platelet where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some embodiments, the concentration of glutathione oxidized is the extracellular concentration of glutathione oxidized or the intracellular concentration of glutathione oxidized. In some embodiments, First Phase is assigned to the buffy coat processed platelet where the extracellular concentration of glutathione oxidized, ratio of acetate:cis-aconitate, and ratio of acetate:lactose are greater than the values on the control indicated as the transition from the first metabolic state to the second metabolic state. In some embodiments, First Phase is assigned to the buffy coat processed platelet sample where the extracellular concentration of glutathione oxidized, ratio of acetate:cis-aconitate, and ratio of acetate:lactose are greater than the values on the control indicated as the transition from the first metabolic state to the second metabolic state and the concentration of sCD40L, value of CD41:Annexin-V, and value of CD41:CD42b are less than the values on the control indicated as the transition from the first metabolic state to the second metabolic state. In some embodiment, First Phase is assigned to the buffy coat processed platelet where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state.

In some embodiments, the extracellular concentration of glutathione oxidized greater than 5.91E-04 mM is associated with First Phase.

In some embodiments, the intracellular concentration of glutathione oxidized greater than 3.6E-05 mM is associated with First Phase.

In some embodiments, the concentration of glutamine greater than 0.42 mM is associated with First Phase.

In some embodiments, the concentration of succinic acid less than 0.0128 mM is associated with First Phase.

In some embodiments, the value of CD41:Annexin-V less than 3.2% is associated with First Phase.

In some embodiments, the value of CD41:CD42b less than 1.7% is associated with First Phase.

In some embodiments, the concentration of sCD40L less than 15 ng/mL is associated with First Phase.

In some embodiments, the ratio of citrate:cis-aconitate greater than 314 is associated with First Phase.

In some embodiments, the ratio of acetate:cis-aconitate greater than 835.7 is associated with First Phase.

In some embodiments, the ratio of acetate:succinate greater than 1644 is associated with First Phase.

In some embodiments, the ratio of acetate:lactose greater than 3 is associated with First Phase.

Platelets Storage Conditions and Additional Features

In some embodiments, a storage condition is correlated to storage time, storage temperature, and/or addition of an additive solution.

In some embodiments, First Phase is correlated to about day 0 to about day 20, about day 1 to about day 15, or about day 1 to about day 10 of storage. In some embodiments, First Phase is correlated to about day 0, 1, 2, 3, 4, 5, 6, or day 7 of storage. In some embodiments, First Phase is correlated to about day 0, 1, 2, 3, 4, or day 5 of storage. In some embodiments, First Phase is correlated to about day 0, 1, 2, 3, or day 4 of storage. In some embodiments, First Phase is correlated to about day 0, 1, 2, or day 3 of storage.

In some embodiments, for apheresis processed platelets, day 0 indicates the day on which the platelets are harvested from a patient and processed for storage. In some embodiments, for apheresis processed platelets, day 1 indicates 24 hours of storage.

In some embodiments, for buffy coat processed platelets, day 1 indicates the day on which the platelets are processed by the buffy coat method. In some embodiments, for buffy coat processed platelets, day 0 indicates the day in which platelets as whole blood is harvested from a patient. In some embodiments, day 2 indicates 24 hours of storage.

In some embodiments, the value of a biomarker is used to predict how long the platelet sample remains in First Phase. In some embodiments, when the concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose, correspond to a value that is not near to the transition value indicated by the control, this indicates that the platelet sample remains in First Phase for 0, 1, 2, 3, 4, 5, 6, 7 or more days. In some embodiments, when the concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose, correspond to a value that is near to the transition value indicated by the control, this indicates that the platelet sample remains in First Phase for less than 0, 1, 2, 3, 4, 5, 6, 7 or more days.

In some embodiments, any platelet sample is characterized as First Phase regardless of storage age, storage condition (e.g. storage temperature or addition of an additive solution) or donor genetic variations (e.g. age, sex or a donor's health). In some embodiments, a platelet sample stored for 1, 2, 3, 4, 5, 6, 7, 8, 9, 10, 11, 12, 13, 14, 15, 16, 17, 18, 19, or 20 days is characterized as First Phase. In some embodiments, a platelet sample which has been in storage for about 5 days or for about 7 days is characterized as First Phase if the concentration of glutathione oxidized, and acetate:cis-aconitate, and either ratio of glucose:lactose or ratio of acetate:lactose as greater than the values on the control indicated as the transition from the first metabolic state to the second metabolic state. In some embodiments, a platelet sample process by apheresis which has been in storage for about 5 days or for about 7 days is characterized as First Phase if the concentration of glutathione oxidized, ratio of acetate:cis-aconitate, and ratio of glucose:lactose are greater than the values on the control indicated as the transition from the first metabolic state to the second metabolic state. In some embodiments, a platelet sample process by apheresis which has been in storage for about 5 days or for about 7 days is characterized as First Phase if the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, a platelet sample process by buffy coat method which has been in storage for about 5 days or for about 7 days is characterized as First Phase if the concentration of glutathione oxidized, ratio of acetate:cis-aconitate, and ratio of acetate:lactose are greater than the values on the control indicated as the transition from the first metabolic state to the second metabolic state. In some embodiments, a platelet sample process by buffy coat method which has been in storage for about 5 days or for about 7 days is characterized as First Phase if the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state.

In some embodiments, the storage condition is a storage temperature. In some embodiments, the storage temperature is from about −80° C. to about 25° C., about 0° C. to about 25° C., or about 20° C. to about 25° C. In some embodiments, a platelet sample which has been in a storage temperature of about 20° C., 21° C., 22° C., 23° C., 24° C., or 25° C. is characterized as First Phase if the concentration of glutathione oxidized, ratio of acetate:cis-aconitate, and either ratio of glucose:lactose or ratio of acetate:lactose as greater than the values on the control indicated as the transition from the first metabolic state to the second metabolic state. In some embodiments, a platelet sample process by apheresis which has been in a storage temperature of about 20° C. to about 25° C. is characterized as First Phase if the concentration of glutathione oxidized, ratio of acetate:cis-aconitate, and ratio of glucose:lactose are greater than the values on the control indicated as the transition from the first metabolic state to the second metabolic state. In some embodiments, a platelet sample process by apheresis which has been a storage temperature of about 20° C. to about 25° C. is characterized as First Phase if the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, a platelet sample process by buffy coat method which has been in a storage temperature of about 20° C. to about 25° C. is characterized as First Phase if the concentration of glutathione oxidized, ratio of acetate:cis-aconitate, and ratio of acetate:lactose are greater than the values on the control indicated as the transition from the first metabolic state to the second metabolic state. In some embodiments, a platelet sample process by buffy coat method which has been in a storage temperature of about 20° C. to about 25° C. is characterized as First Phase if the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state.

In some embodiments, a platelet sample stored under any storage condition is characterized as First Phase. In some embodiments, the storage condition is a storage temperature or the addition of an additive solution. In some embodiments, the additive solution includes Examplary PLT additive solutions include, but are not limited to, PAS-1 (PAS-I plasmalyte), PAS-B (PAS-II or T-Sol), PAS-C(PAS-III or Intersol), PAS-D (ComposolPS), PAS-E (PAS-IIIM SSP+), PAS-F (PlasmaLyte A, Isoplate), PAS-G, or M-Sol. In some embodiments, platelets are not stored in the presence of an additive solution.

In some embodiments, a platelet sample regardless of donor genetic variation (e.g. age, sex or a donor's health) is characterized as First Phase. In some embodiments, a platelet sample regardless of donor genetic variation is characterized as First Phase if the concentration of glutathione oxidized, ratio of acetate:cis-aconitate, and either ratio of glucose:lactose or ratio of acetate:lactose as greater than the values on the control indicated as the transition from the first metabolic state to the second metabolic state. In some embodiments, a platelet sample process by apheresis regardless of donor genetic variation is characterized as First Phase if the concentration of glutathione oxidized, ratio of acetate:cis-aconitate, and ratio of glucose:lactose are greater than the values on the control indicated as the transition from the first metabolic state to the second metabolic state. In some embodiments, a platelet sample process by apheresis regardless of donor genetic variation is characterized as First Phase if the concentration of glutathione oxidized, concentration of glutamine, ratio of acetate:cis-aconitate, ratio of glucose:lactose, ratio of citrate:cis-aconitate, and ratio of citrate:malate are greater than the values on the control indicated as the transition from the first metabolic state to the second metabolic state and concentration of niacinamide, concentration of sCD40L, and value of CD41:CD63 are less than the values on the control indicated as the transition from the first metabolic state to the second metabolic state. In some embodiments, a platelet sample process by buffy coat method regardless of donor genetic variation is characterized as First Phase if the concentration of glutathione oxidized, ratio of acetate:cis-aconitate, and ratio of acetate:lactose are greater than the values on the control indicated as the transition from the first metabolic state to the second metabolic state. In some embodiments, a platelet sample process by buffy coat method regardless of donor genetic variation is characterized as First Phase if the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state.

Second Phase—Platelets

In some embodiments, Second Phase is characterized by a set of biomarkers. In some embodiments, the set of biomarkers is selected from concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combination thereof. In some embodiments, the set of biomarkers is concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose. In some embodiments, the platelet sample is classified as Second Phase based on the concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose. In some instances, the quality of the platelet sample is determined based on the concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose.

In some embodiments, the biomarkers are obtained from the extracellular portion of the platelet sample. In some embodiments, the set of biomarkers obtained from the extracellular portion include concentration of glutamine, concentration of niacinamide, concentration of glutathione oxidized, and concentration of succinic acid. In some embodiments, the set of biomarkers obtained from the extracellular portion is concentration of glutamine, concentration of niacinamide, concentration of glutathione oxidized, and concentration of succinic acid. In some embodiments, Second Phase is characterized by the set of biomarkers obtained from the extracellular portion.

In some embodiments, the biomarkers are obtained from the intracellular portion of the platelet sample. In some embodiments, the set of biomarkers obtained from the intracellular portion include concentration of glutamine, concentration of niacinamide, concentration of glutathione oxidized, and concentration of succinic acid. In some embodiments, the set of biomarkers obtained from the intracellular portion is concentration of glutamine, concentration of niacinamide, concentration of glutathione oxidized, and concentration of succinic acid. In some embodiments, Second Phase is characterized by the set of biomarkers obtained from the intracellular portion.

In some embodiments, the set of biomarkers selected from concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose are indicated with a set of values. In some embodiments, the value is associated with a unit or is unitless. In some embodiments, the value is a ratio. In some embodiments, the unit is in millimolar (mM) concentration, ng/mL, or as a percentage.

Apheresis

In some embodiments, the biomarkers are obtained from an apheresis processed platelet sample. In some embodiments, biomarkers associated with the apheresis processed platelet sample for determining the phase of platelets include concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combinations thereof. In some embodiments, a biomarker associated with the apheresis processed platelet is selected from concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combinations thereof. In some embodiments, a biomarker associated with the apheresis processed platelet is selected from concentration of glutathione oxidized, ratio of acetate:cis-aconitate, ratio of glucose:lactose, concentration of sCD40L, and value of CD41:CD63. In some embodiments, a biomarker associated with the apheresis processed platelet is selected from concentration of glutathione oxidized, ratio of acetate:cis-aconitate, and ratio of glucose:lactose.

In some embodiments, Second Phase is assigned the apheresis processed platelet sample based on concentration of glutamine, concentration of niacinamide, concentration of glutathione oxidized, concentration of sCD40L, value of CD41:CD63, ratio of citrate:cis-aconitate, ratio of citrate:malate, ratio of acetate:cis-aconitate, ratio of glucose:lactose, or any combinations thereof. In some embodiments, Second Phase is assigned the apheresis processed platelet sample based on concentration of glutathione oxidized, ratio of acetate:cis-aconitate, ratio of glucose:lactose, concentration of sCD40L, and value of CD41:CD63. In some embodiments, Second Phase is assigned the apheresis processed platelet sample based on concentration of glutathione oxidized, ratio of acetate:cis-aconitate, and ratio of glucose:lactose.

In some embodiments, Second Phase is assigned to the apheresis processed platelet sample where the concentration of glutathione oxidized, ratio of acetate:cis-aconitate, and ratio of glucose:lactose are less than the values on the control indicated as the transition from the first metabolic state to the second metabolic state. In some embodiments, Second Phase is assigned to the apheresis processed platelet sample where the concentration of glutathione oxidized, ratio of acetate:cis-aconitate, and ratio of glucose:lactose are less than the values on the control indicated as the transition from the first metabolic state to the second metabolic state, and concentration of sCD40L, and value of CD41:CD63 are greater than the values on the control indicated as the transition from the first metabolic state to the second metabolic state. In some embodiments, Second Phase is assigned to the apheresis processed platelet sample where the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, the concentration of glutathione oxidized is the intracellular concentration of glutathione oxidized. In some embodiments, Second Phase is assigned to the apheresis processed platelet sample where the intracellular concentration of glutathione oxidized, ratio of acetate:cis-aconitate, and ratio of glucose:lactose are less than the values on the control indicated as the transition from the first metabolic state to the second metabolic state. In some embodiments, Second Phase is assigned to the apheresis processed platelet sample where the intracellular concentration of glutathione oxidized, ratio of acetate:cis-aconitate, and ratio of glucose:lactose are less than the values on the control indicated as the transition from the first metabolic state to the second metabolic state, and concentration of sCD40L, and value of CD41:CD63 are greater than the values on the control indicated as the transition from the first metabolic state to the second metabolic state. In some embodiments, Second Phase is assigned to the apheresis processed platelet sample where the intracellular concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state.

In some embodiments, the concentration of glutathione oxidized less than 2.22E-05 mM is associated with Second Phase for the apheresis processed platelet sample. In some embodiments, the concentration of glutathione oxidized is the intracellular concentration of glutathione oxidized. In some embodiments, the intracellular concentration of glutathione oxidized less than 2.22E-05 mM is associated with Second Phase for the apheresis processed platelet sample.

In some embodiments, the concentration of glutamine less than 0.11 mM is associated with Second Phase for the apheresis processed platelet sample.

In some embodiments, the concentration of niacinamide greater than 0.0035 mM is associated with Second Phase for the apheresis processed platelet sample.

In some embodiments, the concentration of sCD40L greater than 20.8 ng/mL is associated with Second Phase for the apheresis processed platelet sample.

In some embodiments, the value of CD41:CD63 greater than 24.3% is associated with Second Phase for the apheresis processed platelet sample.

In some embodiments, the ratio of citrate:cis-aconitate less than 228.3 is associated with Second Phase for the apheresis processed platelet sample.

In some embodiments, the ratio of citrate:malate less than 470.6 is associated with Second Phase for the apheresis processed platelet sample.

In some embodiments, the ratio of acetate:cis-aconitate less than 680.6 is associated with Second Phase for the apheresis processed platelet sample.

In some embodiments, the ratio of glucose:lactose less than 0.569 is associated with Second Phase for the apheresis processed platelet sample.

Buffy Coat

In some embodiments, the biomarkers are obtained from a buffy coat processed platelet sample. In some embodiments, biomarkers associated with the buffy coat processed platelet sample for determining the phase of platelets include concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combinations thereof. In some embodiments, a biomarker associated with the buffy coat processed platelet sample is selected from concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, ratio of acetate:lactose, or any combination thereof. In some embodiments, a biomarker associated with the buffy coat processed platelet sample is selected from concentration of glutathione oxidized, ratio of acetate:cis-aconitate, and ratio of acetate:lactose.

In some embodiments, Second Phase is assigned the buffy coat processed platelet sample based on concentration of glutamine, concentration of glutathione oxidized, concentration of succinic acid, concentration of sCD40L, value of CD41:Annexin-V, value of CD41:CD42b, ratio of citrate:cis-aconitate, ratio of acetate:cis-aconitate, ratio of acetate:succinate, and ratio of acetate:lactose. In some embodiments, Second Phase is assigned the buffy coat processed platelet sample based on concentration of glutathione oxidized, ratio of acetate:cis-aconitate, ratio of acetate:lactose, concentration of sCD40L, value of CD41:Annexin-V, and value of CD41:CD42b. In some embodiments, Second Phase is assigned the buffy coat processed platelet sample based on concentration of glutathione oxidized, ratio of acetate:cis-aconitate, and ratio of acetate:lactose.

In some embodiments, Second Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state. In some embodiments, Second Phase is assigned to the buffy coat processed platelet sample where the concentration of glutathione oxidized, ratio of acetate:cis-aconitate, and ratio of acetate:lactose are greater than the values on the control indicated as the transition from the first metabolic state to the second metabolic state and concentration of sCD40L, value of CD41:Annexin-V, and value of CD41:CD42b are less than the values on the control indicated as the transition from the first metabolic state to the second metabolic state. In some embodiments, Second Phase is assigned to the buffy coat processed platelet sample where the concentration of glutathione oxidized, concentration of glutamine, ratio of acetate:cis-aconitate, ratio of acetate:lactose, ratio of citrate:cis-aconitate, and ratio of acetate:succinate are greater than the values on the control indicated as the transition from the first metabolic state to the second metabolic state; and the concentration of succinic acid, concentration of sCD40L, value of CD41:Annexin-V, and value of CD41:CD42b are less than the values on the control indicated as the transition from the first metabolic state to the second metabolic state. In some instances, the concentration of glutathione oxidized is the extracellular concentration of glutathione oxidized or the intracellular concentration of glutathione oxidized. In some embodiments, Second Phase is assigned to the buffy coat processed platelet sample where the extracellular concentration of glutathione oxidized, ratio of acetate:cis-aconitate, and ratio of acetate:lactose are less than the values on the control indicated as the transition from the first metabolic state to the second metabolic state. In some embodiments, Second Phase is assigned to the buffy coat processed platelet sample where the extracellular concentration of glutathione oxidized, intracellular concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state.

In some embodiments, the extracellular concentration of glutathione oxidized less than 5.91E-04 mM is associated with Second Phase for the buffy coat processed platelet sample.

In some embodiments, the intracellular concentration of glutathione oxidized less than 3.6E-05 mM is associated with Second Phase for the buffy coat processed platelet sample.

In some embodiments, the concentration of glutamine less than 0.42 mM is associated with Second Phase for the buffy coat processed platelet sample.

In some embodiments, the concentration of succinic acid greater than 0.0128 mM is associated with Second Phase for the buffy coat processed platelet sample.

In some embodiments, the value of CD41:Annexin-V greater than 3.2% is associated with Second Phase for the buffy coat processed platelet sample.

In some embodiments, the value of CD41:CD42b greater than 1.7% is associated with Second Phase for the buffy coat processed platelet sample.

In some embodiments, the concentration of sCD40L greater than 15 ng/mL is associated with Second Phase for the buffy coat processed platelet sample.

In some embodiments, the ratio of citrate:cis-aconitate less than 314 is associated with Second Phase for the buffy coat processed platelet sample.

In some embodiments, the ratio of acetate:cis-aconitate less than 835.7 is associated with Second Phase for the buffy coat processed platelet sample.

In some embodiments, the ratio of acetate:succinate less than 1644 is associated with Second Phase for the buffy coat processed platelet sample.

In some embodiments, the ratio of acetate:lactose less than 3 is associated with Second Phase for the buffy coat processed platelet sample.

Platelets Storage Conditions and Additional Features

In some embodiments, a storage condition is correlated to storage time, storage temperature, and/or addition of an additive solution.

In some embodiments, Second Phase is correlated to about day 3 to about day 20, about day 3 to about day 15, or about day 3 to about day 10 of storage. In some embodiments, Second Phase is correlated to about day 3, 4, 5, 6, 7, 8, 9, or day 10 of storage. In some embodiments, Second Phase is correlated to about day 4, 5, 6, 7, 8, 9, or day 10 of storage.

In some embodiments, any platelet sample is characterized as Second Phase regardless of storage age, storage condition (e.g. storage temperature or addition of an additive solution) or donor genetic variations (e.g. age, sex or a donor's health). In some embodiments, a platelet sample stored for 3, 4, 5, 6, 7, 8, 9, 10, 11, 12, 13, 14, 15, 16, 17, 18, 19, or 20 days is characterized as Second Phase. In some embodiments, a platelet sample which has been in storage for about 3 days or for about 4 days is characterized as Second Phase if the concentration of glutathione oxidized, ratio of acetate:cis-aconitate, and either ratio of glucose:lactose or ratio of acetate:lactose are less than the values on the control indicated as the transition from the first metabolic state to the second metabolic state. In some embodiments, a platelet sample process by apheresis which has been in storage for about 3 days or for about 4 days is characterized as Second Phase if the concentration of glutathione oxidized, ratio of acetate:cis-aconitate, and ratio of glucose:lactose are less than the values on the control indicated as the transition from the first metabolic state to the second metabolic state. In some embodiments, a platelet sample process by apheresis which has been in storage for about 3 days or for about 4 days is characterized as Second Phase if the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, a platelet sample process by buffy coat method which has been in storage for about 3 days or for about 4 days is characterized as Second Phase if the concentration of glutathione oxidized, ratio of acetate:cis-aconitate, and ratio of acetate:lactose are less than the values on the control indicated as the transition from the first metabolic state to the second metabolic state. In some embodiments, a platelet sample process by buffy coat method which has been in storage for about 3 days or for about 4 days is characterized as Second Phase if the concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state.

In some embodiments, the storage condition is a storage temperature. In some embodiments, the storage temperature is from about −80° C. to about 25° C., about 0° C. to about 25° C., or about 20° C. to about 25° C. In some embodiments, a platelet sample which has been in a storage temperature of about 20° C., 21° C., 22° C., 23° C., 24° C., or 25° C. is characterized as Second Phase if the concentration of glutathione oxidized, ratio of acetate:cis-aconitate, and either ratio of glucose:lactose or ratio of acetate:lactose are less than the values on the control indicated as the transition from the first metabolic state to the second metabolic state. In some embodiments, a platelet sample process by apheresis which has been in a storage temperature of about 20° C. to about 25° C. is characterized as Second Phase if the concentration of glutathione oxidized, ratio of acetate:cis-aconitate, and ratio of glucose:lactose are less than the values on the control indicated as the transition from the first metabolic state to the second metabolic state. In some embodiments, a platelet sample process by apheresis which has been a storage temperature of about 20° C. to about 25° C. is characterized as Second Phase if the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, a platelet sample process by buffy coat method which has been in a storage temperature of about 20° C. to about 25° C. is characterized as Second Phase if the concentration of glutathione oxidized, ratio of acetate:cis-aconitate, and ratio of acetate:lactose are less than the values on the control indicated as the transition from the first metabolic state to the second metabolic state. In some embodiments, a platelet sample process by buffy coat method which has been in a storage temperature of about 20° C. to about 25° C. is characterized as Second Phase if the concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state.

In some embodiments, a platelet sample stored under any storage condition is characterized as Second Phase. In some embodiments, the storage condition is a storage temperature or the addition of an additive solution. In some embodiments, the additive solution includes Examplary PLT additive solutions include, but are not limited to, PAS-1 (PAS-I plasmalyte), PAS-B (PAS-II or T-Sol), PAS-C(PAS-III or Intersol), PAS-D (ComposolPS), PAS-E (PAS-IIIM SSP+), PAS-F (PlasmaLyte A, Isoplate), PAS-G, or M-Sol. In some embodiments, platelets are not stored in the presence of an additive solution.

In some embodiments, a platelet sample regardless of donor genetic variation (e.g. age, sex or a donor's health) is characterized as Second Phase. In some embodiments, a platelet sample regardless of donor genetic variation is characterized as Second Phase if the concentration of glutathione oxidized, ratio of acetate:cis-aconitate, and either ratio of glucose:lactose or ratio of acetate:lactose are less than the values on the control indicated as the transition from the first metabolic state to the second metabolic state. In some embodiments, a platelet sample process by apheresis regardless of donor genetic variation is characterized as Second Phase if the concentration of glutathione oxidized, ratio of acetate:cis-aconitate, and ratio of glucose:lactose are less than the values on the control indicated as the transition from the first metabolic state to the second metabolic state. In some embodiments, a platelet sample process by apheresis regardless of donor genetic variation is characterized as Second Phase if the concentration of glutathione oxidized, concentration of glutamine, ratio of acetate:cis-aconitate, ratio of glucose:lactose, ratio of citrate:cis-aconitate, and ratio of citrate:malate are less than the values on the control indicated as the transition from the first metabolic state to the second metabolic state and concentration of niacinamide, concentration of sCD40L, and value of CD41:CD63 are greater than the values on the control indicated as the transition from the first metabolic state to the second metabolic state. In some embodiments, a platelet sample process by buffy coat method regardless of donor genetic variation is characterized as Second Phase if the concentration of glutathione oxidized, ratio of acetate:cis-aconitate, and ratio of acetate:lactose are less than the values on the control indicated as the transition from the first metabolic state to the second metabolic state. In some embodiments, a platelet sample process by buffy coat method regardless of donor genetic variation is characterized as Second Phase if the concentration of glutathione oxidized, concentration of glutamine, ratio of acetate:cis-aconitate, ratio of acetate:lactose, ratio of citrate:cis-aconitate, and ratio of acetate:succinate are less than the values on the control indicated as the transition from the first metabolic state to the second metabolic state; and the concentration of succinic acid, concentration of sCD40L, value of CD41:Annexin-V, and value of CD41:CD42b are greater than the values on the control indicated as the transition from the first metabolic state to the second metabolic state.

Analytical Techniques and Instrumentation

Sample Preparation

Methods and systems described herein are compatible with a variety of sample preparation techniques. In some embodiments, the RBC and/or PLT samples are prepared by centrifugation, lysis (e.g. vortex), homogenization, or freeze-thaw process and further processed by a filtration step prior to proceeding to an analytical step. In some embodiments, the RBC and/or PLT samples are processed and separated into an extracellular portion and an intracellular portion. In some embodiments, the extracellular portion and the intracellular portion are then separately submitted to an analytical step. In some embodiments, the extracellular portion is process and analyzed to derive the set of biomarkers described herein.

In some embodiments, the extracellular portion comprises the RBC medium. In some embodiments, the RBC medium comprises inosine, hypoxanthine, adenine, $Na^+$, $K^+$, glucose, lactate and pyruvate. In some embodiments, the extracellular portion comprises inosine, hypoxanthine, adenine, $Na^+$, $K^+$, glucose, lactate and pyruvate. In some embodiments, the set of biomarkers obtained from the extracellular portion of RBC include concentration of inosine, concentration of hypoxanthine, concentration of adenine, ratio of hypoxanthine:adenine, ration of $Na^+$:$K^+$, ratio of glucose:lactate, ratio of inosine:adenine, and concentration of pyruvate. In some embodiments, the biomarker obtained from the extracellular portion of RBC is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate.

In some embodiments, the extracellular portion comprises the PLT medium. In some embodiments, the PLT medium comprises glutamine, niacinamide, glutathione oxidized, and succinic acid. In some embodiments, the set of biomarkers obtained from the extracellular portion of PLT include concentration of glutamine, concentration of niacinamide, concentration of glutathione oxidized, and concentration of succinic acid. In some embodiments, the set of biomarkers obtained from the extracellular portion of PLT is concentration of glutamine, concentration of niacinamide, concentration of glutathione oxidized, and concentration of succinic acid.

In some embodiments, the intracellular portion is process and analyzed to derive the set of biomarkers described herein. In some embodiments, the intracellular portion comprises the PLT medium. In some embodiments, the intracellular PLT medium comprises glutathione oxidized. In some embodiments, the biomarker obtained from the intracellular portion of PLT includes concentration of glutathione oxidized.

In some embodiments, the following preparation techniques are for illustrative purposes only and should not be construed as limiting in any manner.

In some embodiments, a methanol water preparation technique is used. In some embodiments, 0.5 mL of methanol-water (7:3) at a temperature of −20° C. is added to an RBC cell pellet and is vortexed for 1 min. In some embodiments, a cell lysis is achieved by performing two consecutive freeze and thaw steps. In some embodiments, the cell lysis is further centrifuged for 15 min at 15,000×g and 3 µL of the cell lysis supernatant is used for the analytical step.

In some embodiments, a methanol water acid (pH2) preparation technique is used. In some embodiments, a solution of methanol-water (7:3) is prepared using water containing 1% of formic acid (pH 2). In some embodiments, 0.5 mL of the methanol-water solution at a temperature of −20° C. is added to the RBC cell pellet and vortexed for 1 min. In some embodiments, the cell lysis is achieved by performing two consecutively freeze and thaw steps. In some embodiments, the cell lysis is further centrifuged for 15 min at 15,000×g and 3 µL of the cell lysis supernatant is used for the analytical step.

In some embodiments, a methanol:water basic (pH10) preparation technique is used. In some embodiments, a solution of methanol-water (7:3) is prepared using water containing 2% of sodium hydroxide (pH 10). In some embodiments, 0.5 mL of the methanol-water solution at a temperature of −20° C. is added to the RBC cell pellet and vortexed for 1 min. In some embodiments, the cell lysis is achieved by performing two consecutively freeze and thaw steps. In some embodiments, the cell lysis is further centrifuged for 15 min at 15,000×g and 3 µL of the cell lysis supernatant is used for the analytical step.

In some embodiments, a hot methanol (80° C.) preparation technique is used. In some embodiments, an RBC cell pellet is resuspended in 0.5 mL of methanol at a temperature of 80° C. and incubated for 15 min at 80° C. In some embodiments, the RBC cell pellet is cooled down in ice for 10 min and vortexed for 1 min before being centrifuged for 15 min at 15,000×g. In some embodiments, a 3 µL volume of the cell lysis supernatant is used for the analytical step.

In some embodiments, a methanol:acetonitrile:water (ACN) preparation technique is used. In some embodiments, a solution of 0.5 mL of methanol:acetonitrile:water (4:4:2) at a temperature of −20° C. is added to an RBC cell pellets and vortexed for 1 min. In some embodiments, the cell lysis is achieved by performing two consecutively freeze and thaw steps. In some embodiments, the cell lysis is further centrifuged for 15 min at 15,000×g and 3 µL of the cell lysis supernatant is used for the analytical step.

In some embodiments, a methanol:chloroform:water ($CHCl_3$) preparation technique is used. In some embodiments, an RBC cell pellet is resuspended in 1.2 mL of methanol at a temperature of −20° C. and vortexed for 1 min. In some embodiments, the cell lysis is achieved by performing two consecutively freeze and thaw steps. In some embodiments, a volume of 0.6 mL of chloroform is added to the RBC cell lysis and vortexed for 30 s during a period of 15 min while maintaining the RBC cell lysis in a cold bath. In some embodiments, a volume of 0.2 mL of ice-cold water is added to the sample and vortexed for 1 min. In some embodiments, the cell lysis is further centrifuged for 1 min at 1000×g and stored at −20° C. for about 4 h. In some embodiments, the organic and water phase is recovered, pooled together, and dried under a gentle stream of nitrogen. In some embodiments, the dried RBC sample is reconstituted in 0.5 mL of methanol:water (7:3) and centrifuged for 15 min at 15,000×g to precipitate residual proteins. In some embodiments, a volume of 3 µL of the RBC sample supernatant is used for the analytical step.

In some embodiments, a methanol:water two-step preparation technique is used. In some embodiments, a volume of 1.4 mL of methanol at a temperature of −20° C. is added to an RBC cell pellet and vortexed for 1 min. In some embodiments, the cell lysis is achieved by performing two consecutively freeze and thaw steps. In some embodiments, the cell lysis is further centrifuged for 5 min at 1500×g. In some embodiments, a second step extraction is achieved by adding a volume of 0.6 mL of ice-cold water and vortexed for 1 min. In some embodiments, the cell lysis is centrifuged for 15 min at 15,000×g. In some embodiments, the water extracts are combined with the methanol extracts. In some embodiments, the cell lysis sample is dried under a gentle stream of nitrogen and reconstituted in a volume of 0.5 mL of methanol:water (7:3). In some embodiments, a volume of 3 µL of the RBC sample supernatant is used for the analytical step.

In some embodiments, the RBC samples are directly used in the methods and systems described herein without any preparation process. In some embodiments, the RBC samples are directly used in a blood-gas analysis method.

In some embodiments, the RBC samples are processed before, during or at the end of storage. In some embodiments, the RBC samples are processed on day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and/or day 60. In some embodiments, the RBC samples are processed on day 1, 4, 8, 11, 15, 18, 22, 25, 29, 32, 36, 39, 43 and/or day 46.

In some embodiments, the PLT samples are directly used in the methods and systems described herein without any preparation process. In some embodiments, the PLT samples are processed such as by a cell lysis step and/or a centrifugation step prior to proceeding into an analysis step. In an illustrative example, cell pellets of platelets is prepared by washing the pellets twice in 1 mL of phosphate-buffered saline, and after centrifugation at 1600×g, at 22° C. for 5 minutes, the supernatant is collected and discharged. In some cases, the cell pellet is used for an analysis step.

Sample Analysis

Methods and systems described herein are compatible with a variety of analytical techniques well known in the art, including blood-gas analysis, biochemical assay (e.g. enzymatic assay), liquid chromatography (LC) (e.g. high performance liquid chromatography), liquid chromatography-mass spectrometry (LC-MS), gas chromatography-mass spectrometry (GC-MS), capillary electrophoresis-mass spectrometry (CE-MS), and nuclear magnetic resonance imaging (NMR).

In some embodiments, blood-gas analysis, biochemical assay (e.g. enzymatic assay), and LC are used with the methods and systems described herein to generate raw data from the RBC sample and/or the PLT sample. In some embodiments, the raw data is then analyzed by data analysis softwares to determine a value of a biomarker. In some embodiments, the RBC sample is a processed RBC sample, a processed extracellular portion of the RBC sample, or an unprocessed RBC sample. In some embodiments, the extracellular portion of the RBC sample is analyzed to generated raw data. In some embodiments, blood-gas analysis, biochemical assay (e.g. enzymatic assay), and LC are used in combination with LC-MS and GC-MS methods. In some embodiments, blood-gas analysis is used in combination with LC method. In some embodiments, blood-gas analysis is used in combination with biochemical assays (e.g. enzymatic assays). In some embodiments, blood-gas analysis is used. In some embodiments, biochemical assay (e.g. enzymatic assay) is used. In some embodiments, LC method is used.

In some embodiments, the PLT sample is a processed PLT sample, a processed extracellular portion of the PLT sample, a processed intracellular portion of the PLT sample, or an unprocessed RBC sample. In some embodiments, biochemical assay (e.g. enzymatic assay), flow cytometry analysis, blood-gas analysis, and LC are used in combination with LC-MS and GC-MS methods. In some embodiments, flow cytometry analysis is used in combination with LC method. In some embodiments, flow cytometry analysis is used in combination with biochemical assays (e.g. enzymatic assays). In some embodiments, flow cytometry analysis is used. In some embodiments, biochemical assay (e.g. enzymatic assay) is used. In some embodiments, LC method is used.

Blood-Gas Analysis

In some embodiments, any suitable blood-gas analysis method is used herein to analyze RBC samples or PLT samples. In some embodiments, any suitable blood-gas analysis method is used herein to analyze the RBC samples. In some embodiments, any suitable blood-gas analysis method is used herein to analyze the PLT samples. In some embodiments, a blood-gas analyzer is used to determine blood gases, acid-base balance, electrolytes, ionized calcium, glucose, lactate, proteins, blood urea nitrogen (BUN), or a combination thereof. In some embodiments, the blood gas analyzer is used to determine the measurement of $K^+$, $Na^+$, $Ca^+$, $Cl^-$, $HCO_3^-$, glucose, lactate, hemoglobin, bilirubin, pH, $pO_2$, $pCO_2$, or a combination thereof. In some embodiments, the blood gas analyzer is used to determine the measurement of $K^+$, $Na^+$, glucose, lactate, pH, $pCO_2$, or a combination thereof. In some embodiments, the blood gas analyzer is used to determine the measurement of $K^+$, $Na^+$, glucose, lactate, pH and $pCO_2$. In some embodiments, the blood gas analyzer is used to determine the measurement of $K^+$. In some embodiments, the blood gas analyzer is used to determine the measurement of $Na^+$. In some embodiments, the blood gas analyzer is used to determine the measurement of glucose. In some embodiments, the blood gas analyzer is used to determine the measurement of lactate. In some embodiments, the blood gas analyzer is used to determine the measurement of pH. In some embodiments, the blood gas analyzer is used to determine the measurement of $pCO_2$.

In some embodiments, the RBC sample is a processed RBC sample, a processed extracellular portion of the RBC sample, or an unprocessed RBC sample. In some embodiments, extracellular portion comprises inosine, hypoxanthine, adenine, $Na^+$, $K^+$, glucose, lactate and pyruvate. In some embodiments, the set of biomarkers obtained from the extracellular portion include concentration of inosine, concentration of hypoxanthine, concentration of adenine, ratio of hypoxanthine:adenine, ration of $Na^+$:$K^+$, ratio of glucose:lactate, ratio of inosine:adenine, and concentration of pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate.

In some embodiments, $pCO_2$ is a measurement of the pressure of $CO_2$ of the RBC sample (e.g. RBC medium) in the RBC unit. In some embodiments, the RBC unit refers to a storage container such as a storage bag. In some embodiments, the RBC unit is defined by volume. In some embodiments, the volume of the RBC unit is about 50 mL, about 75 mL, about 100 mL, about 125 mL, about 150 mL, about 175 mL, about 200 mL, about 225 mL, about 230 mL, about 235 mL, about 240 mL, about 245 mL, about 250 mL, about 255 mL, about 260 mL, about 265 mL, about 270 mL, about 275 mL, about 280 mL, about 300 mL, about 350 mL, about 400 mL, about 450 mL, about 500 mL, about 550 mL, about 600 mL, about 650 mL, about 700 mL, about 750 mL, about 800 mL, about 850 mL, about 900 mL, about 950 mL, or about 1000 mL. In some embodiments, $pCO_2$ is a measurement of the pressure of $CO_2$ of the RBC sample in a about 50 mL, about 75 mL, about 100 mL, about 125 mL, about 150 mL, about 175 mL, about 200 mL, about 225 mL, about 230 mL, about 235 mL, about 240 mL, about 245 mL, about 250 mL, about 255 mL, about 260 mL, about 265 mL, about 270 mL, about 275 mL, about 280 mL, about 300 mL, about 350 mL, about 400 mL, about 450 mL, about 500 mL, about 550 mL, about 600 mL, about 650 mL, about 700 mL, about 750 mL, about 800 mL, about 850 mL, about 900 mL, about 950 mL, or about 1000 mL RBC unit. In some embodiments, $pCO_2$ is a measurement of the pressure of $CO_2$ of the RBC sample in a about 75 mL, about 150 mL, about 200 mL, about 225 mL, about 230 mL, about 235 mL, about 240 mL, about 245 mL, about 250 mL, about 255 mL, about 260 mL, about 265 mL, about 270 mL, about 275 mL, about 280 mL, about 300 mL, about 350 mL, about 400 mL, about 450 mL, or about 500 mL RBC unit. In some embodiments, $pCO_2$ is a measurement of the pressure of $CO_2$ of the RBC sample in a about 200 mL, about 225 mL, about 230 mL, about 235 mL, about 240 mL, about 245 mL, about 250 mL, about 255 mL, about 260 mL, about 265 mL, about 270 mL, about 275 mL, about 280 mL, about 300 mL, about 350 mL, about 400 mL, about 450 mL, or about 500 mL RBC unit.

Exemplary blood-gas analyzers include, but are not limited to, ABL90 FLEX analyzer, ABL80 FLEX analyzer, or ABL800 FLEX analyzer from Radiometer Medical ApS; RAPIDLab® 1200 system, RAPIDPoint® 500 system, RAPIDPoint® 400/405 system, RAPIDPoint 340/350 system, RAPIDLab® 348EX system, RAPIDLab® 248/348 system, or RAPIDChem® 744/754 system from Siemens/Bayer Healthcare LLP; Omni S series, Omni C series, cobas b 121 system, cobas b 123 POC system or cobas b 221 Blood Gas system from Roche Diagnostics; i-STAT® system from Abbott Laboratories Ltd; GEM® Premier 3000 from Instrumentation Laboratory; GEM OPL from Avox System Inc; Immediate Response Mobile Analyser (IRMA) TRUpoint™ from International Technidyne Corporation; EasyStat from Medica Corporation; Critical Care Express (CCX), pHOx series or pHOX CO-oximeter from Nova Biomedical Corporation; or OPTI CCA from Osmetech Inc.

Biochemical Assays

In some embodiments, biochemical assays suitable for the quantification of one or more metabolites disclosed herein include enzymatic assays, immunoassays and enzyme based immunoassays. In some embodiments, enzymatic assays are used for the quantification of one or more metabolites disclosed herein. In some embodiments, the enzymatic assays also include the use of antibodies and are also referred to as enzyme based immunoassays. In some embodiments, the metabolites include inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, and annexin-V. In some embodiments, an enzymatic assay is used to quantify inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, annexin-V, or a combination thereof. In some embodiments, an enzymatic assay is used to quantify inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, or annexin-V. In some embodiments, an enzymatic assay is used to quantify inosine. In some embodiments, an enzymatic assay is used to quantify hypoxanthine. In some embodiments, an enzymatic assay is used to quantify adenine. In some embodiments, an enzymatic assay is used to quantify pyruvate. In some embodiments, an enzymatic assay is used to quantify glucose. In some embodiments, an enzymatic assay is used to quantify lactate. In some embodiments, an enzymatic assay is used to quantify glutamine. In some embodiments, an enzymatic assay is used to quantify niacinamide. In some embodiments, an enzymatic assay is used to quantify glutathione oxidized. In some embodiments, an enzymatic assay is used to quantify citrate. In some embodiments, an enzymatic assay is used to quantify acetate. In some embodiments, an enzymatic assay is used to quantify cis-aconitate. In some embodiments, an enzymatic assay is used to quantify malate. In some embodiments, an enzymatic assay is used to quantify succinic acid. In some embodiments, an enzymatic assay is used to quantify sCD40L. In some embodiments, an enzymatic assay is used to quantify CD41. In some embodiments, an enzymatic assay is used to quantify CD63+. In some embodiments, an enzymatic assay is used to quantify CD42b. In some embodiments, an enzymatic assay is used to quantify annexin-V.

In some embodiments, enzymatic assays utilize enzymes which bind to target analytes (e.g. metabolites) and convert the target analytes into products. In some embodiments, enzyme is used in the broadest sense and covers any of various proteins capable of producing certain chemical changes in an analyte by catalytic action. In some embodiments, enzymes are further categorized into hydrolase, phospholipase, transferase, reductase and isomerase. Hydrolase is an enzyme that catalyzes the hydrolysis of a chemical bond. Phospholipase is an enzyme that converts phospholipids into fatty acids and other lipophilic substances. Transferase is an enzyme that catalyzes the transfer of a functional group (e.g. a methyl or phosphate group) from one molecule called the donor to another molecule called the acceptor. Reductases work in both directions of a reaction, i.e. any reductase, under the proper conditions, can behave as an oxidase and vice versa, hence is also referred to as oxidoreductase. Isomerase is an enzyme that catalyses the structural rearrangement of isomers.

In some embodiments, enzymes used for the quantification of metabolites disclosed herein are selected from one or more of hydrolase, phospholipase, transferase, reductase and/or isomerase. In some embodiments, enzymes used for the quantification of metabolites disclosed herein are selected from transferase and/or reductase. Suitable transferase and reductase used for the quantification of one or more metabolites disclosed herein include, but are not limited to, transferases: purine nucleoside phosphorylase, adenine phosphoriboxyltransferase, and hexokinase phosphorylate; and reductases: lactate dehydrogenase, xanthine oxidase, and glucose oxidase. Purine nucleoside phosphorylase metabolizes inosine into hypoxanthine. Adenine phosphoribosyltransferase converts adenine to adenosine monophosphate. Lactate dehydrogenase (LDH), for example, catalyzes the interconversion of pyruvate and lactate. Xanthine oxidase catalyzes the oxidation of hypoxanthine to xanthine. Hexokinase phosphorylate metabolizes glucose to glucose-6-phosphate. Alternatively, glucose oxidase also processes glucose via oxidation of glucose into hydrogen peroxide and D-glucono-γ-lactone.

In some embodiments, products of enzymatic assays are quantified through changes in light absorptions. In some embodiments, assays that are based on changes in light absorptions are referred to as colorimetric assays or luminescent assays. Therefore, in some embodiments, an enzymatic assay is also a colorimetric assay or a luminescent assay.

In some embodiments, an enzymatic assay is a colorimetric assay. In some embodiments, colorimetric assays utilize chromophores that undergo a change in the absorbance of light at one wavelength in response to a product formation. For example, in a colorimetric glucose assay, glucose oxidase oxidizes glucose into hydrogen peroxide and D-glucono-γ-lactone. The presence of hydrogen peroxide then induces oxidation of a chromophore to produce a color change. The concentration of glucose is correlated to the concentration of hydrogen peroxide produced and is therefore also correlated to the intensity of the color. Hence, the concentration of glucose is measured directly at a particular wavelength of the chromophore used. Exemplary chromophores suitable for a colorimetric assay include, but are not limited to, diaminobenzidine (DAB), 4-chloro-1-naphthol (4CN), 5-bromo-4-chloro-3-indolyl phosphate (BCIP), nitroblue tetrazolium (NBT), p-nitrophenyl phosphate (pNPP), 2-(4-iodophenyl)-3-(4-nitrophenyl)-5-phenyl-2H-tetrazolium chloride (INT), 4-aminophenazone, Opti-4CN™, or BCIP/NBT.

In some embodiments, a colorimetric assay is used to determine the concentration of inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, annexin-V, or a combination thereof. In some embodiments, a colorimetric assay is used to determine the concentration of inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, or annexin-V. In some embodiments, a colorimetric assay is used to determine the concentration of inosine. In some embodiments, a colorimetric assay is used to determine the concentration of hypoxanthine. In some embodiments, a colorimetric assay is used to determine the concentration of adenine. In some embodiments, a colorimetric assay is used to determine the concentration of pyruvate. In some embodiments, a colorimetric assay is used to determine the concentration of glucose. In some embodiments, a colorimetric assay is used to determine the concentration of lactate.

In some embodiments, a colorimetric assay is used to determine the concentration of glutamine. In some embodiments, a colorimetric assay is used to determine the concentration of niacinamide. In some embodiments, a colorimetric assay is used to determine the concentration of glutathione oxidized. In some embodiments, a colorimetric assay is used to determine the concentration of citrate. In some embodiments, a colorimetric assay is used to determine the concentration of acetate. In some embodiments, a colorimetric assay is used to determine the concentration of cis-aconitate. In some embodiments, a colorimetric assay is used to determine the concentration of malate. In some embodiments, a colorimetric assay is used to determine the concentration of succinic acid. In some embodiments, a colorimetric assay is used to determine the concentration of sCD40L. In some embodiments, a colorimetric assay is used to determine the concentration of CD41. In some embodiments, a colorimetric assay is used to determine the concentration of CD63+. In some embodiments, a colorimetric assay is used to determine the concentration of CD42b. In some embodiments, a colorimetric assay is used to determine the concentration of annexin-V. Exemplary colorimetric assays include assays and kits obtained from manufacturers such as Abnova GmbH, BioVision Inc, Abcam, Cayman Chemical, Sigma-Aldrich, RayBiotech Inc., Cambridge Bioscience, Life Technologies, Eton Bioscience Inc., EMD4Biociences, and so forth.

In some embodiments, an enzymatic assay is a luminescent assay. In some embodiments, luminescent assays utilize luminescent agents that emit light as a byproduct of biochemical reactions. In some embodiments, luminescent assays are classified as chemiluminescent assay, fluorometric assays, chemifluorescent assay, or radioluminescent assays.

In some embodiments, a luminescent assay is used to determine the concentration of inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, annexin-V, or a combination thereof. In some embodiments, a luminescent assay is used to determine the concentration of inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, or annexin-V. In some embodiments, a luminescent assay is used to determine the concentration of inosine. In some embodiments, a luminescent assay is used to determine the concentration of hypoxanthine. In some embodiments, a luminescent assay is used to determine the concentration of adenine. In some embodiments, a luminescent assay is used to determine the concentration of pyruvate. In some embodiments, a luminescent assay is used to determine the concentration of glucose. In some embodiments, a luminescent assay is used to determine the concentration of lactate. In some embodiments, a luminescent assay is used to determine the concentration of glutamine. In some embodiments, a luminescent assay is used to determine the concentration of niacinamide. In some embodiments, a luminescent assay is used to determine the concentration of glutathione oxidized. In some embodiments, a luminescent assay is used to determine the concentration of citrate. In some embodiments, a luminescent assay is used to determine the concentration of acetate. In some embodiments, a luminescent assay is used to determine the concentration of cis-aconitate. In some embodiments, a luminescent assay is used to determine the concentration of malate. In some embodiments, a luminescent assay is used to determine the concentration of succinic acid. In some embodiments, a luminescent assay is used to determine the concentration of sCD40L. In some embodiments, a luminescent assay is used to determine the concentration of CD41. In some embodiments, a luminescent assay is used to determine the concentration of CD63+. In some embodiments, a luminescent assay is used to determine the concentration of CD42b. In some embodiments, a luminescent assay is used to determine the concentration of annexin-V.

In some embodiments, luminescent assays are classified as fluorometric assays. In some embodiments, fluorometric assays utilize chromophores that emit light at one wavelength after absorbance of light at another wavelength in response to a product formation. For example, in a fluorometric glucose assay, glucose oxidase oxidizes glucose into hydrogen peroxide and D-glucono-γ-lactone. The presence of hydrogen peroxide induces oxidation of a chromophore which emits light at a wavelength and is then measured by a spectrophotometer. Exemplary chromophores suitable for a fluorometric assays include 10-acetyl-3,7-dihydroxyphenoxazine (Ample Red) and 7-ethoxyresorufin.

In some embodiments, a fluorometric assay is used to determine the concentration of inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, or annexin-V, or a combination thereof. In some embodiments, a fluorometric assay is used to determine the concentration of inosine, hypoxanthine, adenine, pyruvate, glucose or lactate. In some embodiments, a fluorometric assay is used to determine the concentration of inosine. In some embodiments, a fluorometric assay is used to determine the concentration of hypoxanthine. In some embodiments, a fluorometric assay is used to determine the concentration of adenine. In some embodiments, a fluorometric assay is used to determine the concentration of pyruvate. In some embodiments, a fluorometric assay is used to determine the concentration of glucose. In some embodiments, a fluorometric assay is used to determine the concentration of lactate. In some embodiments, a fluorometric assay is used to determine the concentration of glutamine. In some embodiments, a fluorometric assay is used to determine the concentration of niacinamide. In some embodiments, a fluorometric assay is used to determine the concentration of glutathione oxidized. In some embodiments, a fluorometric assay is used to determine the concentration of citrate. In some embodiments, a fluorometric assay is used to determine the concentration of acetate. In some embodiments, a fluorometric assay is used to determine the concentration of cis-aconitate. In some embodiments, a fluorometric assay is used to determine the concentration of malate. In some embodiments, a fluorometric assay is used to determine the concentration of succinic acid. In some embodiments, a fluorometric assay is used to determine the concentration of sCD40L. In some embodiments, a fluorometric assay is used to determine the concentration of CD41. In some embodiments, a fluorometric assay is used to determine the concentration of CD63+. In some embodiments, a fluorometric assay is used to determine the concentration of CD42b. In some embodiments, a fluorometric assay is used to determine the concentration of annexin-V. Exemplary fluorometric assays include assays and kits obtained from manufacturers such as Abnova GmbH, BioVision Inc, Abcam, Cayman Chemical, Sigma-Aldrich, RayBiotech Inc., Cambridge Bioscience, Life Technologies, Eton Bioscience Inc., EMD4Biociences, and so forth.

In some embodiments, chromophores are molecules capable of selective light absorption resulting in the coloration of these molecule containing compounds. The color arises when a molecule either absorbs light in one wavelength (e.g. color in a visible range) or absorbs light at a first wavelength and releases light in an excited state at a second wavelength (e.g. fluorescence). Exemplary chromophores include, but are not limited to, fluorochrome, non-fluorochrome chromophore, quencher (e.g. fluorescence quencher and a dark quencher), absorption chromophore, fluorophore, any organic or inorganic dye, metal chelate, or any fluorescent enzyme substrate.

In certain embodiments, the chromophores described herein, comprise both colorimetric properties (e.g. absorbs light in one wavelength) and fluorescent properties (e.g. absorbs light at a first wavelength and releases light in an excited state at a second wavelength). In some embodiments, the dual property of the chromophore allows both colorimetric and fluorometric measurements in one assay. For example, in a glucose assay, glucose oxidase oxidizes glucose into hydrogen peroxide and D-glucono-γ-lactone. The presence of hydrogen peroxide then interact with Amplex® Red (10-acetyl-3,7-dihydroxyphenoxazine) to produce resorufin. Resorufin is then measured either by absorbance at 570 nm or by fluorescence absorption and emission at 570 nm and 590 nm. Hence, the product of the glucose assay is measured either through absorbance or by fluorescence. In certain embodiments, the concentration of inosine, hypoxanthine, adenine, pyruvate, glucose, lactate, glutamine, niacinamide, glutathione oxidized, citrate, acetate, cis-aconitate, malate, succinic acid, sCD40L, CD41, CD63+, CD42b, and/or annexin-V is quantified either by absorbance or by fluorescence in the same enzymatic assay.

In some embodiments, the enzymatic assays utilize a measuring device to perform photometric measurements for the quantification of light. In some embodiments, the quantification of light is visible, ultraviolet or infrared light. In some embodiments, the measuring device measures light absorption, transmission, emission, and/or scattering. In some embodiments, when an optical property is monitored, a change in light absorption, transmission, emission, or scattering by the RBC sample is measured by the measuring device. In some embodiments, the measuring device used for taking photometric measurements contains a light source that is located adjacent to one surface of the device and a detector that is adjacent to the opposite surface (two parts of a reaction chamber). In some embodiments, the detector measures light transmitted through a fluid sample such as an RBC sample. Alternatively, the light source and the detector is located on the same side of the reaction chamber. Alternatively, light that is scattered from a fluid sample or light that passes through the sample is reflected back through a second time (by a reflector on that opposite side) and is detected by a detector on the same side as the light source. In some embodiments, the change in absorbed, transmitted, emitted, or scattered light is a measurement of the metabolite of the RBC sample. In some embodiments, the measuring device is a spectrophotometer. In some embodiments, the method is a photometry method. In some embodiments, the enzymatic assays utilize a photometry method.

In some embodiments, changes in optical properties in an enzymatic assay are monitored by photometric measurements. In some embodiments, the enzymatic assay is monitored by photometric measurements. In some embodiments, the enzymatic assay is a colorimetric assay or a luminescent assay. In some embodiments, the colorimetric assay is monitored by photometric measurements. In some embodiments, the luminescent assay is monitored by photometric measurements. In some embodiments, the luminescent assay is a fluorometric assay. In some embodiments, the fluorometric assay is monitored by photometric measurements.

Chromatography and Mass Spectrometry

In some embodiments, chromatographic methods suitable for the analysis of one or more metabolites disclosed herein include liquid chromatography (LC) method, gas chromatography (GC) method and capillary electrophoresis (CE) method. In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is used to determine the concentration of inosine, hypoxanthine, adenine, pyruvate, glucose, lactate, or a combination thereof. In some embodiments, the LC method is used to determine the concentration of inosine, hypoxanthine, adenine, pyruvate, glucose and lactate. In some embodiments, the LC method is used to determine the concentration of inosine. In some embodiments, the LC method is used to determine the concentration of hypoxanthine. In some embodiments, the LC method is used to determine the concentration of adenine. In some embodiments, the LC method is used to determine the concentration of pyruvate. In some embodiments, the LC method is used to determine the concentration of glucose. In some embodiments, the LC method is used to determine the concentration of lactate.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method of the present disclosure is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC).

In some embodiments, a hydrophilic interaction liquid chromatography (HILIC) method is employed. In some embodiments, a reverse phase liquid chromatography (RPLC) method is employed. In some embodiments, the HILIC method and the RPLC method utilizes an Acquity UPLC column, an XBridge column or an Atlantis column. In some embodiments, the extracellular and intracellular samples are analyzed 1, 2, 3, 4, 5 or more times in positive ionization mode and/or in negative ionization mode using either acidic or basic chromatographic conditions. In some embodiments, the flow rate, in both negative and positive mode, is about 0.4 or more milliliters per minute. In some embodiments, any suitable buffers for the HILIC method are used. Exemplary buffers include trifluoroacetic acid (TFA), acetic acid, acetonitrile, formic acid, methanol, acetate, formate, 4-methylmorpholine, ammonia, ammonium bicarbonate, ammonium acetate, ammonium formate, triethylamine and pyrrolidine. In some embodiments, different buffers are used in the positive mode and the negative mode. In some embodiments, the same buffers are used in the positive mode and the negative mode. In some embodiments, each mode utilizes two buffers, a buffer A and a buffer B. In some embodiments, an acetonitrile:water buffer (buffer A:B) is used for positive mode and an acetonitrile:sodium bicarbonate buffer (A:B) is used for negative mode. In some embodiments, the ratio of acetonitrile:water is about 100:0 in positive mode. In some embodiments, the ratio of acetonitrile:sodium bicarbonate is about 95:5. In some embodiments, a methanol:water buffer (A:B) is used for both modes. In some embodiments, the ratio is represented as a percentage. In some embodiments, an additive is added to the buffer. In some embodiments, 0.1% formic acid is added to the buffer. In some embodiments, an elution gradient is used to elude the sample from the column. In some embodiments, the elution gradient is tailored to the elution of a particular sample. Exemplary elution gradient include 0 min 99% buffer A; 8 min 20% buffer A; 8.5 min 99% buffer A; 10 min 99% buffer A or 0 min 99% A; 2 min 80% A; 5 min 20% A; 6 min 20% A; 6.5 min 99% A; 10 min 99% A.

In some embodiments, the HPLC method is used to determine the concentration of inosine, hypoxanthine, adenine, pyruvate, glucose, lactate, or a combination thereof. In some embodiments, the HPLC method is used to determine the concentration of inosine, hypoxanthine, adenine, pyruvate, glucose and lactate. In some embodiments, the HPLC method is used to determine the concentration of inosine. In some embodiments, the HPLC method is used to determine the concentration of hypoxanthine. In some embodiments, the HPLC method is used to determine the concentration of adenine. In some embodiments, the HPLC method is used to determine the concentration of pyruvate. In some embodiments, the HPLC method is used to determine the concentration of glucose. In some embodiments, the HPLC method is used to determine the concentration of lactate.

In some embodiments, the LC is coupled to a mass spectroscopy as a LC-MS method. In some embodiments, the LC-MS method includes ultra-performance liquid chromatography-electrospray ionization quadrupole time-of-flight mass spectrometry (UPLC-ESI-QTOF-MS), ultra-performance liquid chromatography-electrospray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ERLIC-MS), liquid chromatography time-of-flight mass spectrometry (LC-QTOF-MS) and liquid chromatography-tandem mass spectrometry (LC-MS/MS). In some embodiments, the LC-MS method of the present disclosure is performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

Nuclear Magnetic Resonance

In some embodiments, the nuclear magnetic resonance (NMR) method is any suitable method well known in the art for the detection of one or more metabolites disclosed herein. In some embodiments, the NMR method includes one dimensional (1D) NMR methods, two dimensional (2D) NMR methods, solid state NMR methods and NMR chromatography. Exemplary 1D NMR methods include $^{1}$Hydrogen, $^{13}$Carbon, $^{15}$Nitrogen, $^{17}$Oxygen, $^{19}$Fluorine, $^{3}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and 1D-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR chromatography include diffusion ordered spectroscopy (DOSY), DOSY-TOCSY and DOSY-HSQC.

Flow Cytometry Analysis

In some embodiments, a flow cytometry method is used to analyze one or more of the biomarkers described herein. In some embodiments, flow cytometry is used to determine expression of soluble CD40 ligand (sCD40L), CD41, CD42b, CD63+, and/or annexin V. In some embodiments, flow cytometry is used to determine expression of soluble CD40 ligand (sCD40L). In some embodiments, flow cytometry is used to determine expression of CD41. In some embodiments, flow cytometry is used to determine expression of CD42b. In some embodiments, flow cytometry is used to determine expression of CD63+. In some embodiments, flow cytometry is used to determine expression of annexin V.

Data Analysis

In some embodiments, any suitable data analysis methods and softwares is applied to the methods described herein. In some embodiments, the raw data generated from the blood-gas analysis, enzymatic assay, flow cytometry analysis, HPLC, LC-MS, GC-MS, CE-MS, and/or NMR methods are processed and analyzed using any suitable analysis methods and softwares. In some embodiments, the raw data generated from the blood-gas analysis and/or LC-MS methods from an RBC sample or from a PLT sample are processed and analyzed using a QuanLynx analysis software or a MarkerLynx analysis software. In some embodiments, the raw data is further processed and analyzed using a principal component analysis (PCA) method. In some embodiments, a standard deviation is calculated. In some embodiments, the raw data of one or more biomarkers described herein is compiled into a dataset. In some embodiments, the dataset also includes the results from one or more of the analysis methods. In some embodiments, the dataset further includes the values of the biomarkers described herein. In some embodiments, a report is generated using the dataset. In some embodiments, the report is transmitted to an end-user.

Control

As used herein, a control is a signature profile of a biomarker. In some embodiments, the signature profile is a biomarker profile over storage time. In some embodiments, the value of the biomarker is determined from one or more RBC samples or one or more PLT samples. For example, the concentration of inosine from one RBC sample over storage time is referred to as a signature profile of inosine. For example, the mean concentration of inosine from 20 RBC samples over storage time is also referred to as a signature profile of inosine. In some embodiments, the value of the biomarker is generated from 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 1000 or more RBC samples. In some embodiments, the value of the biomarker is represented as a value, a mean value, a medium value, a mode value, a weighted average value or a normalized value. In some embodiments, the signature profile is represented as a value, a mean value, a medium value, a mode value, a weighted average value or a normalized value.

In some embodiments, the signature profile contains a plurality of values. In some embodiments, a profile curve is generated from the plurality of values. In some embodiments, each individual value from the plurality of values correlates to the biomarker at a specific time point. In some embodiments, the profile curve contains an initial value correlating to the biomarker at a first time point and an end-point value correlating to the biomarker at a second time point.

In some embodiments, a signature profile is categorized based on time. In some embodiments, the time is represented as 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 days. In some embodiments, a signature profile for an RBC sample is categorized into three phases with First Phase (Healthy Phase) from about day 0 to about day 10, Second Phase (Transition Phase) from about day 11 to about day 18 and Third Phase (Old Phase) from about day 19 to about day 46. In some embodiments, a signature profile for a PLT sample is categorized into two phases with First Phase from day 0 to about day 3 and Second Phase from about day 4 to about day 10. In some embodiments, the signature profile is presented as a graph, a chart, a table or a diagram.

In some embodiments, the signature profile is generated from different types of detection experiments. As described elsewhere herein, the different types of detection experiments involved utilizing one or more methods selected from the group consisting of blood-gas analysis, enzymatic assay, flow cytometry, high performance liquid chromatography (HPLC), liquid chromatography-mass spectrometry (LC-MS), gas chromatography-mass spectrometry (GC-MS), capillary electrophoresis-mass spectrometry (CE-MS), nuclear magnetic resonance imaging (NMR) and data analysis method. In some embodiments, the signature profile is generated from detection experiments using blood-gas analysis method, enzymatic assay, flow cytometry, HPLC method, or a combination thereof. In some embodiments, the signature profile is generated from detection experiments using a blood-gas analysis method. In some embodiments, the signature profile is generated from detection experiments using an enzymatic assay. In some embodiments, the signature profile is generated from detection experiments using a flow cytometry method. In some embodiments, the signature profile is generated from detection experiments using an HPLC method. In some embodiments, the enzymatic assay is a colorimetric assay, a luminescent assay, or a combination thereof. In some embodiments, the signature profile is generated from detection experiments using a colorimetric assay. In some embodiments, the signature profile is generated from detection experiments using a luminescent assay. In some embodiments, the luminescent assay is a fluorometric assay. In some embodiments, the signature profile is generated from detection experiments using a fluorometric assay.

In some embodiments, a signature profile is a control. In some embodiments, the control is a control for an RBC sample or a PLT sample. In some embodiments, the control is an RBC control. In some embodiments, the RBC control is categorized into three phases. In some embodiments, the three phases are First Phase (Healthy Phase), Second Phase (Transition Phase) and Third Phase (Old Phase). In some embodiments, the RBC control is presented as a graph, a chart, a table or a diagram. In some embodiments, the RBC control is generated utilizing one or more methods selected from the group consisting of blood-gas analysis, enzymatic assay, high performance liquid chromatography (HPLC), liquid chromatography-mass spectrometry (LC-MS), gas chromatography-mass spectrometry (GC-MS), capillary electrophoresis-mass spectrometry (CE-MS), nuclear magnetic resonance imaging (NMR) and data analysis method. In some embodiments, the RBC control is generated utilizing a blood-gas analysis method, an enzymatic assay, a HPLC method, or a combination thereof. In some embodiments, the RBC control is generated utilizing a blood-gas analysis method. In some embodiments, the RBC control is generated utilizing an enzymatic assay. In some embodiments, the RBC control is generated utilizing an HPLC method. In some embodiments, the enzymatic assay is a colorimetric assay, a luminescent assay, or a combination thereof. In some embodiments, the RBC control is generated utilizing a colorimetric assay. In some embodiments, the luminescent assay is a fluorometric assay. In some embodiments, the RBC control is generated utilizing a fluorometric assay.

In some embodiments, the control is a PLT control. In some embodiments, the PLT control is categorized into two phases. In some embodiments, the two phases are First Phase and Second Phase. In some embodiments, the PLT control is presented as a graph, a chart, a table or a diagram. In some embodiments, the PLT control is generated utilizing one or more methods selected from the group consisting of blood-gas analysis, enzymatic assay, flow cytometry, high performance liquid chromatography (HPLC), liquid chromatography-mass spectrometry (LC-MS), gas chromatography-mass spectrometry (GC-MS), capillary electrophoresis-mass spectrometry (CE-MS), nuclear magnetic resonance imaging (NMR) and data analysis method. In some embodiments, the PLT control is generated utilizing a blood-gas analysis method. In some embodiments, the PLT control is generated utilizing an enzymatic assay. In some embodiments, the PLT control is generated utilizing a flow cytometry method. In some embodiments, the PLT control is generated utilizing an HPLC method. In some embodiments, the enzymatic assay is a colorimetric assay, a luminescent assay, or a combination thereof. In some embodiments, the PLT control is generated utilizing a colorimetric assay. In some embodiments, the luminescent assay is a fluorometric assay. In some embodiments, the PLT control is generated utilizing a fluorometric assay.

RBC Storage Device

Disclosed herein are RBC storage devices for use with the methods and systems described herein. In some embodiments, disclosed herein is a storage device comprising: a container containing a composition comprising red blood cells (RBCs) and an additive solution, wherein the container comprises an indicator which displays a phase of red blood cells (RBCs) stored therein. In some embodiments, the phase is indicated by an electronic or a non-electronic display system. In some embodiments, the phase is First Phase, Second Phase, or Third Phase. In some embodiments, First Phase is associated with about day 1 to about day 10. In some embodiments, Second Phase is associated with about day 11 to about day 18. In some embodiments, Third Phase is associated with about day 18 to about day 46. In some embodiments, Third Phase is associated with about day 19 to about day 46. In some embodiments, the phase is indicated by a date, dates or a range of dates. In some embodiments, the biomarker value is selected from one or more of: concentration of inosine, concentration of hypoxanthine, concentration of adenine, ratio of hypoxanthine:adenine, ratio of glucose:lactate, ratio of $Na^+$:$K^+$, ratio of inosine:adenine, concentration of pyruvate. In some embodiments, disclosed herein is a storage device comprising: a container; a composition comprising red blood cells (RBCs) and an additive solution in the container; and an indicator which displays the metabolic state of RBCs stored therein; wherein the indicator has a testing module which contains reagents and analytes for carrying out a test reaction to allow detection of one or more biomarkers; and the metabolic state of the RBCs is displayed as one of a First, a Second or a Third Phase; wherein the metabolic state of the RBCs is classified as: (a) First Phase by comparing the measured ratio of glucose:lactate and the ratio of $Na^+$:$K^+$ match the values on the control indicated for the First Phase; and optionally when one or more of the concentration of inosine, the ratio of hypoxanthine:adenine, the ratio of inosine:adenine and the concentration of pyruvate match the values on the control indicated for First Phase; (b) Second Phase when the ratio of hypoxanthine:adenine matches the value on the control indicated for the Second Phase; and optionally when concentration of inosine and/or the ratio of inosine:adenine matches the values on the control indicated for Second Phase; or (c) Third Phase when the ratio of hypoxanthine:adenine, the concentration of hypoxanthine and the concentration of adenine match the values on the control indicated for the Third Phase; and optionally when one or more of $pCO_2$:pH, the ratio of inosine:adenine and the concentration of inosine match the values on the control indicated for the Third Phase.

Electronic Display System for RBCs

In some embodiments, the indicator is an electronic display system. In some embodiments, the electronic display system is any suitable electronic display system for use, such as for example, but not limited to, LCD display system (e.g. TN segment, TFT-LCD), LED display system, OLED display system, or pixel-based (e.g. E-paper) display system. In some embodiments, the electronic display system is an electronic label. In some embodiments, the electronic display system is able to detect one or more biomarkers selected from: concentration of inosine, concentration of hypoxanthine, concentration of adenine, ratio of hypoxanthine:adenine, ratio of glucose:lactate, ratio of $Na^+$:$K^+$, ratio of inosine:adenine, and concentration of pyruvate.

In some embodiments, the electronic label is a pictorial label, a color label, an alpha-numerical label, a sound label, or a combination thereof. In some embodiments, the electronic label displays a set of dates correspond to First Phase, Second Phase and Third Phase. In some embodiments, the electronic label displays a phase of the RBC unit in a particular color, a set of dates associated with the phase and a tracking code unique to this RBC unit.

In some embodiments, the electronic label is updated either locally or remotely. In some embodiments, the electronic label is updated locally through touch-screen interface, buttons, joy stick, track ball and so forth. In some embodiments, the electronic label is updated remotely by communicating wirelessly to a digital processing device. In some embodiments, the digital processing device wirelessly communicates a change in phase to the electronic label and updates the set of days to correspond to the newly updated phase. In some embodiments, the change in phase is reflected through a pictorial change, a color change, an alpha-numerical change, a sound change, or a combination thereof.

Figure 2:
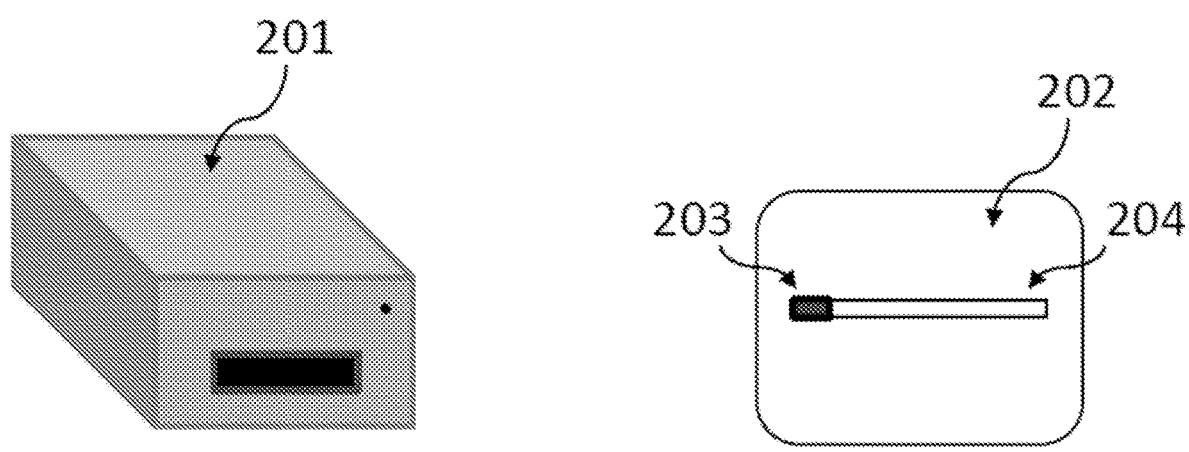
FIG. 2 illustrates a conceptual schematic of an exemplary electronic test label.

In some embodiments, the electronic label is an electronic test label (or a smart test label). In some embodiments, the electronic test label includes an analytical module 201 and a testing module 202 (FIG. 2). In some embodiments, the testing module contains a sample receiving portion 203 and a detection portion 204 which contains the reagents and analytes necessary for carrying out the test reaction to allow detection of one or more biomarkers disclosed herein. In some embodiments, testing module further contains submodules such as valves, pumps, electrodes, channels, or additional submodules necessary to allow for sample movement into the detection portion and thereby for analysis by the analytical module. In some embodiments, the analytical module further communicates wirelessly with a digital processing device and thereby sends updated information and also receives information. In some embodiments, the digital processing device wirelessly communicates a change in phase to the electronic test label and updates the set of dates to correspond to the newly updated phase. In some embodiments, the change in phase is reflected through pictorial means, color means, alpha-numerical means, sound means, or a combination thereof.

In some embodiments, the electronic test label indicates the phase of the RBCs. In some embodiments, the electronic test label indicates the phase of RBCs through pictorial means, color means, alpha-numerical means, sound means, or a combination thereof. In some embodiments, the electronic test label indicates the phase of RBCs through a color. In some embodiments, the electronic test label indicates a change which is reflected through pictorial means, color means, alpha-numerical means, sound means, or a combination thereof. In some embodiments, the electronic test label indicates a change through a change in color.

In some embodiments, the electronic display system displays the metabolic state of RBCs stored therein; wherein the electronic display system has a testing module which contains reagents and analytes for carrying out a test reaction to allow detection of one or more biomarkers; and the metabolic state of the RBCs is displayed as one of a First, a Second or a Third Phase; wherein the metabolic state of the RBCs is classified as: (a) First Phase by comparing the measured ratio of glucose:lactate and the ratio of Na+:K+ match the values on the control indicated for the First Phase; and optionally when one or more of the concentration of inosine, the ratio of hypoxanthine:adenine, the ratio of inosine:adenine and the concentration of pyruvate match the values on the control indicated for First Phase; (b) Second Phase when the ratio of hypoxanthine:adenine matches the value on the control indicated for the Second Phase; and optionally when concentration of inosine and/or the ratio of inosine:adenine matches the values on the control indicated for Second Phase; or (c) Third Phase when the ratio of hypoxanthine:adenine, the concentration of hypoxanthine and the concentration of adenine match the values on the control indicated for the Third Phase; and optionally when one or more of pCO2:pH, the ratio of inosine:adenine and the concentration of inosine match the values on the control indicated for the Third Phase.

Non-Electronic Display System for RBCs

In some embodiments, the indicator is a non-electronic display system. In some embodiments, the non-electronic display system comprises a non-electronic label, a color display, a tracking code, a barcode, a test strip, or a combination thereof. In some embodiments, the non-electronic label is a pictorial label, a color label, an alpha-numerical label, a non-electronic test label, or a combination thereof. In some embodiments, the non-electronic label displays a set of dates correspond to First Phase, Second Phase and Third Phase. In some embodiments, the non-electronic label displays a phase of the RBC unit in a particular color, a set of dates associated with the phase and a tracking code or a barcode unique to this RBC unit. In some embodiments, bar code includes one dimensional barcodes and two dimensional barcodes. Exemplary one dimensional and two dimensional barcodes include, but are not limited to, Codabar, Code 25, Code 11, Code 39, Code 93, Code 128, CPC binary, EAN-2, EAN-5, EAN-8, EAN-13, GS1-128, GS1 databar, HIBCC, ITF-14, JAN, MSI, Pharmacode, Plessey, UPC, Aztec Code, Code 1, ColorCode, Data Matrix, EZcode, High Capacity Color Barcode, MaxiCode, NexCode, PDF417, QR Code, ShotCode and SPARQCode. In some embodiments, the barcodes is readable by any barcode readers such as handheld scanners, pen scanners (or wand scanners), stationary scanners, fixed-position scanners, PDA scanners, automatic readers, cordless scanners, or portable electronic communication devices (e.g. cell phones or tablets). In some embodiments, the non-electronic display system is able to detect one or more biomarkers selected from: concentration of inosine, concentration of hypoxanthine, concentration of adenine, ratio of hypoxanthine:adenine, ratio of glucose:lactate, ratio of $Na^+:K^+$, ratio of inosine:adenine, and concentration of pyruvate.

In some embodiments, the non-electronic display system is printed on any suitable materials. In some embodiments, the suitable materials include polyester based, polypropylene based, vinyl based, polyolefin based, acetate based, or polystyrene based materials, paper, cloth, foil, or a combination thereof.

Figure 3:
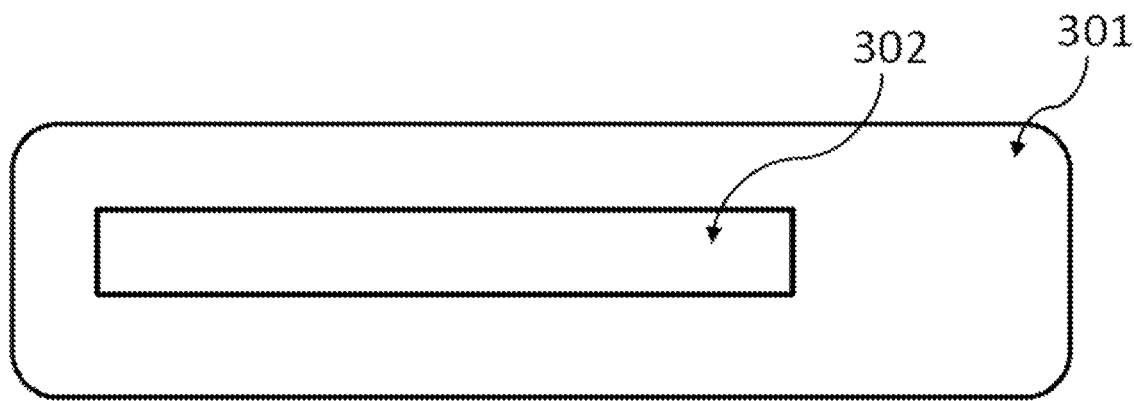
FIG. 3 illustrates a conceptual schematic of an exemplary non-electronic test label.

In some embodiments, the non-electronic display system is a non-electronic test label 301 (FIG. 3). In some embodiments, the non-electronic test label 301 contains a test portion 302. In some embodiments, the test portion contains reagents and analytes necessary for carrying out the test reaction to allow testing of one or more biomarkers disclosed herein. In some embodiments, the test portion detects one or more biomarkers in an RBC sample by a lateral flow assay, including biochemical assays such as immunoassays, enzymatic assays, enzyme-based immunoassays, and chemical assays. In some embodiments, the test portion contains a sample receiving zone 303, a reaction zone 304, a detection zone 305 and an absorbent pad or wick 306 for receiving the fluid and promoting capillary flow through the test portion. In some embodiments, the lateral flow assay is carried out when the sample is in contact with the receiving zone 303 and allowing it to travel along the test portion by capillary action, to react with the reagents provided in the reaction zone 304 and further downstream to be captured and concentrated at the detection zone 305. In some embodiments, the lateral flow assay is carried out by applying the sample at the receiving zone 303 and allowing it to travel along the remaining zones. In some embodiments, a color change is triggered by a reaction from the detection zone 305. In some embodiments, the color change is associated with the presence, increase or decrease of one or more biomarkers.

In some embodiments, a change in one or more biomarker levels is indicated by a change in one or more colors. For example, the set of biomarkers associated with First Phase, Second Phase, and Third Phase corresponds to a color and a change in each set of biomarker levels triggers a color change. The changes in colors indicate a change in phase. Alternatively, each individual biomarker corresponds to an individual color. A change in each color indicates a change in the biomarker level. Then the panels of colors are matched to a color code such as a color palette, a color chart and so forth to derive the phase.

In some embodiments, the non-electronic test label indicates the phase of the RBCs. In some embodiments, the non-electronic test label indicates the phase of RBCs through pictorial means, color means, alpha-numerical means, or a combination thereof. In some embodiments, the non-electronic test label indicates the phase of RBCs through a color. In some embodiments, the non-electronic test label indicates a change is reflected through a pictorial change, a color change, an alpha-numerical change, a sound change, or a combination thereof. In some embodiments, the non-electronic test label indicates a change through a change in color.

In some embodiments, the non-electronic test label is a test strip or a test patch. In some embodiments, the non-electronic test label is a test strip. In some embodiments, the test strip indicates the phase of the RBCs. In some embodiments, the test strip indicates the phase of RBCs through pictorial means, color means, alpha-numerical means, or a combination thereof. In some embodiments, the test strip indicates the phase of RBCs through a color. In some embodiments, the test strip indicates a change is reflected through a pictorial change, a color change, an alpha-numerical change, a sound change, or a combination thereof. In some embodiments, the test strip indicates a change through a change in color. In some embodiments, the test strip is further analyzed by a test meter to measure the levels of each biomarker.

In some embodiments, the non-electronic display system displays (e.g., test strip, test patch) the metabolic state of RBCs stored therein; wherein the non-electronic display system has a testing module which contains reagents and analytes for carrying out a test reaction to allow detection of one or more biomarkers; and the metabolic state of the RBCs is displayed as one of a First, a Second or a Third Phase; wherein the metabolic state of the RBCs is classified as: (a) First Phase by comparing the measured ratio of glucose:lactate and the ratio of Na+:K+ match the values on the control indicated for the First Phase; and optionally when one or more of the concentration of inosine, the ratio of hypoxanthine:adenine, the ratio of inosine:adenine and the concentration of pyruvate match the values on the control indicated for First Phase; (b) Second Phase when the ratio of hypoxanthine:adenine matches the value on the control indicated for the Second Phase; and optionally when concentration of inosine and/or the ratio of inosine:adenine matches the values on the control indicated for Second Phase; or (c) Third Phase when the ratio of hypoxanthine:adenine, the concentration of hypoxanthine and the concentration of adenine match the values on the control indicated for the Third Phase; and optionally when one or more of pCO2:pH, the ratio of inosine:adenine and the concentration of inosine match the values on the control indicated for the Third Phase.

RBC Containers

In some embodiments, the container is any containers suitable for the long term storage of RBCs. In some embodiments, the container is permeable to oxygen or at least semi-permeable to oxygen. In some embodiments, the container includes one or more container walls which define an interior chamber for receiving the RBC composition. In one embodiment, the container wall is made of a single layer of a polymeric material, such as a polyvinyl chloride (PVC) or non-PVC polymer or polymer blend. In another embodiment, the container wall is made of a multiple sheet laminate wherein the inner surface is made of one material and the outer surface is made of a different material. In some embodiments, the container contains one or more access ports for connection with tubing, docking devices and the like to establish flow into and out from the interior chamber of the container.

In one embodiment, containers useful in the storage of RBCs as described above include container walls that are made of a polymeric material comprising in whole or at least in part of a plastic material that include at least one or more polymeric compounds. In one embodiment, the one or more plastic and/or polymeric compounds is blended together and formed into flat sheets that are sealed together. In another embodiment, the polymeric material is made from or otherwise includes polyvinyl chloride (PVC) or one or more non-PVC plastics such as non-PVC polyolefin homopolymers, copolymers or blends thereof, or plasticizer-free polyolefin. Exemplary non-PVC polyolefins include polypropylene, polyethylene, including ultra-low density polyethylene (ULDPE) and very low density polyethylene (VLDPE). In another embodiment, other suitable compounds that are used in the polymeric material of the container include ethylene vinyl acetate (EVA) and block copolymers such as Kraton®.

In some embodiments, containers suitable for use in the devices, systems and methods of the present disclosure also contain a plasticizer. The plasticizer is incorporated into the polymeric materials including the PVC plastics and the non-PVC plastics. For example, a container in which its polymeric material is a PVC plastic will have to be plasticized due to the brittle nature of the PVC. In one embodiment, the plasticizer includes families of phthalate esters such as di-2-ethylhexylphthalate (DEHP), mono-(2-ethylhexyl) phthalate (MEHP), and triethylhexyltrimellitate (TEHTM) and citrate esters such as acetyltri-n-hexyl citrate, acetyltri-n-(hexyl/octyl/decyl) citrate, acetyltri-n-(octyl/decyl) citrate, and n-butyryltri-n-hexyl citrate. In another embodiment, the plasticizer includes non-phthalate plasticizers or at least substantially free of phthalate plasticizers. In some embodiments, the non-phthalate plasticizers include TEHTM, di(isononyl) cyclohexane-1,2-dicarboxylate (DINCH) or n-butyryltri-n-hexyl citrate.

In some embodiments, containers suitable for storage of RBCs are not limited to any shape, size or volume. In some embodiments, the container is a bag, a box, a bottle, ajar, or a canister. In some embodiments, the container is a bag. Exemplary bags for RBC storage include, but are not limited to, Teruflex® blood bags from Terumo BCT; Fenwal, Terumo, or Pedi-Pak from Genesis BPS, Top and Top system or T-BEX system from JMS CO., LTD.; or PVC or PVC-free bags from Grifols International, S.A.

In some embodiments, the indicator is adherent to the container. In some embodiments, the indicator is adherent to the surface of the container, the wall (interior chamber) of the container or is embedded within the container. In some embodiments, the indicator is adherent to the wall of the container. In some embodiments, the indicator is an electronic display system. In some embodiments, the indicator is a non-electronic display system. In some embodiments, the non-electronic display system comprises a non-electronic label, a color display, a tracking code, a barcode, a test strip, or a combination thereof. In some embodiments, the test strip is adherent to the wall of the container. In some embodiments, the test strip is in contact with the composition comprising red blood cells (RBCs) and an additive solution. In some embodiments, the test strip is visible through the polymeric material. In some embodiments, the color displayed by the test strip is visible through the polymeric material. In some embodiments, the indicator is able to detect one or more biomarkers selected from: concentration of inosine, concentration of hypoxanthine, concentration of adenine, ratio of hypoxanthine:adenine, ratio of glucose:lactate, ratio of Na$^+$:K$^+$, ratio of inosine:adenine, and concentration of pyruvate.

Platelet Storage Device

Disclosed herein are platelet storage devices for use with the methods and systems described herein. In some embodiments, disclosed herein is a storage device which comprises (a) a container; (b) a composition comprising platelets (PLTs) in the container; and (c) an indicator which displays the metabolic state of platelets stored therein. In some embodiments, disclosed herein is a storage device which comprises (a) a container; (b) a composition comprising platelets (PLTs) in the container; and (c) an indicator which displays the metabolic state of platelets stored therein; wherein the indicator has a testing module which contains reagents and analytes for carrying out a test reaction to allow detection of one or more biomarkers; and the metabolic state of the platelets is displayed as one of First Phase or Second Phase; wherein the metabolic state of the RBCs is classified as: First Phase by comparing the measured concentration of glutathione oxidized, ratio of acetate:cis-aconitate, and either ratio of glucose:lactose or ratio of acetate:lactose as greater than the values on the control indicated as the transition from the first metabolic state to the second metabolic state; or Second Phase by comparing the measured concentration of glutathione oxidized, ratio of acetate:cis-aconitate, and either ratio of glucose:lactose or ratio of acetate:lactose as less than the values on the control indicated as the transition from the first metabolic state to the second metabolic state. In some embodiments, the phase is indicated by an electronic or a non-electronic display system. In some embodiments, the phase is First Phase or Second Phase. In some embodiments, First Phase is associated with about day 0 to about day 3. In some embodiments, Second Phase is associated with about day 4 to about day 10. In some embodiments, the phase is indicated by a date, dates or a range of dates.

Electronic Display System for Platelets

In some embodiments, the indicator is an electronic display system. In some embodiments, the electronic display system is any suitable electronic display system for use, such as for example, but not limited to, LCD display system (e.g. TN segment, TFT-LCD), LED display system, OLED display system, or pixel-based (e.g. E-paper) display system. In some embodiments, the electronic display system is an electronic label. In some embodiments, the electronic display system is able to detect one or more biomarkers selected from: concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose.

In some embodiments, the electronic label is a pictorial label, a color label, an alpha-numerical label, a sound label, or a combination thereof. In some embodiments, the electronic label displays a set of dates correspond to First Phase and Second Phase. In some embodiments, the electronic label displays a phase of the platelet unit in a particular color, a set of dates associated with the phase and a tracking code unique to this platelet unit.

In some embodiments, the electronic label is updated either locally or remotely. In some embodiments, the electronic label is updated locally through touch-screen interface, buttons, joy stick, track ball and so forth. In some embodiments, the electronic label is updated remotely by communicating wirelessly to a digital processing device. In some embodiments, the digital processing device wirelessly communicates a change in phase to the electronic label and updates the set of days to correspond to the newly updated phase. In some embodiments, the change in phase is reflected through a pictorial change, a color change, an alpha-numerical change, a sound change, or a combination thereof.

In some embodiments, the electronic label is an electronic test label (or a smart test label). As described elsewhere herein, in some embodiments, the electronic test label includes an analytical module 201 and a testing module 202 (FIG. 2). In some embodiments, the testing module contains a sample receiving portion 203 and a detection portion 204 which contains the reagents and analytes necessary for carrying out the test reaction to allow detection of one or more biomarkers disclosed herein. In some embodiments, testing module further contains submodules such as valves, pumps, electrodes, channels, or additional submodules necessary to allow for sample movement into the detection portion and thereby for analysis by the analytical module. In some embodiments, the analytical module further communicates wirelessly with a digital processing device and thereby sends updated information and also receives information. In some embodiments, the digital processing device wirelessly communicates a change in phase to the electronic test label and updates the set of dates to correspond to the newly updated phase. In some embodiments, the change in phase is reflected through pictorial means, color means, alpha-numerical means, sound means, or a combination thereof.

In some embodiments, the electronic test label indicates the phase of the PLTs. In some embodiments, the electronic test label indicates the phase of PLTs through pictorial means, color means, alpha-numerical means, sound means, or a combination thereof. In some embodiments, the electronic test label indicates the phase of PLTs through a color. In some embodiments, the electronic test label indicates a change which is reflected through pictorial means, color means, alpha-numerical means, sound means, or a combination thereof. In some embodiments, the electronic test label indicates a change through a change in color.

In some embodiments, the electronic display system displays the metabolic state of platelets stored therein; wherein the electronic display system has a testing module which contains reagents and analytes for carrying out a test reaction to allow detection of one or more biomarkers; and the metabolic state of the platelets is displayed as one of First Phase or Second Phase; wherein the metabolic state of the RBCs is classified as: First Phase by comparing the measured concentration of glutathione oxidized, ratio of acetate:cis-aconitate, and either ratio of glucose:lactose or ratio of acetate:lactose as greater than the values on the control indicated as the transition from the first metabolic state to the second metabolic state; or Second Phase by comparing the measured concentration of glutathione oxidized, ratio of acetate:cis-aconitate, and either ratio of glucose:lactose or ratio of acetate:lactose as less than the values on the control indicated as the transition from the first metabolic state to the second metabolic state.

Non-Electronic Display System for Platelets

In some embodiments, the indicator is a non-electronic display system. In some embodiments, the non-electronic display system comprises a non-electronic label, a color display, a tracking code, a barcode, a test strip, or a combination thereof. In some embodiments, the non-electronic label is a pictorial label, a color label, an alpha-numerical label, a non-electronic test label, or a combination thereof. In some embodiments, the non-electronic label displays a set of dates correspond to First Phase and Second Phase. In some embodiments, the non-electronic label displays a phase of the platelet unit in a particular color, a set of dates associated with the phase and a tracking code or a barcode unique to this platelet unit. In some embodiments, bar code includes one dimensional barcodes and two dimensional barcodes. Exemplary one dimensional and two dimensional barcodes include, but are not limited to, Codabar, Code 25, Code 11, Code 39, Code 93, Code 128, CPC binary, EAN-2, EAN-5, EAN-8, EAN-13, GS1-128, GS1 databar, HIBCC, ITF-14, JAN, MSI, Pharmacode, Plessey, UPC, Aztec Code, Code 1, ColorCode, Data Matrix, EZcode, High Capacity Color Barcode, MaxiCode, NexCode, PDF417, QR Code, ShotCode and SPARQCode. In some embodiments, the barcodes is readable by any barcode readers such as handheld scanners, pen scanners (or wand scanners), stationary scanners, fixed-position scanners, PDA scanners, automatic readers, cordless scanners, or portable electronic communication devices (e.g. cell phones or tablets). In some embodiments, the non-electronic display system is able to detect one or more biomarkers selected from: concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, or ratio of acetate:lactose.

In some embodiments, the non-electronic display system is printed on any suitable materials. In some embodiments, the suitable materials include polyester based, polypropylene based, vinyl based, polyolefin based, acetate based, or polystyrene based materials, paper, cloth, foil, or a combination thereof.

As described elsewhere herein, in some embodiments, the non-electronic display system is a non-electronic test label 301 (FIG. 3). In some embodiments, the non-electronic test label 301 contains a test portion 302. In some embodiments, the test portion contains reagents and analytes necessary for carrying out the test reaction to allow testing of one or more biomarkers disclosed herein. In some embodiments, the test portion detects one or more biomarkers in a platelet sample by a lateral flow assay, including biochemical assays such as immunoassays, enzymatic assays, enzyme-based immunoassays, and chemical assays. In some embodiments, the test portion contains a sample receiving zone 303, a reaction zone 304, a detection zone 305 and an absorbent pad or wick 306 for receiving the fluid and promoting capillary flow through the test portion. In some embodiments, the lateral flow assay is carried out when the sample is in contact with the receiving zone 303 and allowing it to travel along the test portion by capillary action, to react with the reagents provided in the reaction zone 304 and further downstream to be captured and concentrated at the detection zone 305. In some embodiments, the lateral flow assay is carried out by applying the sample at the receiving zone 303 and allowing it to travel along the remaining zones. In some embodiments, a color change is triggered by a reaction from the detection zone 305. In some embodiments, the color change is associated with the presence, increase or decrease of one or more biomarkers.

In some embodiments, a change in one or more biomarker levels is indicated by a change in one or more colors. For example, the set of biomarkers associated with First Phase and Second Phase corresponds to a color and a change in each set of biomarker levels triggers a color change. The changes in colors indicate a change in phase. Alternatively, each individual biomarker corresponds to an individual color. A change in each color indicates a change in the biomarker level. Then the panels of colors are matched to a color code such as a color palette, a color chart and so forth to derive the phase.

In some embodiments, the non-electronic test label indicates the phase of the PLTs. In some embodiments, the non-electronic test label indicates the phase of PLTs through pictorial means, color means, alpha-numerical means, or a combination thereof. In some embodiments, the non-electronic test label indicates the phase of PLTs through a color. In some embodiments, the non-electronic test label indicates a change is reflected through a pictorial change, a color change, an alpha-numerical change, a sound change, or a combination thereof. In some embodiments, the non-electronic test label indicates a change through a change in color.

In some embodiments, the non-electronic test label is a test strip or a test patch. In some embodiments, the non-electronic test label is a test strip. In some embodiments, the test strip indicates the phase of the PLTs. In some embodiments, the test strip indicates the phase of PLTs through pictorial means, color means, alpha-numerical means, or a combination thereof. In some embodiments, the test strip indicates the phase of PLTs through a color. In some embodiments, the test strip indicates a change is reflected through a pictorial change, a color change, an alpha-numerical change, a sound change, or a combination thereof. In some embodiments, the test strip indicates a change through a change in color. In some embodiments, the test strip is further analyzed by a test meter to measure the levels of each biomarker.

In some embodiments, the non-electronic display system (e.g., test strip, test patch) displays the metabolic state of platelets stored therein; wherein the non-electronic display system has a testing module which contains reagents and analytes for carrying out a test reaction to allow detection of one or more biomarkers; and the metabolic state of the platelets is displayed as one of First Phase or Second Phase; wherein the metabolic state of the RBCs is classified as: First Phase by comparing the measured concentration of glutathione oxidized, ratio of acetate:cis-aconitate, and either ratio of glucose:lactose or ratio of acetate:lactose as greater than the values on the control indicated as the transition from the first metabolic state to the second metabolic state; or Second Phase by comparing the measured concentration of glutathione oxidized, ratio of acetate:cis-aconitate, and either ratio of glucose:lactose or ratio of acetate:lactose as less than the values on the control indicated as the transition from the first metabolic state to the second metabolic state.

Platelet Containers

In some embodiments, the container is any containers suitable for the long term storage of PLTs. In some embodiments, the container is permeable to oxygen or at least semi-permeable to oxygen. In some embodiments, the container includes one or more container walls which define an interior chamber for receiving the platelet composition. In one embodiment, the container wall is made of a single layer of a polymeric material, such as a polyvinyl chloride (PVC) or non-PVC polymer or polymer blend. In another embodiment, the container wall is made of a multiple sheet laminate wherein the inner surface is made of one material and the outer surface is made of a different material. In some embodiments, the container contains one or more access ports for connection with tubing, docking devices and the like to establish flow into and out from the interior chamber of the container.

In one embodiment, containers useful in the storage of PLTs as described above include container walls that are made of a polymeric material comprising in whole or at least in part of a plastic material that include at least one or more polymeric compounds. In one embodiment, the one or more plastic and/or polymeric compounds is blended together and formed into flat sheets that are sealed together. In another embodiment, the polymeric material is made from or otherwise includes polyvinyl chloride (PVC) or one or more non-PVC plastics such as non-PVC polyolefin homopolymers, copolymers or blends thereof, or plasticizer-free polyolefin. Exemplary non-PVC polyolefins include polypropylene, polyethylene, including ultra-low density polyethylene (ULDPE) and very low density polyethylene (VLDPE). In another embodiment, other suitable compounds that are used in the polymeric material of the container include ethylene vinyl acetate (EVA) and block copolymers such as Kraton®.

In some embodiments, containers suitable for use in the devices, systems and methods of the present disclosure also contain a plasticizer. The plasticizer is incorporated into the polymeric materials including the PVC plastics and the non-PVC plastics. For example, a container in which its polymeric material is a PVC plastic will have to be plasticized due to the brittle nature of the PVC. In one embodiment, the plasticizer includes families of phthalate esters such as di-2-ethylhexylphthalate (DEHP), mono-(2-ethylhexyl) phthalate (MEHP), and triethylhexyltrimellitate (TEHTM) and citrate esters such as acetyltri-n-hexyl citrate, acetyltri-n-(hexyl/octyl/decyl) citrate, acetyltri-n-(octyl/decyl) citrate, and n-butyryltri-n-hexyl citrate. In another embodiment, the plasticizer includes non-phthalate plasticizers or at least substantially free of phthalate plasticizers. In some embodiments, the non-phthalate plasticizers include TEHTM, di(isononyl) cyclohexane-1,2-dicarboxylate (DINCH) or n-butyryltri-n-hexyl citrate.

In some embodiments, containers suitable for storage of platelets are not limited to any shape, size or volume. In some embodiments, the container is a bag, a box, a bottle, ajar, or a canister. In some embodiments, the container is a bag. Exemplary bags for RBC storage include, but are not limited to, Teruflex® blood bags from Terumo BCT; Fenwal, Terumo, or Pedi-Pak from Genesis BPS, Top and Top system or T-BEX system from JMS CO., LTD.; or PVC or PVC-free bags from Grifols International, S.A.

In some embodiments, the indicator is adherent to the container. In some embodiments, the indicator is adherent to the surface of the container, the wall (interior chamber) of the container or is embedded within the container. In some embodiments, the indicator is adherent to the wall of the container. In some embodiments, the indicator is an electronic display system. In some embodiments, the indicator is a non-electronic display system. In some embodiments, the non-electronic display system comprises a non-electronic label, a color display, a tracking code, a barcode, a test strip, or a combination thereof. In some embodiments, the test strip is adherent to the wall of the container. In some embodiments, the test strip is in contact with the composition comprising platelets. In some embodiments, the test strip is in contact with the composition comprising platelets and an additive solution. In some embodiments, the test strip is visible through the polymeric material. In some embodiments, the color displayed by the test strip is visible through the polymeric material. In some embodiments, the indicator is able to detect one or more biomarkers selected from: concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate: cis-aconitate, ratio of glucose:lactose, ratio of acetate:succinate, or ratio of acetate:lactose.

Compositions and Kits

Disclosed herein, in certain embodiments, are compositions and kits for use with the methods and systems described herein. In some embodiments, disclosed herein is a kit for determining the phase or metabolic state of a red blood cell (RBC) sample, comprising: (a) a plurality of reagents and analytes for determining a dataset for a biomarker, wherein the biomarker is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate; (b) at least one software module for analyzing the dataset to determine a value of the biomarker, matching the value of the biomarker to an equivalent value on a control; and assigning the RBC sample as First Phase, Second Phase or Third Phase, wherein the value of the biomarker indicates the phase of the RBC sample; and (c) instruction manuals for utilizing the plurality of reagents and analytes and the at least one software module. In some embodiments, the compositions comprise any reagents, reaction mixtures, and/or analytes described herein, as well as any combination thereof. In some embodiments, any suitable reagents are provided, including reagent for solubilizing the RBC samples, reagents used for blood-gas analysis methods, reagents used for enzymatic assays, reagents used for facilitating HPLC, reagents used for mass spectrometry and internal standards for use with the disclosed analytical methods. In some embodiments, the plurality of reagents and analytes comprise reagents and analytes for separating the RBC sample into an extracellular portion and an intracellular portion. In some embodiments, the extracellular portion of the RBC sample comprises inosine, hypoxanthine, adenine, $Na^+$, $K^+$, glucose, lactate and pyruvate. In some embodiments, the biomarker obtained from the extracellular portion is concentration of inosine, concentration of hypoxanthine, concentration of adenine, ratio of hypoxanthine:adenine, ratio of glucose:lactate, ratio of $Na^+$:$K^+$, ratio of $pCO_2$:pH, ratio of inosine:adenine, or concentration of pyruvate. In some embodiments, the plurality of reagents and analytes comprise reagents and analytes for analyzing the RBC sample to determine a raw data for inosine, hypoxanthine, adenine, glucose, lactate, $Na^+$, $K^+$, $pCO_2$, pH, and pyruvate. In some embodiments, the raw data is determined utilizing a method selected from the group consisting of high-performance liquid chromatography (HPLC), blood-gas analysis and enzymatic assays. In some embodiments, the enzymatic assay is a colorimetric assay or a luminescent assay. In some embodiments, the luminescent assay is a fluorometric assay. In some embodiments, the enzymatic assay is a colorimetric assay. In some embodiments, the enzymatic assay is a fluorometric assay. In some embodiments, the enzymatic assay is monitored by photometric measurements. In some embodiments, the colorimetric assay is monitored by photometric measurements. In some embodiments, the luminescent assay is monitored by photometric measurements. In some embodiments, the fluorometric assay is monitored by photometric measurements. In some embodiments, any suitable analytes are provided, such as for example, for use in biochemical assays such as enzymatic assays for detection of an RBC phase. In some embodiments, analytes include enzymes or antibodies for use in biochemical assays such as enzymatic assays for detection of an RBC phase.

In some embodiments, disclosed herein is a kit for determining the phase or metabolic state of a platelet (PLT) sample, comprising: (a) a plurality of reagents and analytes for determining a dataset for a biomarker, wherein the biomarker is concentration of glutamine, concentration of niacinamide, concentration of glutathione oxidized, concentration of succinic acid, concentration of sCD40L, value of CD41:CD63, value of CD41:Annexin-V, value of CD41:CD42b, ratio of citrate:cis-aconitate, ratio of citrate:malate, ratio of acetate:cis-aconitate, ratio of glucose:lactose, ratio of acetate:succinate, ratio of acetate:lactose, or any combination thereof; (b) at least one software module for analyzing the dataset to determine a value of the biomarker, comparing the value of the biomarker to a respective biomarker value in a control dataset; and assigning the PLT sample as First Phase or Second Phase, wherein the value of the biomarker indicates the phase of the PLT sample; and (c) instruction manuals for utilizing the plurality of reagents and analytes and the at least one software module. In some embodiments, the compositions comprise any reagents, reaction mixtures, and/or analytes described herein, as well as any combination thereof. In some embodiments, any suitable reagents are provided, including reagent for solubilizing the PLT samples, reagents used for flow cytometry method, reagents used for enzymatic assays, reagents used for facilitating HPLC, reagents used for mass spectrometry and internal standards for use with the disclosed analytical methods. In some embodiments, the plurality of reagents and analytes comprise reagents and analytes for separating the PLT sample into an extracellular portion and an intracellular portion. In some embodiments, the extracellular portion of the PLT sample comprises glutamine, niacinamide, glutathione oxidized, and succinic acid. In some embodiments, the biomarker obtained from the extracellular portion is concentration of glutamine, concentration of niacinamide, concentration of glutathione oxidized, and concentration of succinic acid. In some embodiments, the plurality of reagents and analytes comprise reagents and analytes for analyzing the PLT sample to determine a raw data for glutamine, niacinamide, glutathione oxidized, succinic acid, sCD40L, CD41, CD63+, Annexin-V+, CD42b, citrate, cis-aconitate, malate, acetate, glucose, lactose, and succinate. In some embodiments, the raw data is determined utilizing a method selected from the group consisting of high-performance liquid chromatography (HPLC), flow cytometry, and enzymatic assays. In some embodiments, the enzymatic assay is a colorimetric assay or a luminescent assay. In some embodiments, the luminescent assay is a fluorometric assay. In some embodiments, the enzymatic assay is a colorimetric assay. In some embodiments, the enzymatic assay is a fluorometric assay. In some embodiments, the enzymatic assay is monitored by photometric measurements. In some embodiments, the colorimetric assay is monitored by photometric measurements. In some embodiments, the luminescent assay is monitored by photometric measurements. In some embodiments, the fluorometric assay is monitored by photometric measurements. In some embodiments, any suitable analytes are provided, such as for example, for use in biochemical assays such as enzymatic assays for detection of a PLT phase. In some embodiments, analytes include enzymes or antibodies for use in biochemical assays such as enzymatic assays for detection of a PLT phase.

Disclosed herein, in certain embodiments, are kits for carrying out the methods and system of the invention. Accordingly, a variety of kits are provided in suitable packaging. In some embodiments, the kits are used for any one or more of the uses described herein, and, accordingly, contain instructions for determining the biomarkers of an RBC sample and/or a PLT sample. In some embodiments, a kit comprises an electronic label. In some embodiments, the electronic label is an electronic test label. In some embodiments, the electronic test label indicates the phase of the RBCs or PLTs. In some embodiments, the electronic test label indicates the phase of RBCs or PLT through pictorial means, color means, alpha-numerical means, sound, or a combination thereof. In some embodiments, the electronic test label indicates the phase of RBCs or PLT through a color. In some embodiments, the electronic test label indicates a change which is reflected through pictorial means, color means, alpha-numerical means, sound, or a combination thereof. In some embodiments, the electronic test label indicates a change through a change in color.

In some embodiments, the kit comprises a non-electronic label. In some embodiments, the non-electronic label is a non-electronic test label. In some embodiments, the non-electronic test label is a test strip. In some embodiments, the test strip indicates the phase of the RBCs or PLTs. In some embodiments, the test strip indicates the phase of RBCs or PLTs through pictorial means, color means, alpha-numerical means, or a combination thereof. In some embodiments, the test strip indicates the phase of RBCs or PLTs through a color. In some embodiments, the test strip indicates a change which is reflected through pictorial means, color means, alpha-numerical means, or a combination thereof. In some embodiments, the test strip indicates a change in phase through a change in color.

In some embodiments, the kit is a test (or diagnostic) kit, for example, a test (or diagnostic) kit containing electronic test labels or non-electronic test strips suitable for the detection of a phase of an RBC sample or a PLT sample recited herein. In some embodiments, a test (or diagnostic) kit contains any of the compositions provided in this disclosure, including those recited above.

Digital Processing Device

In some embodiments, the systems and methods described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect™, Leap Motion™, or the like. In still further embodiments, the input device is a combination of devices such as those disclosed herein.

Non-transitory Computer Readable Storage Medium

In some embodiments, the systems and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems and methods disclosed herein include at least one computer program, or use of the same. A computer program includes a sequence of instructions, executable in the digital processing device's CPU, written to perform a specified task. In some embodiments, computer readable instructions are implemented as program modules, such as functions, objects, Application Programming Interfaces (APIs), data structures, and the like, that perform particular tasks or implement particular abstract data types. In light of the disclosure provided herein, those of skill in the art will recognize that a computer program, in certain embodiments, is written in various versions of various languages.

In some embodiments, the functionality of the computer readable instructions are combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. In some embodiments, a web application is written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the systems and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the methods and systems disclosed herein include one or more databases, or use of the same. In view of the disclosure provided herein, those of skill in the art will recognize that many databases are suitable for storage and retrieval of analytical information described elsewhere herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Services

Disclosed herein in certain embodiments, are methods and systems performed as a service. In some embodiments, a service provider obtains RBC samples and/or PLT samples that a customer wishes to analyze. In some embodiments, the service provider then encodes each RBC sample or PLT sample to be analyzed by any of the methods described herein, performs the analysis and provides a report to the customer. In some embodiments, the customer also performs the analysis and provides the results to the service provider for decoding. In some embodiments, the service provider then provides the decoded results to the customer. In some embodiments, the customer also encodes the RBC samples and/or the PLT samples, analyzes the samples and decodes the results by interacting with softwares installed locally (at the customer's location) or remotely (e.g. on a server reachable through a network). In some embodiments, the softwares generate a report and transmit the report to the costumer. Exemplary customers include clinical laboratories, hospitals, blood banks, industrial manufacturers and the like. In some embodiments, a customer or party is any suitable customer or party with a need or desire to use the methods, systems, compositions, and kits of the invention.

Server

Figure 4:
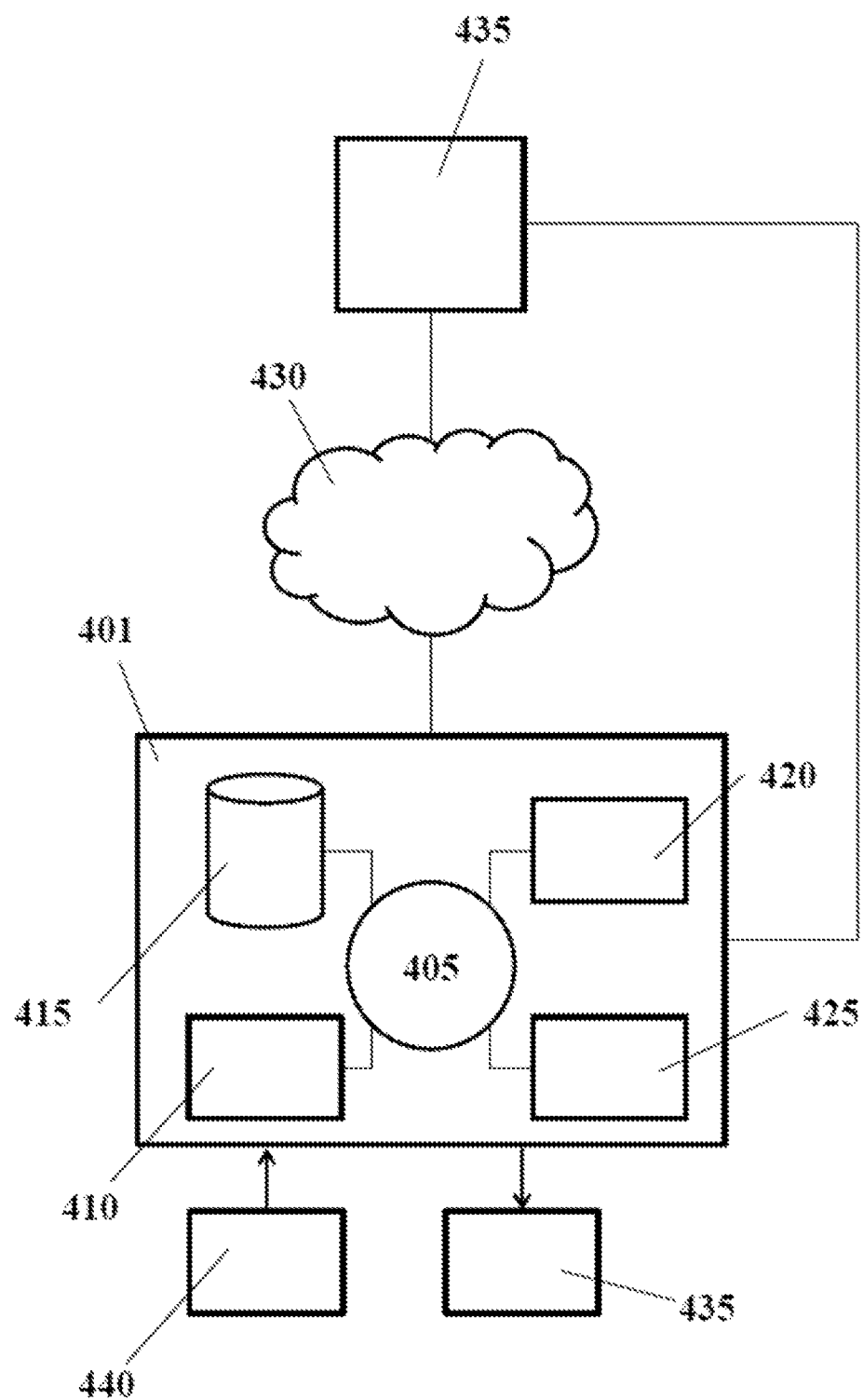
FIG. 4 illustrates a conceptual schematic of an exemplary computer server to be used for processing a system and a method described herein.
Figures 5A, 5B:
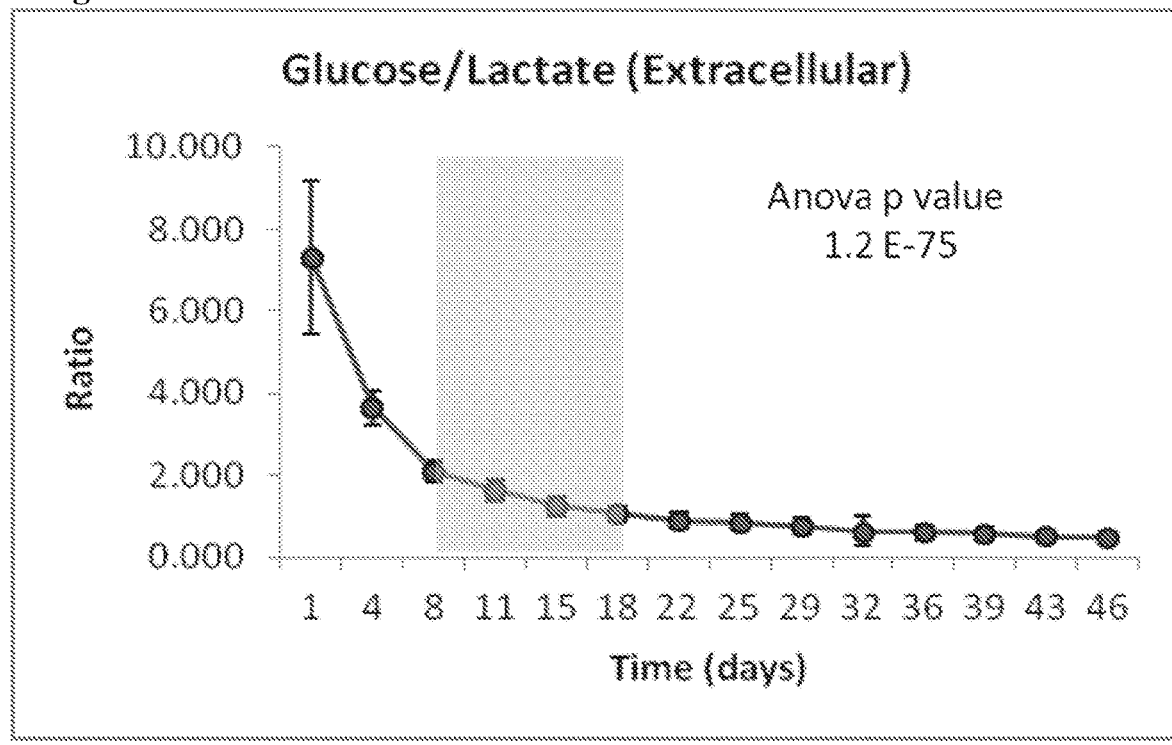
FIGS. 5A-5E illustrate an exemplary signature profile of glucose:lactate.
Figure 5C:
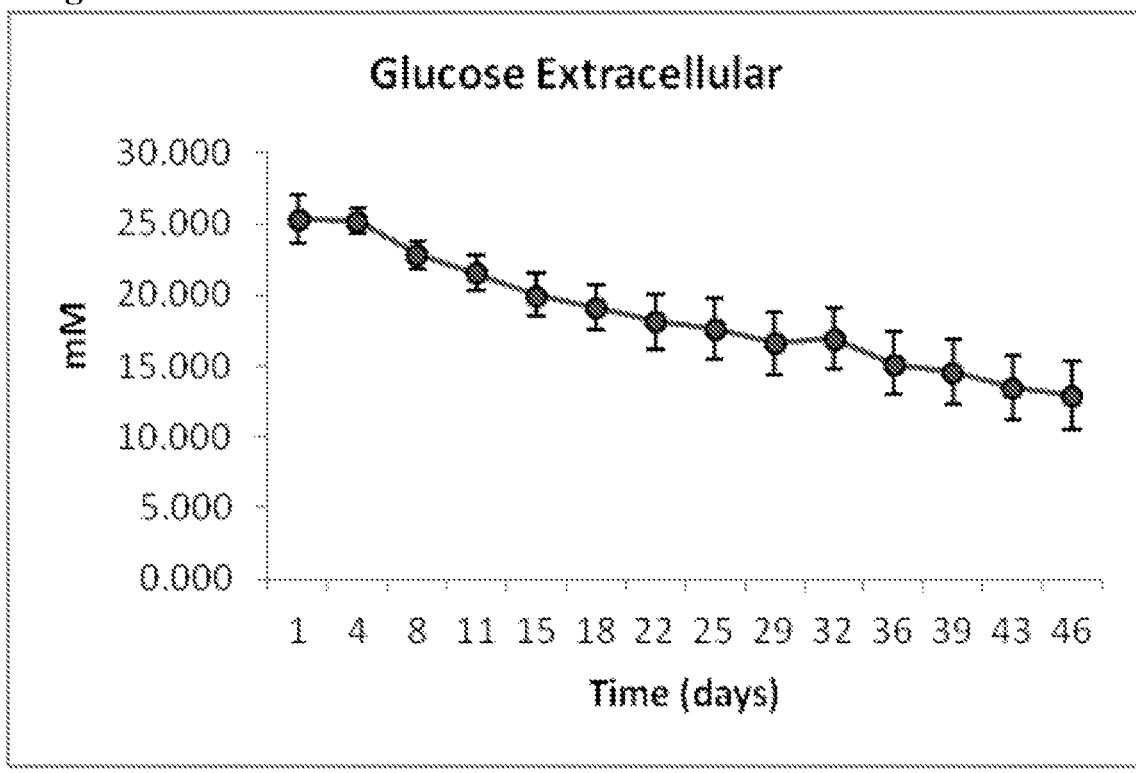
Figure 5D:
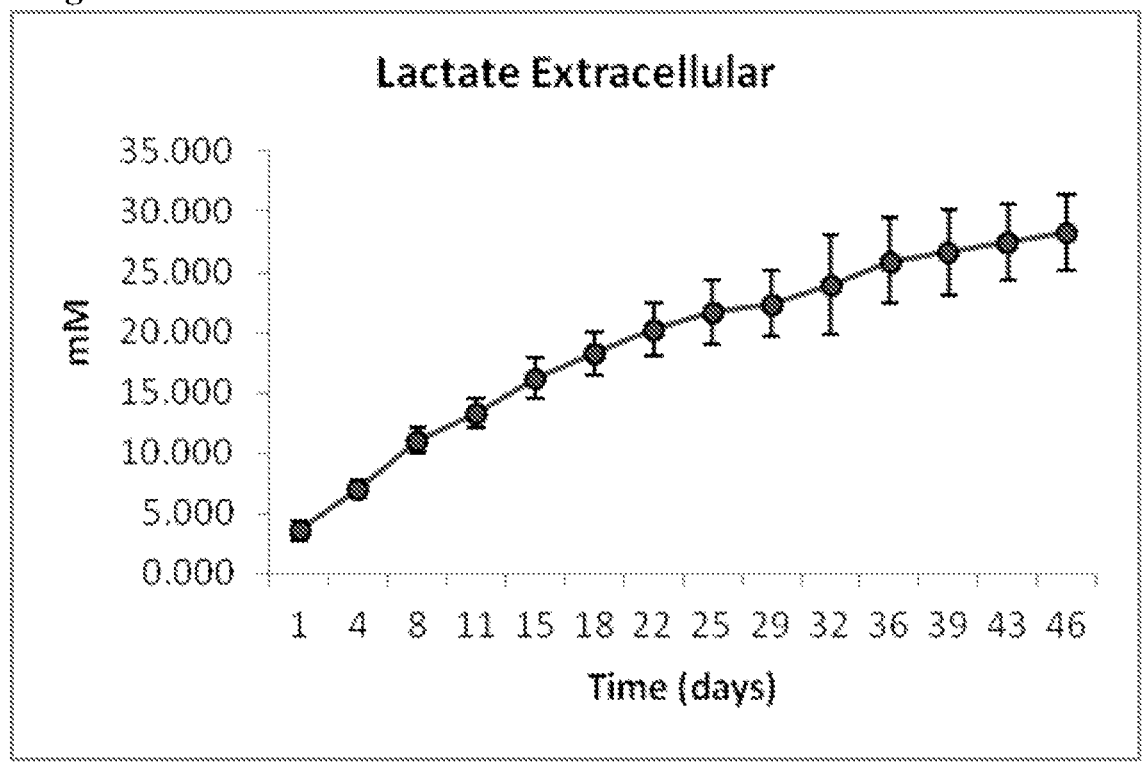
Figure 5E:
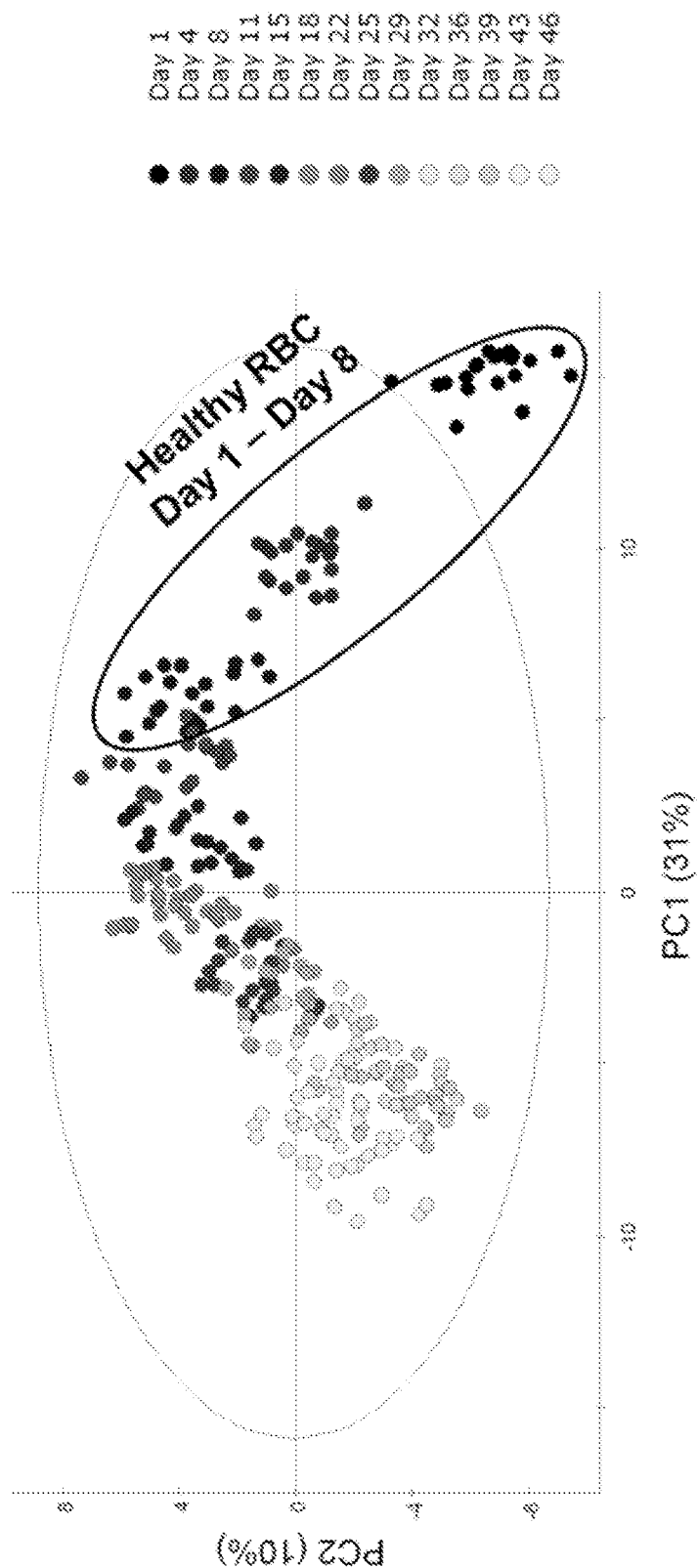
Figures 6A, 6B:
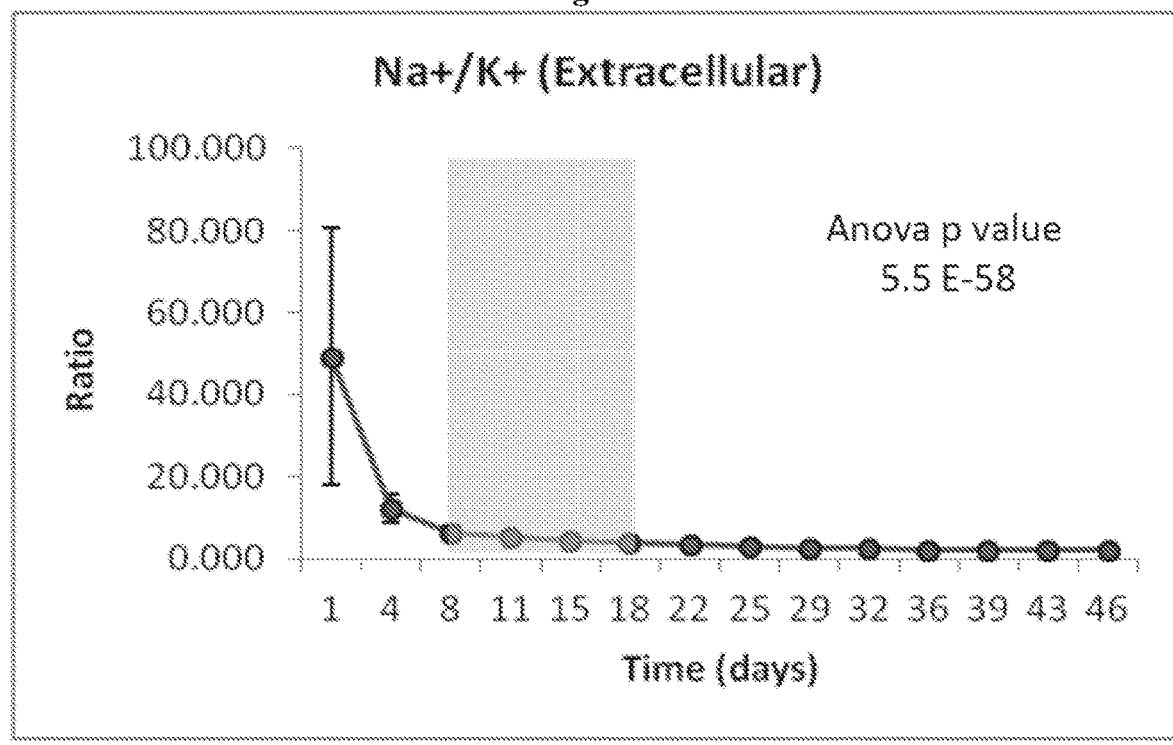
FIGS. 6A-6E illustrate an exemplary signature profile of $Na^+$:$K^+$.
Figure 6C:
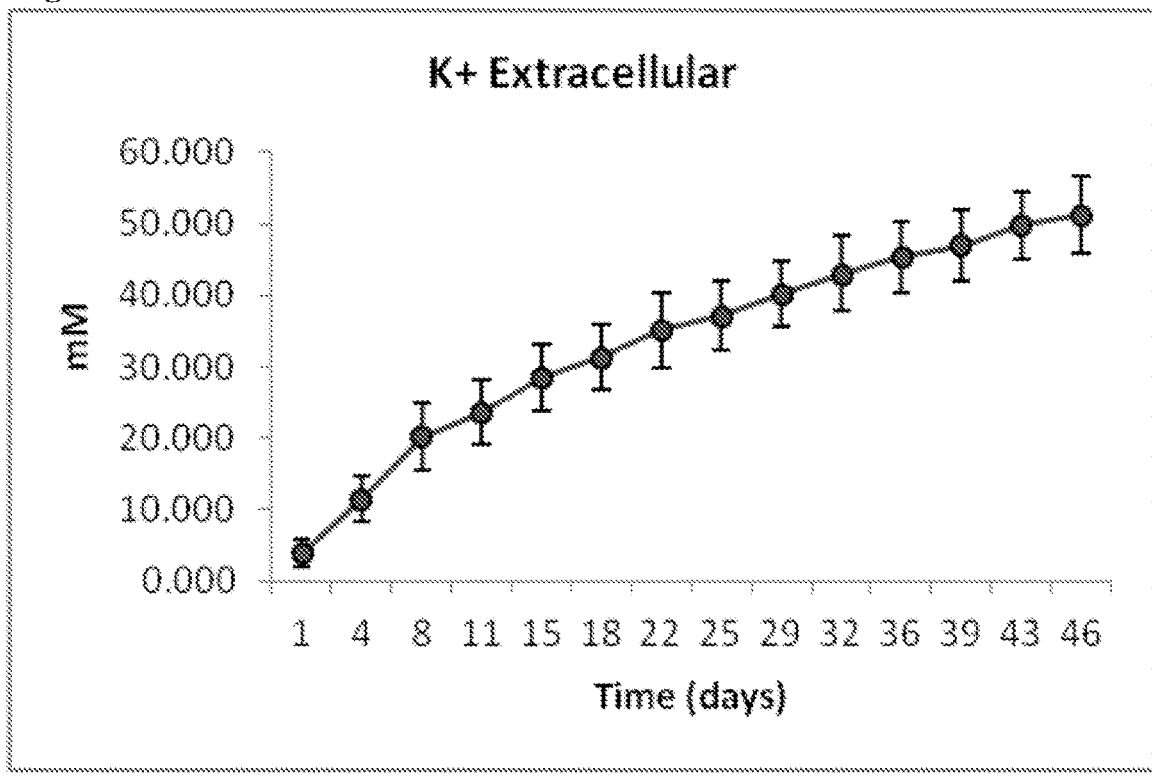
Figure 6D:
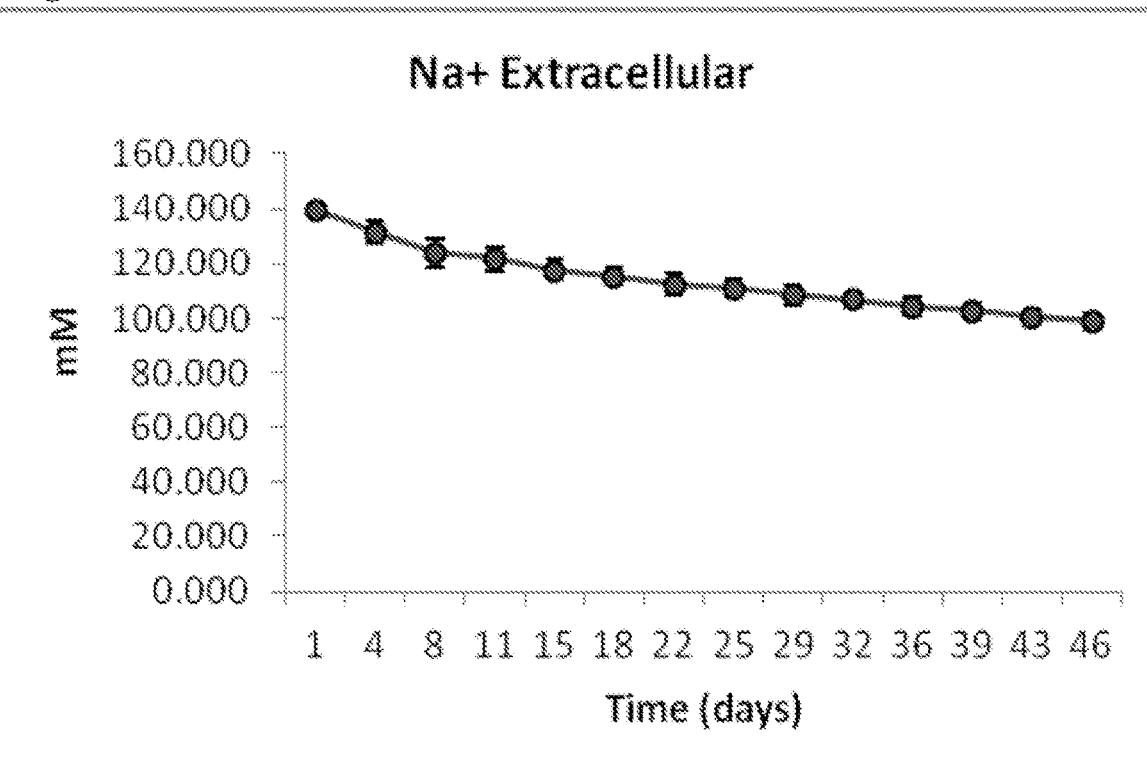
Figure 6E:
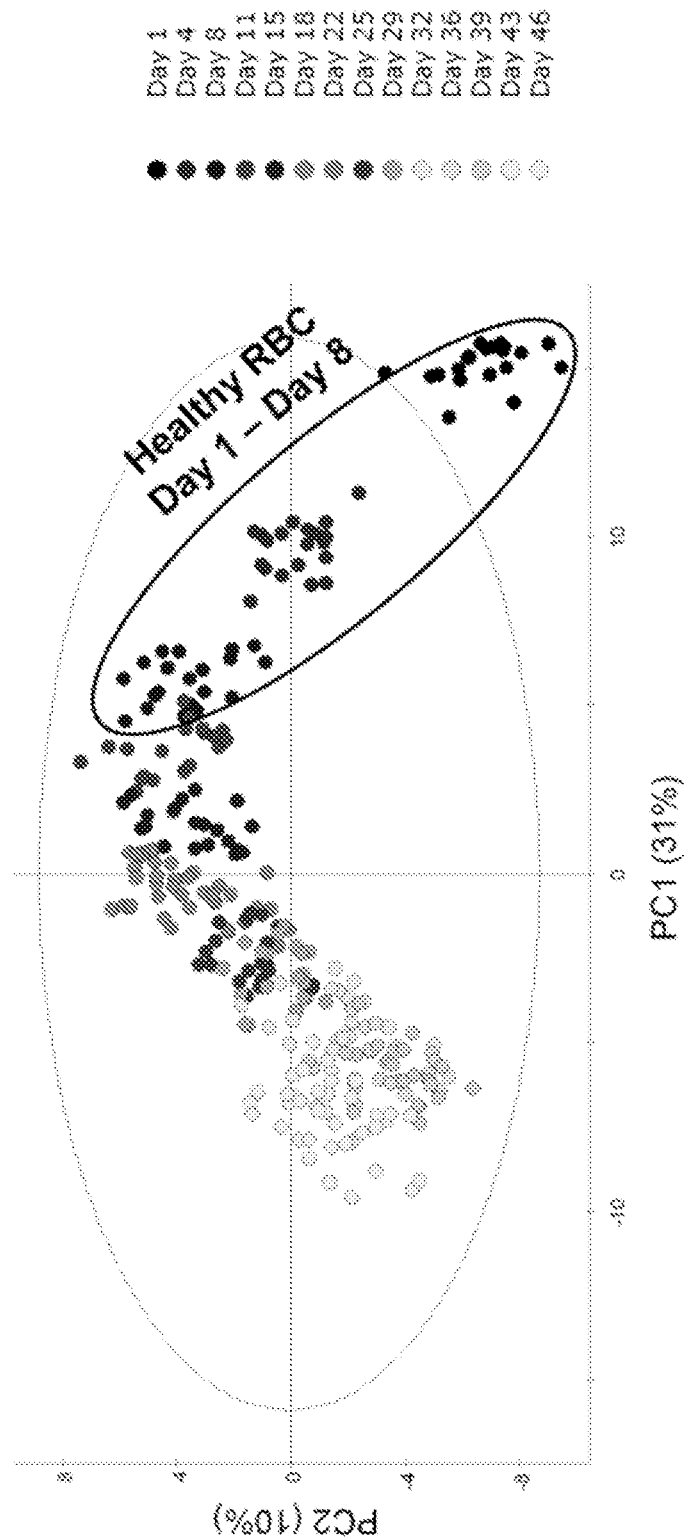
Figures 7A, 7B:
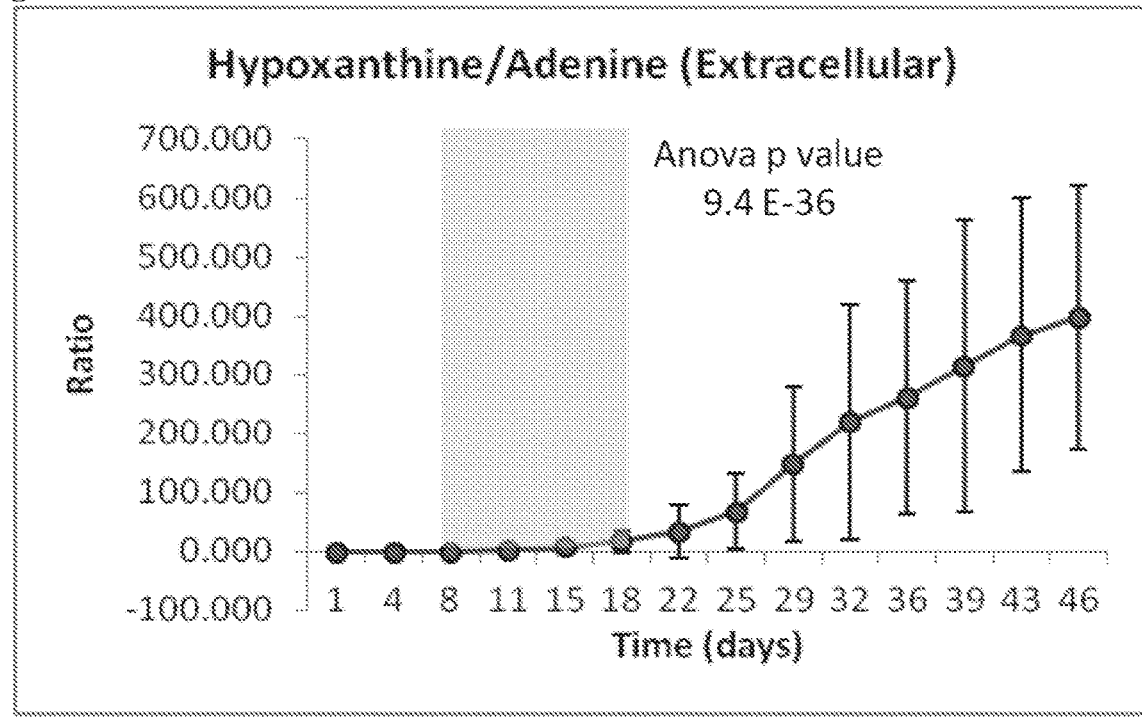
FIGS. 7A-7F illustrate an exemplary signature profile of hypoxanthine:adenine.
Figure 7C:
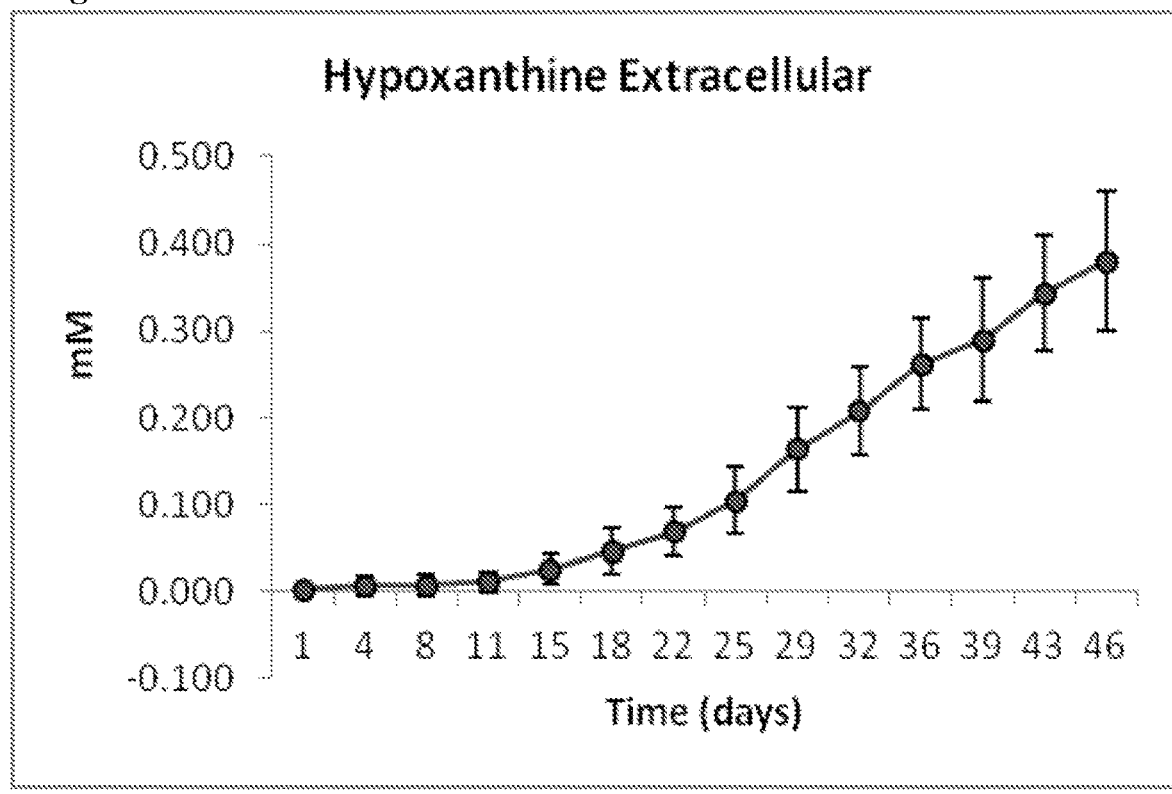
Figure 7D:
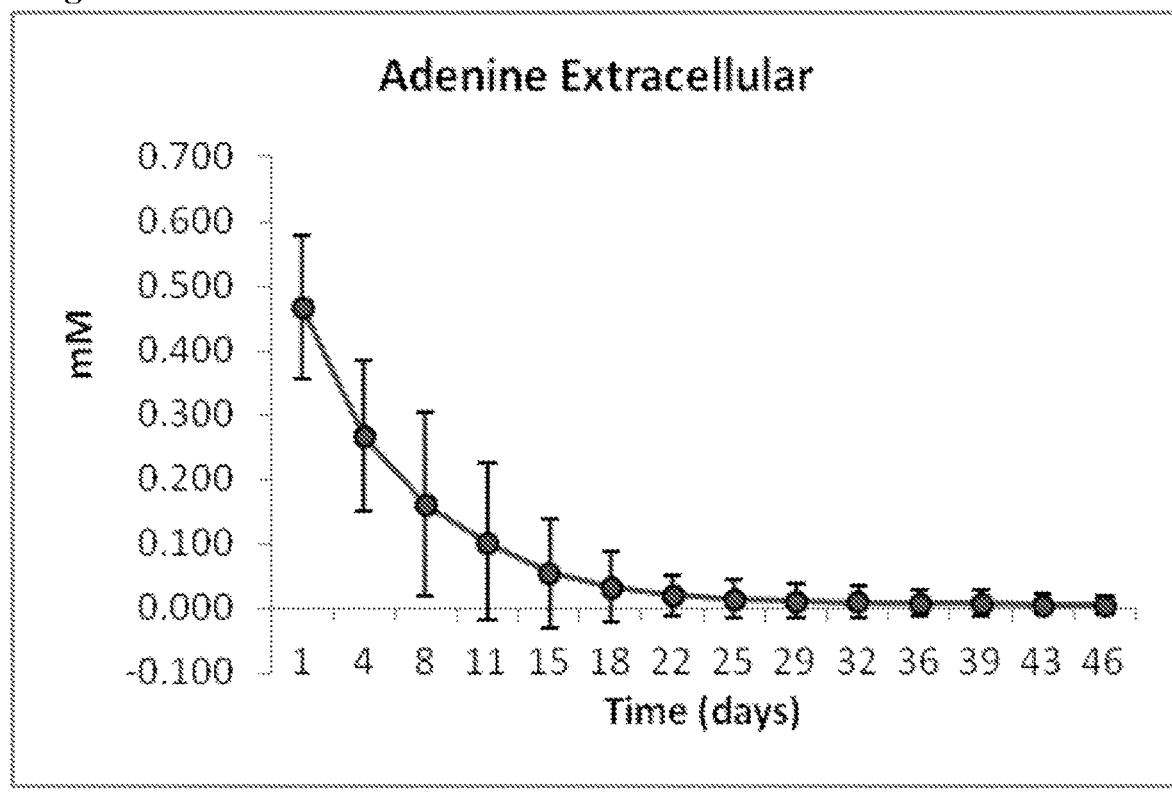
Figure 7E:
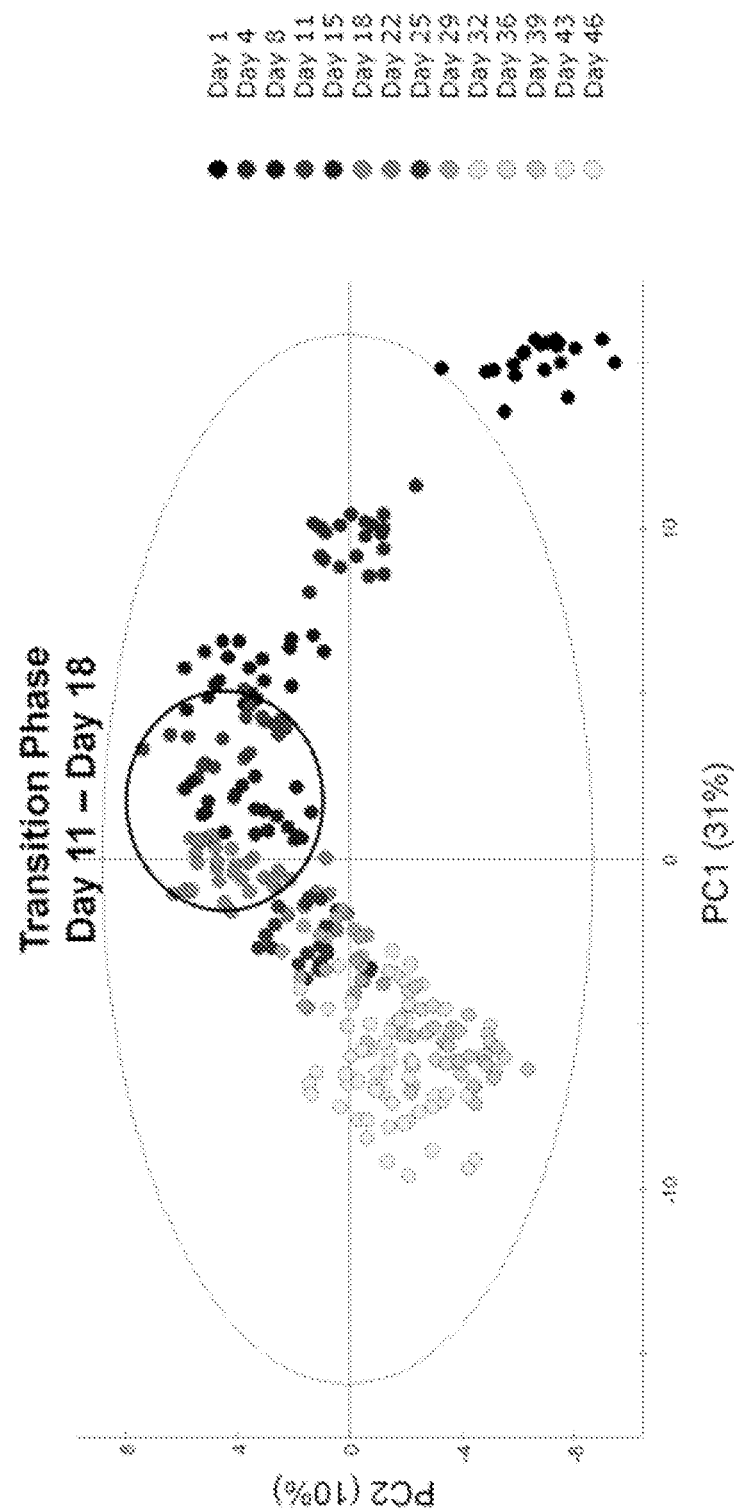
Figure 7F:
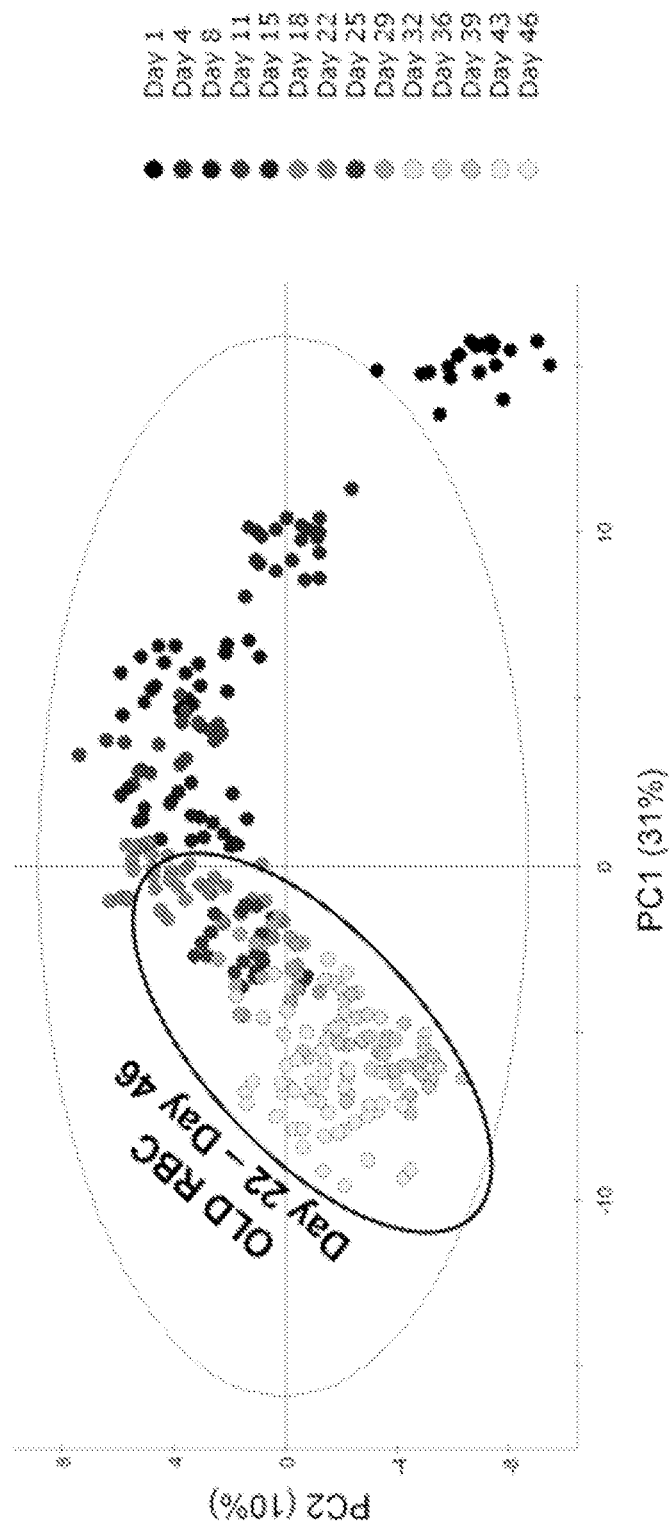
Figures 8A, 8B:
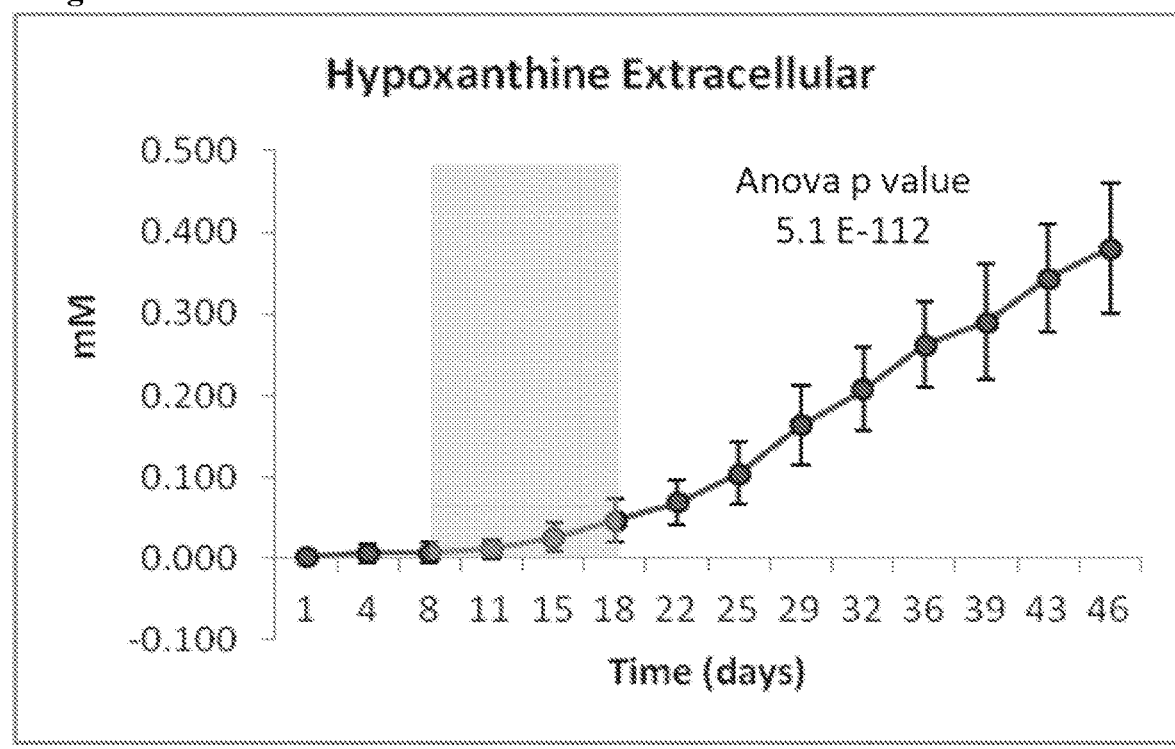
Figures 9A, 9B:
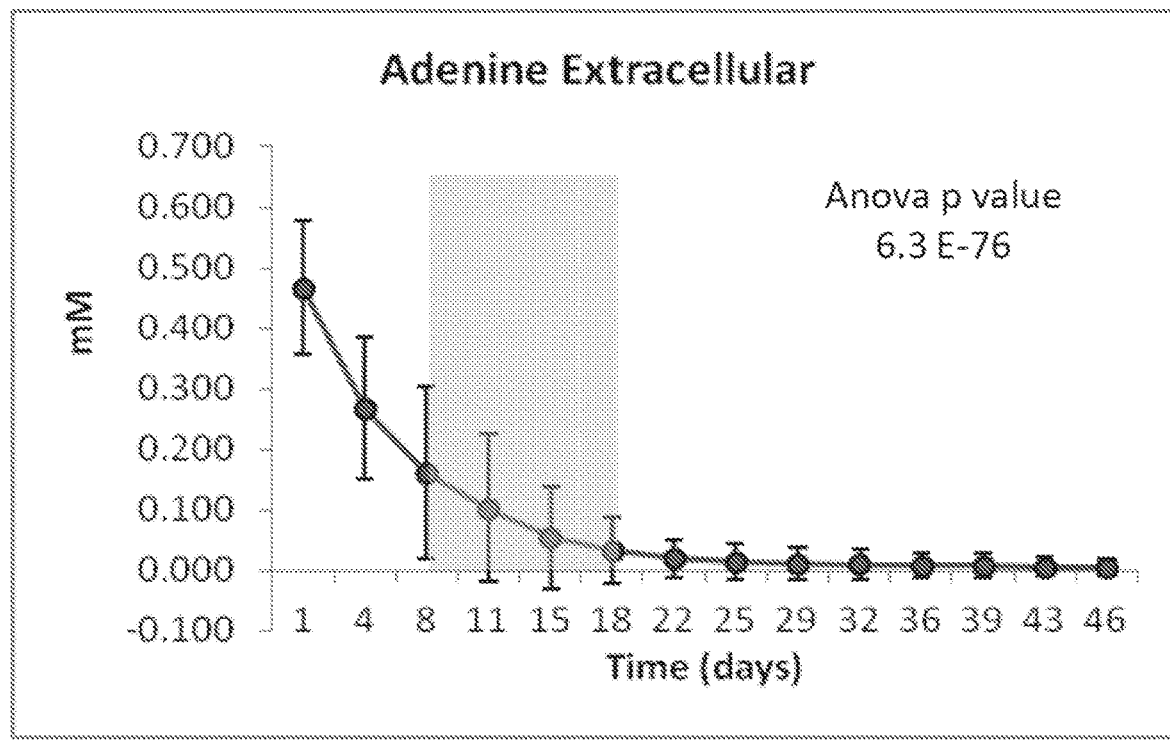
FIGS. 9A-9D illustrate an exemplary signature profile of adenine.
Figure 9C:
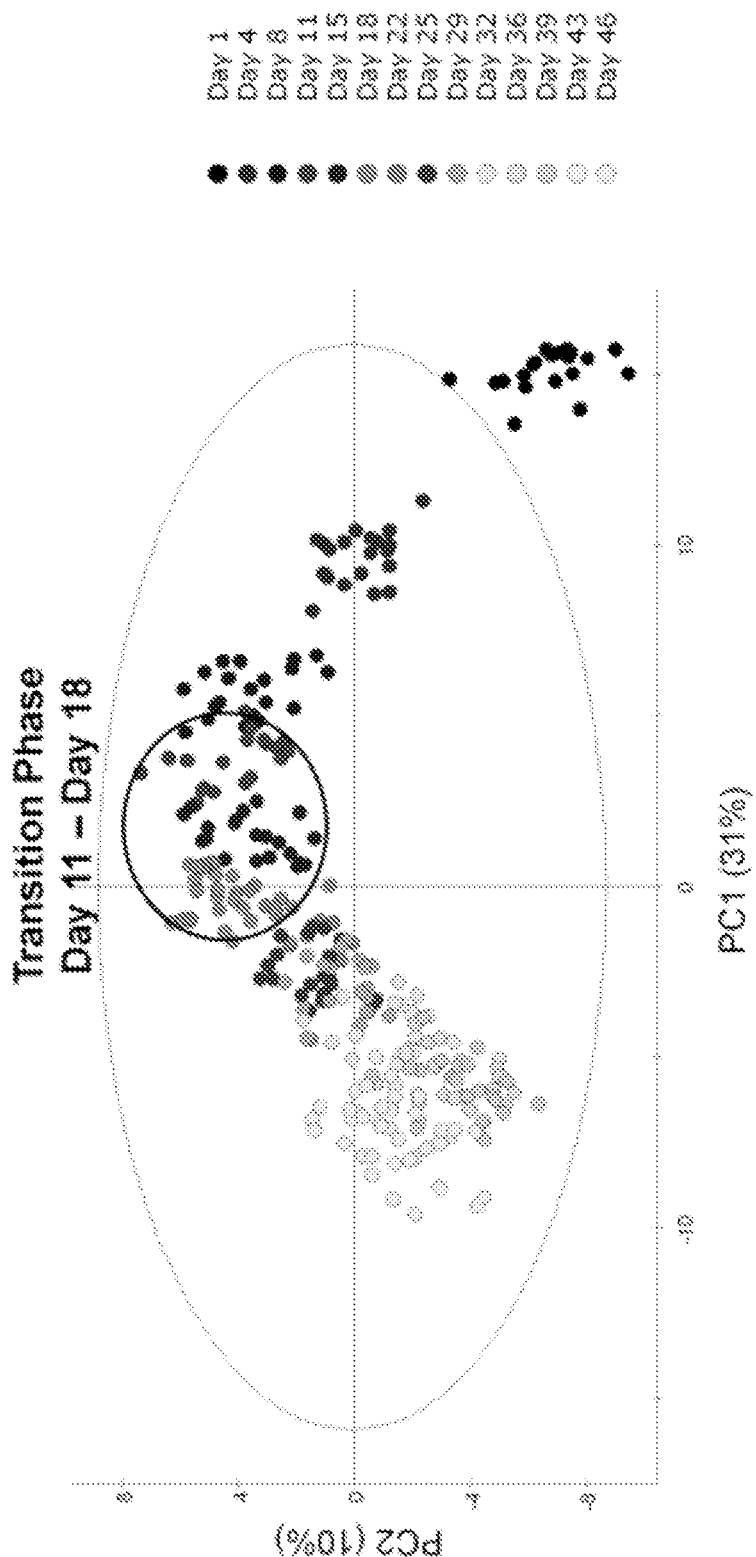
Figure 9D:
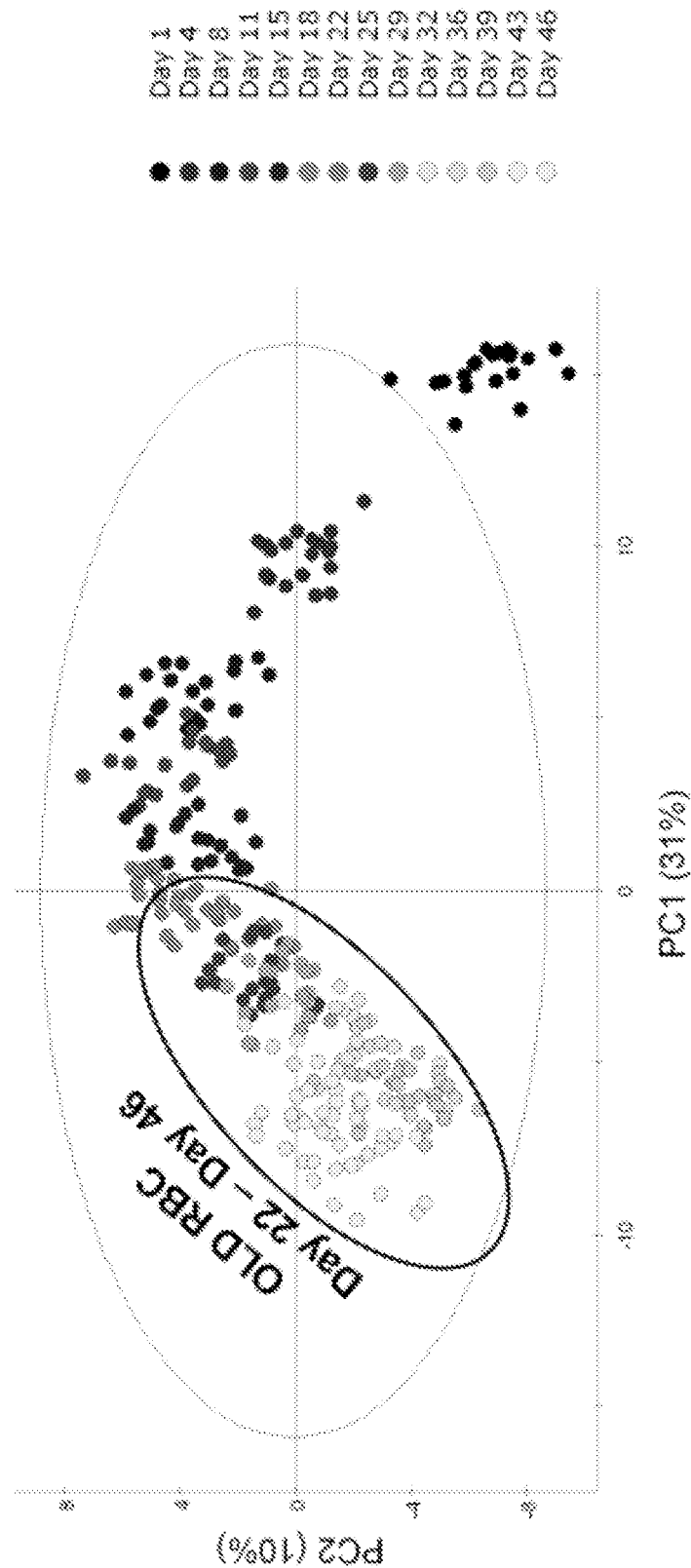
Figures 10A, 10B:
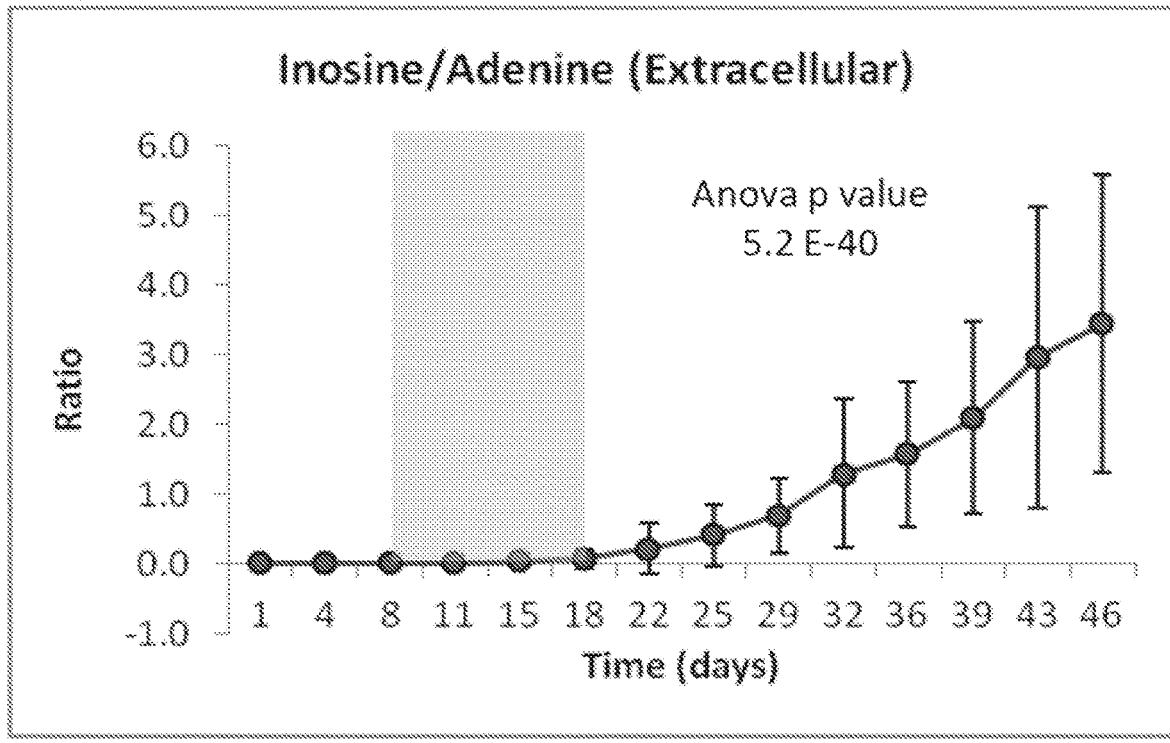
FIGS. 10A-10F illustrate an exemplary signature profile of inosine:adenine.
Figure 10C:
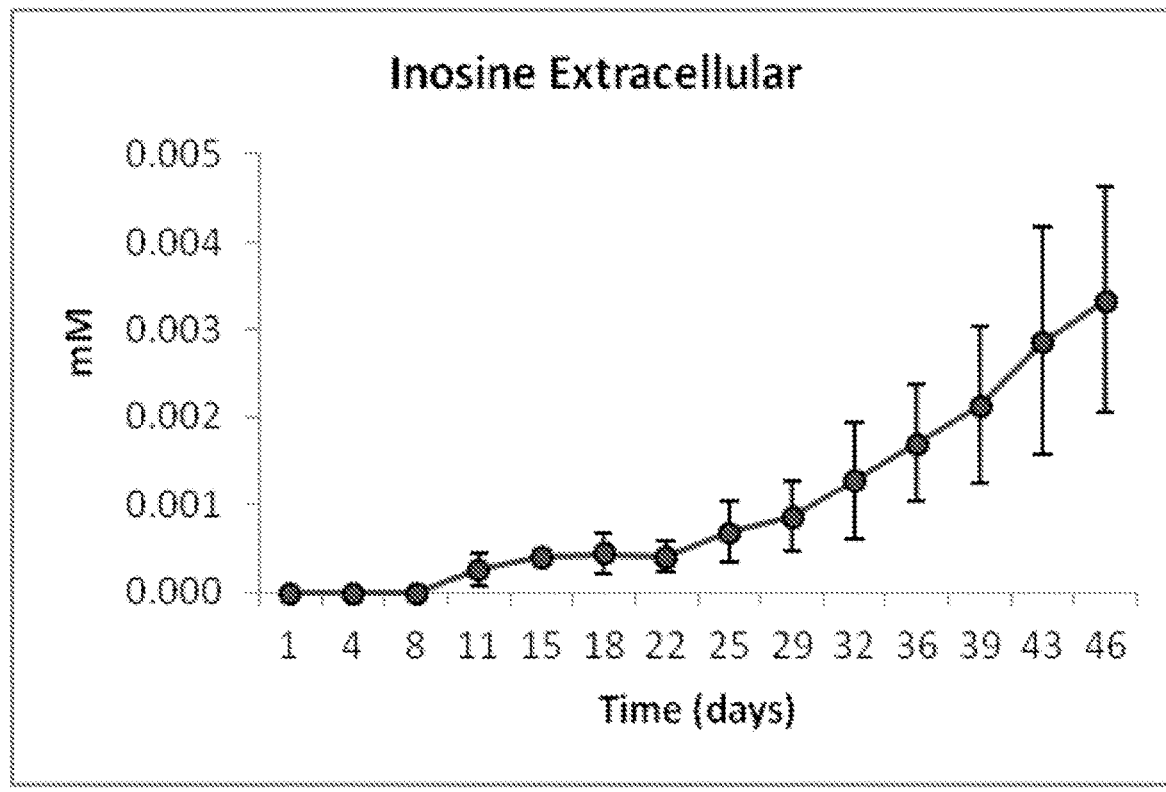
Figure 10D:
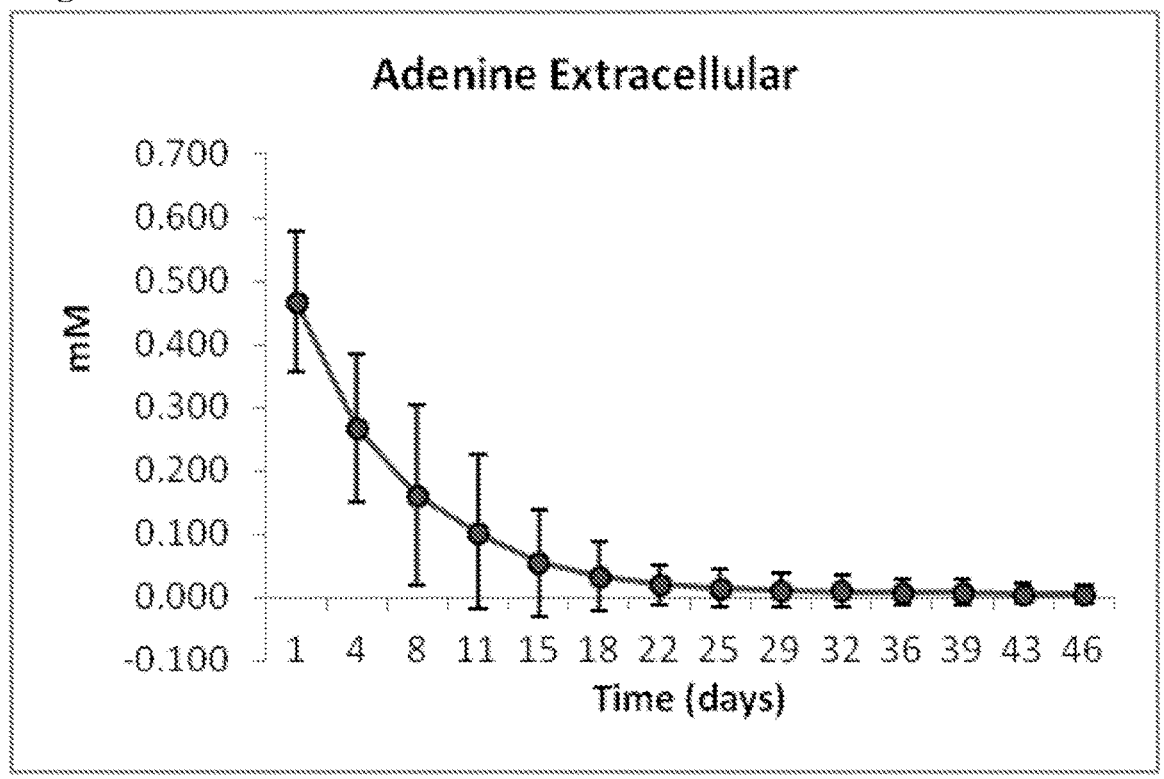
Figure 10E:
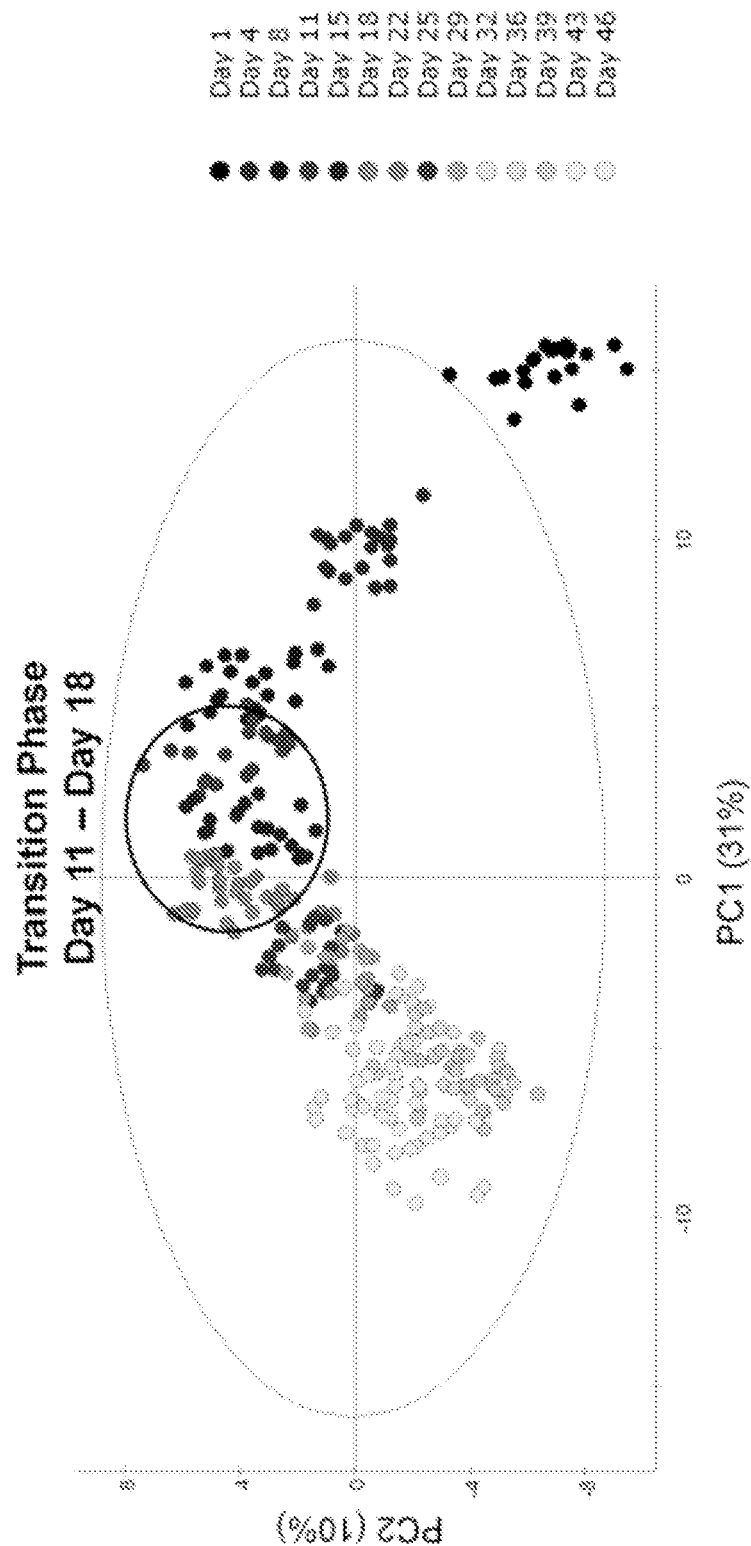
Figure 10F:
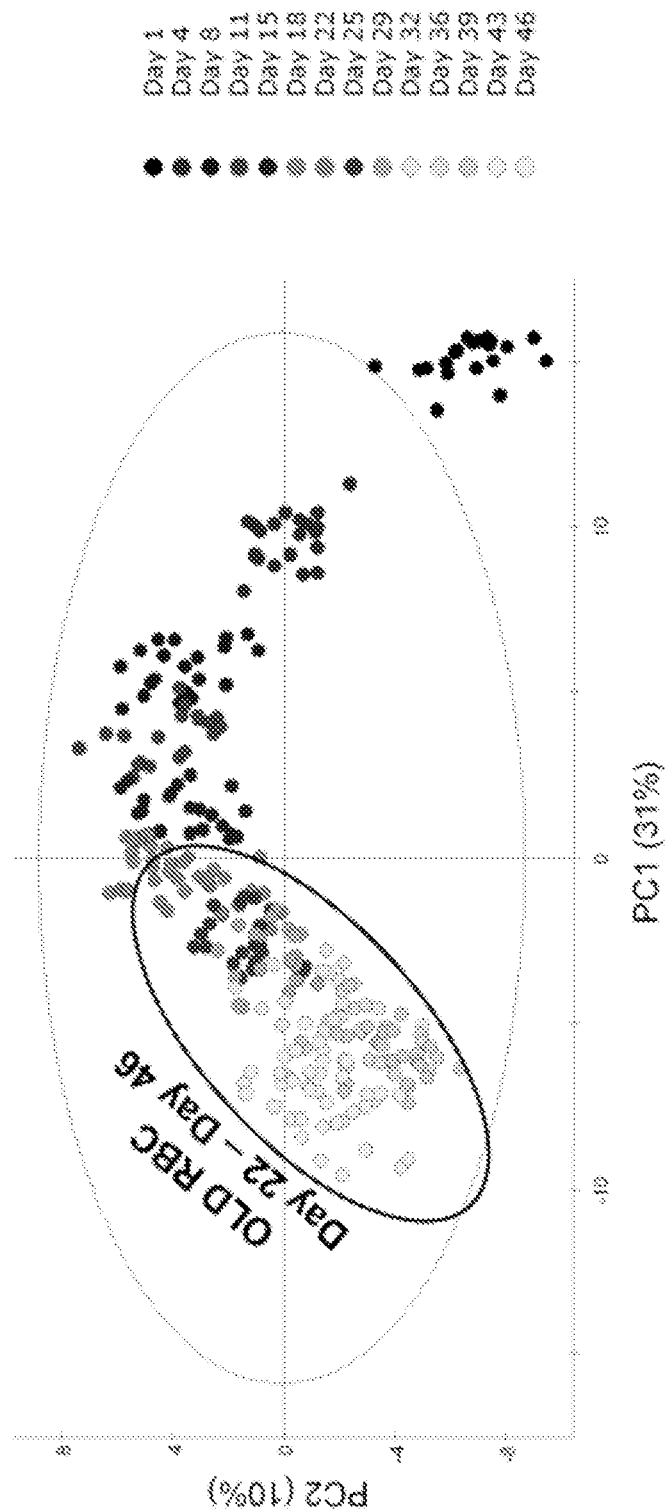
Figures 11A, 11B:
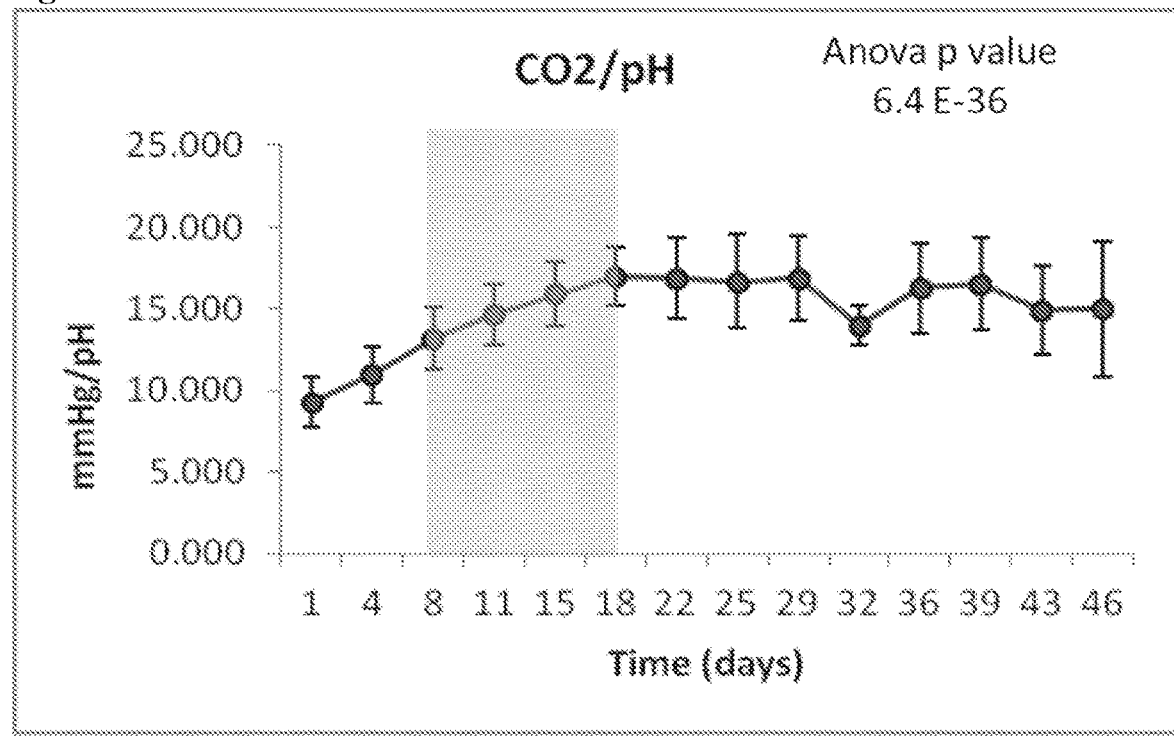
FIGS. 11A-11F illustrate an exemplary signature profile of $pCO_2$:pH.
Figure 11C:
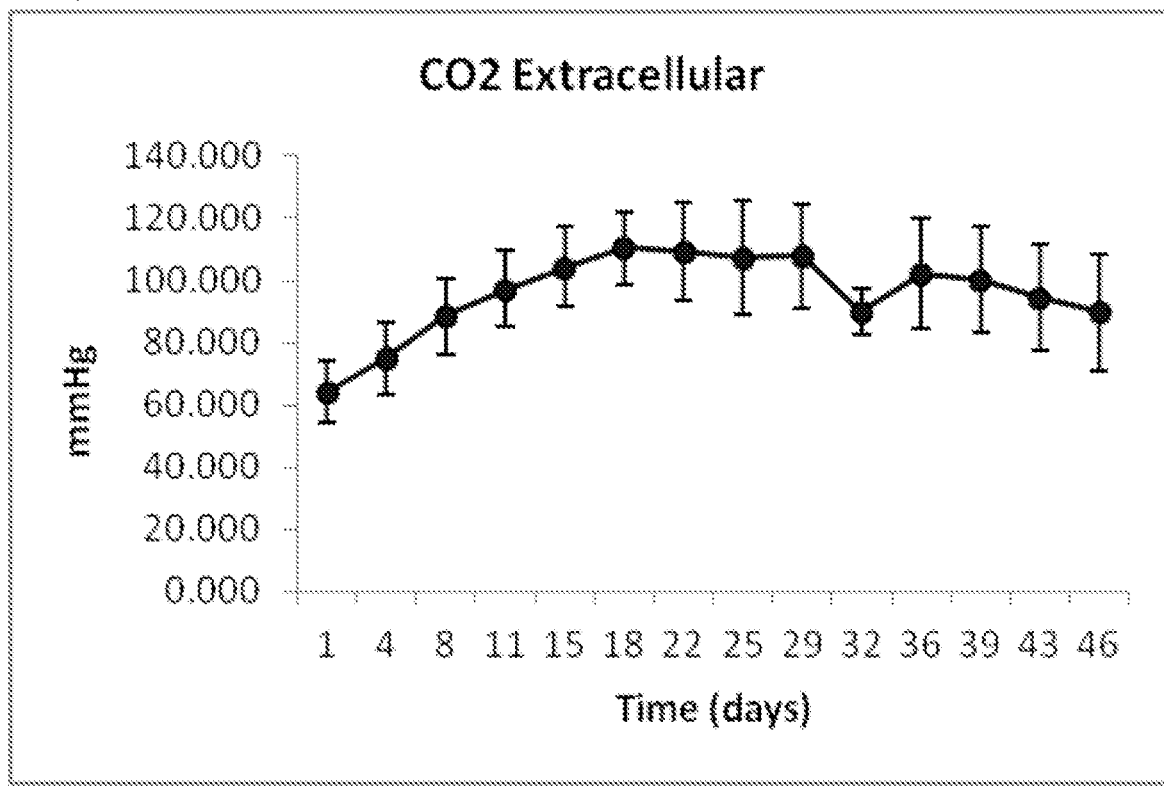
Figure 11D:
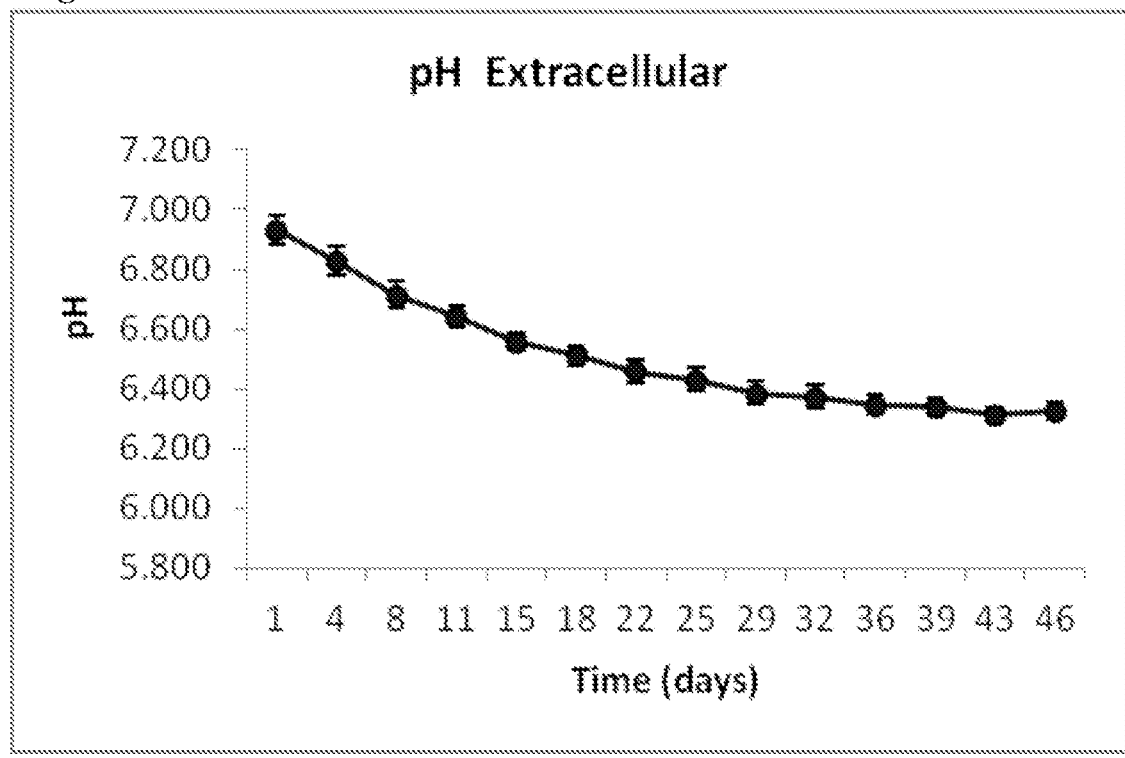
Figure 11E:
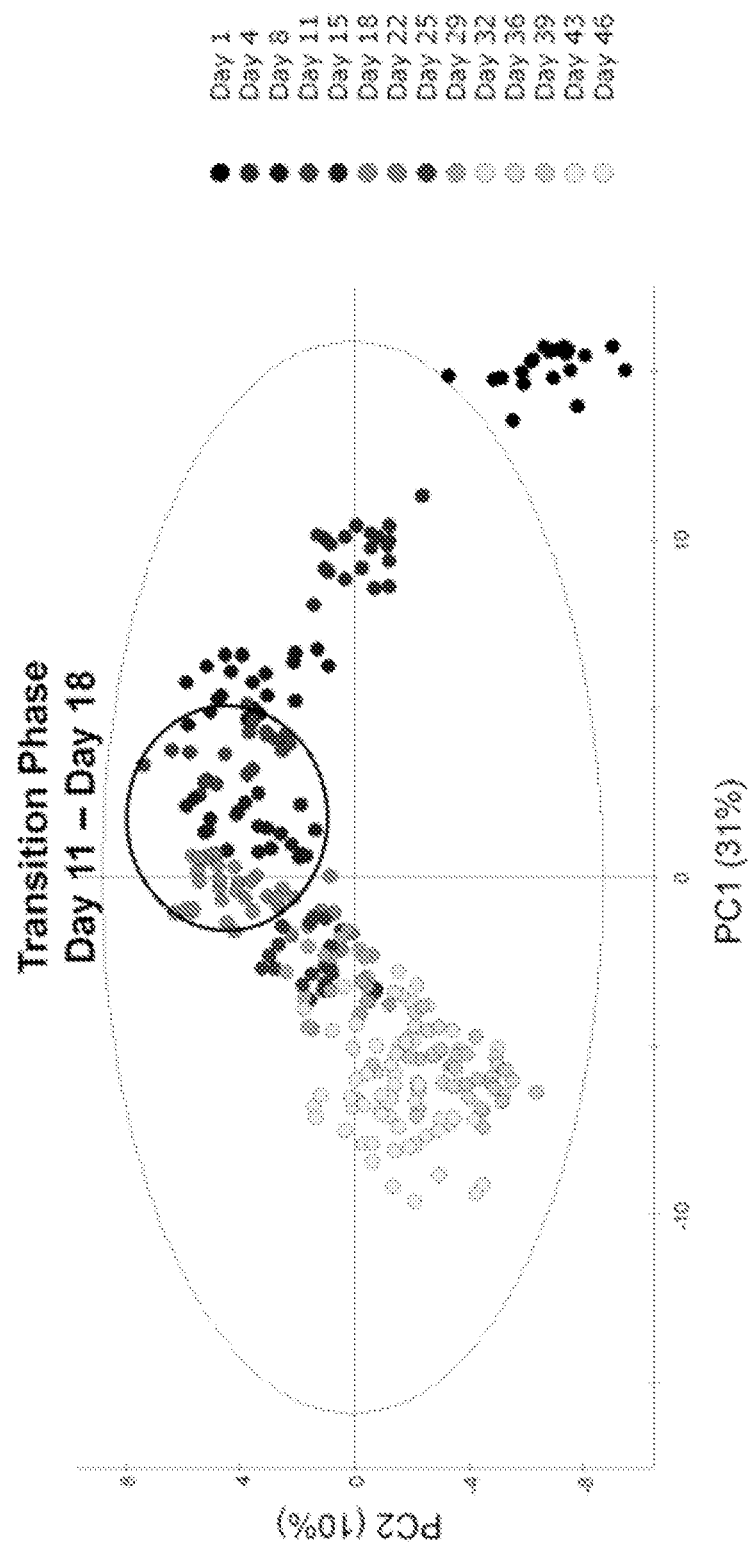
Figure 11F:
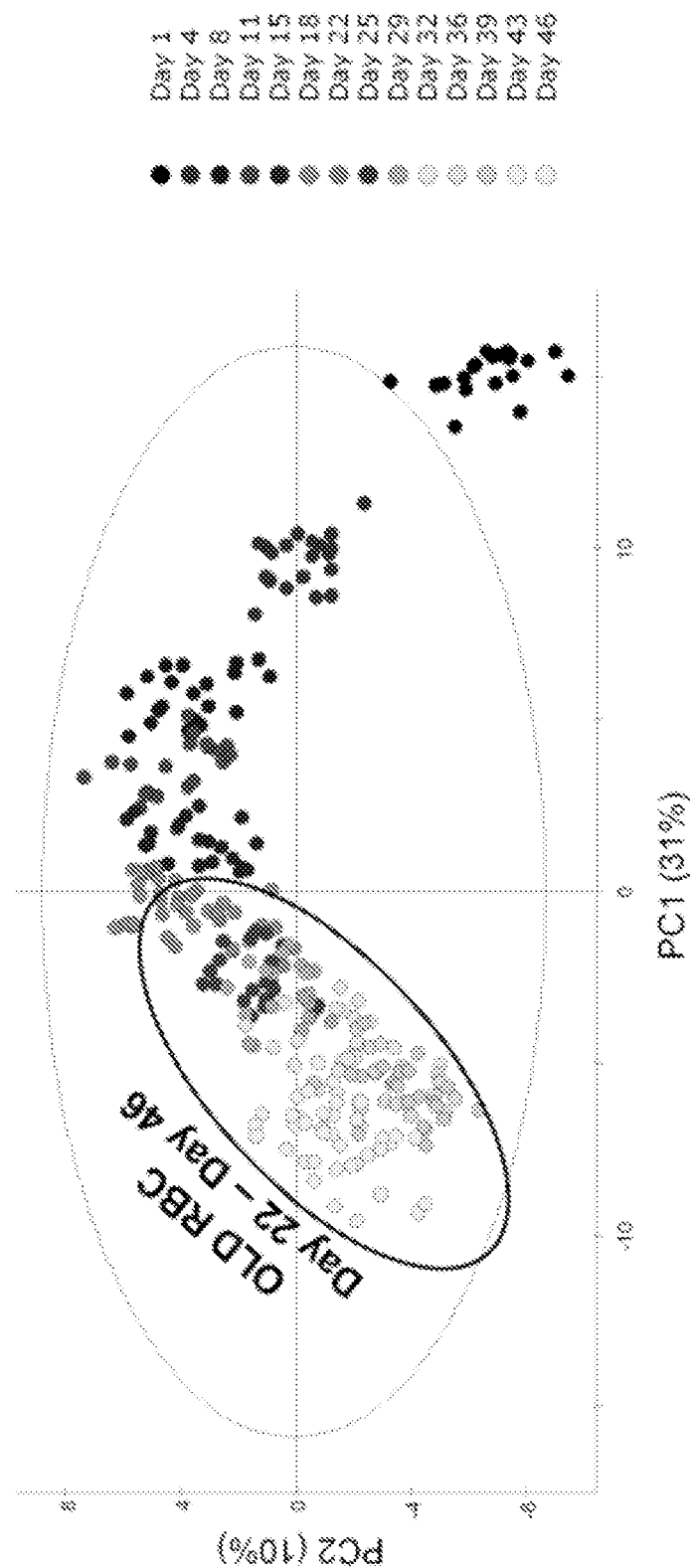
Figures 12A, 12B:
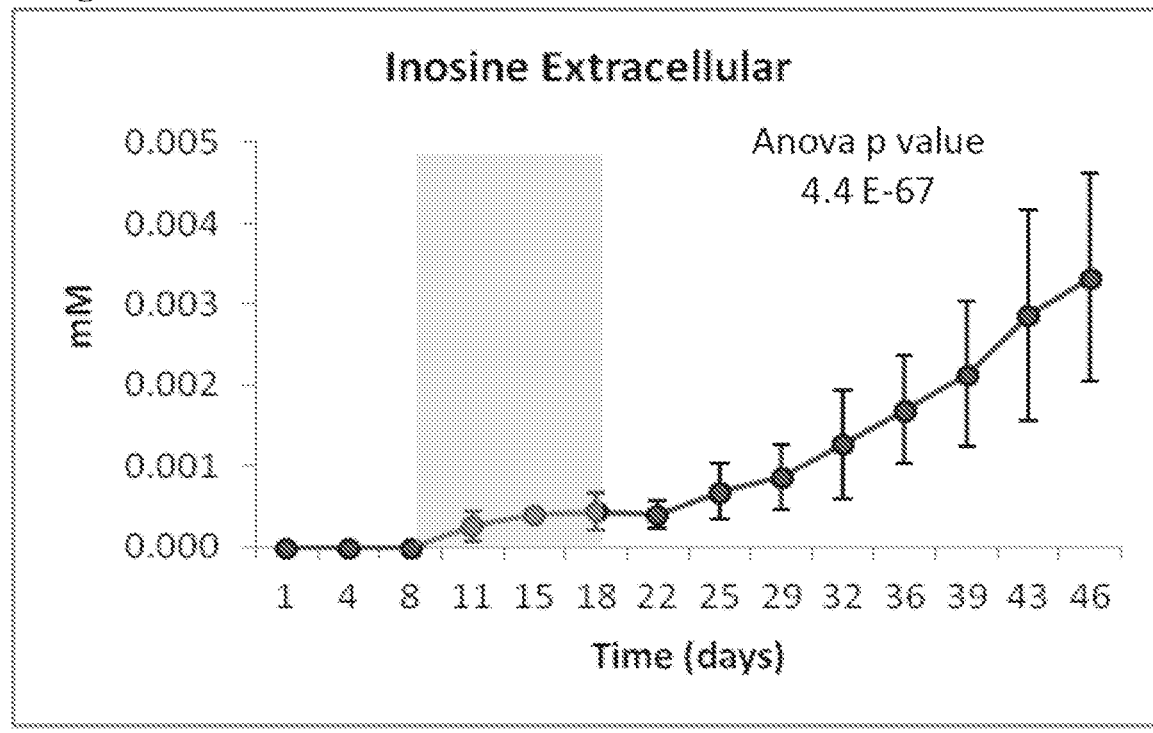
FIGS. 12A-12D illustrate an exemplary signature profile of inosine.
Figure 12C:
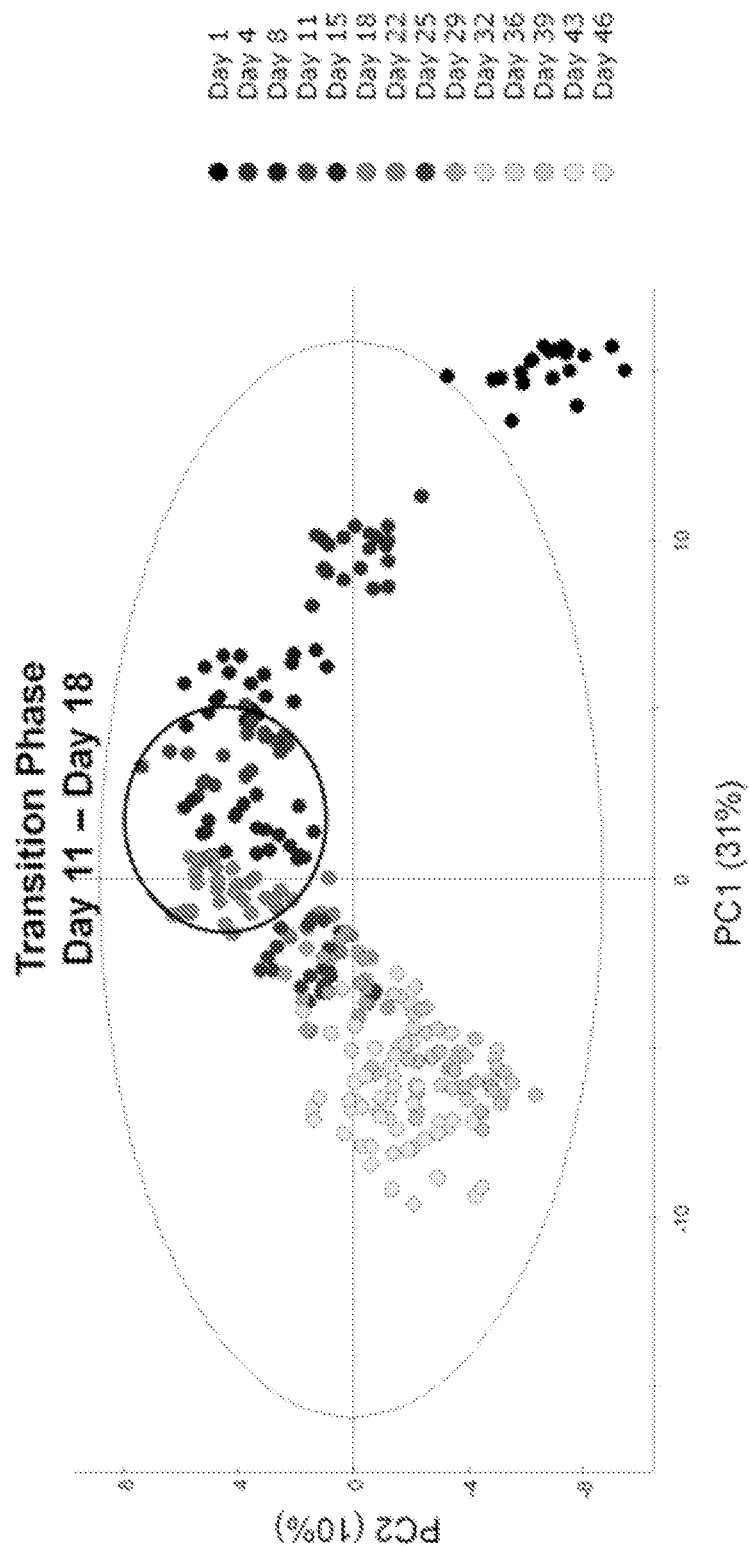
Figure 12D:
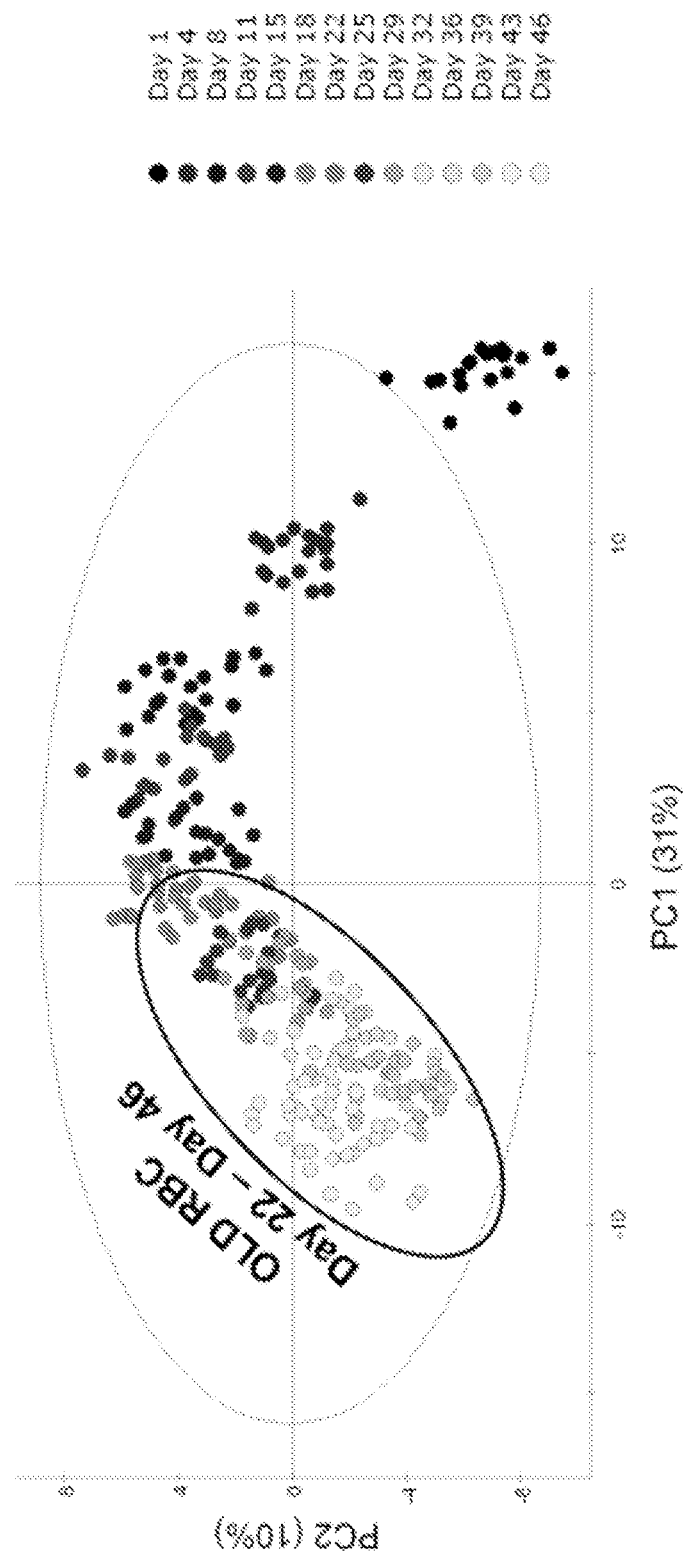
Figure 13:
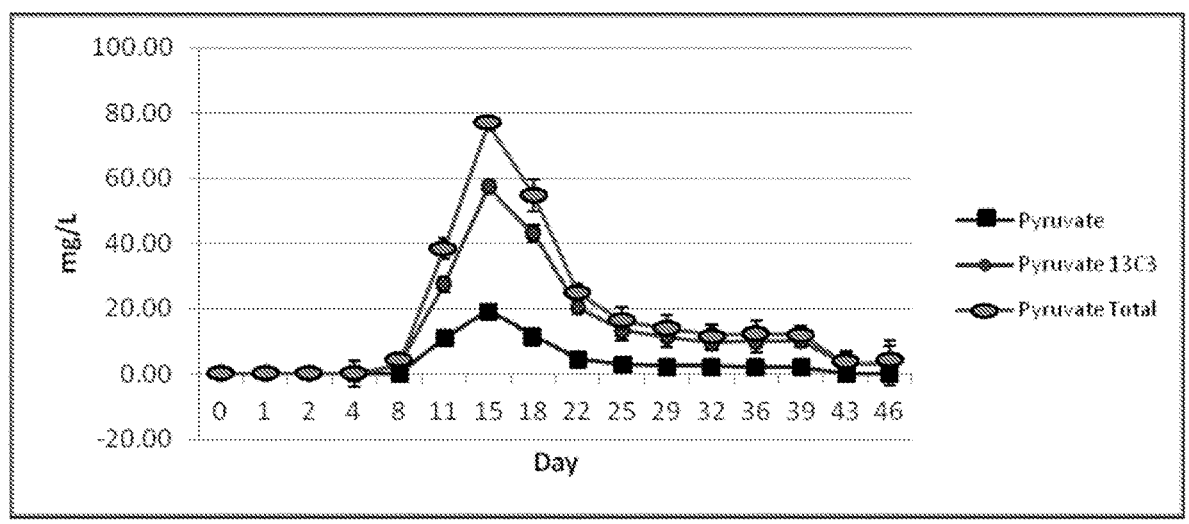
FIG. 13 illustrates an exemplary signature profile of pyruvate.

In some embodiments, the methods provided herein are processed on a server or a computer server (FIG. 4). In some embodiments, the server 401 includes a central processing unit (CPU, also "processor") 405 which is a single core processor, a multi core processor, or plurality of processors for parallel processing. In some embodiments, a processor used as part of a control assembly is a microprocessor. In some embodiments, the server 401 also includes memory 410 (e.g. random access memory, read-only memory, flash memory); electronic storage unit 415 (e.g. hard disk); communications interface 420 (e.g. network adaptor) for communicating with one or more other systems; and peripheral devices 425 which includes cache, other memory, data storage, and/or electronic display adaptors. The memory 410, storage unit 415, interface 420, and peripheral devices 425 are in communication with the processor 405 through a communications bus (solid lines), such as a motherboard. In some embodiments, the storage unit 415 is a data storage unit for storing data. The server 401 is operatively coupled to a computer network ("network") 430 with the aid of the communications interface 420. In some embodiments, a processor with the aid of additional hardware is also operatively coupled to a network. In some embodiments, the network 430 is the Internet, an intranet and/or an extranet, an intranet and/or extranet that is in communication with the Internet, a telecommunication or data network. In some embodiments, the network 430 with the aid of the server 401, implements a peer-to-peer network, which enables devices coupled to the server 401 to behave as a client or a server. In some embodiments, the server is capable of transmitting and receiving computer-readable instructions (e.g., device/system operation protocols or parameters) or data (e.g., sensor measurements, raw data obtained from detecting metabolites, analysis of raw data obtained from detecting metabolites, interpretation of raw data obtained from detecting metabolites, etc.) via electronic signals transported through the network 430. Moreover, in some embodiments, a network is used, for example, to transmit or receive data across an international border.

In some embodiments, the server 401 is in communication with one or more output devices 435 such as a display or printer, and/or with one or more input devices 440 such as, for example, a keyboard, mouse, or joystick. In some embodiments, the display is a touch screen display, in which case it functions as both a display device and an input device. In some embodiments, different and/or additional input devices are present such an enunciator, a speaker, or a microphone. In some embodiments, the server uses any one of a variety of operating systems, such as for example, any one of several versions of Windows®, or of MacOS®, or of Unix®, or of Linux®.

In some embodiments, the storage unit 415 stores files or data associated with the operation of a device, systems or methods described herein.

In some embodiments, the server communicates with one or more remote computer systems through the network 430. In some embodiments, the one or more remote computer systems include, for example, personal computers, laptops, tablets, telephones, Smart phones, or personal digital assistants.

In some embodiments, a control assembly includes a single server 401. In other situations, the system includes multiple servers in communication with one another through an intranet, extranet and/or the Internet.

In some embodiments, the server 401 is adapted to store device operation parameters, protocols, methods described herein, and other information of potential relevance. In some embodiments, such information is stored on the storage unit 415 or the server 401 and such data is transmitted through a network.

EXAMPLES

These examples are provided for illustrative purposes only and not to limit the scope of the claims provided herein.

Example 1

Sample Collection for RBC

Red blood cell (RBC) units were drawn from healthy human volunteers after the approval of The National Bioethics Committee of Iceland and the Icelandic Data Protection Authority. 20 RBC units were collected from 20 healthy donor volunteers during two different experiments categorized as Unit 1, 2, 3, and so forth. Whole blood was collected from healthy donor volunteers into CPD anticoagulant (63 mL). After separation of plasma by centrifugation, RBCs were suspended in 100 mL of SAGM (Saline, Adenine, Glucose, Mannitol) additive solution.

RBC units were stored for 46 days under standard conditions (Celsius Degree) and samples were collected for the analysis at the following days: Day 1, 4, 8, 11, 15, 18, 22, 25, 29, 32, 36, 39, 43 and 46. Experiment 1 utilized the following RBC units: Unit 1, 2, 3, 4, 5, 6, 7, 8, 9 and 10. Experiment 2 utilized the following RBC units: Units 11, 12, 13, 14, 15, 16, 17, 18, 19 and 20.

Sample Preparation for RBC

A 0.5 mL of RBC sample was separated by centrifugation (1600 g, 4° C., 15 min) into supernatant and cell pellet. Immediately after centrifugation, cell-free supernatant was removed from centrifuged tubes and collected in separates tubes. Cell pellets were washed twice by adding 1 mL of PBS, and after centrifugation (1600 g, 4° C., 15 min), the supernatant was discharged. Cells and free cells supernatant were processed separately.

Example 2

Extracellular Sample Preparation for RBC

A volume of 80 μL of supernatant sample was processed by adding 30 μL of internal standard mixture (Phenylalanine d2 (72 mg/L), Succinate d4 (50 mg/L), Glucose 13C6 (2100 mg/L), Carnitine d9 (20 mg/L), Glutamic Acid d5 (30 mg/L), Lysine d4 (90 mg/L)) and 0.5 mL of MeOH. Samples were vortexed and centrifuged (15000 g, 4° C., 15 min). Supernatant was transferred into a new tube and dried using a vacuum concentrator. Samples were reconstituted in 200 μL of $H_2O$:ACN (50:50) and filtered to remove residual hemoglobin by centrifugation using a 0.5 mL filters (15000 g, 4° C., 60 min).

Intracellular Sample Preparation for RBC

A volume of 30 μL of internal standard mixture (Phenylalanine d2 (50 mg/L), Succinate d4 (50 mg/L), Glucose 13C6 (2000 mg/L), Carnitine d9 (5 mg/L), Glutamic Acid d5 (40 mg/L), Lysine d4 60 mg/L), Alanine d4 (300 mg/L), AMP 13C1015N5 (50 mg/L) and 1 mL of cold (−20° C.) methanol-water (7:3) was added to the cell pellets. Cell lysis was achieved by performing two consecutive freeze and thaw steps. Samples were centrifuged (15000 g, 4° C., 20 min) and supernatant was transferred in a new tube. 1 mL of cold (−20° C.) methanol-water (7:3) was added to the pellets. Samples were vortexed for 1 minute and after centrifugation (15000 g, 4° C., 20 min) the supernatant was added to the precedent. Samples were dried using a vacuum concentrator, reconstituted in 300 μL $H_2O$:ACN (50:50), and filtered to remove residual hemoglobin by centrifugation using an Amicon Ultra 0.5 mL filters (15000 g, 4° C., 60 min).

Blood Bank Quality Controls-RBC

Immediately after sample collection, a blood gas analyzer was used for determination of pH, $pO_2$ and $pCO_2$, concentration of total hemoglobin, and concentrations of $K^+$, $Na^+$, $Cl^-$, glucose, and lactate in the RBC media.

Example 3

Ultra Performance Liquid Chromatography-Mass Spectrometry (UPLC-MS) for RBC Analysis Inosine, hypoxanthine, adenine, and pyruvate were analyzed using a UPLC-MS method. Ultra performance liquid chromatography (UPLC) was coupled with a quadrupole-time of flight mass spectrometer. Chromatographic separation was achieved by hydrophilic interaction liquid chromatography (HILIC) using an Acquity amide column, 1.7 μm (2.1×150 mm). All intracellular and extracellular samples were analyzed three times: once in positive ionization mode and twice in negative ionization mode using acidic and basic chromatographic conditions. In positive and in negative acidic conditions, mobile phase A was 100% ACN and B was 100% $H_2O$, both containing 0.1% formic acid. The following elution gradient was used: 0 min 99% A; 0.1 min 99% A; 6 min 40% A; 8 min 60% A; 8.5 min 99% A; 14 min 99% A. In negative mode basic conditions, mobile phase A contained ACN:sodium bicarbonate 10 mM (95:5) and mobile phase B contained ACN:sodium bicarbonate 10 mM (5:95). The following elution gradient was used: 0 min 99% A; 0.1 min 99% A; 5 min 42% A; 6 min 60% A; 7 min 99% A; 14 min 99% A. In all conditions, the flow rate was 0.4 mL/min, the column temperature was 45° C., and the injection volume was 3.5 μL.

In all conditions, the mass spectrometer operated using a capillary voltage of 1.5 kV, the sampling cone and the extraction cone were of 30 V and 5 V, respectively. The cone and the desolvation gas flow were 50 L/h and 800 L/h, respectively, while the source and desolvation gas temperatures were 120 and 500° C., respectively. MS spectra were acquired in centroid mode from m/z 50 to 1000 using scan time of 0.3 s. Leucine enkephalin (2 ng/μL) was used as lock mass (m/z 556.2771 and 554.2615 in positive and negative experiments, respectively).

An analytical block consisted of pooled QC samples to equilibrate the system, calibrators, samples and spiked pooled QC samples.

An internal standard was used prior to start of the experiment. The internal standard used for the experiments to detect inosine, hypoxanthine, and adenine was L-phenylalanine-3,3-$d_2$. The internal standard used for the experiments to detect pyruvate and lactate was succinic acid-2,2,3,3-$d_4$. The internal standard used for the experiment to detect glucose was D-glucose-$^{13}C_6$.

The ionization mode during the experiment was ES− for inosine, pyruvate and lactate and ES+ for hypoxanthine, adenine and glucose.

The following table listed peak (m/z) and UPLC retention time in minutes for the metabolites inosine, pyruvate, lactate, hypoxanthine, adenine and glucose.

TABLE 1

| Metabolites | Peak (m/z) | UPLC Retention Time (min.) |
| --- | --- | --- |
| Inosine | 267.0729 | 3.65 |
| Hypoxanthine | 137.0463 | 3.26 |
| Adenine | 136.0618 | 3.75 |
| Pyruvate | 87.0088 | 1.9 |
| Glucose | 203.054 | 4.2 |
| Lactate | 89.0239 | 2.2 |

Data Processing and Analysis-RBC

The identification of the metabolites was achieved by integration, alignment, and conversion of MS data points into exact mass retention time pairs. The identity of the metabolites was established by verifying peak retention time, accurate mass measurements, and tandem mass spectrometry against our in-house database and/or online databases, including HMDB and METLIN. TargetLynx was used to integrate chromatograms of targeted metabolites. Extracted ion chromatograms were extracted using a 0.02 mDa window centered on the expected m/z for each targeted compound. Quantitation was performed by external calibration with reference standards.

Principal Component Analysis (PCA) was performed on all significant measurements ($p<0.05$ one way Anova test). Before PCA, data was scaled (unit variance scaling).

Normalization was performed before PCA analysis to minimize the differences between two different experiments (Experiment 1 (Exp1): RBC units 1-2-3-4-5-6-7-8-9-10. Experiment 2 (Exp2): RBC units 11-12-13-14-15-16-17-18-19-20). Normalized Exp1 (Exp1') was obtained by applying the following formula to each parameter: Exp1'=(Exp1+average Exp2)−average Exp1.

Blood-Gas Analysis-RBC

Glucose, lactate, $Na^+$, $K^+$, $pCO_2$, and pH were analyzed using a blood gas analyzer. Samples were analyzed following the manufacture's protocol.

Results

Nine biomarkers were analyzed (FIG. 5-FIG. 13). The ratio of glucose:lactate (FIG. 5), the ratio of $Na^+$:$K^+$ (FIG. 6), and optionally the ratio of hypoxanthine:adenine (FIG. 7), the ratio of inosine:adenine (FIG. 10), the value of inosine (FIG. 12) and the value of pyruvate (FIG. 13) were used to determine and assign First Phase (Healthy Phase) to the RBC sample. The ratio of hypoxanthine:adenine (FIG. 7) and optionally the ratio of inosine:adenine (FIG. 10) and the value of inosine (FIG. 12) were used to determine and assign Second Phase (Transition Phase). The ratio of hypoxanthine:adenine (FIG. 7), the value of hypoxanthine (FIG. 8), the value of adenine (FIG. 9) and optionally the ratio of inosine:adenine (FIG. 10), the ratio of $pCO_2$:pH (FIG. 11) and the value of inosine (FIG. 12) were used to determine and assign Third Phase (Old Phase).

Example 4

Metabolome Baseline Study for Platelet Concentrates

The metabolome baseline for platelet concentrates (PCs) stored for a period of 10 days at 22° C. was evaluated. The metabolome (both intracellular and extracellular) were analyzed at CSBui by mass spectrometry (MS).

Eight PC (platelet concentrates) bags were collected by apheresis (2-3 units collected on the same day). On the day of collection, 2 to 3 PC bags were obtained which were collected by apheresis from different donors. A sterile Clave sampler was welded to each bag to minimize the length of tubing between the valve and the bag. The PC bags were placed in a platelet incubator at standard storage conditions (e.g., 22° C., gentle agitation).

The PC bags were sampled on days 0, 1, 3, 4, 5, 6, 7, and 10. Day 0 was defined as the day the platelets were collected from the donor). Sample collection between Day 0 and Day 1 was about 23-25 hours apart (in this set of experiment was done in the afternoon). Sample collection on the remaining days took place between the hours of 8:00 and 11:00 in the morning. After regular sampling on day 10, collect an additional end-of-study sample was collected from the bags. The bags were then discarded.

The study was repeated with 2-3 more PC bags per experiment, until data from 8 PC bags were collected.

PC Bag Sampling

Using a syringe, 3.2 mL of sample was collect. Immediately after sample collection, the sample was analyzed directly from the syringe on a ABL90. The following parameters were recorded: pH, $pO_2$, $pCO_2$, ctHb, $cK^+$, $cNa^+$, $cCa^+$, $cCl^-$, cGlu, and cLac.

For the remaining sample in the syringe, the syringe was first gently inverted 5 times and the remaining sample was dispensed into a 5-mL tube. The sample was aliquoted from the 5-mL tube into six 1.7-mL microcentrifuge tubes, creating four 0.5-mL aliquots and two 0.25-mL aliquots. The tubes were kept at room temperature. Three of the 0.5-mL aliquots and both 0.25-mL aliquots were transferred to CSBui within 1 hour of preparation.

The cells from spent media in the remaining 0.5-mL aliquot were separated by centrifugation. Centrifugation was done within 15 minutes of tube preparation. After centrifugation, the PC supernatant was aliquoted into ten 1.5-mL microcentrifuge tubes (40 µL per tube). One of the PC supernatant aliquots was placed in the refrigerator and the remaining 9 PC supernatant aliquots were stored at −80° C. These aliquots were used for assays performed after the end of the experiment.

The remainder of the sample in the 5-mL tube was used for the hematology analyzer and flow cytometry. The hematology analyzer was used in Open Mode. The following parameters were recorded: PLT, MPV, PCT, and PDW. Hematoanalysis and flow cytometry sample dilution were performed within 15 minutes of tube preparation.

End-of-study Sample

Just prior to terminating the bags on day 10, 10 mL of sample was collected into a syringe. The sample was dispensed from the syringe into a 15-mL centrifuge tube and the cells were separated from the spent media by centrifugation. Additional sample was collected and used for bacterial contamination analysis. After centrifugation, the PC supernatant was aliquoted into five 1.5-mL microcentrifuge tubes (1 mL per tube). The PC supernatant aliquots were stored in −80° C. freezer. The cell pellets were discarded.

End-of-Study Assays

Within 4 days of completing an experiment, LDH assay was performed on the PC supernatant samples stored in the refrigerator. Within 2 months of completing an experiment, the levels of soluble CD62p, soluble CD40L, and cytokines in the PC supernatant samples stored at −80° C. were measured. Within 2 months of completing an experiment, the amount of plasma in PC supernatants collected on day 0 and stored at −80° C. were quantified.

Example 5

Evaluation of Platelets by Flow Cytometry

Platelet viability, degree of activation, and mitochondrial activity were evaluated by flow cytometry. The following reagents and kits were used: CD41a-FITC (BD 555466), CD42b-PE (BD 555473), CD62p-PE (BD 348107), CD63-PE (BD 556020), AnnexinV-PE (BD 556421), JC-1 kit (Invitrogen M34152), IgG1-PE (control) (BD 340013).

Three 15-mL centrifuge tubes were prepared with the first tube containing 9 mL of HEPES buffered saline solution (HBS) (10 mM HEPES, 140 mM NaCl, 5 mM KCl, 1 mM $MgSO_4*7H_2O$, pH 5-5.5), the second tube containing 2 mL of the HEPES buffered saline solution, and the third tube containing 5 mL of HEPES buffered saline solution supplemented with calcium chloride (ca-HBS) (10 mM HEPES, 140 mM NaCl, 5 mM KCl, 1 mM $MgSO_4*7H_2O$, 3.5 mM $CaCl_2*2H_2O$, pH 5-5.5). The first tube and the third tube were kept on ice. The second tube was kept at room temperature prior to use.

Table 2 shows the assay setup and final volumes of the reagents used.

TABLE 2

| Tube | Sample (μL) | Buffer (mL) | Reagent 1 (μL) | Reagent 2 (μL) |
|---|---|---|---|---|
| A | diluted PC sample (5) | HBS (2) | IgG1-PE (20) | CD41-FITC (10) |
| B | diluted PC sample (5) | HBS (2) | CD42b-PE (20) | CD41-FITC (10) |
| C | diluted PC sample (5) | HBS (2) | CD62p-PE (20) | CD41-FITC (10) |
| D | diluted PC sample (5) | HBS (2) | CD63-PE (20) | CD41-FITC (10) |
| E | diluted PC sample (5) | ca-HBS (2.19) | ca-HBS (10) | CD41-FITC (10) |
| F | diluted PC sample (5) | ca-HBS (2.19) | AnnexinV-PE (10) | CD41-FITC (10) |
| G | diluted PC sample (Eq. 1) | HBS (Eq. 2) | JC-1 (2.5) | carbonyl cyanide 3-chlorophenyl-hydrazone (CCCP) (0.5) |
| H | diluted PC sample (Eq. 1) | HBS (Eq. 2) | JC-1 (2.5) | none |

Sample and Tube Preparation

Platelet concentrates (PC) was dilute 1:10 by mixing 100 μL of PC sample with 900 μL of room-temperature HBS solution in a 5-mL tube. The PC sample was gently agitated first by flicking the tube 5 times to ensure cells did not settle to the bottom. The diluted sample was referred to as "diluted PC sample" in the subsequent experiment. Eight 5-mL tubes (A through H) were labeled for each sample to be tested (see assay setup in Table 2).

Tubes A-F (Platelet Activation and Apoptosis Markers)

Reagents 1 and 2 (volumes as shown in Table 2) were pipetted into tubes A-D. Reagent 2 (CD41-FITC) (volume as shown in Table 2) was pipetted into tubes E and F.

The tube containing the diluted PC sample was gently agitated 5 times to prevent clumping of the cells. To the tubes A-F, 5 μL of diluted PC sample was added to each tube. Tubes A-F were then incubated in the dark at room temperature for 20 minutes. After 20-minute incubation, 200 μL of ca-HBS was added to tube E, 190 μL of ca-HBS was added to tube F, and 10 μL of AnnexinV-PE to tube F. Tubes E and F were incubated in the dark at room temperature for 15 minutes. Meanwhile, 2 mL of ice-cold HBS was added to tubes A-D. The tubes were kept on ice and protect from light until flow cytometry analysis.

After completion of tubes E and F incubation, 2 mL of ca-HBS was added to each tube, and the tubes were kept on ice and protect from light until flow cytometry analysis. The flow cytometry analysis (FACSCalibur flow cytometer) was performed within 2 hours of sample preparation.

Tubes G-H (Mitochondrial Membrane Potential)

Fresh JC-1 solution was prepared by dissolving the contents of one vial of JC-1 powder in 230 μL of DMSO. Room-temperature HBS solution and diluted PC sample were added to tubes G and H such that the volume and platelet concentration in the tubes were 1 mL and $3 \times 10^{10}$ cells/L, respectively. The following equations were used to calculate the required volumes of diluted PC sample and HBS buffer. The cell concentration (PLT) was obtained from the hematology analyzer.

$$\text{volume of diluted } PC \text{ sample } (\mu L) = \frac{3 \times 10^{14}}{PLT \text{ (cells/L)}} \quad (1)$$

$$\text{volume of } HBS \text{ buffer } (\mu L) = \quad (2)$$
$$1000 - \text{volume of diluted } PC \text{ sample } (\mu L)$$

Reagents 1 and 2 were added into both tubes (volumes as shown in Table 2). The tubes were incubated in the dark in a 37° C. incubator for 20 minutes. After the 20-minute incubation period, the tubes were left at room temperature protected from light. Flow cytometry analysis (FACSCalibur flow cytometer) was performed within 2 hours of sample preparation.

FIGS. 15-21 illustrate exemplary signature profiles of platelet biomarkers described herein. FIG. 15A illustrates a signature profile of platelets processed by apheresis by principal component analysis. FIG. 15B illustrates a signature profile of platelets processed by buffy coat method by principal component analysis. Stage 1 illustrates First Phase. Stage 2 illustrates Second Phase. FIG. 16A and FIG. 16B illustrate exemplary signature profiles of glutathione oxidized. FIG. 16A illustrates signature profile of glutathione oxidized from platelets processed by apheresis. The glutathione oxidized was obtained from the intracellular medium of the apheresis processed platelets. FIG. 16B illustrates signature profile of glutathione oxidized from platelets processed by buffy coat method. The glutathione oxidized was obtained from the extracellular medium of the buffy coat processed platelets. FIG. 17A-FIG. 17E illustrate exemplary signature profiles of glutamine, niacinamide, succinic acid, and a second signature profile for glutathione oxidized. FIG. 17A illustrates signature profile of glutamine from platelets processed by apheresis. FIG. 17B illustrates signature profile of niacinamide from platelets processed by apheresis. FIG.

Figure 17A:
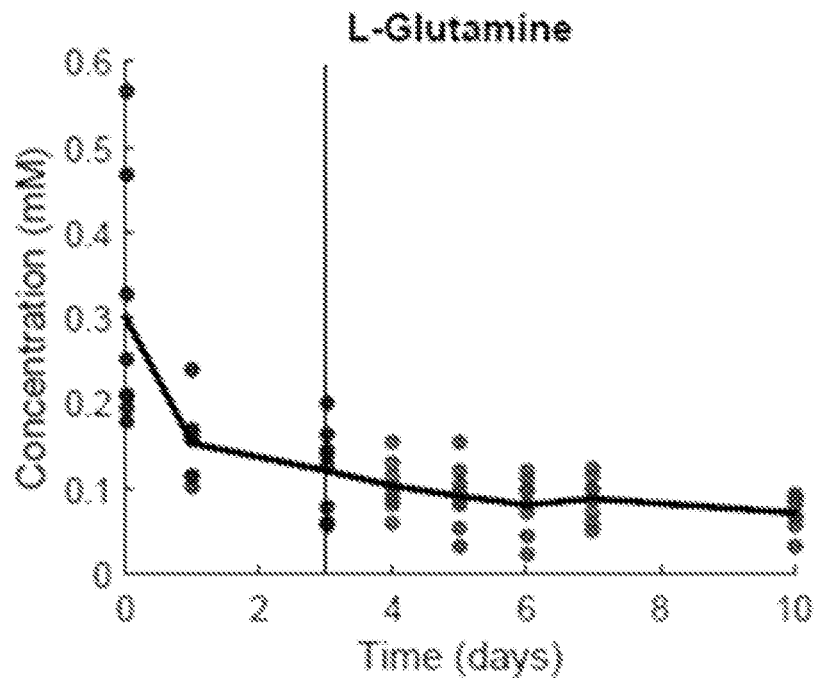
FIG. 17A-FIG. 17E illustrate exemplary signature profiles of glutamine, niacinamide, succinic acid, and a second signature profile for glutathione oxidized.
Figure 17B:
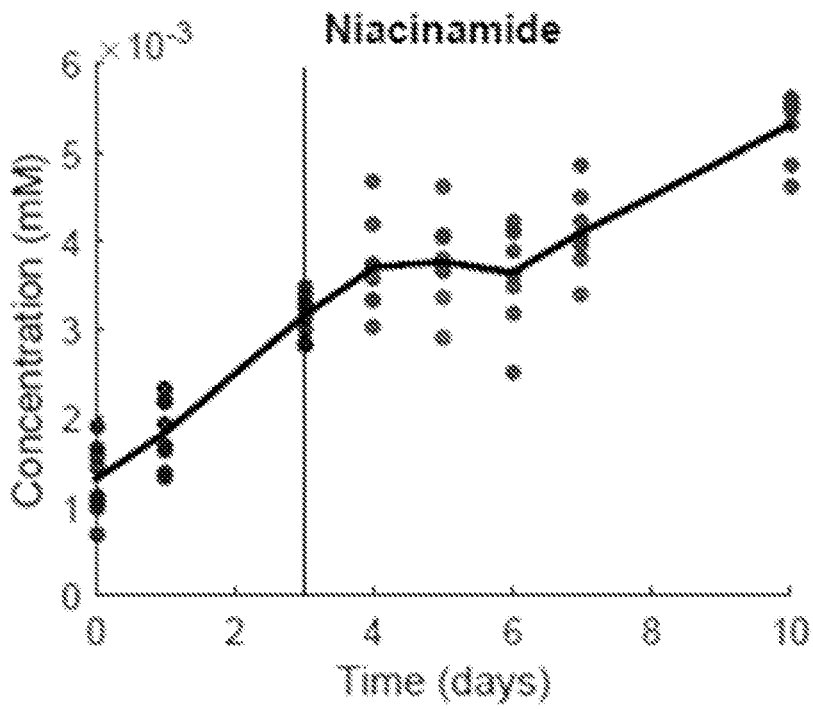
Figure 17C:
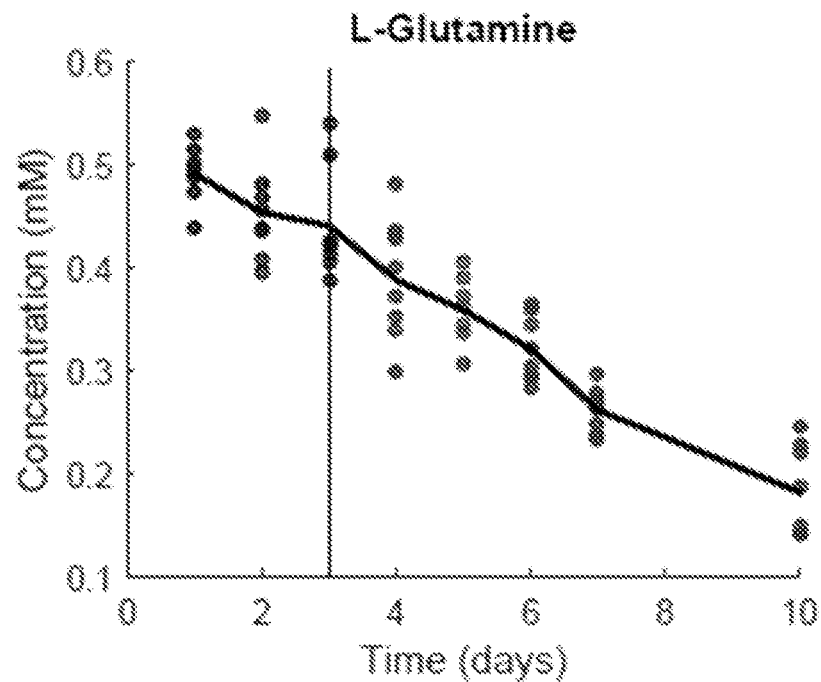
Figure 17D:
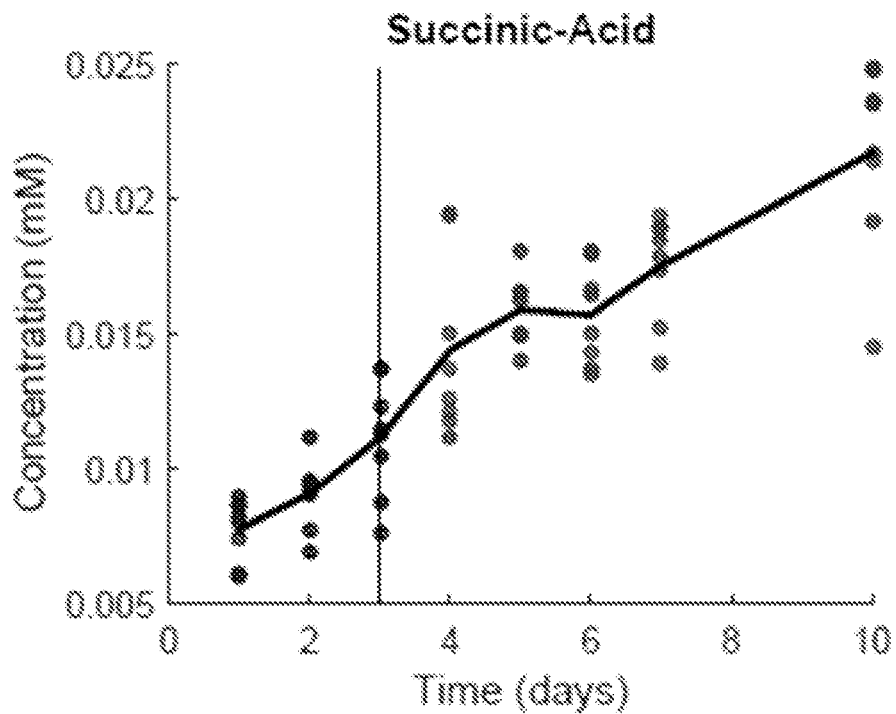
Figure 17E:
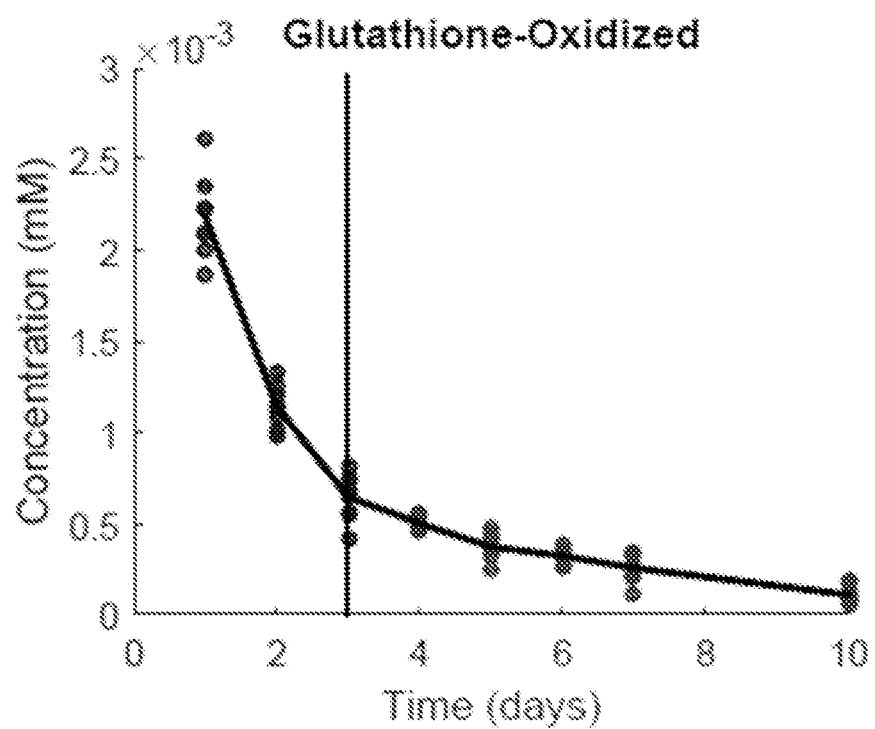
Figure 18:
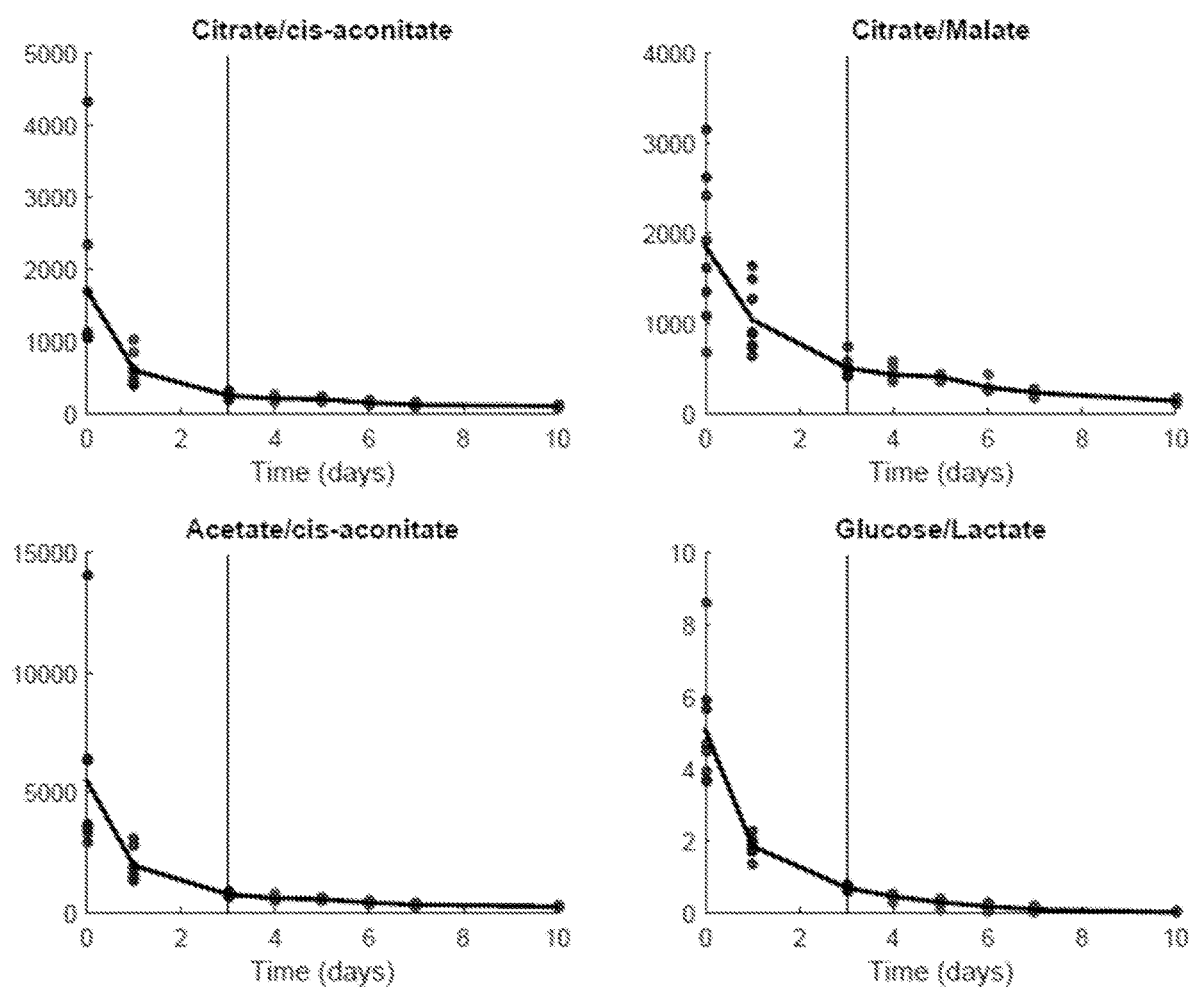
FIG. 18 illustrates exemplary signature profiles of citrate:cis-aconitate; citrate:malate; acetate:cis-aconitate; and glucose:lactate from platelets processed by apheresis.
Figure 19:
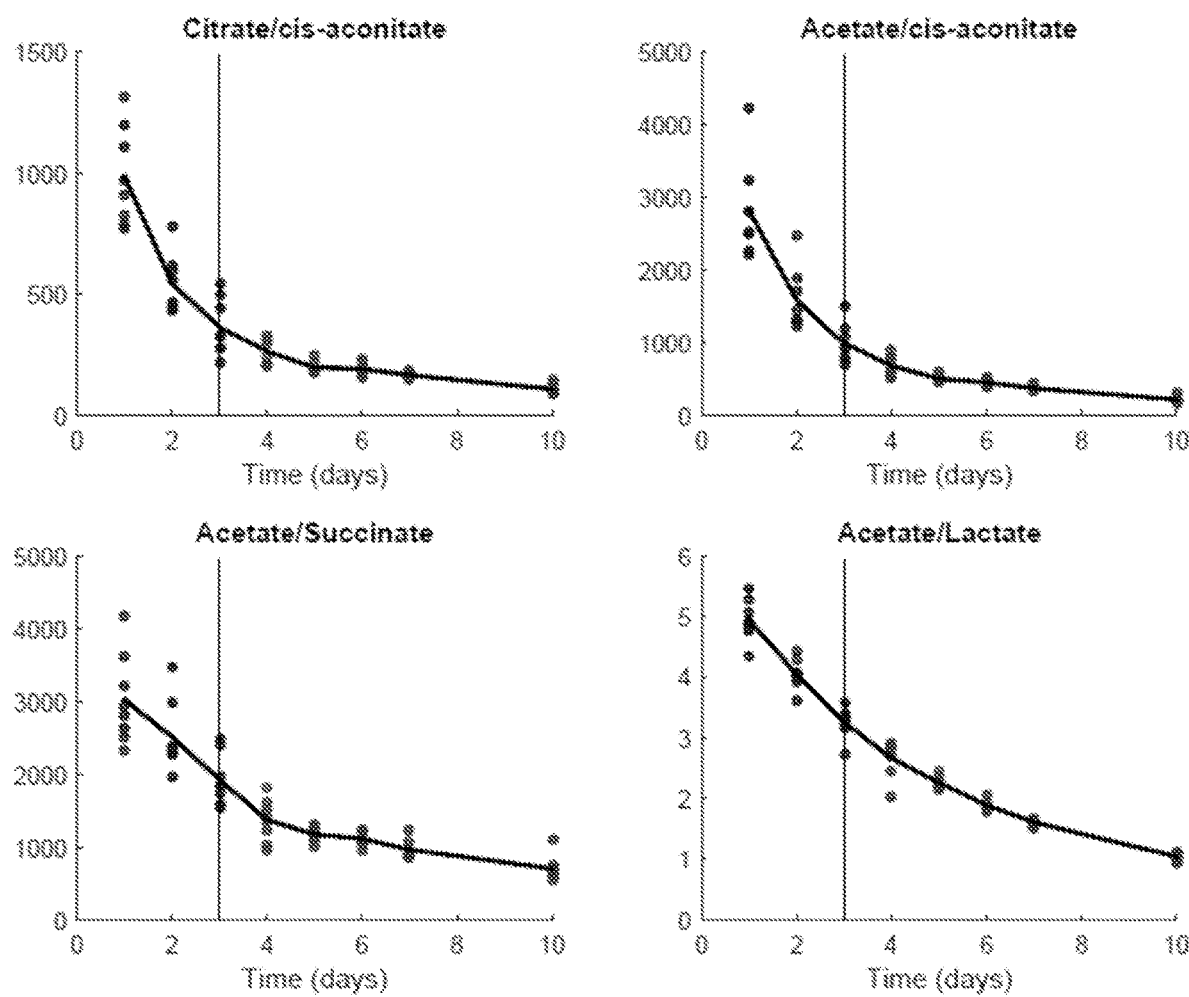
FIG. 19 illustrates exemplary signature profiles of citrate:cis-aconitate; acetate:cis-aconitate; acetate:succinate; and acetate:lactate from platelets processed by buffy coat method.
Figure 20:
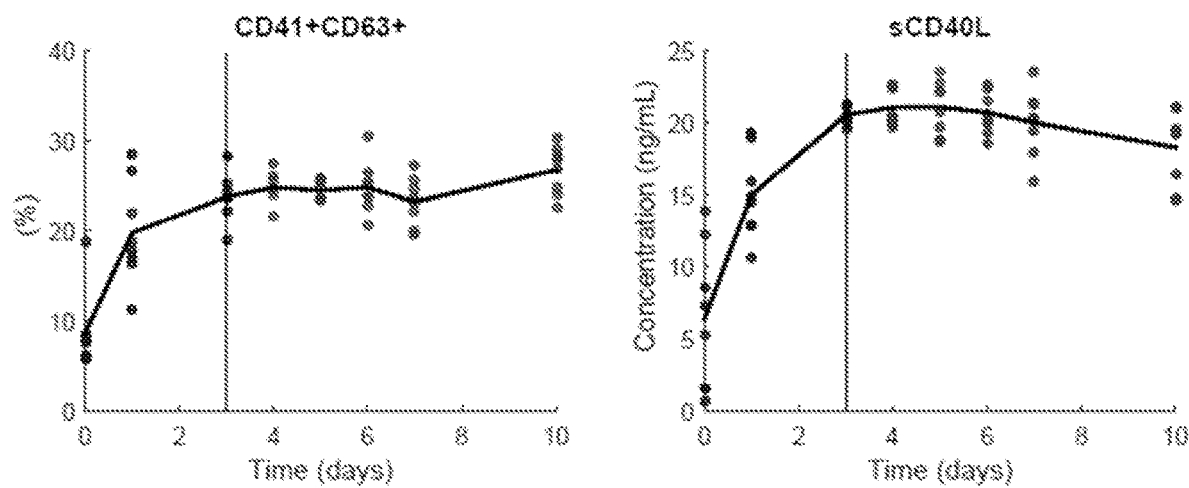
FIG. 20 illustrates exemplary signature profile of CD41-CD63+ and signature profile of sCD40L from platelets processed by apheresis.
Figure 21:
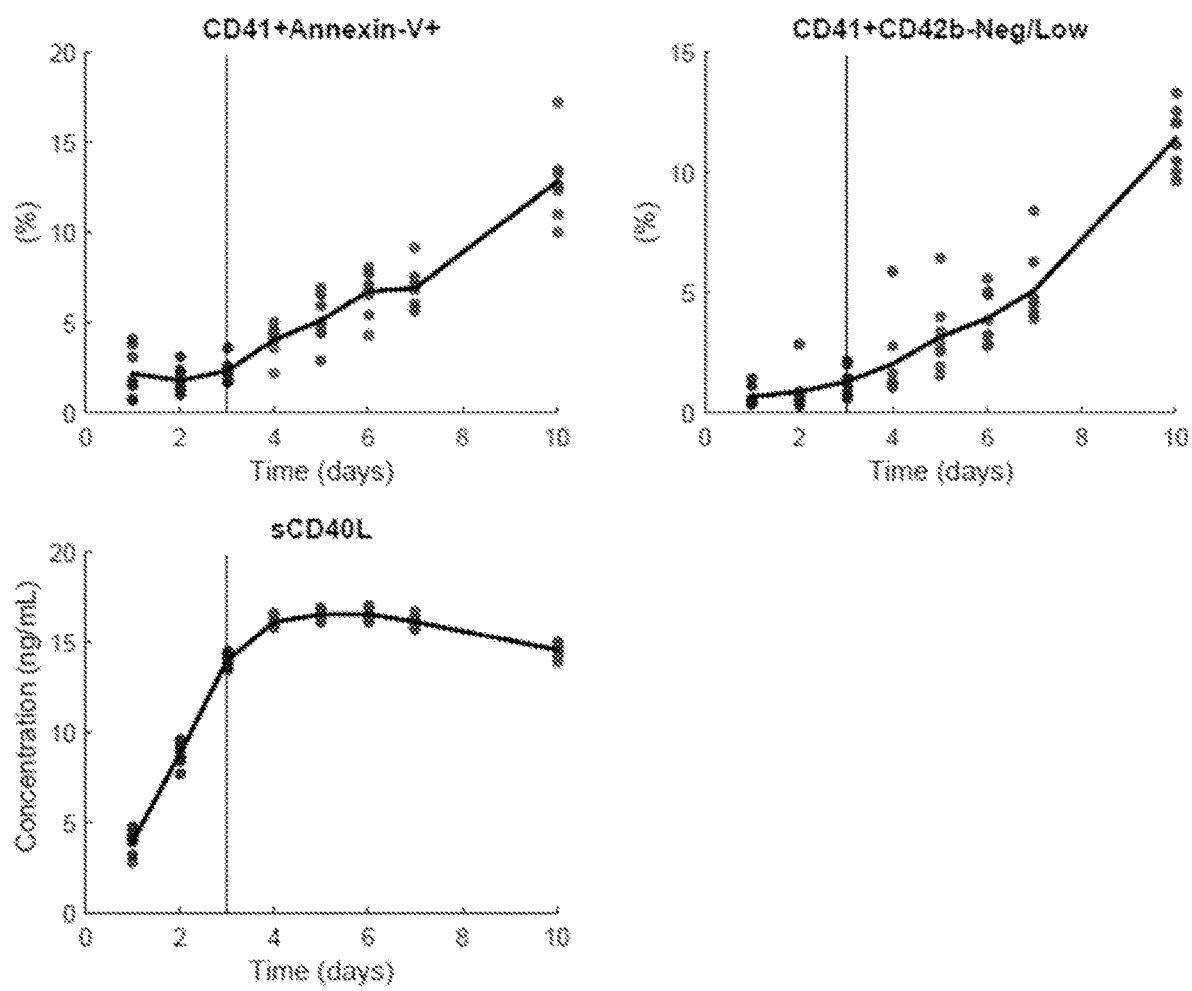
FIG. 21 illustrates exemplary signature profiles of CD41-annexin-V+; CD41-CD42b; and sCD40L from platelets processed by buffy coat method.

17C illustrates signature profile of glutamine from platelets processed by buffy coat method. FIG. 17D illustrates signature profile of succinic acid from platelets processed by buffy coat method. FIG. 17E illustrates a second signature profile of glutathione oxidized from platelets processed by buffy coat method. The glutathione oxidized used to generate the second signature profile was obtained from the intracellular medium of the buffy coat processed platelets. FIG. 18 illustrates exemplary signature profiles of citrate:cis-aconitate; citrate:malate; acetate:cis-aconitate; and glucose:lactate from platelets processed by apheresis. FIG. 19 illustrates exemplary signature profiles of citrate:cis-aconitate; acetate:cis-aconitate; acetate:succinate; and acetate:lactate from platelets processed by buffy coat method. FIG. 20 illustrates exemplary signature profile of CD41-CD63+ and signature profile of sCD40L from platelets processed by apheresis. FIG. 21 illustrates exemplary signature profiles of CD41-annexin-V+; CD41-CD42b; and sCD40L from platelets processed by buffy coat method.

Example 6

The metabolic phases of RBCs in different additive solutions (e.g., AS-1, AS-3, and PAGGSM) were examined. Tables 3-5 illustrate the values associated with the RBC biomarkers in AS-1, AS-3 and PAGGSM additive solutions.

TABLE 3

| Biomarker | Metabolic Shift | First Phase Range | Second Phase Range | Third Phase Range | Units |
|---|---|---|---|---|---|
| Inosine | 1 to 2 | 0 | in between | >0.0932 | uM |
| Adenine | 1 to 2 | >0.0814 | <0.0814 | — | mM |
| Acetyl-Carnitine | 2 to 3 | — | <1.24 | >1.24 | uM |
| Hypoxanthine | 1 to 2 | <0.0367 | >0.0367 | — | mM |
| Ratios | | | | | |
| Glucose/Lactate | 1 to 2 | >3.4 | <3.4 | — | — |
| Na+/K+ | 1 to 2 | >7 | <7 | — | — |
| pCO2/pH | 2 to 3 | — | <18.5 | >18.5 | — |
| Inosine/Adenine | 2 to 3 | — | <0.0025 | >0.0025 | — |
| Hypoxanthine/Adenine | 2 to 3 | — | <5 | >5 | — |

TABLE 4

| Biomarker | Metabolic Shift | First Phase Range | Second Phase Range | Third Phase Range | Units |
|---|---|---|---|---|---|
| Inosine | 2 to 3 | — | <0 | >0.01 | uM |
| Adenine | N/A | — | — | — | — |
| Hypoxanthine | 1 to 2 | <0.125 | >0.125 | — | mM |
| Ratios | | | | | |
| Glucose/Lactate | 1 to 2 | >4 | <4 | — | — |
| Na+/K+ | 1 to 2 | >7.5 | <7.5 | — | — |
| pCO2/pH | N/A | — | — | — | — |
| Inosine/Adenine | 2 to 3 | — | 0 | >0.001 | — |
| Hypoxanthine/Adenine | 2 to 3 | — | <6.5 | >6.5 | — |

TABLE 5

| Biomarker | Metabolic Shift | First Phase Range | Second Phase Range | Third Phase Range | Units |
|---|---|---|---|---|---|
| Inosine | 1 to 2 | <0.1 | — | — | uM |
| Adenine | 1 to 2 | >0.05 | <0.05 | — | mM |
| Hypoxanthine | N/A | — | — | — | — |
| Ratios | | | | | |
| Glucose/Lactate | 1 to 2 | >2.25 | <2.25 | — | — |
| Na+/K+ | 1 to 2 | >5.5 | <5.5 | — | — |
| pCO2/pH | 1 to 2 | <16 | >16 | — | — |
| Inosine/Adenine | 1 to 2 | <0.002 | >0.002 | — | — |
| Hypoxanthine/Adenine | 1 to 2 | <5 | >5 | — | — |

Figure 22:
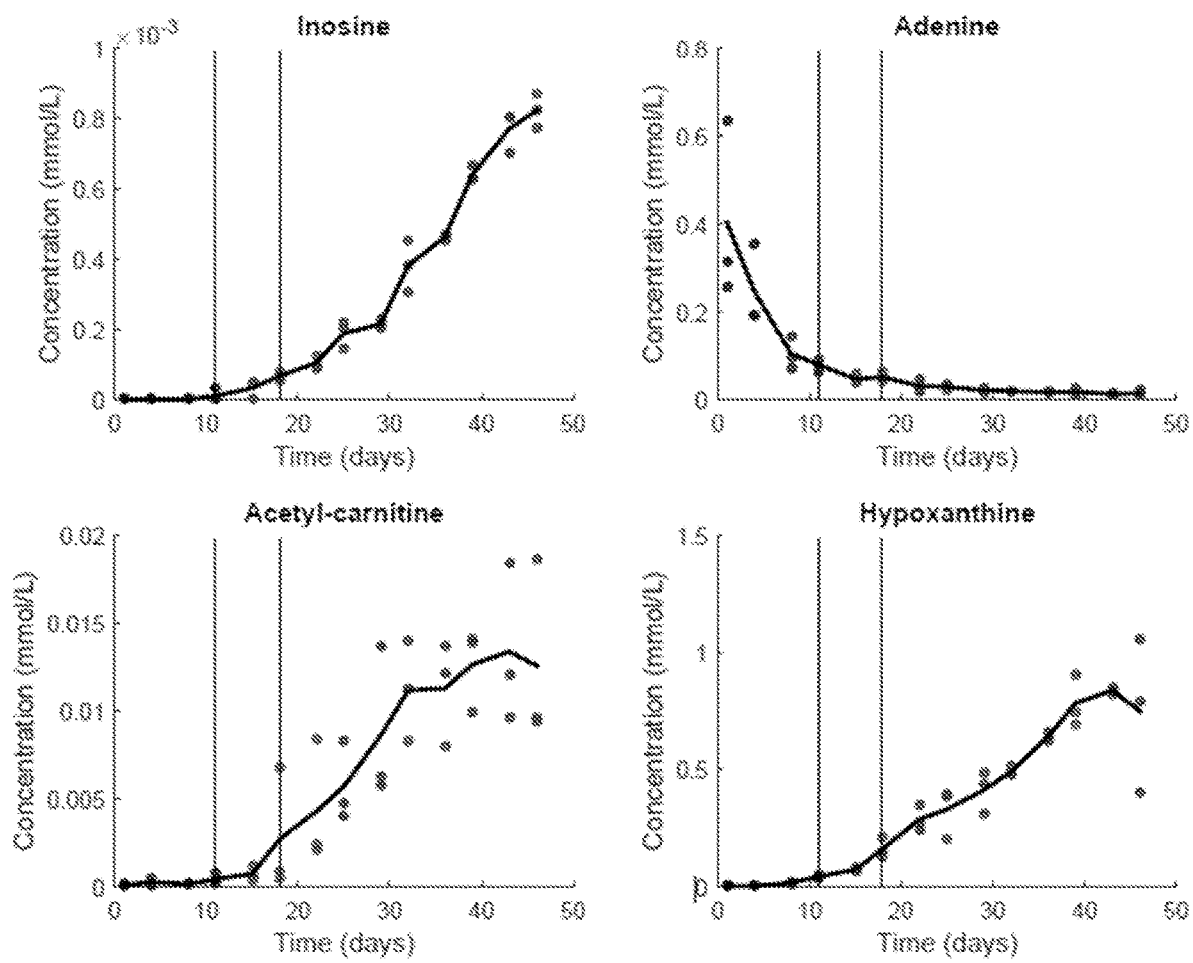
FIG. 22 illustrates exemplary signature profiles of inosine, adenine, acetyl-carnitine, and hypoxanthine from RBCs in AS-1 additive solution.
Figure 23:
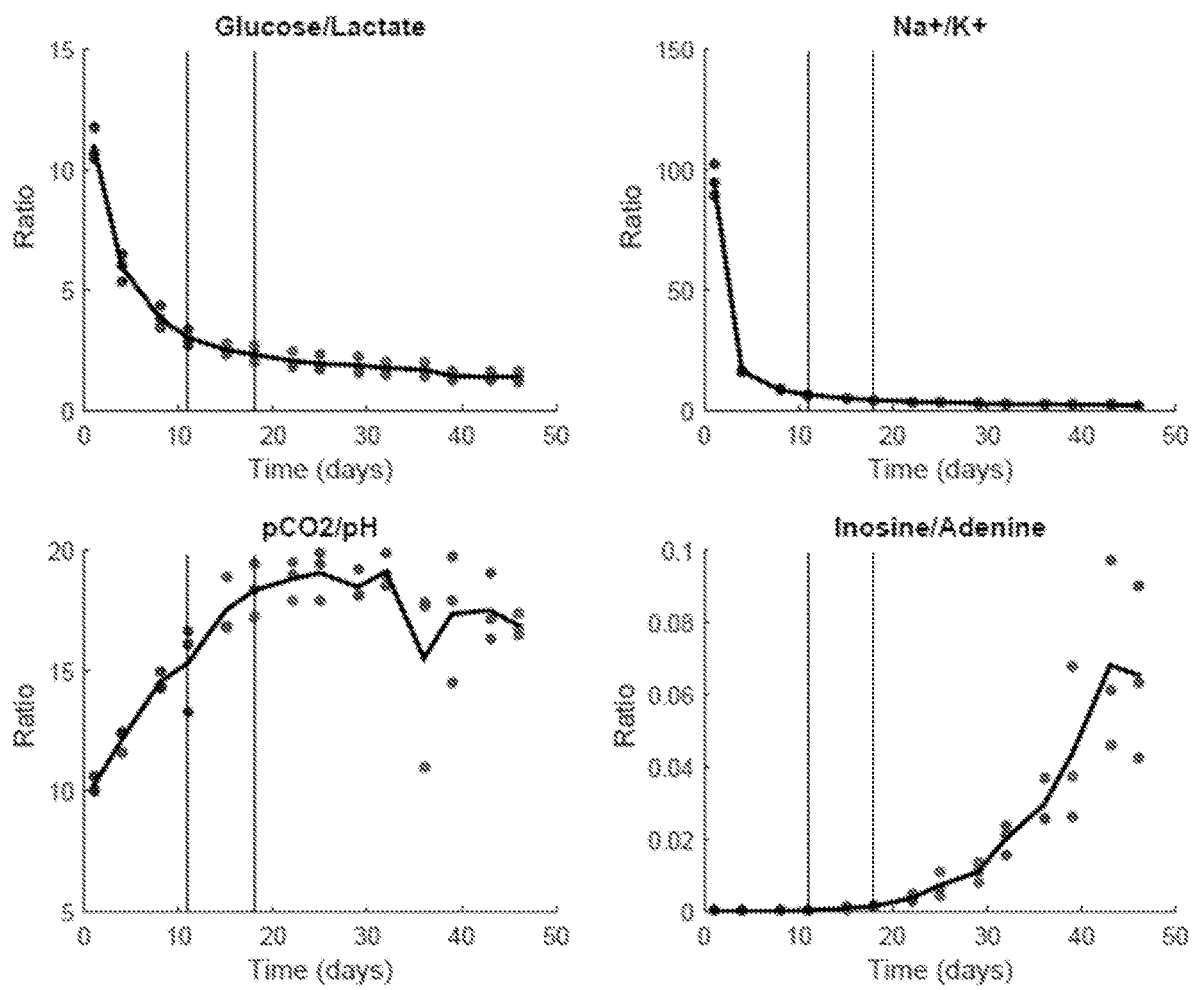
FIG. 23 illustrates exemplary signature profiles of glucose:lactate; $Na^+:K^+$; $pCO_2:pH$; and inosine:adenine from RBCs in AS-1 additive solution.
Figure 24:
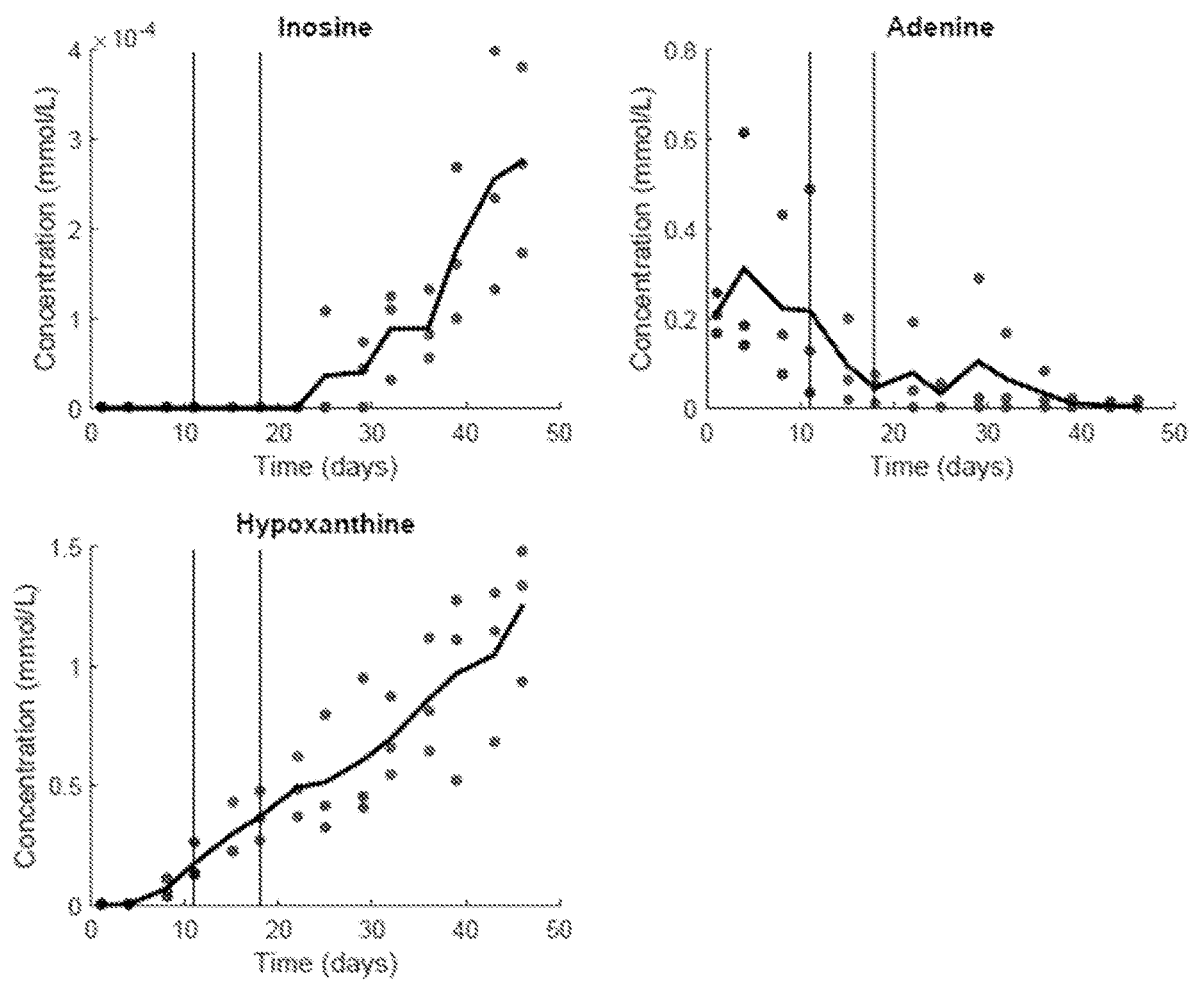
FIG. 24 illustrates exemplary signature profiles of inosine, adenine, and hypoxanthine from RBCs in AS-3 additive solution.
Figure 25:
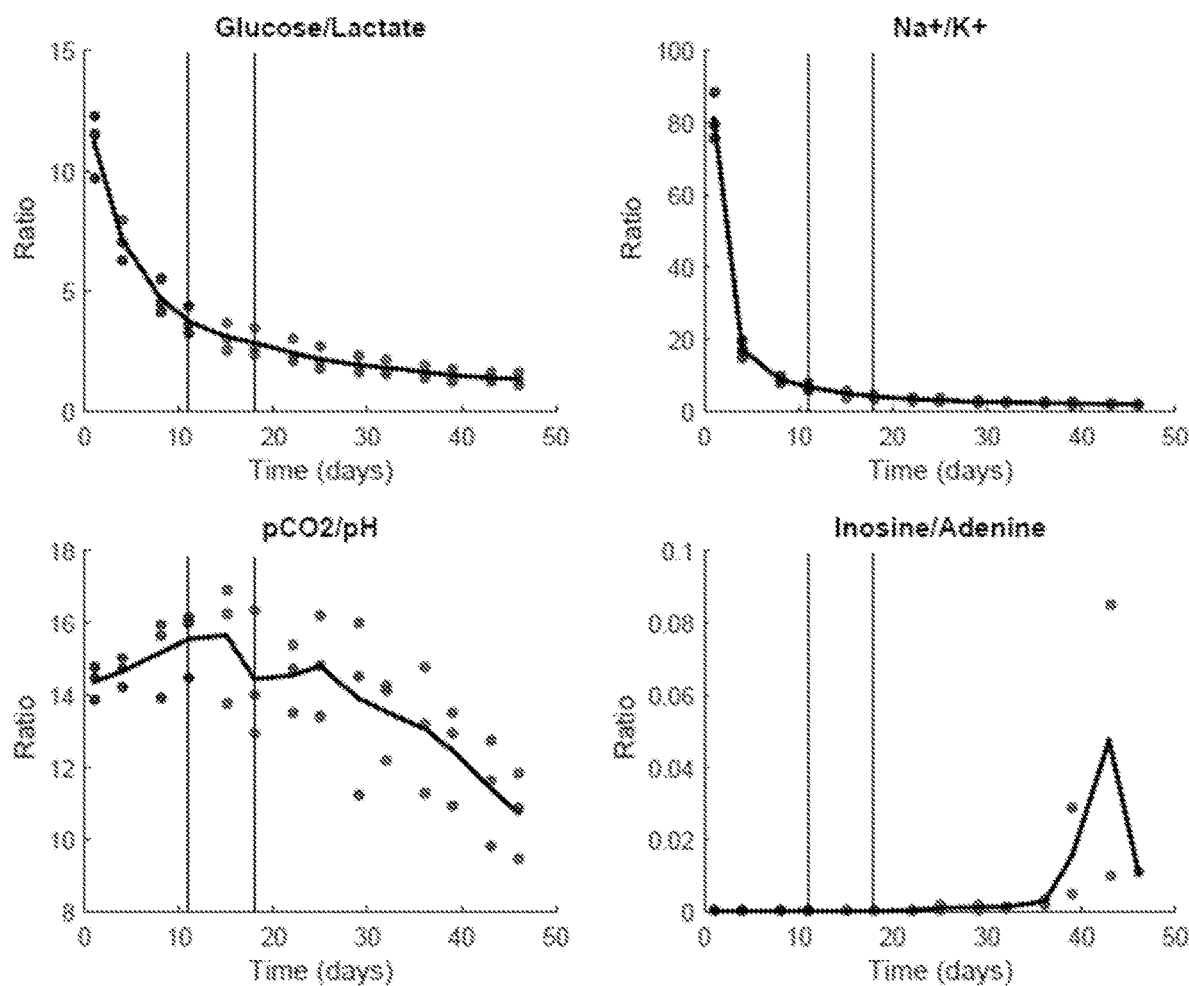
FIG. 25 illustrates exemplary signature profiles of glucose:lactate; $Na^+:K^+$; $pCO_2:pH$; and inosine:adenine from RBCs in AS-3 additive solution.
Figure 26:
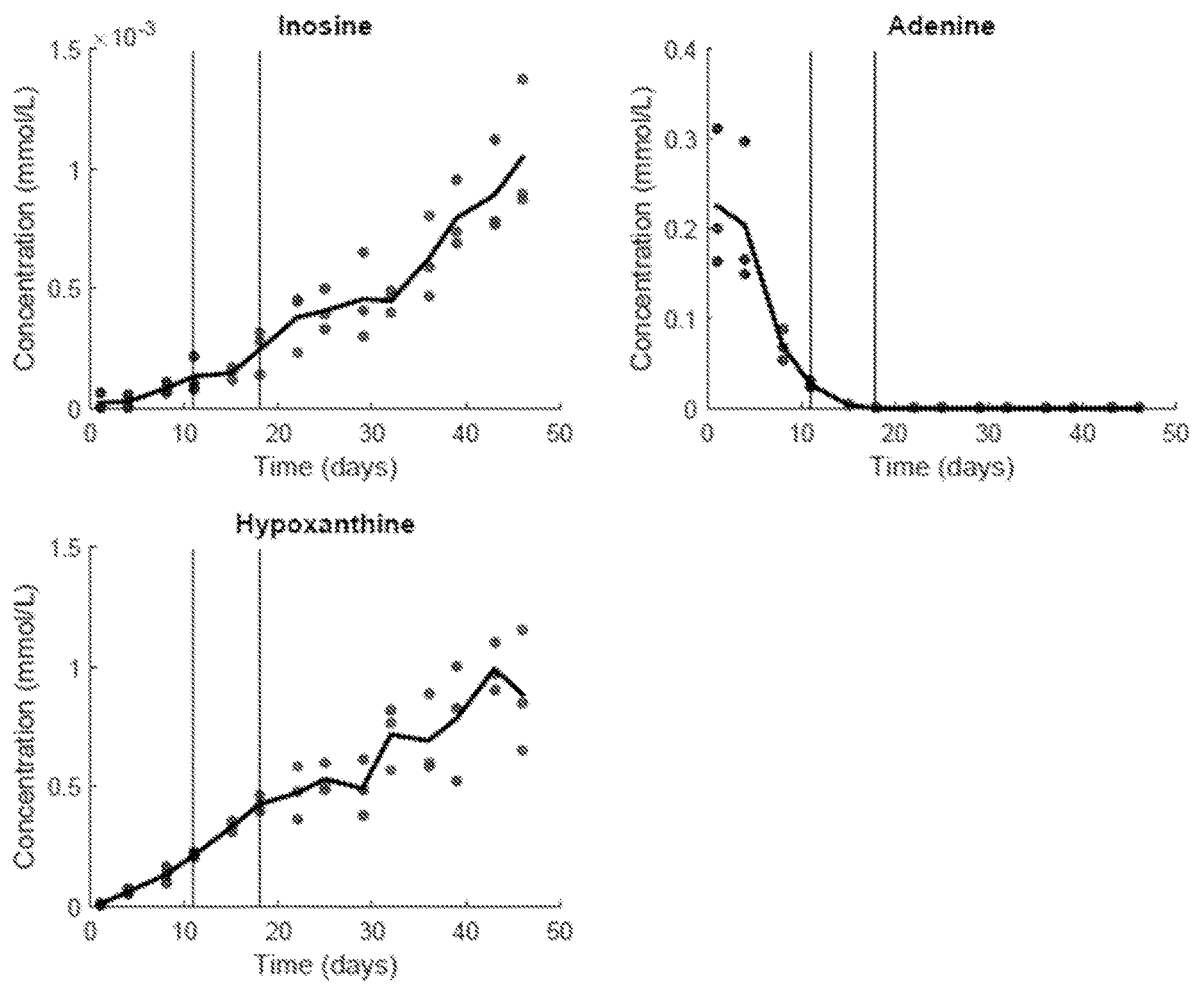
FIG. 26 illustrates exemplary signature profiles of inosine, adenine, and hypoxanthine from RBCs in PAGGSM additive solution.
Figure 27:
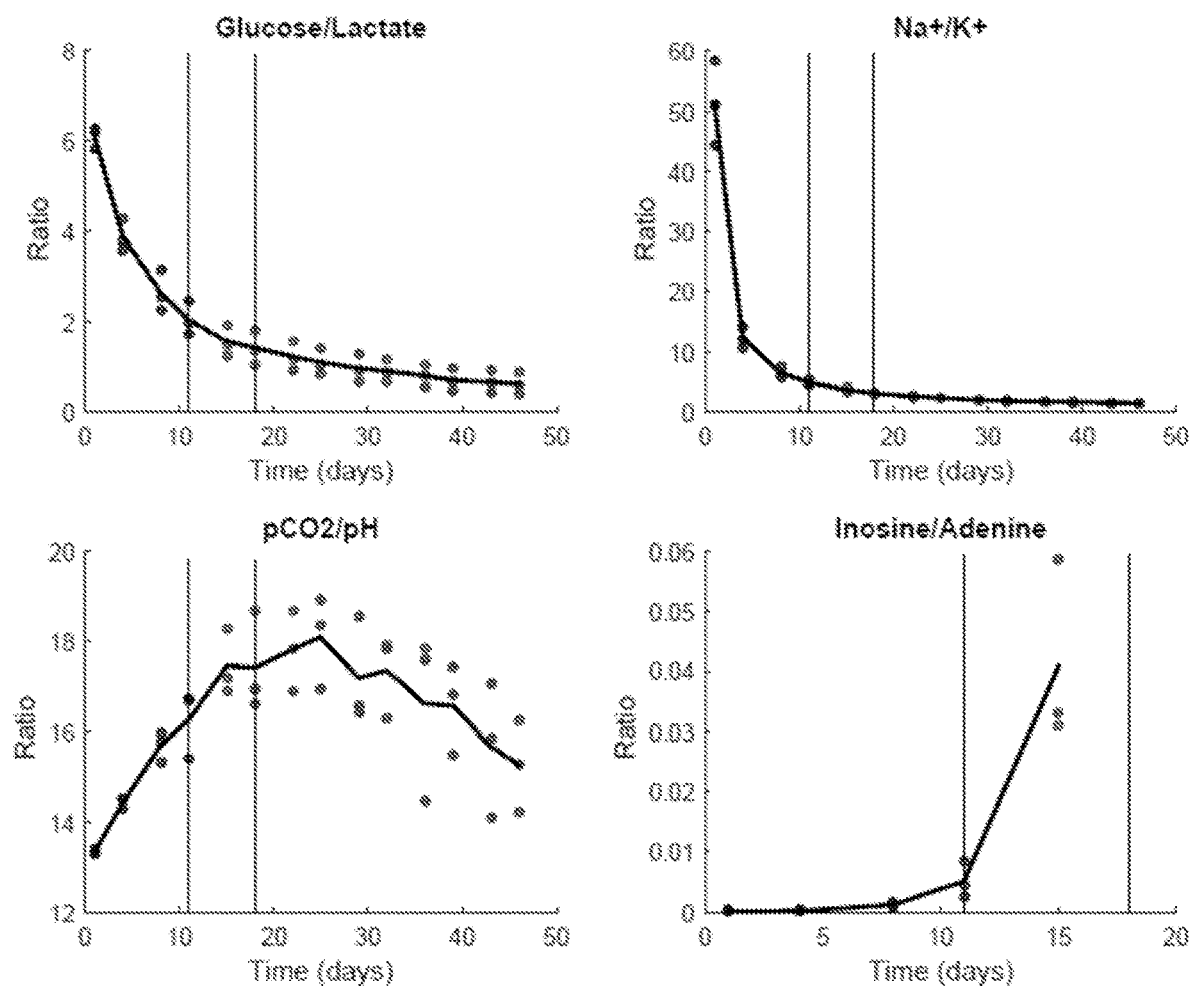
FIG. 27 illustrates exemplary signature profiles of glucose:lactate; $Na^+:K^+$; $pCO_2:pH$; and inosine:adenine from RBCs in PAGGSM additive solution.

FIGS. 22-27 illustrate exemplary signature profiles of RBC biomarker described herein obtained from RBCs with AS-1, AS-3 or PAGGSM additive solutions. FIG. 22 illustrates exemplary signature profiles of inosine, adenine, acetyl-carnitine, and hypoxanthine from RBCs in AS-1 additive solution. FIG. 23 illustrates exemplary signature profiles of glucose:lactate; $Na^+$:$K^+$; $pCO_2$:pH; and inosine:adenine from RBCs in AS-1 additive solution. FIG. 24 illustrates exemplary signature profiles of inosine, adenine, and hypoxanthine from RBCs in AS-3 additive solution. FIG. 25 illustrates exemplary signature profiles of glucose:lactate; $Na^+$:$K^+$; $pCO_2$:pH; and inosine:adenine from RBCs in AS-3 additive solution. FIG. 26 illustrates exemplary signature profiles of inosine, adenine, and hypoxanthine from RBCs in PAGGSM additive solution. FIG. 27 illustrates exemplary signature profiles of glucose:lactate; $Na^+$:$K^+$; $pCO_2$:pH; and inosine:adenine from RBCs in PAGGSM additive solution.

The examples and embodiments described herein are for illustrative purposes only and various modifications or changes suggested to persons skilled in the art are to be included within the spirit and purview of this application and scope of the appended claims.

What is claimed is:

1. An analytical storage device comprising:
   a storage container configured to store a composition comprising red blood cells (RBCs) and an additive solution;
   a test portion comprising a test label, the test portion mechanically coupled to the storage container, the test label comprising:
   (a) a testing module comprising a detector comprising reagents and configured to carry out a test reaction of the RBCs with the reagents to detect a metabolic state of red blood cells (RBCs) as indicated by a concentration of one or more biomarkers of the metabolic state of RBCs selected from the group consisting of hypoxanthine, inosine, adenine, glucose, lactate, $Na^+$, $K^+$, and pyruvate, wherein the hypoxanthine and adenine are extracellular; and
   (b) an analytical module configured to assign one phase out of three possible phases to the RBC sample indicative of the metabolic state of the RBCs and based on the concentration of the one or more biomarkers of the metabolic state of RBCs, the three possible phases comprising:
   (i) a First Phase when a comparison of a measured ratio of glucose:lactate and a ratio of Na+:K+ matches the values of an RBC control having predetermined values indicated for the metabolic state of the RBCs for the First Phase; and optionally, when one or more of a concentration of inosine, a ratio of hypoxanthine:adenine, a ratio of inosine:adenine, and a concentration of pyruvate, match values of the RBC control having predetermined values indicated for the metabolic state of the RBCs for First Phase;

(ii) a Second Phase when the ratio of hypoxanthine:adenine matches a value of an RBC control having predetermined values indicated for the metabolic state of the RBCs for the Second Phase; and optionally when the concentration of inosine and/or the ratio of inosine:adenine matches values of the RBC control having predetermined values indicated for the metabolic state of the RBCs for Second Phase; and (iii) a Third Phase when the concentration of hypoxanthine or the ratio of hypoxanthine:adenine, matches values of an RBC control having predetermined values indicated for the metabolic state of the RBCs for the Third Phase; and optionally when one or more of the concentration of adenine, $pCO_2$:pH, the ratio of inosine:adenine and the concentration of inosine match values of the RBC control having predetermined values indicated for the metabolic state of the RBCs for the Third Phase; and an indicator operably connected to the test portion comprising the test label and configured to (i) receive, from the analytical module of the test label, the assigned phase and (ii) display the phase.

2. The analytical storage device of claim 1, wherein the RBC control is a signature profile of one, two or more biomarkers of the metabolic state of RBCs over time.

3. The analytical storage device of claim 1, wherein a ratio of glucose:lactate greater than 2.0 mM/mM is associated with the First Phase and a ratio of glucose:lactate of between 0-2.0 mM/mM, inclusive, is associated with both the Second Phase and the Third Phase.

4. The analytical storage device of claim 1, wherein a ratio of $Na^+$:$K^+$ greater than 6.5 mM/mM is associated with the First Phase and a ratio of between 0-6.5 mM/mM, inclusive, is associated with both the Second Phase and the Third Phase.

5. The analytical storage device of claim 1, wherein a ratio of hypoxanthine:adenine of between 0-1.0 mM/mM, inclusive, is associated with the First Phase, a ratio of between 1.0-16 mM/mM is associated with the Second Phase and a ratio greater than 16 mM/mM is associated with the Third Phase.

6. The analytical storage device of claim 1, wherein a concentration of extracellular hypoxanthine of between 0-0.1 mM, inclusive, is associated with both the First Phase and the Second Phase and a concentration greater than 0.1 mM is associated with the Third Phase.

7. The analytical storage device of claim 1, wherein a concentration of adenine greater than 0.1 mM is associated with both the First Phase and the Second Phase and a concentration of adenine of between 0-0.1 mM is associated with the Third Phase.

8. The analytical storage device of claim 1, wherein a ratio of inosine:adenine of 0 mM/mM is associated with the First Phase, a ratio of inosine:adenine of between 0-0.05 mM/mM, inclusive, is associated with the Second Phase and a ratio greater than 0.05 mM/mM is associated with the Third Phase.

9. The analytical storage device of claim 1, wherein a ratio of $pCO_2$:pH of between 0-16 mmHg/pH, inclusive, is associated with the First Phase and the Second Phase, and a ratio greater than 16 mmg/pH is associated with the Third Phase.

10. The analytical storage device of claim 1, wherein a concentration of inosine of 0 mM is associated with the First Phase, a concentration of inosine of between 0-0.0005 mM, inclusive, is associated with the Second Phase and a concentration greater than 0.0005 mM is associated with the Third Phase.

11. The analytical storage device of claim 1, wherein a concentration of pyruvate of 0 mM is associated with the First Phase and a concentration greater than 0 mM is associated with both the Second Phase and the Third Phase.

12. The analytical storage device of claim 1, wherein the indicator is configured to indicate the phase through a color.

13. The analytical storage device of claim 12, wherein the indicator is configured to indicate a change in the phase through a change in the color.

14. The analytical storage device of claim 1, wherein the storage container comprises the composition comprising the RBCs and the additive solution.

15. The analytical storage device of claim 1, wherein the test portion is mechanically coupled to an inner wall of the container.

16. The analytical storage device of claim 1, wherein the test label comprises a test strip.

17. The analytical storage device of claim 1, wherein the test reaction is high-performance liquid chromatography (HPLC), blood-gas analysis, enzymatic assay, biochemical assay, luminescence assay, mass spectrometry, or photometry.

18. The analytical storage device of claim 1, wherein at least one of the inosine, $Na^+$, $K^+$, glucose, lactate, and pyruvate is extracellular.

19. The analytical storage device of claim 1, wherein the indicator operably connected to the test portion is connected to the test portion via a computer network.

20. The analytical storage device of claim 1, wherein the storage container and the test portion comprising the test label are integrated into a single device.

* * * * *